(12) United States Patent
Baumann et al.

(10) Patent No.: US 8,962,834 B2
(45) Date of Patent: Feb. 24, 2015

(54) MODULATORS OF AMYLOID BETA

(71) Applicant: Hoffmann-La Roche Inc., Nutley, NJ (US)

(72) Inventors: Karlheinz Baumann, Efringen-Kirchen (DE); Alexander Flohr, Loerrach (DE); Erwin Goetschi, Reinach BL (CH); Helmut Jacobsen, Schopfheim (DE); Synese Jolidon, Blauen (CH); Thomas Luebbers, Loerrach (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 41 days.

(21) Appl. No.: 13/749,865

(22) Filed: Jan. 25, 2013

(65) Prior Publication Data
US 2013/0190302 A1  Jul. 25, 2013

Related U.S. Application Data

(63) Continuation of application No. 12/731,729, filed on Feb. 16, 2009, now abandoned.

(30) Foreign Application Priority Data

Feb. 22, 2008 (EP) ..................... 08151825

(51) Int. Cl.
| | | |
|---|---|---|
| C07D 403/12 | (2006.01) | |
| C07D 401/12 | (2006.01) | |
| C07D 401/14 | (2006.01) | |
| C07D 403/14 | (2006.01) | |
| C07D 409/14 | (2006.01) | |
| C07D 413/12 | (2006.01) | |
| C07D 413/14 | (2006.01) | |
| C07D 417/12 | (2006.01) | |
| C07D 405/14 | (2006.01) | |
| C07D 417/14 | (2006.01) | |
| A61P 25/28 | (2006.01) | |

(52) U.S. Cl.
CPC ............ *C07D 403/12* (2013.01); *C07D 401/12* (2013.01); *C07D 401/14* (2013.01); *C07D 403/14* (2013.01); *C07D 409/14* (2013.01); *C07D 413/12* (2013.01); *C07D 413/14* (2013.01); *C07D 417/12* (2013.01); *C07D 405/14* (2013.01); *C07D 417/14* (2013.01)
USPC ......................................................... 544/331

(58) Field of Classification Search
USPC ......................................................... 544/331
See application file for complete search history.

(56) References Cited

U.S. PATENT DOCUMENTS 5,686,070 A  11/1997  Doerschuk et al.
6,399,773 B1  6/2002  Liu et al.

| 2003/0134838 A1 | 7/2003 | Bornemann et al. |
|---|---|---|
| 2003/0176454 A1 | 9/2003 | Yamada et al. |
| 2004/0034008 A1 | 2/2004 | Stamford et al. |
| 2005/0176772 A1 | 8/2005 | Calabrese et al. |
| 2006/0004013 A1 | 1/2006 | Kimura et al. |
| 2007/0117798 A1 | 5/2007 | Kimura et al. |
| 2007/0117839 A1 | 5/2007 | Kimura et al. |
| 2007/0219181 A1 | 9/2007 | Kimura et al. |
| 2008/0280948 A1 | 11/2008 | Baumann et al. |
| 2009/0163485 A1 | 6/2009 | Knust et al. |
| 2009/0181965 A1 | 7/2009 | Baumann et al. |
| 2009/0215759 A1 | 8/2009 | Baumann et al. |

FOREIGN PATENT DOCUMENTS

| EP | 0233461 | 8/1987 |
|---|---|---|
| EP | 1201661 | 5/2002 |
| EP | 1479397 | 11/2004 |
| EP | 1947098 | 7/2008 |
| EP | 1950211 | 7/2008 |
| EP | 2019093 | 1/2009 |
| EP | 2243785 | 10/2010 |
| WO | 93/19050 | 9/1993 |
| WO | 94/04487 | 3/1994 |
| WO | 97/21704 | 6/1997 |
| WO | 99/65884 | 12/1999 |

(Continued)

OTHER PUBLICATIONS (Translation of Chinese Off Act in Corres Chinese Appl 20098010598.3 Oct. 22, 2012).

(Continued)

*Primary Examiner* — James O Wilson
*Assistant Examiner* — Cecilia M Jaisle

(57) ABSTRACT

The invention relates to compounds of formula

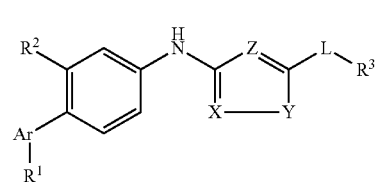

wherein the substituents are as described in claim 1. Compounds of formula I are modulators for amyloid beta and thus, they may be useful for the treatment or prevention of a disease associated with the deposition of β-amyloid in the brain, in particular Alzheimer's disease, and other diseases such as cerebral amyloid angiopathy, hereditary cerebral hemorrhage with amyloidosis, Dutch-type (HCHWA-D), multi-infarct dementia, dementia pugilistica and Down syndrome.

11 Claims, No Drawings

(56) References Cited

FOREIGN PATENT DOCUMENTS

| | | |
|---|---|---|
| WO | 00/25780 | 5/2000 |
| WO | 00/27842 | 5/2000 |
| WO | 00/78731 | 12/2000 |
| WO | 01/47897 | 7/2001 |
| WO | 01/87845 | 11/2001 |
| WO | 02/057240 | 7/2002 |
| WO | 03/002561 | 1/2003 |
| WO | 03/040141 | 5/2003 |
| WO | 03/040141 A1 | 5/2003 |
| WO | 03/044014 | 5/2003 |
| WO | 03/047512 | 6/2003 |
| WO | 03/053939 | 7/2003 |
| WO | 2004/046118 | 6/2004 |
| WO | 2004/069185 | 8/2004 |
| WO | 2004/087699 | 10/2004 |
| WO | 2004/110350 | 12/2004 |
| WO | 2005/003103 | 1/2005 |
| WO | 2005/013996 | 2/2005 |
| WO | 2005/040120 | 5/2005 |
| WO | 2005/044785 | 5/2005 |
| WO | 2005/063022 | 7/2005 |
| WO | 2005/115990 | 12/2005 |
| WO | 2006/040192 | 4/2006 |
| WO | 2006/044457 | 4/2006 |
| WO | 2006/058905 | 6/2006 |
| WO | 2006/111549 | 10/2006 |
| WO | 2006/112550 | 10/2006 |
| WO | 2006/112551 | 10/2006 |
| WO | 2006/113704 | 10/2006 |
| WO | 2007/013673 | 2/2007 |
| WO | 2007/051333 | 5/2007 |
| WO | 2007/053452 | 5/2007 |
| WO | 2007/054480 | 5/2007 |
| WO | 2007/058304 | 5/2007 |
| WO | 2007/058305 | 5/2007 |
| WO | 2007/060810 | 5/2007 |
| WO | 2007/060821 | 5/2007 |
| WO | 2007/076161 | 5/2007 |
| WO | 2007/102580 | 9/2007 |
| WO | 2007/120333 | 10/2007 |
| WO | 2007/125405 | 11/2007 |
| WO | 2007/131953 | 11/2007 |
| WO | 2007/135969 | 11/2007 |
| WO | 2007/135970 | 11/2007 |
| WO | 2007/139149 | 12/2007 |
| WO | 2008/006103 | 1/2008 |
| WO | 2008/013213 | 1/2008 |
| WO | 2008/065626 | 6/2008 |
| WO | 2008/097538 | 8/2008 |
| WO | 2008/099210 | 8/2008 |
| WO | 2008/099210 A2 | 8/2008 |
| WO | 2008/100412 | 8/2008 |
| WO | 2008/107096 | 9/2008 |
| WO | 2008/138753 | 11/2008 |
| WO | 2008/156580 | 12/2008 |
| WO | 2009/032277 | 2/2009 |
| WO | 2009/032861 | 3/2009 |
| WO | 2009/064388 | 5/2009 |
| WO | 2009/076337 | 6/2009 |
| WO | 2009/103652 | 8/2009 |
| WO | 2009/155551 | 12/2009 |
| WO | 2010/010188 | 1/2010 |
| WO | 2010/027500 | 3/2010 |
| WO | 2010/098487 | 9/2010 |

OTHER PUBLICATIONS

Nettekoven et al., Synthesis 11:1649-1652 (2003).
Maiti et al., JOC Note 75:1791-1794 (2010).
Nilsson et al., J. Med. Chem. 46:3985-4001 (2003).
Paul et al, "Preparation of substituted N-phenyl-4-aryl-2-pyrimidinamines as mediator release inhibitors," J. Med Chem., 1993, 36 (19), pp. 2716-2725, pp. 10.
The Japanese Office Action, issued on Mar. 5, 2013, in the corresponding Japanese application No. 2010-547156., pp. 6.
Wilkins et al., Science of Synthesis 13:277-295 (2004).
Jantzen et al., Neuroscience 22:226-254 (2002).
Delecea et al., Proc. Natl. Acad. Sci. USA 95:322-327 (1998).
Sakamoto et al., Regul. Pept. 118:183-191 (2004).
Kumita et al., Nippon Noyaku Gakkaishi 26(1):60-66 (2001).
Takahashi et al., Biol. Chem. 278:18644-18670 (2003).
Dhar et al., Bioorganic & Medicinal Chemistry Letters (XP002522864), 12(12):3125-3128 (2002).
Suzuki et al., Brain Research 1044:116-121 (2005).
Yang et al., Org. Chem. vol. 67(21):7429-7431 (2002).
Perretto et al., Med. Chem. 48:5705-5720 (2005).
Clarke et al., Biol. Chem. 281:31279-31289 (2006).
(Office Action in copending U.S. Appl. No. 12/114,852, Jun. 28, 2010).
Kidwai et al., Chemical Papers:231-234 (2000).
Cai et al., Expert Opin. Ther. Patents 16(5):631-646 (2006).
Albaneze-Walker et al., Tetrahedron 61:6330-6336 (2005).
Piper et al., Eur. J. Neuroscience 12:726-730 (2000).
Winsky Sommerer et al., J. Neuroscience 24:11439-11448 (2004).
Menicagli et al., Synth. Commun. 24:2153-2158 (1994).
Ida et al., Biochem. Biophys. Res. Comm. 270:318-323 (2000).
Sakurai et al., Cell 92:573-585 (1998).
Cooke et al., Tetrahedron 57:2787-2789 (2001).
Kuru et al., Neuroreport 11:1977-1980 (2000).
(EPO Communication in EP Appl. 09713519.8 Dec. 30, 2011).
Ringold et al., Am. Chem. Soc. 78:2477-2479 (1956).
Narlawar et al., Med. Chem. 49:7588-7591 (2006).
Schulte et al., Synlett:2331-2336 (2007).
Reinke, A. et al., Chem. Biol. Drug Des. 70:206-215 (2007).
(International Search Report PCT/EP 2008/055290 Oct. 8, 2008).
Siegel, Annu. Rev. Psychol. 55:125-148 (2004).
(Translation of Israeli Off Act in Corres Israeli App 206945 dated Feb. 29, 2012).
Beher et al., Biol. Chem. 279:43419-43426 (2004).
Iwanowicz et al., Bioorg. Med. Chem. Lett. 13:2059-2063 (2003).
Morihara et al., Neurochem. 83:1009-1012 (2002).
Grundmann et al., Am. Chem. Soc. 79:944-948 (1957).
Tilley et al., Helv. Chim. Acta 63:832-840 (1980).
Pitts et al., Bioorganic & Medicinal Chemistry Letters 12(16):2137-2140 (2002).
Chang et al., Neurosci. Res. 56:356-362 (2006).
Nishino et al., Lancet 355:39-40 (2000).
Kukar et al., Nature Med. 11:545-550 (2005).
(International Search Report PCT/EP2009/064497 Apr. 8, 2010).
(International Search Report for PCT/EP2008/067273 May 15, 2009).
Paul et al., Jour. Of Medicinal Chemistry (XP002522865), 36(19):2716-2725 (1999).
Caubere et al., Bull. Soc. Chim. Fr.:2112-2115 (1973).
Chemelli et al., Cell 98:437-451 (1999).
Malherbe et al., Mol. Pharmacol. 64:823-832 (2003).
McPhee et al., Med. Chem. Soc. 66:1132-1136 (1944).
Bingham et al., Current Opinion in Drug Discovery & Development 9(5):551-559 (2006).
Olson, R. et al., Current Topics in Medicinal Chemistry 8:17-33 (2008).
Lin et al., Cell 98:365-376 (1999).
(International Search Report for PCT/EP2009/062570 Dec. 4, 2009).
Dorwald F. A. Side Reactions in Organic Systhesis "1 & Preface"Wiley,:1-16 (2005).
Peyron et al., Nature Medicine 6:991-997 (2000).
Bourgin et al., J. Neurosci. 20(20):7760-7765 (2000).
(Office Action in copending U.S. Appl. No. 12/334,559, Sep. 30, 2009).
Lleo et al., Nature Med. 10:1065-1066 (2004).
Weggen et al., Nature 414:212-216 (2001).
(International Search Report for PCT/EP2009/051613 Apr. 22, 2004).
Hirt et al., Helv. 33:1365-1369 (1950).
Kubinyi 3D QSAR in Drug Design: Ligand Protein Interactions & Molecular SimilaritySpringer, vol. 2-3:243-244 (1998).
Mignot et al., Sleep 11:1012-1020 (1997).

(56) References Cited

OTHER PUBLICATIONS

Sakurai, Regulatory Peptides 126:3-10 (2005).
(Office Action in copending U.S. Appl. No. 12/334,559, May 20, 2010).
Peyron et al., Neurosci. 18:9996-10015 (1998).
Nambu et al., Brain Res. 18:243-260 (1999).
Bessard et al., Tetrahedron 55:405-412 (1999).
Smith et al., Neurosci. Lett. 341(3):256-258 (2003).
Schaeffer et al., Am. Chem. Soc. 73:2990-2992 (1951).
Stock et al., Bioorg. Med. Chem. Lett. 16:2219-2223 (2006).
Digby et al., J. Endocrinol. 191:129-136 (2006).
Wu et al., Tet. Lett. 49:2869-2871 (2008).

MODULATORS OF AMYLOID BETA

PRIORITY TO RELATED APPLICATION(S)

This application is a Continuation of application Ser. No. 12/371,729, filed Feb. 16, 2009, now pending which claims the benefit of European Patent Application No. 08151825.0, filed Feb. 22, 2008, which is hereby incorporated by reference in its entirety.

BACKGROUND OF THE INVENTION

Alzheimer's disease (AD) is the most common cause of dementia in later life. Pathologically, AD is characterized by the deposition of amyloid in extracellular plaques and intracellular neurofibrillary tangles in the brain. The amyloid plaques are mainly composed of amyloid peptides (Aβ peptides) which originate from the β-Amyloid Precursor Protein (APP) by a series of proteolytic cleavage steps. Several forms of APP have been identified of which the most abundant are proteins of 695, 751 and 770 amino acids length. They all arise from a single gene through differential splicing. The Aβ peptides are derived from the same domain of the APP.

Aβ peptides are produced from APP through the sequential action of two proteolytic enzymes termed β- and γ-secretase. β-Secretase cleaves first in the extracellular domain of APP just outside of the trans-membrane domain (TM) to produce a C-terminal fragment of APP containing the TM- and cytoplasmatic domain (CTFβ). CTFβ is the substrate for γ-secretase which cleaves at several adjacent positions within the TM to produce the Aβ peptides and the cytoplasmic fragment. Various proteolytic cleavages mediated by γ-secretase result in Aβ peptides of different chain length, e.g. Aβ38, Aβ40 and Aβ42. The latter one is regarded to be the more pathogenic amyloid peptide because of its strong tendency to form neurotoxic aggregates.

The β-secretase is a typical aspartyl protease. The γ-secretase is a proteolytic activity consisting of several proteins, its exact composition is incompletely understood. However, the presenilins are essential components of this activity and may represent a new group of atypical aspartyl proteases which cleave within the TM of their substrates and which are themselves polytopic membrane proteins. Other essential components of γ-secretase may be nicastrin and the products of the aph1 and pen-2 genes. Proven substrates for γ-secretase are the APP and the proteins of the Notch receptor family, however, γ-secretase has loose substrate specificity and may cleave further membrane proteins unrelated to APP and Notch.

The γ-secretase activity is absolutely required for the production of Aβ peptides. This has been shown both by genetic means, i.e., ablation of the presenilin genes and by low-molecular-weight inhibitory compounds. Since according to the amyloid hypothesis for AD the production and deposition of Aβ is the ultimate cause for the disease, it is thought that selective and potent inhibitors of γ-secretase will be useful for the prevention and treatment of AD.

An alternative mode of treatment is the modulation of the γ-secretase activity which results in a selective reduction of the Aβ42 production. This will result in to an increase of shorter Aβ isoforms, such as Aβ38, Aβ37 or others, which have reduced capability for aggregation and plaque formation, and hence less neurotoxic. Compounds which show this effect on modulating γ-secretase activity include certain non-steroidal anti-inflammatory drugs (NSAIDs) and related analogues (Weggen et al. Nature, 414 (2001) 212-16).

Numerous documents describe the current knowledge on γ-secretase modulation, for example the following publications:
Morihara et al, J. Neurochem., 83 (2002) 1009-12
Jantzen et al, J. Neuroscience, 22 (2002) 226-54
Takahashi et al, J. Biol. Chem., 278 (2003) 18644-70
Beher et al, J. Biol. Chem. 279 (2004) 43419-26
Lleo et al, Nature Med. 10 (2004) 1065-6
Kukar et al, Nature Med. 11 (2005) 545-50
Perretto et al, J. Med. Chem. 48 (2005) 5705-20
Clarke et al, J. Biol. Chem. 281 (2006) 31279-89
Stock et al, Bioorg. Med. Chem. Lett. 16 (2006) 2219-2223
Narlawar et al, J. Med. Chem. 49 (2006) 7588-91

SUMMARY OF THE INVENTION

The invention provides a compound of formula

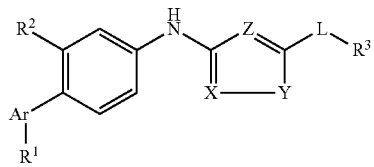

I wherein
$R^1$ is hydrogen, lower alkyl or lower alkyl substituted by hydroxy;
$R^2$ is hydrogen, lower alkoxy, lower alkyl, cyano or halogen;
$R^3$ i) for any definition of L, $R^3$ is lower alkyl, lower alkenyl, lower alkyl substituted by fluoro, $(CH_2)_2$O-lower alkyl, $(CH_2)_2NR^8{}_2$, or is 4H-benzo[1,4]oxazin-3-one, cycloalkyl optionally substituted by hydroxy, or is heterocycloalkyl, which heterocycloalkyl is optionally substituted by hydroxy or $S(O)_2$-lower alkyl, or is $(CH_2)_m$-aryl or is a five-or six-membered heteroaryl group, wherein the rings in the heteroaryl group are optionally substituted by one or more R', or
ii) for L is a bond, $R^3$ is halogen, hydroxy, —C(O)O-lower alkyl, OC(O)-lower alkyl or C(O)NH$_2$, or
iii) for L is —CR$^6$R$^7$—, $R^3$ is lower alkoxy, hydroxy, —C(O)O-lower alkyl, OC(O)-lower alkyl or C(O)NH$_2$, or
iv) for L is NR$^8$, $R^3$ is CH$_2$—C(O)O-lower alkyl, or
v) for L is C(O), $R^3$ is lower alkoxy, hydroxy or NR$^8{}_2$;
R' is halogen, lower alkyl, lower alkoxy, cyano, lower alkyl substituted by fluoro, lower alkoxy substituted by fluoro, SF$_5$, or is a five-membered heteroaryl group, which is optionally substituted by lower alkyl;
Ar is a five-membered heteroaryl group or is pyridinyl;
Z is CH or N;
X—Y is N—CR$^4$=CR$^5$, CH—CR$^4$=N, CH—CR$^4$=CR$^5$ or N—NH; and wherein $R^4$ and $R^5$ together with the corresponding carbon atoms to which they are attached optionally form an additional ring with —(CH$_2$)$_n$, with the proviso that if X—Y is CH—CR$^4$=CR$^5$ or CH—CR$^4$=N, then Z is N; or
$R^4$ and $R^5$ are each independently hydrogen, halogen, lower alkyl, lower alkoxy, C(O)O—lower alkyl, lower alkyl substituted by one or more groups selected from fluoro, hydroxy, cyano and cycloalkyl,
or are cyano, phenyl, benzyl or a five-or six-membered heteroaryl group wherein the rings in the heteroaryl group are optionally substituted by one or more R', or are cycloalkyl or heterocycloalkyl, each of which is optionally substituted by lower alkyl and hydroxy, with the proviso that $R^4$ also is optionally hydroxy or $NR^8{}_2$;

L is a bond, $-CR^6R^7-$, $-O-$, $-NR^8-$ or $-C(O)-$;

$R^6$ and $R^7$ are each independently hydrogen, lower alkyl, cycloalkyl, or phenyl or $R^6$ and $R^7$ together with the carbon atom to which they are attached form a $C_{3-6}$-cycloalkyl group, with the proviso that $R^6$ also is optionally hydroxy or lower alkoxy;

$R^8$ is hydrogen or lower alkyl;

m 0 or 1; and n is 3 or 4;

or a pharmaceutically active acid addition salt thereof.

The invention also provides all forms of optically pure enantiomers, racemates or diastereomeric mixtures for compounds of formula I.

The invention further provides pharmaceutical compositions containing compounds of formula I and methods for the preparation of such compounds and compositions.

The present compounds of formula I are modulators for amyloid beta and, thus, they may be useful for the treatment or prevention of a disease associated with the deposition of β-amyloid in the brain, in particular Alzheimer's disease, and other diseases such as cerebral amyloid angiopathy, hereditary cerebral hemorrhage with amyloidosis, Dutch-type (HCHWA-D), multi-infarct dementia, dementia pugilistica and Down syndrome.

DETAILED DESCRIPTION OF THE INVENTION

The following definitions of general terms used herein apply irrespective of whether the terms in question appear alone or in combination. It must be noted that, as used in the specification and the appended claims, the singular forms "a", "an," and "the" include plural forms unless the context clearly dictates otherwise.

As used herein, the term "lower alkyl" denotes a saturated straight- or branched-chain hydrocarbon group containing from 1 to 7 carbon atoms, for example, methyl, ethyl, propyl, isopropyl, n-butyl, i-butyl, 2-butyl, t-butyl and the like. Preferred alkyl groups are groups with 1-4 carbon atoms.

As used herein "halogen" denotes fluorine, chlorine, bromine, and iodine.

As used herein, the term "cycloalkyl" denotes a saturated carbon ring system, containing from 3 to 6 carbon atoms, for example cyclopropyl, cyclobutyl, cyclopentyl or cyclohexyl.

As used herein, the term "lower alkoxy" denotes a group containing an alkyl group as defined above which is attached via an oxygen atom.

As used herein, the term "lower alkyl substituted by halogen" denotes an alkyl group as defined above, wherein at least one hydrogen atom is replaced by halogen.

As used herein, the term "lower alkyl substituted by fluoro" denotes an alkyl group as defined above, wherein at least one hydrogen atom is replaced by fluoro, for example $CF_3$, $CHF_2$, $CH_2F$, $CH_2CF_3$, $CH_2CH_2CF_3$, $CH_2CF_2CF_3$, $CH_2CF_2CF_2CF_3$, $CH_2CH_2CF_2CF_3$ and the like.

As used herein, the term "lower alkoxy substituted by fluoro" denotes an alkoxy group as defined above, wherein at least one hydrogen atom is replaced by fluoro, for example $OCF_3$, $OCHF_2$, $OCH_2F$, $OCH_2CF_3$, $OCH_2CH_2CF_3$, $OCH_2CF_2CF_3$, $OCH_2CF_2CF_2CF_3$, $OCH_2CH_2CF_2CF_3$ and the like.

The term "lower alkenyl" denotes a straight- or branched-chain carbon group containing from 2-7, preferably from 2-4, carbon atoms, wherein at least one bond is a double bond.

As used herein, the term "five-membered heteroaryl group" denotes an heterocyclic group, containing at least two heteroatoms, selected from the group consisting of N, O and S, wherein at least one of the rings in the heterocyclic group is aromatic, for example oxazol-5-yl, [1,2,4]triazol-1-yl, [1,2,4]triazol-3-yl, [1,2,3]triazol-1-yl, imidazol-1-yl, thiazol-5-yl, thiazol-2-yl, furan-2-yl, thiophen-2-yl, pyrazol-4-yl, pyrazol-3-yl, pyrazol-1-yl, [1,2,4]-oxadiazol-5-yl, [1,3,4]-oxadiazol-2-yl or [1,2,4]thiadiazol-5-yl. Preferred are the imidazol-1-yl, pyrazol-4-yl, [1,2,4]triazol-1-yl or oxazol-5-yl groups.

The term "six-membered heteroaryl group" denotes a heterocyclic group, containing at least one heteroatom, selected from the group consisting of N, O and S, wherein at least one ring in the heterocyclic group is aromatic, for example pyridinyl, pyrazinyl, pyrimidinyl or pyridazinyl.

The term "aryl" denotes an aromatic mono or bicyclic carbon ring system, for example phenyl or naphthyl.

The term "heterocycloalkyl" denotes a non-aromatic ring system, containing at least one heteroatom, selected from the group consisting of N, O and S, for example tetrahydropyran-4-yl, piperidin-4-yl, pyrrolidin-1-yl, morpholinyl, 1,1-dioxo-6-thiomorpholin-4-yl, oxetan-3-yl or piperazin-1-yl.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluene-sulfonic acid and the like.

"Therapeutically effective amount" means an amount that is effective to prevent, alleviate or ameliorate symptoms of disease or prolong the survival of the subject being treated.

One embodiment of the invention provides compounds of formula

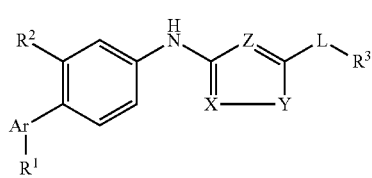

I-1 wherein $R^1$ is hydrogen, lower alkyl, lower alkyl substituted by halogen or by hydroxy, or is lower alkoxy or lower alkoxy substituted by halogen;

$R^2$ is hydrogen, lower alkoxy, lower alkyl, cyano or halogen;

$R^3$ is lower alkyl, lower alkyl substituted by fluoro or is aryl or a five-or six membered heteroaryl group wherein the rings in the heteroaryl group are optionally substituted by one or more R' for any definition of L, or when L is a bond, $R^3$ is halogen, or when L is a bond or $-CR^6R^7-$, $R^3$ is hydroxy, C(O)O-lower alkyl or C(O)NH$_2$;

R' is halogen, lower alkyl, lower alkoxy, cyano, lower alkyl substituted by fluoro, lower alkoxy substituted by fluoro or is a five-membered heteroaryl group;

Ar is a five-membered heteroaryl group;

Z is CH or N;

X—Y is N—CR$^4$=CR$^5$, N—CR$^4$=N, CH—CR$^4$=N, CH—CR$^4$=CR$^5$ or N—NH; with the proviso that if X—Y is CH—CR$^4$=CR$^5$ or CH—CR$^4$=N, then Z is N;

R$^4$ and R$^5$ are each independently hydrogen, halogen, hydroxy, lower alkyl, lower alkoxy, C(O)O-lower alkyl, lower alkyl substituted by fluoro, or are cyano, phenyl, benzyl or a five-or six-membered heteroaryl group, wherein the rings in the five-or six-membered heteroaryl group are optionally substituted by one or more R';

L is a bond, —CR$^6$R$^7$—, —O—, —NR$^8$— or —C(O)—;

R$^6$ and R$^7$ are each independently hydrogen, lower alkyl, lower alkoxy, hydroxy, phenyl or R$^6$ and R$^7$ together with the carbon atom to which they are attached form a C$_{3-6}$-cycloalkyl group; and R$^8$ is hydrogen or lower alkyl;

or pharmaceutically active acid addition salts.

Preferred are compounds of formula I-A

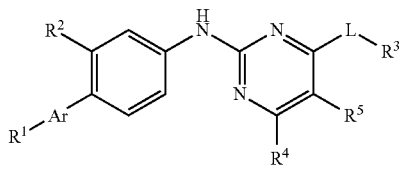

I-A wherein

R$^1$ is hydrogen, lower alkyl or lower alkyl substituted by hydroxy;

R$^2$ is hydrogen, lower alkoxy, lower alkyl, cyano or halogen;

R$^3$ i) for any definitions of L, R$^3$ is lower alkyl, lower alkenyl, lower alkyl substituted by fluoro, (CH$_2$)$_2$O-lower alkyl, (CH$_2$)$_2$NR$^8$$_2$, or is 4H-benzo[1,4]oxazin-3-one, cycloalkyl optionally substituted by hydroxy, or is heterocycloalkyl, which heterocycloalkyl is optionally substituted by hydroxy or S(O)$_2$-lower alkyl, or is (CH$_2$)$_m$-aryl or is a five-or six-membered heteroaryl group wherein the rings in the heteroaryl group are optionally substituted by one or more R' or ii) for L is a bond, R$^3$ is halogen, hydroxy, —C(O)O-lower alkyl, OC(O)-lower alkyl or C(O)NH$_2$, or iii) for L is —CR$^6$R$^7$—, R$^3$ is lower alkoxy, hydroxy, —C(O)O-lower alkyl, OC(O)-lower alkyl or C(O)NH$_2$, or iv) for L is NR$^8$, R$^3$ is CH$_2$—C(O)O-lower alkyl, or v) for L is C(O), R$^3$ is lower alkoxy, hydroxy or NR$^8$$_2$;

R' is halogen, lower alkyl, lower alkoxy, cyano, lower alkyl substituted by fluoro, lower alkoxy substituted by fluoro, SF$_5$, or is a five-membered heteroaryl group optionally substituted by lower alkyl;

Ar is a five-membered heteroaryl group or is pyridinyl;

R$^4$ and R$^5$ are each independently hydrogen, halogen, lower alkyl, lower alkoxy, C(O)O-lower alkyl, lower alkyl substituted by one or more groups selected from fluoro, hydroxy, cyano and cycloalkyl, or are cyano, phenyl, benzyl or a five-or six membered heteroaryl group, wherein the rings in the heteroaryl group are optionally substituted by one or more R', or are cycloalkyl or heterocycloalkyl, each of which is optionally substituted by lower alkyl and hydroxy, with the proviso that R$^4$ also is optionally hydroxy or NR$^8$$_2$, or wherein R$^4$ and R$^5$ together with the corresponding carbon atoms to which they are attached optionally form an additional ring with —(CH$_2$)$_n$;

L is a bond, —CR$^6$R$^7$—, —O—, —NR$^8$— or —C(O)—;

R$^6$ and R$^7$ are each independently hydrogen, lower alkyl, cycloalkyl, or phenyl or R$^6$ and R$^7$ together with the carbon atom to which they are attached form a C$_{3-6}$-cycloalkyl group, with the proviso that R$^6$ also is optionally hydroxy or lower alkoxy;

R$^8$ is hydrogen or lower alkyl;

m is 0 or 1; and n is 3 or 4;

or pharmaceutically active acid addition salts thereof.

Preferred compounds from formula I-A are those of formula I-A-1

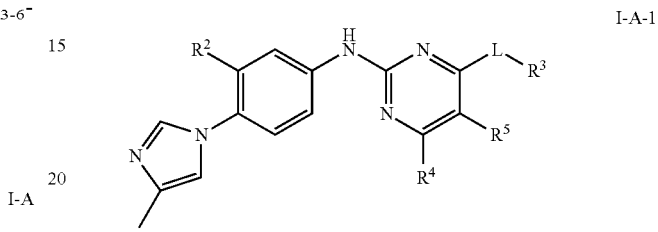

I-A-1 wherein

R$^2$ is hydrogen, lower alkoxy, lower alkyl, cyano or halogen;

R$^3$ i) for any definitions of L, R$^3$ is lower alkyl, lower alkenyl, lower alkyl substituted by fluoro, (CH$_2$)$_2$O-lower alkyl, (CH$_2$)$_2$NR$^8$$_2$, or is 4H-benzo[1,4]oxazin-3-one, cycloalkyl optionally substituted by hydroxy, or is heterocycloalkyl, which heterocycloalkyl is optionally substituted by hydroxy or S(O)$_2$-lower alkyl, or is (CH$_2$)$_m$-aryl or is a five-or six-membered heteroaryl group wherein the rings in the heteroaryl group are optionally substituted by one or more R' or ii) for L is a bond, R$^3$ is halogen, hydroxy, —C(O)O-lower alkyl, OC(O)-lower alkyl or C(O)NH$_2$, or iii) for L is —CR$^6$R$^7$—, R$^3$ is lower alkoxy, hydroxy, —C(O)O-lower alkyl, OC(O)-lower alkyl or C(O)NH$_2$, or iv) for L is NR$^8$, R$^3$ is CH$_2$—C(O)O-lower alkyl, or v) for L is C(O), R$^3$ is lower alkoxy, hydroxy or NR$^8$$_2$;

R' is halogen, lower alkyl, lower alkoxy, cyano, lower alkyl substituted by fluoro, lower alkoxy substituted by fluoro, SF$_5$, or is a five-membered heteroaryl group, which is optionally substituted by lower alkyl;

R$^4$ and R$^5$ are each independently hydrogen, halogen, lower alkyl, lower alkoxy, C(O)O-lower alkyl, lower alkyl substituted by one or more groups selected from fluoro, hydroxy, cyano and cycloalkyl, or are cyano, phenyl, benzyl or a five-or six-membered heteroaryl group wherein the rings in the heteroaryl group are optionally substituted by one or more R', or are cycloalkyl or heterocycloalkyl, each of which is optionally substituted by lower alkyl and hydroxy, with the proviso that R$^4$ also is optionally hydroxy or NR$^8$$_2$, or wherein R$^4$ and R$^5$ together with the corresponding carbon atoms to which they are attached optionally form an additional ring with —(CH$_2$)$_n$;

L is a bond, —CR$^6$R$^7$—, —O—, —NR$^8$— or —C(O)—;

R$^6$ and R$^7$ are each independently hydrogen, lower alkyl, cycloalkyl, phenyl or R$^6$ and R$^7$ together with the carbon atom to which they are attached form a C$_{3-6}$-cycloalkyl group, with the proviso that R$^6$ also is optionally hydroxy or lower alkoxy;

R$^8$ is hydrogen or lower alkyl;

m is 0 or 1; and n is 3 or 4;

or pharmaceutically active acid addition salts thereof.

Preferred compounds from this group are the following compounds:

(4-benzyl-pyrimidin-2-yl)-[3-methoxy-4-(4-methyl-imidazol-1-yl)-phenyl]-amine;
[3-methoxy-4-(4-methyl-imidazol-1-yl)-phenyl]-[4-(3,4,5-trifluoro-benzyl)-pyrimidin-2-yl]-amine;
[4-(3-chloro-benzyl)-pyrimidin-2-yl]-[3-methoxy-4-(4-methyl-imidazol-1-yl)-phenyl]-amine;
[3-methoxy-4-(4-methyl-imidazol-1-yl)-phenyl]-[5-methyl-4-(1-phenyl-ethyl)-pyrimidin-2-yl]-amine;
[3-methoxy-4-(4-methyl-imidazol-1-yl)-phenyl]-[4-methyl-6-(3,4,5-trifluoro-phenoxy)-pyrimidin-2-yl]-amine;
[4-(3,4-difluoro-phenoxy)-6-methyl-pyrimidin-2-yl]-[3-methoxy-4-(4-methyl-imidazol-1-yl)-phenyl]-amine;
[4-(4-chloro-phenoxy)-6-methyl-pyrimidin-2-yl]-[3-methoxy-4-(4-methyl-imidazol-1-yl)-phenyl]-amine;
[4-(2,6-dichloro-phenoxy)-pyrimidin-2-yl]-[3-methoxy-4-(4-methyl-imidazol-1-yl)-phenyl]-amine;
[3-methoxy-4-(4-methyl-imidazol-1-yl)-phenyl]-[4-methyl-6-(2-trifluoromethyl-phenoxy)-pyrimidin-2-yl]-amine;
[3-methoxy-4-(4-methyl-imidazol-1-yl)-phenyl]-[4-methyl-6-(3-trifluoromethoxy-phenoxy)-pyrimidin-2-yl]-amine;
[3-methoxy-4-(4-methyl-imidazol-1-yl)-phenyl]-[4-methyl-6-(3-trifluoromethyl-phenoxy)-pyrimidin-2-yl]-amine;
[3-methoxy-4-(4-methyl-imidazol-1-yl)-phenyl]-[4-methyl-6-(3,3,4,4,4-pentafluoro-butoxy)-pyrimidin-2-yl]-amine;
{4-[1-(4-chloro-phenyl)-1-methyl-ethyl]-5-methyl-pyrimidin-2-yl}-[3-methoxy-4-(4-methyl-imidazol-1-yl)-phenyl]-amine;
{4-[1-(4-chloro-phenyl)-1-methyl-ethyl]-pyrimidin-2-yl}-[3-methoxy-4-(4-methyl-imidazol-1-yl)-phenyl]-amine;
{4-[1-(4-chloro-phenyl)-1-methyl-ethyl]-pyrimidin-2-yl}-[3-fluoro-4-(4-methyl-imidazol-1-yl)-phenyl]-amine;
ethyl 4-(4-chloro-phenyl)-2-[3-methoxy-4-(4-methyl-imidazol-1-yl)-phenylamino]-pyrimidine-5-carboxylate;
[3-methoxy-4-(4-methyl-imidazol-1-yl)-phenyl]-[4-(4-trifluoromethyl-phenyl)-pyrimidin-2-yl]-amine;
(4-benzyl-6-methyl-pyrimidin-2-yl)-[3-methoxy-4-(4-methyl-imidazol-1-yl)-phenyl]-amine;
(4-ethoxy-6-methyl-pyrimidin-2-yl)-[3-methoxy-4-(4-methyl-imidazol-1-yl)-phenyl]-amine;
N4-(2,2,3,3,4,4,4-heptafluoro-butyl)-N2-[3-methoxy-4-(4-methyl-imidazol-1-yl)-phenyl]-6-methyl-pyrimidine-2,4-diamine;
[4-(4-chloro-phenyl)-5-(4-methoxy-benzyl)-pyrimidin-2-yl]-[3-methoxy-4-(4-methyl-imidazol-1-yl)-phenyl]-amine;
[3-methoxy-4-(4-methyl-imidazol-1-yl)-phenyl]-(4-methoxy-6-methyl-pyrimidin-2-yl)-amine;
(4-isopropoxy-6-methyl-pyrimidin-2-yl)-[3-methoxy-4-(4-methyl-imidazol-1-yl)-phenyl]-amine;
[4-(4-Fluoro-phenoxy)-6-methyl-pyrimidin-2-yl]-[3-methoxy-4-(4-methyl-imidazol-1-yl)-phenyl]-amine;
[4-(4-tert-butyl-phenoxy)-6-methyl-pyrimidin-2-yl]-[3-methoxy-4-(4-methyl-imidazol-1-yl)-phenyl]-amine;
2-{6-ethoxy-2-[3-methoxy-4-(4-methyl-imidazol-1-yl)-phenylamino]-pyrimidin-4-yl}-propan-2-ol;
N4-(3-chloro-phenyl)-N2-[3-methoxy-4-(4-methyl-imidazol-1-yl)-phenyl]-6-methyl-pyrimidine-2,4-diamine;
N4-(4-chloro-phenyl)-N2-[3-methoxy-4-(4-methyl-imidazol-1-yl)-phenyl]-6-methyl-pyrimidine-2,4-diamine;
N4,N4-diethyl-N2-[3-methoxy-4-(4-methyl-imidazol-1-yl)-phenyl]-6-methyl-pyrimidine-2,4-diamine;
1-{2-[3-methoxy-4-(4-methyl-imidazol-1-yl)-phenylamino]-6-methyl-pyrimidin-4-yl}-piperidin-4-ol;
[3-methoxy-4-(4-methyl-imidazol-1-yl)-phenyl]-(4-methyl-6-pyrrolidin-1-yl-pyrimidin-2-yl)-amine;
[3-methoxy-4-(4-methyl-imidazol-1-yl)-phenyl]-(4-methyl-6-piperidin-1-yl-pyrimidin-2-yl)-amine;
2-({2-[3-methoxy-4-(4-methyl-imidazol-1-yl)-phenylamino]-6-methyl-pyrimidin-4-yl}-methyl-amino)-ethanol;
2-{2-[3-methoxy-4-(4-methyl-imidazol-1-yl)-phenylamino]-6-piperidin-1-yl-pyrimidin-4-yl}-propan-2-ol;
2-{2-[3-methoxy-4-(4-methyl-imidazol-1-yl)-phenylamino]-6-pyrrolidin-1-yl-pyrimidin-4-yl}-propan-2-ol;
[4-butyl-6-(4-chloro-phenyl)-pyrimidin-2-yl]-[3-methoxy-4-(4-methyl-imidazol-1-yl)-phenyl]-amine;
[3-methoxy-4-(4-methyl-imidazol-1-yl)-phenyl]-(4-phenyl-pyrimidin-2-yl)-amine;
5-(4,6-dimethyl-pyrimidin-2-ylamino)-2-(4-methyl-imidazol-1-yl)-benzonitrile;
5-[4-(4-chloro-phenyl)-pyrimidin-2-ylamino]-2-(4-methyl-imidazol-1-yl)-benzonitrile;
[5-ethyl-4-(4-trifluoromethyl-phenyl)-pyrimidin-2-yl]-[3-methoxy-4-(4-methyl-imidazol-1-yl)-phenyl]-amine;
[3-methoxy-4-(4-methyl-imidazol-1-yl)-phenyl]-[4-(3,4,5-trifluoro-phenyl)-pyrimidin-2-yl]-amine;
[4-(2,5-dichloro-phenyl)-pyrimidin-2-yl]-[3-methoxy-4-(4-methyl-imidazol-1-yl)-phenyl]-amine;
[4-(3,4-dichloro-phenyl)-pyrimidin-2-yl]-[3-methoxy-4-(4-methyl-imidazol-1-yl)-phenyl]-amine;
[4-(2,4-dichloro-phenyl)-pyrimidin-2-yl]-[3-methoxy-4-(4-methyl-imidazol-1-yl)-phenyl]-amine;
[4-(4-chloro-3-methyl-phenyl)-pyrimidin-2-yl]-[3-methoxy-4-(4-methyl-imidazol-1-yl)-phenyl]-amine;
[4-(4-chloro-phenyl)-5-propyl-pyrimidin-2-yl]-[3-methoxy-4-(4-methyl-imidazol-1-yl)-phenyl]-amine;
[3-methoxy-4-(4-methyl-imidazol-1-yl)-phenyl]-(5-methoxy-4-phenyl-pyrimidin-2-yl)-amine;
(4-cyclopropyl-pyrimidin-2-yl)-[3-methoxy-4-(4-methyl-imidazol-1-yl)-phenyl]-amine;
ethyl 4-benzyl-2-[3-methoxy-4-(4-methyl-imidazol-1-yl)-phenylamino]-pyrimidine-5-carboxylate;
[3-methoxy-4-(4-methyl-imidazol-1-yl)-phenyl]-[4-(4-methyl-pent-3-enyl)-5-phenyl-pyrimidin-2-yl]-amine;
6-{2-[3-methoxy-4-(4-methyl-imidazol-1-yl)-phenylamino]-pyrimidin-4-yl}-4H-benzo[1,4]oxazin-3-one;
[4-(2-chloro-phenyl)-pyrimidin-2-yl]-[3-methoxy-4-(4-methyl-imidazol-1-yl)-phenyl]-amine;
(4-isobutyl-6-methyl-pyrimidin-2-yl)-[3-methoxy-4-(4-methyl-imidazol-1-yl)-phenyl]-amine;
(4,6-diethyl-pyrimidin-2-yl)-[3-methoxy-4-(4-methyl-imidazol-1-yl)-phenyl]-amine;
[3-methoxy-4-(4-methyl-imidazol-1-yl)-phenyl]-(4-methyl-6-phenyl-pyrimidin-2-yl)-amine;
(4-furan-2-yl-6-trifluoromethyl-pyrimidin-2-yl)-[3-methoxy-4-(4-methyl-imidazol-1-yl)-phenyl]-amine;
[3-methoxy-4-(4-methyl-imidazol-1-yl)-phenyl]-(4-phenyl-5,6,7,8-tetrahydro-quinazolin-2-yl)-amine;
(4,6-dimethyl-pyrimidin-2-yl)-[3-methoxy-4-(4-methyl-imidazol-1-yl)-phenyl]-amine;
(4,6-bis-trifluoromethyl-pyrimidin-2-yl)-[3-methoxy-4-(4-methyl-imidazol-1-yl)-phenyl]-amine;
(4-isopropyl-6-trifluoromethyl-pyrimidin-2-yl)-[3-methoxy-4-(4-methyl-imidazol-1-yl)-phenyl]-amine;
(4,6-diisopropyl-pyrimidin-2-yl)-[3-methoxy-4-(4-methyl-imidazol-1-yl)-phenyl]-amine;
[4-(2-chloro-phenyl)-6-methyl-pyrimidin-2-yl]-[3-methoxy-4-(4-methyl-imidazol-1-yl)-phenyl]-amine;
ethyl 2-[3-methoxy-4-(4-methyl-imidazol-1-yl)-phenylamino]-6-thiophen-2-yl-pyrimidine-4-carboxylate;
ethyl 6-Isopropyl-2-[3-methoxy-4-(4-methyl-imidazol-1-yl)-phenylamino]-pyrimidine-4-carboxylate;

ethyl 6-cyclopropyl-2-[3-methoxy-4-(4-methyl-imidazol-1-yl)-phenylamino]-pyrimidine-4-carboxylate;
ethyl 2-[3-methoxy-4-(4-methyl-imidazol-1-yl)-phenylamino]-6-pyridin-2-yl-pyrimidine-4-carboxylate;
ethyl 2-[3-methoxy-4-(4-methyl-imidazol-1-yl)-phenylamino]-6-(4-trifluoromethyl-phenyl)-pyrimidine-4-carboxylate;
ethyl 6-(4-chloro-benzyl)-2-[3-methoxy-4-(4-methyl-imidazol-1-yl)-phenylamino]-pyrimidine-4-carboxylate;
2-{2-[3-methoxy-4-(4-methyl-imidazol-1-yl)-phenylamino]-6-methyl-pyrimidin-4-yl}-propan-2-ol;
2-{6-ethyl-2-[3-methoxy-4-(4-methyl-imidazol-1-yl)-phenylamino]-pyrimidin-4-yl}-propan-2-ol;
2-{6-isopropyl-2-[3-methoxy-4-(4-methyl-imidazol-1-yl)-phenylamino]-pyrimidin-4-yl}-propan-2-ol;
2-{6-cyclopropyl-2-[3-methoxy-4-(4-methyl-imidazol-1-yl)-phenylamino]-pyrimidin-4-yl}-propan-2-ol;
2-{6-tert-butyl-2-[3-methoxy-4-(4-methyl-imidazol-1-yl)-phenylamino]-pyrimidin-4-yl}-propan-2-ol;
2-{2-[3-methoxy-4-(4-methyl-imidazol-1-yl)-phenylamino]-6-thiophen-2-yl-pyrimidin-4-yl}-propan-2-ol;
2-{2-[3-methoxy-4-(4-methyl-imidazol-1-yl)-phenylamino]-6-pyridin-2-yl-pyrimidin-4-yl}-propan-2-ol;
2-{6-(4-chloro-benzyl)-2-[3-methoxy-4-(4-methyl-imidazol-1-yl)-phenylamino]-pyrimidin-4-yl}-propan-2-ol;
2-[2-[3-methoxy-4-(4-methyl-imidazol-1-yl)-phenylamino]-6-(4-trifluoromethyl-phenyl)-pyrimidin-4-yl]-propan-2-ol;
1-[2-[3-methoxy-4-(4-methyl-imidazol-1-yl)-phenylamino]-6-(4-trifluoromethyl-phenyl)-pyrimidin-4-yl]ethanone;
3-{2-[3-methoxy-4-(4-methyl-imidazol-1-yl)-phenylamino]-pyrimidin-4-yl}-pentan-3-ol;
2-[2-[3-methoxy-4-(4-methyl-imidazol-1-yl)-phenylamino]-6-(3,4,5-trifluoro-phenyl)-pyrimidin-4-yl]-propan-2-ol;
2-{6-(2,4-dichloro-phenyl)-2-[3-methoxy-4-(4-methyl-imidazol-1-yl)-phenylamino]-pyrimidin-4-yl}-propan-2-ol;
2-{6-(4-chloro-phenyl)-2-[3-methoxy-4-(4-methyl-imidazol-1-yl)-phenylamino]-pyrimidin-4-yl}-propan-2-ol;
2-{6-(2-chloro-phenyl)-2-[3-methoxy-4-(4-methyl-imidazol-1-yl)-phenylamino]-pyrimidin-4-yl}-propan-2-ol;
2-{2-[3-methoxy-4-(4-methyl-imidazol-1-yl)-phenylamino]-5,6,7,8-tetrahydro-quinazolin-4-yl}-propan-2-ol;
2-{2-[3-fluoro-4-(4-methyl-imidazol-1-yl)-phenylamino]-6-isopropyl-pyrimidin-4-yl}-propan-2-ol;
2-[2-[3-fluoro-4-(4-methyl-imidazol-1-yl)-phenylamino]-6-(4-trifluoromethyl-phenyl)-pyrimidin-4-yl]-propan-2-ol;
2-{6-dimethylamino-2-[3-methoxy-4-(4-methyl-imidazol-1-yl)-phenylamino]-pyrimidin-4-yl}-propan-2-ol;
1-{6-(1-hydroxy-1-methyl-ethyl)-2-[3-methoxy-4-(4-methyl-imidazol-1-yl)-phenylamino]-pyrimidin-4-yl}-4-methyl-piperidin-4-ol;
1-[2-[3-methoxy-4-(4-methyl-imidazol-1-yl)-phenylamino]-6-(4-trifluoromethyl-phenyl)-pyrimidin-4-yl]-cyclopentanol;
5-[4-(1-hydroxy-1-methyl-ethyl)-6-(4-trifluoromethyl-phenyl)-pyrimidin-2-ylamino]-2-(4-methyl-imidazol-1-yl)-benzonitrile; and
2-[2-[3-methyl-4-(4-methyl-imidazol-1-yl)-phenylamino]-6-(4-trifluoromethyl-phenyl)-pyrimidin-4-yl]-propan-2-ol.

Preferred compounds of formula I-A are further those, wherein R¹—Ar is 2-methyl-imidazol-1-yl, 3-methyl-[1,2,4]triazol-1-yl, thiazol-5-yl, 2-methyl-thiazol-5-yl, 2-methyl-oxazol-5-yl, 2-methyl-pyridin-4-yl, 1-methyl-1H-pyrazol-4-yl, 3-methyl-[1,2,4]triazol-1-yl, [1,2,4]triazol-1-yl, 5-methyl-[1,2,4]triazol-1-yl, [1,3,4]oxadiazol-2-yl, 4-pyridin-4-yl, 2-methyl-pyridin-4-yl, 3-methyl-[1,2,4]thiadiazol-5-yl, or oxazol-5-yl, for example the following compounds
(4-benzyl-6-methyl-pyrimidin-2-yl)-[3-methoxy-4-(3-methyl-[1,2,4]triazol-1-yl)-phenyl]-amine;
(4-benzyl-6-methyl-pyrimidin-2-yl)-[3-methoxy-4-(2-methyl-thiazol-5-yl)-phenyl]-amine;
(4-benzyl-6-methyl-pyrimidin-2-yl)-[3-methoxy-4-(2-methyl-oxazol-5-yl)-phenyl]-amine;
2-[2-[3-methoxy-4-(2-methyl-thiazol-5-yl)-phenylamino]-6-(4-trifluoromethyl-phenyl)-pyrimidin-4-yl]-propan-2-ol;
(4,6-dimethyl-pyrimidin-2-yl)-[4-(2-methyl-pyridin-4-yl)-phenyl]-amine; and
(4-benzyl-6-methyl-pyrimidin-2-yl)-[4-(2-methyl-pyridin-4-yl)-phenyl]-amine.

Preferred are further compounds of formula

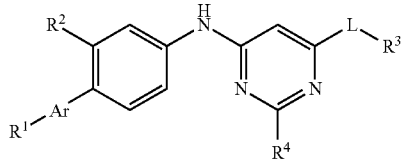

I-B wherein
R¹ is hydrogen, lower alkyl or lower alkyl substituted by hydroxy;
R² is hydrogen, lower alkoxy, lower alkyl, cyano or halogen;
R³ i) for any definitions of L, R³ is lower alkyl, lower alkenyl, lower alkyl substituted by fluoro, $(CH_2)_2O$-lower alkyl, $(CH_2)_2NR^8{}_2$, or is 4H-benzo[1,4]oxazin-3-one, cycloalkyl optionally substituted by hydroxy, or is heterocycloalkyl, which heterocycloalkyl is optionally substituted by hydroxy or $S(O)_2$-lower alkyl, or is $(CH_2)_m$-aryl or is a five- or six-membered heteroaryl group wherein the rings in the heteroaryl group are optionally substituted by one or more R' or
ii) for L is a bond, R³ is halogen, hydroxy, —C(O)O-lower alkyl, OC(O)-lower alkyl or $C(O)NH_2$, or
iii) for L is —CR⁶R⁷—, R³ is lower alkoxy, hydroxy, —C(O)O-lower alkyl, OC(O)-lower alkyl or $C(O)NH_2$, or
iv) for L is NR⁸, R³ is $CH_2$—C(O)O-lower alkyl, or
v) for L is C(O), R³ is lower alkoxy, hydroxy or $NR^8{}_2$;
R' is halogen, lower alkyl, lower alkoxy, cyano, lower alkyl substituted by fluoro, lower alkoxy substituted by fluoro, $SF_5$, or is a five-membered heteroaryl group, which is optionally substituted by lower alkyl;
Ar is a five-membered heteroaryl group or is pyridinyl;
R⁴ is hydrogen, halogen, lower alkyl, lower alkoxy, C(O)O-lower alkyl, lower alkyl substituted by one or more groups selected from fluoro, hydroxy, cyano or cycloalkyl, or is cyano, phenyl, benzyl or a five- or six membered heteroaryl group in which the rings of the heteroaryl group are optionally substituted by one or more R', or is cycloalkyl or heterocycloalkyl, each of which is optionally substituted by lower alkyl and hydroxy, or is hydroxy or $NR^8{}_2$;
L is a bond, —CR⁶R⁷—, —O—, —NR⁸— or —C(O)—;
R⁶ and R⁷ are each independently hydrogen, lower alkyl, cycloalkyl, phenyl or R⁶ and R⁷ together with the carbon atom to which they are attached form a $C_{3-6}$-cycloalkyl group, with the proviso that R⁶ also is optionally hydroxy or lower alkoxy;

$R^8$ is hydrogen or lower alkyl;
m is 0 or 1; and
n is 3 or 4;
or pharmaceutically active acid addition salts.

Preferred compounds from formula I-B are for example the following compounds
(6-benzyl-2-chloro-pyrimidin-4-yl)-[3-methoxy-4-(4-methyl-imidazol-1-yl)-phenyl]-amine and
{6-[1-(4-chloro-phenyl)-cyclobutyl]-2-methyl-pyrimidin-4-yl}-[3-methoxy-4-(4-methyl-imidazol-1-yl)-phenyl]-amine.

Preferred are further compounds of formula

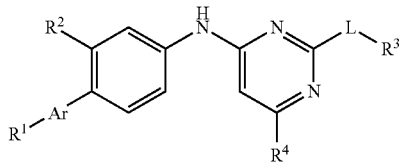

I-C wherein
$R^1$ is hydrogen, lower alkyl or lower alkyl substituted by hydroxy;
$R^2$ is hydrogen, lower alkoxy, lower alkyl, cyano or halogen;
$R^3$ i) for any definitions of L, $R^3$ is lower alkyl, lower alkenyl, lower alkyl substituted by fluoro, $(CH_2)_2$O-lower alkyl, $(CH_2)_2NR^8{}_2$, or is 4H-benzo[1,4]oxazin-3-one, cycloalkyl optionally substituted by hydroxy, or is heterocycloalkyl, which heterocycloalkyl is optionally substituted by hydroxy or S(O)$_2$-lower alkyl, or is $(CH_2)_m$-aryl or is a five-or six-membered heteroaryl group wherein the rings in the heteroaryl group are optionally substituted by one or more R' or
  ii) for L is a bond, $R^3$ is halogen, hydroxy, —C(O)O-lower alkyl, OC(O)-lower alkyl or C(O)NH$_2$, or
  iii) for L is —CR$^6$R$^7$—, $R^3$ is lower alkoxy, hydroxy, —C(O)O-lower alkyl, OC(O)-lower alkyl or C(O)NH$_2$, or
  iv) for L is NR$^8$, $R^3$ is CH$_2$—C(O)O-lower alkyl, or
  v) for L is C(O), $R^3$ is lower alkoxy, hydroxy or NR$^8{}_2$;
R' is halogen, lower alkyl, lower alkoxy, cyano, lower alkyl substituted by fluoro, lower alkoxy substituted by fluoro, SF$_5$, or is a five-membered heteroaryl group, which is optionally substituted by lower alkyl;
Ar is a five-membered heteroaryl group or is pyridinyl;
$R^4$ is hydrogen, halogen, lower alkyl, lower alkoxy, C(O)O-lower alkyl, lower alkyl substituted by one or more groups selected from fluoro, hydroxy, cyano or cycloalkyl, or are cyano, phenyl, benzyl or a five-or six-membered heteroaryl group, wherein the rings in the heteroaryl group are optionally substituted by one or more R', or are cycloalkyl or heterocycloalkyl, each of which is optionally substituted by lower alkyl and hydroxy or is hydroxy or NR$^8{}_2$;
L is a bond, —CR$^6$R$^7$—, —O—, —NR$^8$— or —C(O)—;
$R^6$ and $R^7$ are each independently hydrogen, lower alkyl, cycloalkyl, phenyl or $R^6$ and $R^7$ form together with the carbon atom to which they are attached form a C$_{3-6}$-cycloalkyl group, with the proviso that $R^6$ also is hydroxy or lower alkoxy;
$R^8$ is hydrogen or lower alkyl;
m is 0 or 1; and
n is 3 or 4;
or pharmaceutically active acid addition salts, for example the compound (2-benzyl-6-chloro-pyrimidin-4-yl)-[3-methoxy-4-(4-methyl-imidazol-1-yl)-phenyl]-amine.

Preferred are further compounds of formula

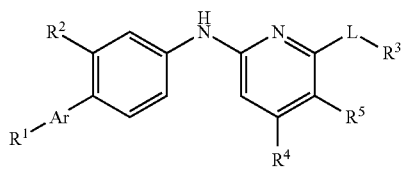

I-D wherein
$R^1$ is hydrogen, lower alkyl or lower alkyl substituted by hydroxy;
$R^2$ is hydrogen, lower alkoxy, lower alkyl, cyano or halogen;
$R^3$ i) for any definitions of L, $R^3$ is lower alkyl, lower alkenyl, lower alkyl substituted by fluoro, $(CH_2)_2$O-lower alkyl, $(CH_2)_2NR^8{}_2$, or is 4H-benzo[1,4]oxazin-3-one, cycloalkyl optionally substituted by hydroxy, or is heterocycloalkyl, which heterocycloalkyl is optionally substituted by hydroxy or S(O)$_2$-lower alkyl, or is $(CH_2)_m$-aryl or is a five-or six-membered heteroaryl group wherein the rings in the heteroaryl group are optionally substituted by one or more R' or
  ii) for L is a bond, $R^3$ is halogen, hydroxy, —C(O)O-lower alkyl, OC(O)-lower alkyl or C(O)NH$_2$, or
  iii) for L is —CR$^6$R$^7$—, $R^3$ is lower alkoxy, hydroxy, —C(O)O-lower alkyl, OC(O)-lower alkyl or C(O)NH$_2$, or
  iv) for L is NR$^8$, $R^3$ is CH$_2$—C(O)O-lower alkyl, or
  v) for L is C(O), $R^3$ is lower alkoxy, hydroxy or NR$^8{}_2$;
R' is halogen, lower alkyl, lower alkoxy, cyano, lower alkyl substituted by fluoro, lower alkoxy substituted by fluoro, SF$_5$, or is a five-membered heteroaryl group, which is optionally substituted by lower alkyl;
Ar is a five-membered heteroaryl group or is pyridinyl;
$R^4$ and $R^5$ are each independently hydrogen, halogen, lower alkyl, lower alkoxy, C(O)O-lower alkyl, lower alkyl substituted by one or more groups selected from fluoro, hydroxy, cyano and cycloalkyl, or are cyano, phenyl, benzyl or a five-or six-membered heteroaryl group, wherein the rings of the heteroaryl group are optionally substituted by one or more R', or are cycloalkyl or heterocycloalkyl, each of which is optionally substituted by lower alkyl and hydroxy', with the proviso that $R^4$ also is optionally hydroxy or NR$^8{}_2$, or wherein $R^4$ and $R^5$ together with the corresponding carbon atoms to which they are attached optionally form an additional ring with —(CH$_2$)$_n$;
L is a bond, —CR$^6$R$^7$—, —O—, —NR$^8$— or —C(O)—;
$R^6$ and $R^7$ are each independently hydrogen, lower alkyl, cycloalkyl, phenyl or $R^6$ and $R^7$ together with the carbon atom to which they are attached form a C$_{3-6}$-cycloalkyl group, with the proviso that $R^6$ also optionally is hydroxy or lower alkoxy;
$R^8$ is hydrogen or lower alkyl;
m is 0 or 1; and
n is 3 or 4;
or pharmaceutically active acid addition salts thereof.

Preferred compounds from this group are for example the following compounds
N-[3-methoxy-4-(4-methyl-imidazol-1-yl)-phenyl]-N'-phenyl-pyridine-2,6-diamine;

N-[3-methoxy-4-(4-methyl-imidazol-1-yl)-phenyl]-N'-(4-trifluoromethoxy-phenyl)-pyridine-2,6-diamine;
N-[3-methoxy-4-(4-methyl-imidazol-1-yl)-phenyl]-N'-(3-trifluoromethoxy-phenyl)-pyridine-2,6-diamine;
N-[3-methoxy-4-(4-methyl-imidazol-1-yl)-phenyl]-N'-(4-pentafluorosulfanyl-phenyl)-pyridine-2,6-diamine;
N-[3-methoxy-4-(4-methyl-imidazol-1-yl)-phenyl]-N'-(4-trifluoromethyl-phenyl)-pyridine-2,6-diamine;
N-[3-methoxy-4-(4-methyl-imidazol-1-yl)-phenyl]-N'-(4-trifluoromethoxy-phenyl)-4-trifluoromethyl-pyridine-2,6-diamine;
N-[3-methoxy-4-(4-methyl-imidazol-1-yl)-phenyl]-N'-(3-trifluoromethoxy-phenyl)-4-trifluoromethyl-pyridine-2,6-diamine;
N-[3-methoxy-4-(4-methyl-imidazol-1-yl)-phenyl]-4-trifluoromethyl-N'-(4-trifluoromethyl-phenyl)-pyridine-2,6-diamine; and
[2-[3-methoxy-4-(4-methyl-imidazol-1-yl)-phenylamino]-6-(4-trifluoromethoxy-phenylamino)-pyridin-4-yl]-methanol.

Preferred are further compounds of formula

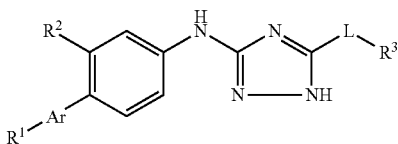

I-E wherein
$R^1$ is hydrogen, lower alkyl or lower alkyl substituted by hydroxy;
$R^2$ is hydrogen, lower alkoxy, lower alkyl, cyano or halogen;
$R^3$ i) for any definitions of L, $R^3$ is lower alkyl, lower alkenyl, lower alkyl substituted by fluoro, $(CH_2)_2$O-lower alkyl, $(CH_2)_2NR^8_2$, or is 4H-benzo[1,4]oxazin-3-one, cycloalkyl optionally substituted by hydroxy, or is heterocycloalkyl, which heterocycloalkyl is optionally substituted by hydroxy or $S(O)_2$-lower alkyl, or is $(CH_2)_m$-aryl or is a five-or six-membered heteroaryl group wherein the rings in the heteroaryl group are optionally substituted by one or more R' or
ii) for L is a bond, $R^3$ is halogen, hydroxy, —C(O)O-lower alkyl, OC(O)-lower alkyl or C(O)NH$_2$, or
iii) for L is —CR$^6$R$^7$—, $R^3$ is lower alkoxy, hydroxy, —C(O)O-lower alkyl, OC(O)-lower alkyl or C(O)NH$_2$, or
iv) for L is NR$^8$, $R^3$ is CH$_2$—C(O)O-lower alkyl, or
v) for L is C(O), $R^3$ is lower alkoxy, hydroxy or NR$^8_2$;
R' is halogen, lower alkyl, lower alkoxy, cyano, lower alkyl substituted by fluoro, lower alkoxy substituted by fluoro, SF$_5$, or is a five-membered heteroaryl group, which is optionally substituted by lower alkyl;
Ar is a five-membered heteroaryl group or is pyridinyl;
L is a bond, —CR$^6$R$^7$—, —O—, —NR$^8$— or —C(O)—;
R$^6$R$^7$ are each independently hydrogen, lower alkyl, cycloalkyl, or phenyl or R$^6$ and R$^7$ together with the carbon atom to which they are attached form a C$_{3-6}$-cycloalkyl group, with the proviso that R$^6$ also optionally is hydroxy or lower alkoxy;
R$^8$ is hydrogen or lower alkyl; and
m is 0 or 1;
or pharmaceutically active acid addition salts thereof.

Preferred compounds from this group are the following compounds

[5-(4-chloro-benzyl)-4H-[1,2,4]triazol-3-yl]-[3-methoxy-4-(4-methyl-imidazol-1-yl)-phenyl]-amine and
[5-(4-fluoro-benzyl)-4H-[1,2,4]triazol-3-yl]-[3-methoxy-4-(4-methyl-imidazol-1-yl)-phenyl]-amine.

The present compounds of formula I and their pharmaceutically acceptable salts can be prepared by methods known in the art, for example, by processes described below, which processes comprise a) reacting a compound of formula

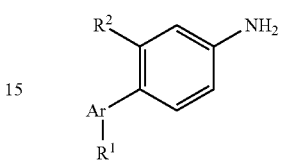

II with a compound of formula

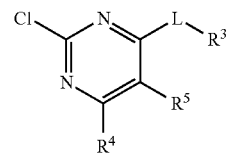

III or, alternatively, reacting a compound

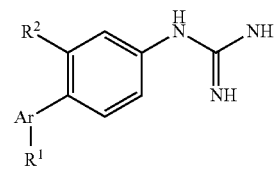

IV with a compound of formula

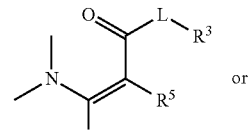

V or

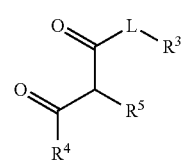

VI to obtain a compound of formula

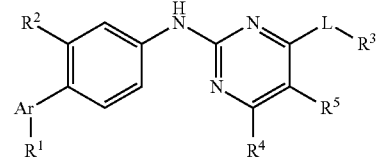

I-A wherein the substituents have the meaning as described above, or, alternatively, reacting a compound of formula

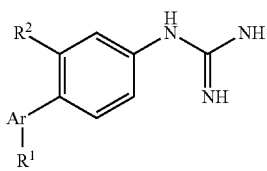

with a compound of formula

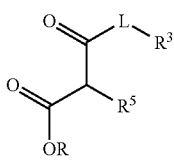

wherein R is $C_{1-4}$-alkyl, to obtain a compound of formula

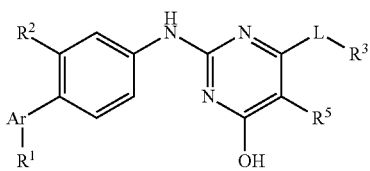

XXVI which may be further converted to a compound I-A, or b) reacting a compound of formula II

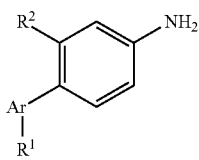

II with a compound of formula

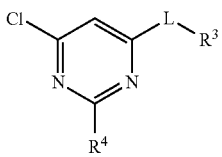

VIII to obtain a compound of formula

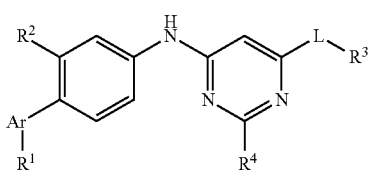

I-B wherein the substituents have the meaning as described above, or c) reacting a compound of formula

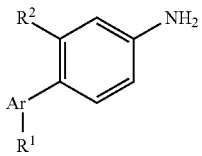

II with a compound of formula

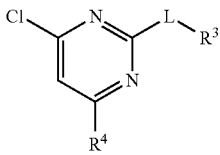

IX to obtain a compound of formula

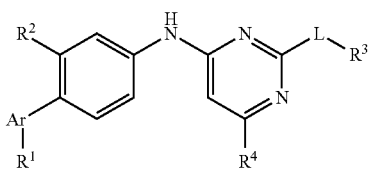

I-C wherein the substituents have the meaning as described above, or d) reacting a compound of formula

II with a compound of formula

X

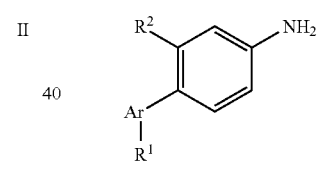

or, alternatively, a compound of formula

XI with a compound of formula

HL-R³  XII to obtain a compound of formula

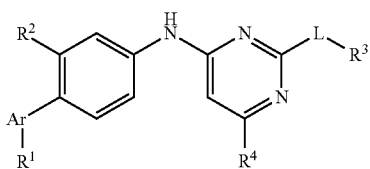

I-D wherein the substituents have the meaning as described above, or e) reacting a compound of formula

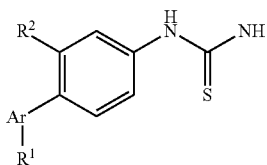

XIII with a compound of formula

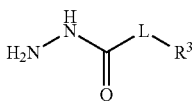

XIV to obtain a compound of formula

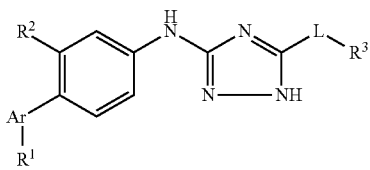

I-E wherein the substituents have the meaning as described above, and if desired, converting the compounds obtained into pharmaceutically acceptable acid addition salts.

The detailed description can be found below and in Examples 1-238.

The preparation of compounds of formula I of the present invention can be carried out in sequential or convergent synthetic routes. Syntheses of the compounds of the invention are shown in the following schemes 1 to 7. The skills required for carrying out the reaction and purification of the resulting products are known to those skilled in the art. The substituents and indices used in the following description of the processes have the significance given herein before unless indicated to the contrary.

In more detail, the compounds of formula I can be manufactured by the methods given below, by the methods given in the examples or by analogous methods. Appropriate reaction conditions for the individual reaction steps are known to a person skilled in the art. The reaction sequence is not limited to the one displayed in the schemes, however, depending on the starting materials and their respective reactivity the sequence of reaction steps can be freely altered. Starting materials are either commercially available or can be prepared by methods analogous to the methods given below, by methods described in the examples, or by methods known in the art.

An aniline II, a guanidine IV or a thiourea XIII can be prepared as described in Scheme 1. Nucleophilic substitution at room temperature or elevated temperature (e.g. reflux or under pressure using a microwave oven) under neutral conditions or in the presence of a base (like e.g. potassium carbonate), neat or in a polar solvent (like e.g. THF or DMSO etc.) of a substituted 4-nitro-phenyl halide XVI (hal=F, Cl, Br, I) with a compound $R^1ArH$, (like 4-methyl-imidazole) yields a nitro derivative XV. The nitro derivative XV can be also obtained by a Suzuki or Stille coupling of a 4-nitro-phenyl halide XVI (hal=Cl, Br, I) and a corresponding aryl boronic acid or aryl tin derivative $R^1ArM$ under palladium(0) catalysis in the presence of a base in a polar or apolar solvent and ambient or high temperature or by Suzuki coupling of a 4-nitro-phenyl boronic acid XVIII with a halide $R^1Arhal$ (hal=Cl, Br, I). Alternatively, a nitro derivative XV can be prepared from a suitable precursor, such as e.g. a carbonyl derivative XVIII (R=H, $NH_2$, alkoxy or $C_{1-4}$-alkyl), by applying standard reaction sequences for the formation of the substituent $ArR^1$. A nitro compound XV can be reduced to an aniline II using generally known procedures, e.g. hydrogenation in the presence of a catalyst (like e.g. 10% palladium on carbon) in a solvent (like e.g. ethanol or ethyl acetate) or, by using a metal (like e.g. iron) or a metal salt (like e.g. stannous chloride) in a polar solvent (like e.g. acetic acid or tetrahydrofuran). Alternatively, aniline II can be prepared by introducing a substituent $ArR^1$ into a N-protected aniline derivative XIX (PG=protecting group) using generally known procedures, e.g. displacement reactions under catalytic conditions (like e.g. palladium(0) or copper(II) catalysis) or, by forming a group $ArR^1$ in a N-protected carbonyl derivative XX, respectively, and subsequently cleaving off the protecting group. The aniline derivative II can be also prepared directly in a Suzuki reaction of the boronic acid derivative XXI with a corresponding aryl halide $R^1Arhal$ (hal=Cl, Br, I) under palladium(0) catalysis in the presence of a base in a polar or apolar solvent and ambient or high temperature. A guanidine IV can be prepared from an aniline II by reaction with cyanamide under acidic conditions (e.g. hydrochloric acid or nitric acid) in a protic solvent (like ethanol) or, by treatment with a carboxamidine derivative, like 3,5-dimethyl-pyrazole-1-carboxamidine, 2-methyl-isothiourea or sulfphoguanidine, in a polar or apolar solvent, optionally in the presence of base. A thiourea XIII can be prepared by either reacting an aniline II with a thiophosgene derivative (like e.g. 1,1'-thiocarbonyldi-2(1H)-pyridone) followed by aminolysis with ammonia or, by treatment of II with an acyl isothiocyanate (like e.g. benzoyl isothiocyanate) and subsequent hydrolysis of the intermediate formed.

Scheme 1

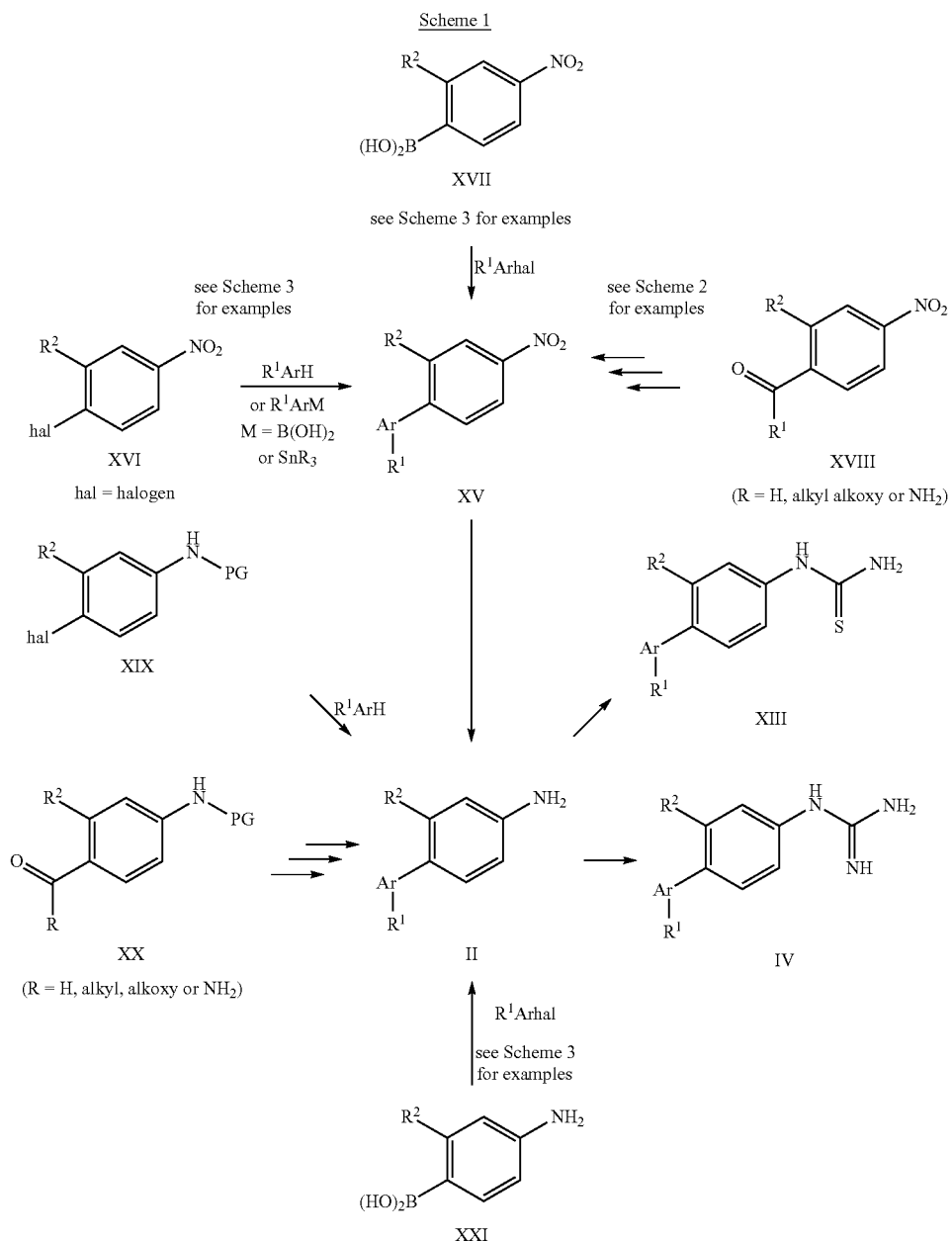

Heterocyclic anilines II like an oxadiazole derivative IIa (Scheme 2) may be prepared from a corresponding ester XVIIIa by conversion to a acylated carboxylic acid hydrazide and subsequent cyclization to an oxadiazole XVa followed by reduction of the latter using generally known methods as described above. Treatment of an aldehyde XVIIIb with TosMIC (tosylmethyl isocyanide) yields an oxazole XVb. A ketone XIIIc can be converted into a substituted oxazole XVc by treatment with iodobenzene diacetate, trifluoromethane-sulfonic acid and a nitrile $R^1CN$. A thiadiazoles XVd can be prepared from a thioamide XXII in the presence of N,N-dimethylacetamide dimethyl acetal and hydroxyl-amine-O-sulfonic acid. A thioamide XXII can be obtained by treatment of a corresponding amide XVIIId with Lawesson's reagent according to known procedures. Reduction of nitro derivatives XVa-d provides the respective anilines IIa-d.

Scheme 2

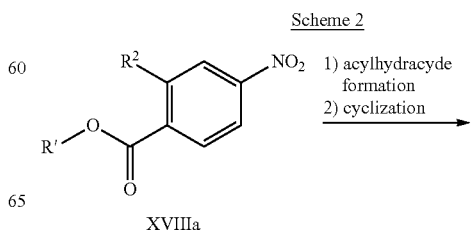

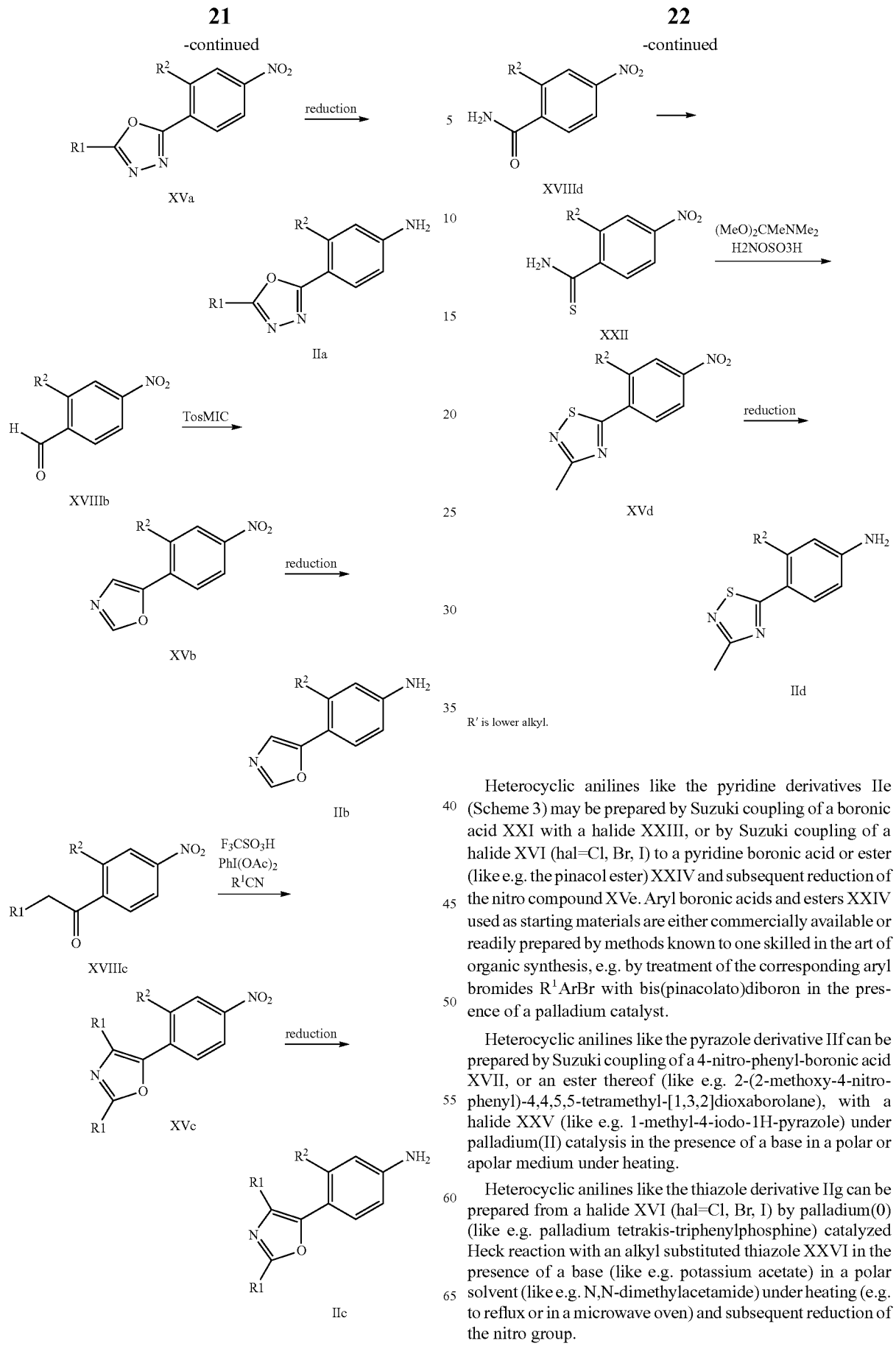

R' is lower alkyl.

Heterocyclic anilines like the pyridine derivatives IIe (Scheme 3) may be prepared by Suzuki coupling of a boronic acid XXI with a halide XXIII, or by Suzuki coupling of a halide XVI (hal=Cl, Br, I) to a pyridine boronic acid or ester (like e.g. the pinacol ester) XXIV and subsequent reduction of the nitro compound XVe. Aryl boronic acids and esters XXIV used as starting materials are either commercially available or readily prepared by methods known to one skilled in the art of organic synthesis, e.g. by treatment of the corresponding aryl bromides $R^1$ArBr with bis(pinacolato)diboron in the presence of a palladium catalyst.

Heterocyclic anilines like the pyrazole derivative IIf can be prepared by Suzuki coupling of a 4-nitro-phenyl-boronic acid XVII, or an ester thereof (like e.g. 2-(2-methoxy-4-nitro-phenyl)-4,4,5,5-tetramethyl-[1,3,2]dioxaborolane), with a halide XXV (like e.g. 1-methyl-4-iodo-1H-pyrazole) under palladium(II) catalysis in the presence of a base in a polar or apolar medium under heating.

Heterocyclic anilines like the thiazole derivative IIg can be prepared from a halide XVI (hal=Cl, Br, I) by palladium(0) (like e.g. palladium tetrakis-triphenylphosphine) catalyzed Heck reaction with an alkyl substituted thiazole XXVI in the presence of a base (like e.g. potassium acetate) in a polar solvent (like e.g. N,N-dimethylacetamide) under heating (e.g. to reflux or in a microwave oven) and subsequent reduction of the nitro group.

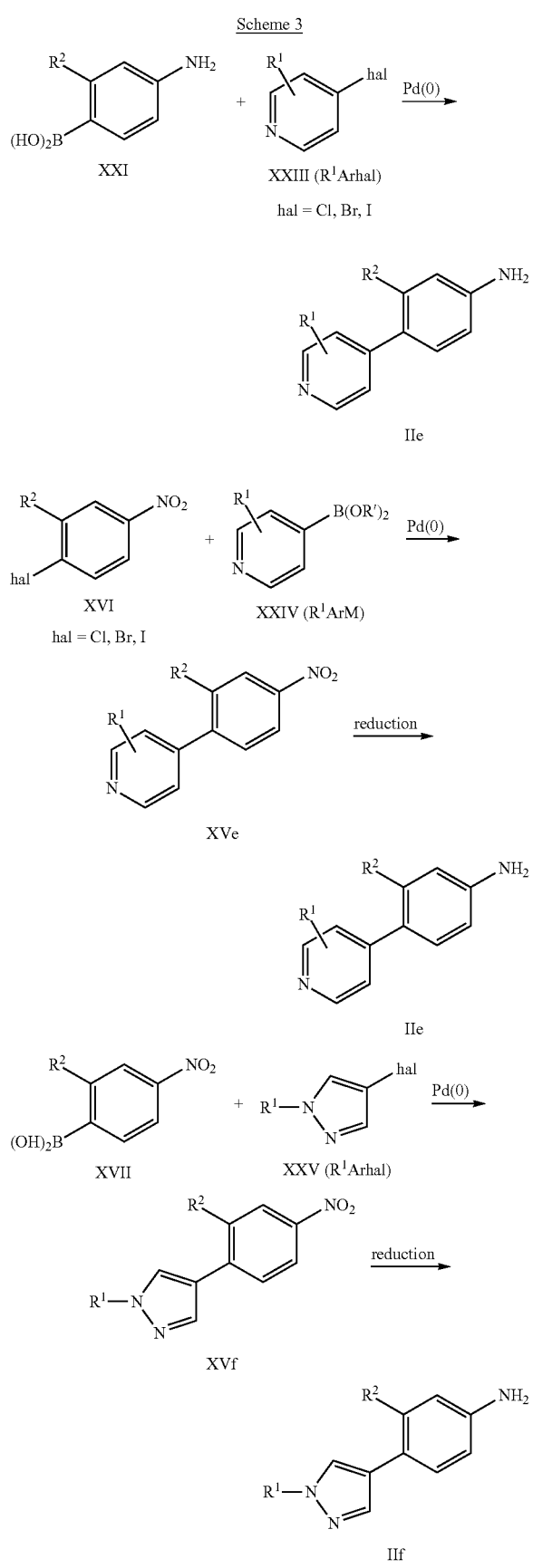

hal is halide (like e.g. chlorine, bromine or iodine), R' is lower alkyl or hydrogen Compounds of formula I-A (Scheme 4) can be prepared by firstly converting a ketone XXIX to an enamine V or a diketone VI, respectively, followed by condensating these intermediates with a guanidine IV (Scheme 2). A ketone XXVIII can be prepared by generally known methods, e.g. by treating a nitrile XXVII in an inert solvent (like toluene) with a solution of a Grignard reagent (like methylmagnesium chloride in tetrahydrofuran) at temperatures from 20 to 100° C.). Preparation of an enamine V can be achieved by reaction of XXVIII with an aminal of DMF (like N,N-diemethylformamide dimethyl acetal or Bredereck's reagent (tert.-butoxy-bis(dimethylamino)methane)). A diketone VI can be prepared from a ketone XXVIII by known methods, e.g. by reaction with a carboxylic acid ester in the presence of a strong base (like sodium hydride, potassium tert.-butoxide, lithium diisopropylamide) in a polar o apolar solvent (like ethanol, tetrahydrofuran or toluene). Condensation of the guanidine IV with an enamine V or a ketone VI in a polar or unpolar solvent, optionally in the presence of base (like triethylamine), at temperatures from 20 to 150° C., optionally using an microwave oven at 100 to 250° C., yields the pyrimidine I-A. Alternatively, compounds of structure I-A can be prepared by reacting a keto-ester VII with a guanidine IV and subsequently converting the resulting pyrimidine XXIX to a compound I-A by further reactions on the hydroxy substituent of the pyrimidine ring, e.g. by preparing a corresponding chloropyrimidine which can be converted to a compound I-A carrying a specific group $R^4$. A keto-ester VII can be prepared from a ketone XXVIII by known methods, e.g. by reaction with a dialkyl carbonate (like diethyl carbonate) in the presence of a strong base (like sodium hydride) in an aprotic solvent (like tetrahydrofuran or N,N-dimethylformamide).

Scheme 4

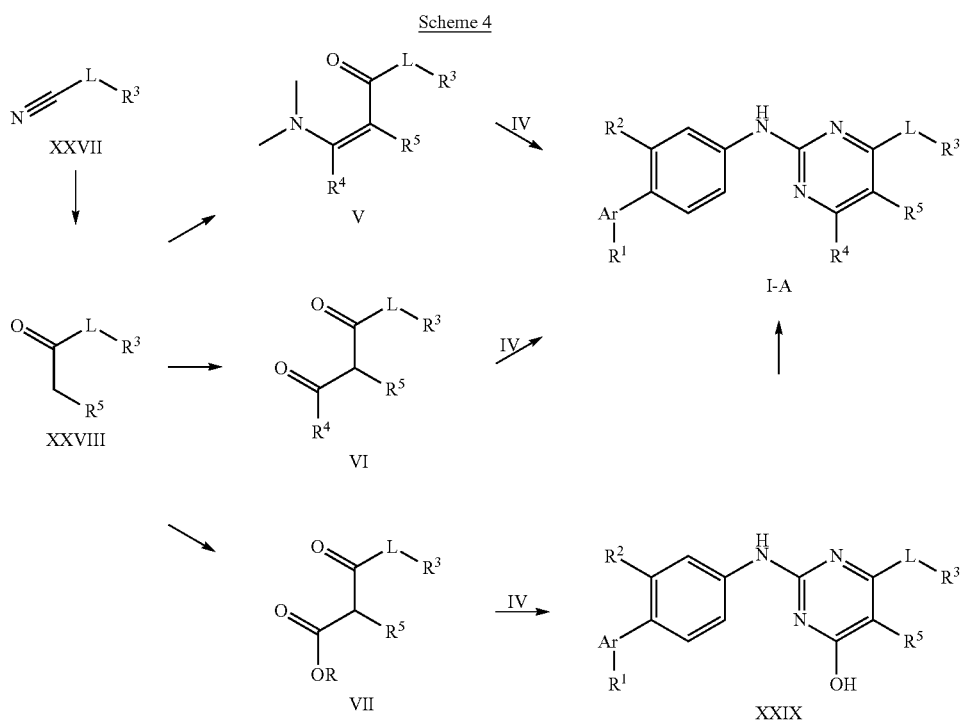

Further route for the preparation of compounds of formula I-A consists in reacting a 2-chloro-pyrimidine III with an aniline II (Scheme 5). In an analogous manner, compounds of formula I-B and I-C can be prepared by reacting an aniline II with a chloro-pyridine VIII or IX, respectively. The intermediates III, VIII and IX can be prepared by generally known methods. A trichloro-pyrimidine XXX can first be reduced to a dichloro-derivative XXXI, e.g. by treatment with zink in aqueous ammonia at 0° C., and subsequently, the 4-chloro substituent of XXXI is replaced by a group HL-R³ using a nucleophilic substitution reaction (like reaction with a Grignard reagent, e.g. benzylmagnesium chloride in tetrahydrofuran at −80 to +20° C.) or, by a metal catalyst assisted displacement reaction (e.g. using palladium acetate, 2-(dicyclohexylphosphino-biphenyl, tetrahydrofuran, microwave oven, 30 min, 200° C.). Alternatively, one of the reactive chloro atoms of XXX is first replaced by a group Q-R³, followed by replacement of a second chloro-substituent in the intermediate XXXII by a group R⁴, to afford III. A chloropyrimidine VIII is prepared by replacement of one chloro atom by a group HL-R³, analogously as described for the preparation of III. In analogous manner, a chloro-pyrimidine IX is prepared by replacement of one chloro atom of a compound XXXIV by a group R⁴. The coupling of intermediates III, VIII, and IX, respectively, with an aniline II is accomplished by applying a metal catalyst assisted displacement reaction (e.g. using palladium acetate, 2-(dicyclohexylphosphino-biphenyl, potassium carbonate, dioxane, microwave oven, 30 min, 200° C.).

Scheme 5

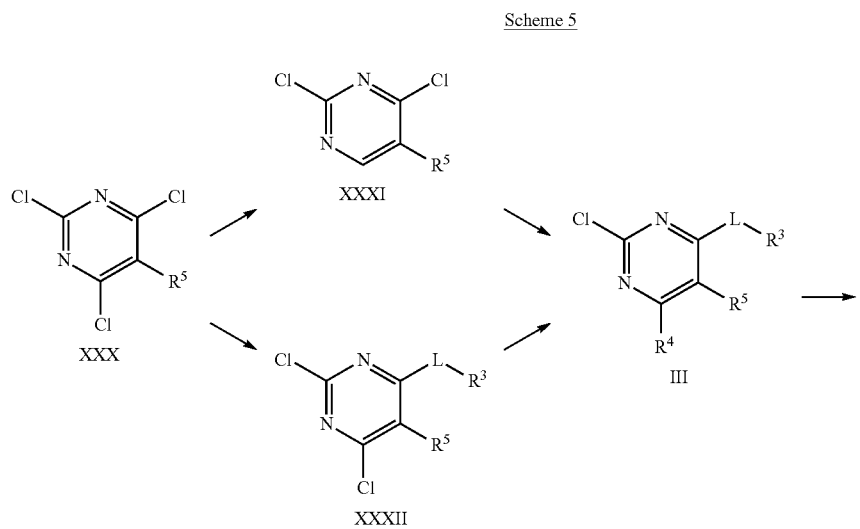

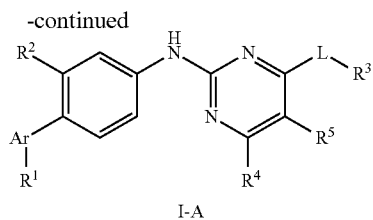

I-A

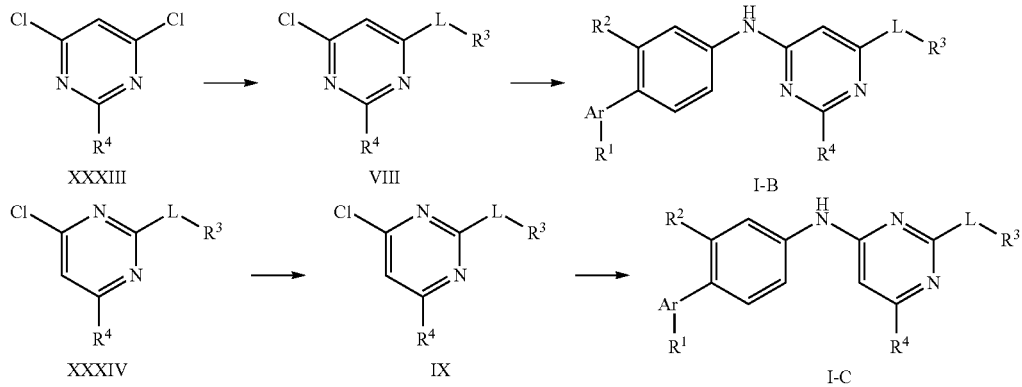

The preparation of a compound of formula I-D (Scheme 6) can be achieved by reacting a 1,6-dichloro-pyridine XXX with a compound HL-R³ (XII) followed by coupling of the resulting intermediate X with an aniline II. Alternatively, a compound XXX is at first coupled to an aniline II and the resulting chloro-pyridine XI is then reacted with XII. The chloro displacement reactions used in these syntheses can be achieved by thermal nucleophilic displacement reactions, preferably in the presence of a suitable catalyst (like an Pd(0) compound).

For the preparation of a compound I-E (Scheme 7), a thiourea XIII is converted to a reactive derivative, such as a thio-amidino ether hydroiodide XXXVI which can be obtained by the treatment of XIII with methyl iodide in acetone at 20° C. Condensation of XXXVI with a carboxylic acid hydrazide XIV, e.g. by heating the two components in a polar solvent (like ethanol), affords compounds I-E.

Scheme 6

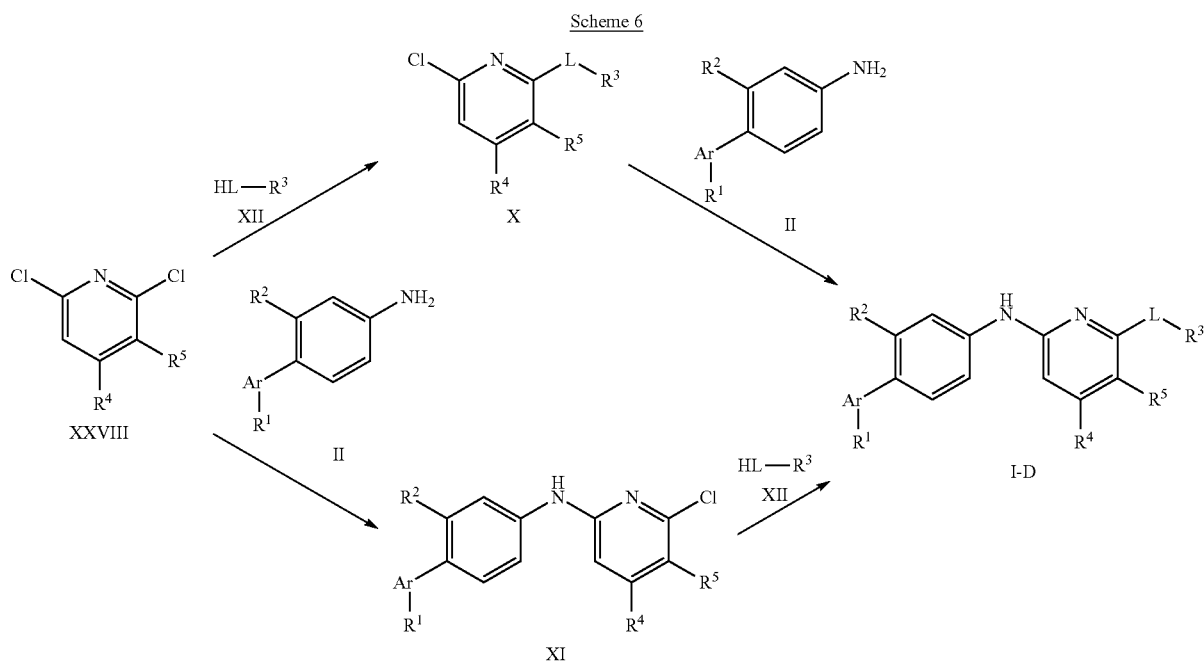

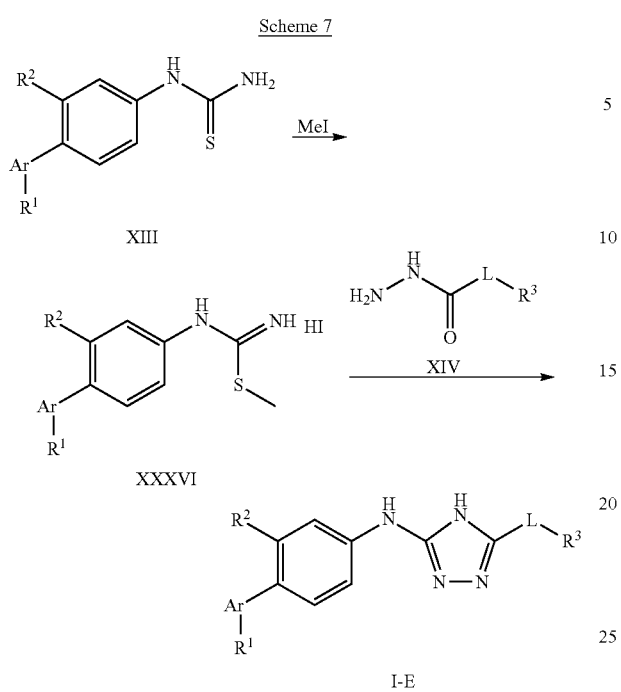

Scheme 7

XIII

XXXVI

I-E

The compounds were investigated in accordance with the test given hereinafter.

Cellular Assay

Human neuroglioma H4 cells overexpressing human APP were plated at 30,000 cells/well/200 µl in 96-well plates in IMDM media containing 10% FCS, 0.2 mg/l Hygromycin B and incubated for 2 h at 37° C., 5% $CO_2$ prior to adding test compounds.

Compounds for testing were dissolved in 100% $Me_2SO$ yielding in a 10 mM stock solution. Typically 12 µl of these solutions were further diluted in 1000 µl of IMDM media (w/o FCS). Sub sequential 1:1 dilutions gave a ten point dose response curve. 100 µl of each dilution was added to the cells in 96-well plates. Appropriate controls using vehicle only and reference compound were applied to this assay. The final concentration of $Me_2SO$ was 0.4%.

After incubation for 22 hrs at 37° C., 5% $CO_2$, 50 µl supernatant was transferred into round-bottom 96-well polypropylene plates for detection of Aβ42. 50 µl assay buffer (50 mM Tris/Cl, pH 7.4, 60 mM NaCl, 0.5% BSA, 1% TWEEN 20) was added to the wells followed by the addition of 100 µl of detection antibody (ruthenylated Aβ42-specific antibody BAP15 0.0625 µg/mL in assay buffer). 50 µl of a premix of capture antibody (biotinylated 6E10 antibody, 1 µg/mL) and Steptavidin-coated magnetic beads (Dynal M-280, 0.125 mg/mL) were preincubated for 1 hr at room temperature before adding the assay plates. Assay plates were incubated on a shaker for 3 hrs at room temperature and finally read in the Bioveris M8 Analyser according to the manufacturer's instructions (Bioveris).

Toxicity of compounds was monitored by a cell viability test of the compound-treated cells using a colorimetric assay (CellTiter 96™ AQ assay, Promega) according to the manufacturer's instructions. Briefly, after removal of 50 µl cell culture supernatant for detection of Aβ42, 20 µl of 1×MTS/PES solution was added to the cells and incubated for 30 min at 37° C., 5% $CO_2$. Optical density was then recorded at 490 nm.

$IC_{50}$ values for inhibition of Aβ42 secretion were calculated by nonlinear regression fit analysis using XLfit 4.0 software (IDBS).

The preferred compounds show an $IC_{50}$<0.5 (nM). In the list below are described some data to the γ-secretase inhibition:

| Example No./Formula | $IC_{50}$ in vitro (nM) |
|---|---|
| 1/I-A | 0.22 |
| 2/I-A | 0.21 |
| 3/I-A | 0.24 |
| 5/I-A | 0.20 |
| 9/I-A | 0.19 |
| 11/I-A | 0.23 |
| 12/I-A | 0.38 |
| 13/I-A | 0.43 |
| 16/I-A | 0.21 |
| 17/I-A | 0.30 |
| 18/I-A | 0.23 |
| 19/I-A | 0.46 |
| 20/I-A | 0.44 |
| 21/I-A | 0.47 |
| 22/I-A | 0.49 |
| 28/IA | 0.49 |
| 38/I-A | 0.32 |
| 43/I-A | 0.15 |
| 46/I-A | 0.27 |
| 47/I-A | 0.19 |
| 61/I-A | 0.50 |
| 62/I-B | 0.98 |
| 64/I-B | 0.67 |
| 65/I-C | 2.51 |
| 70/I-D | 0.26 |
| 72/I-E | 0.10 |
| 73/I-E | 0.22 |
| 75/I-A | 0.31 |
| 76/I-A | 0.49 |
| 81/I-A | 0.34 |
| 82/I-A | 0.48 |
| 88/I-A | 0.39 |
| 90/I-A | 0.17 |
| 91/I-A | 0.07 |
| 92/I-A | 0.45 |
| 94/I-A | 0.32 |
| 95/I-A | 0.42 |
| 97/I-A | 0.2 |
| 104/I-A | 0.42 |
| 105/I-A | 0.44 |
| 106/I-A | 0.12 |
| 108/I-A | 0.28 |
| 109/I-A | 0.32 |
| 112/I-A | 0.32 |
| 113/I-A | 0.22 |
| 115/I-A | 0.4 |
| 116/I-A | 0.36 |
| 117/I-A | 0.15 |
| 118/I-A | 0.27 |
| 119/I-A | 0.11 |
| 120/I-A | 0.16 |
| 121/I-A | 0.25 |
| 122/I-A | 0.46 |
| 131/I-A | 0.32 |
| 134/I-A | 0.38 |
| 136/I-A | 0.29 |
| 137/I-A | 0.43 |
| 140/I-A | 0.18 |
| 145/I-A | 0.39 |
| 146/I-A | 0.3 |
| 147/I-A | 0.25 |
| 149/I-A | 0.26 |
| 150/I-A | 0.23 |
| 152/I-A | 0.22 |
| 153/I-A | 0.21 |
| 154/I-A | 0.43 |
| 155/I-A | 0.13 |
| 156/I-A | 0.41 |
| 157/I-A | 0.13 |
| 159/I-A | 0.12 |

-continued

| Example No./Formula | IC$_{50}$ in vitro (nM) |
|---|---|
| 161/I-A | 0.28 |
| 162/I-A | 0.17 |
| 163/I-A | 0.36 |
| 164/I-A | 0.21 |
| 165/I-A | 0.23 |
| 166/I-A | 0.28 |
| 167/I-A | 0.07 |
| 168/I-A | 0.06 |
| 169/I-A | 0.17 |
| 170/I-A | 0.32 |
| 172/I-A | 0.45 |
| 173/I-A | 0.09 |
| 174/I-A | 0.1 |
| 175/I-A | 0.1 |
| 176/I-A | 0.47 |
| 179/I-A | 0.08 |
| 180/I-A | 0.14 |
| 181/I-A | 0.09 |
| 182/I-A | 0.26 |
| 183/I-A | 0.43 |
| 187/I-D | 0.22 |
| 188/I-D | 0.24 |
| 189/I-D | 0.31 |
| 192/I-D | 0.27 |
| 196/I-D | 0.28 |
| 197/I-D | 0.45 |
| 198/I-D | 0.31 |
| 202/I-D | 0.33 |
| 205/I-A | 0.49 |
| 209/I-A | 0.43 |
| 218/I-A | 0.36 |
| 220/I-A | 0.37 |
| 221/I-A | 0.34 |
| 223/I-A | 0.34 |
| 226/I-A | 0.13 |
| 228/I-A | 0.18 |
| 233/I-A | 0.29 |
| 234/I-A | 0.22 |
| 235/I-A | 0.28 |
| 236/I-A | 0.45 |
| 237/I-A | 0.5 |

The present invention also provides pharmaceutical compositions containing compounds of the invention, for example, compounds of formula I or pharmaceutically acceptable salts thereof and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical composition can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The present invention also provides a method for the manufacture of pharmaceutical compositions. Such process comprises bringing one or more compounds of formula I and/or pharmaceutically acceptable acid addition salts thereof and, if desired, one or more other therapeutically valuable substances into a galenical administration form together with one or more therapeutically inert carriers.

In accordance with the invention compounds of formula I as well as their pharmaceutically acceptable salts are useful in the control or prevention of illnesses based on the inhibition of the γ-secretase, such as of Alzheimer's disease.

The dosage at which compounds of the invention can be administered can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage may be administered as single dose or in divided doses and, in addition, the upper limit can also be exceeded when this is found to be indicated.

| | | Tablet Formulation (Wet Granulation) mg/tablet | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure

1. Mix items 1, 2, 3 and 4 and granulate with purified water.

2. Dry the granules at 50° C.

3. Pass the granules through suitable milling equipment.

4. Add item 5 and mix for three minutes; compress on a suitable press.

| | | Capsule Formulation mg/capsule | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure

1. Mix items 1, 2 and 3 in a suitable mixer for 30 minutes.

2. Add items 4 and 5 and mix for 3 minutes.

3. Fill into a suitable capsule.

Example 1

(4-Benzyl-pyrimidin-2-yl)-[3-methoxy-4-(4-methyl-imidazol-1-yl)-phenyl]-amine

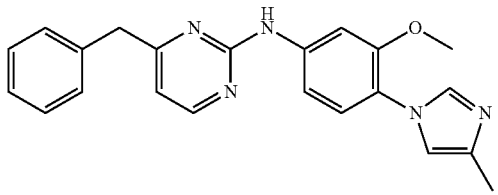 [SMILES: COc1cc(Nc2nccc(Cc3ccccc3)n2)ccc1-n1cnc(C)c1]

a) 1-(2-Methoxy-4-nitro-phenyl)-4-methyl-1H-imidazole

A solution of 2-chloro-5-nitroanisole (187 mg, 1 mmol), of 4-methyl-1H-imidazole (335 mg, 4 mmol) and of potassium hydroxide (99 mg, 1.5 mmol) in DMSO (0.86 mL) was stirred for 5 h at 80° C. under an atmosphere of nitrogen. After cooling to 20° C. the reaction was poured onto ice-water. A precipitation was formed and the suspension was stirred for 15 min. The solid was filtered off, washed with water, dissolved in dichloromethane, dried over sodium sulfate, filtered and the solvent was evaporated under reduced pressure to yield a yellow solid. The crude product was purified on silica gel using dichloromethane/methanol (19:1 v/v) as eluent to yield the title compound (106 mg, 45%) as a pale-yellow solid. Alternatively the product can be also crystallized from the crude material from diethyl ether.

MS ISP (m/e): 234.3 (100) [(M+H)$^+$].

$^1$H NMR (CDCl$_3$, 300 MHz): δ (ppm)=7.97 (d, 1H), 7.96 (s, 1H), 7.83 (s, 1H), 7.42 (d, 1H), 7.00 (s, 1H), 4.00 (s, 3H), 2.31 (s, 3H).

b) 3-Methoxy-4-(4-methyl-imidazol-1-yl)-phenylamine 1-(2-Methoxy-4-nitro-phenyl)-4-methyl-1H-imidazole (2.52 g, 10.8 mmol) dissolved in ethanol (110 mL) was stirred under an atmosphere of hydrogen at 20° C. for 3.5 h in the presence of 10% palladium on charcoal (0.25 g). The catalyst was filtered off and washed with ethanol. The solvent of the filtrate was evaporated under reduced pressure. The crude product was purified on silica gel using dichloromethane/methanol (19:1 v/v) as eluent. The fraction containing the product was suspended in diethyl ether, stirred for 15 min, filtered and dried to yield the title compound (1.72 g, 78%) as a yellow solid.

MS ISP (m/e): 204.3 (100) [(M+H)$^+$].

$^1$H NMR (CDCl$_3$, 300 MHz): δ (ppm)=7.48 (s, 1H), 6.91 (d, 1H), 6.88 (s, 1H), 6.35 (s, 1H), 6.17 (d, 1H), 3.68 (s, 3H), 2.11 (s, 3H).

c) 6-Benzyl-2,4-dichloro-pyrimidine

To a solution of 2,4,6-trichloropyrimidine (936 mg, 5.0 mmol) in tetrahydrofuran (50 mL) was added at −78° C. under an atmosphere of nitrogen and stirring drop wise 1 M benzylmagnesium chloride solution in diethyl ether (5 mL, 5.0 mmol). The reaction was let to warm up to 20° C. over 16 h. The solvent was removed under reduced pressure and the residue was dissolved in water. The aqueous layer was extracted twice with dichloromethane. The combined organic layers were washed once with brine, dried over sodium sulfate, filtered and the solvent was removed under reduced pressure. The residue was purified by column chromatography on silica gel using heptane and then heptane/ethyl acetate (9:1 v/v) as eluent to yield the title compound (778 mg, 65%) as a pale-yellow viscous oil.

MS ISP (m/e): 238.9/241.0 (100/70) [(M+H)$^+$].

$^1$H NMR (DMSO-D$_6$, 300 MHz): δ (ppm)=7.73 (s, 1H), 7.26-7.34 (m, 5H), 4.12 (s, 2H).

d) 4-Benzyl-2-chloro-pyrimidine

To an emulsion of 6-benzyl-2,4-dichloro-pyrimidine (239 mg, 1 mmol) in 25% aqueous ammonia solution (1 mL) was added after stirring for 10 min at 0° C. zinc powder (82 mg, 1.25 mmol). The reaction was stirred at 20° C. for 16 h. The yellow suspension was diluted with ethyl acetate an insoluble material was filtered off. The layers were separated and the aqueous layer was extracted with ethyl acetate. The combined organic layers were washed with brine, dried over sodium sulfate and evaporated under reduced pressure to yield the crude title compound (210 mg, 92%) as a yellow oil.

MS EI (m/e): 203.1/204.2 (100/50) [M$^+$].

$^1$H NMR (DMSO-D$_6$, 300 MHz): δ (ppm)=8.66 (d, 1H), 7.73 (d, 1H), 7.25-7.45 (m, 5H), 4.11 (s, 2H).

e) (4-Benzyl-pyrimidin-2-yl)-[3-methoxy-4-(4-methyl-imidazol-1-yl)-phenyl]-amine Palladium acetate (2.7 mg, 0.012 mmol) and 2-(dicyclohexylphosphino)-biphenyl (8.7 mg, 0.024 mmol) were dissolved under an atmosphere of nitrogen in dioxane (1 mL) and stirred for 10 min at 20° C. This solution was added at 20° C. under an atmosphere of nitrogen to a microwave flask containing 3-methoxy-4-(4-methyl-imidazol-1-yl)-phenylamine (61 mg, 0.3 mmol), 4-benzyl-2-chloro-pyrimidine (68 mg, 0.3 mmol) and potassium carbonate (829 mg, 6.0 mmol). The mixture was diluted with dioxane (1.7 mL) and heated for 30 min to 200° C. in a microwave oven. The reaction was poured onto water and extracted twice with ethyl acetate. The combined organic solutions were washed with brine, dried over sodium sulfate, filtered and the residue was purified by column chromatography on silica gel using dichloromethane/methanol (19:1 v/v) as eluent to yield the title compound (50 mg, 45%) as a yellow solid.

MS ISP (m/e): 372.2 (100) [(M+H)$^+$].

$^1$H NMR (DMSO-D$_6$, 300 MHz): δ (ppm)=9.77 (s, 1H), 8.41 (d, 1H), 7.83 (s, 1H), 7.65 (s, 1H), 7.18-7.39 (m, 7H), 7.02 (s, 1H), 6.79 (d, 1H), 4.00 (s, 2H), 3.73 (s, 3H), 2.14 (s, 3H).

Example 2

[3-Methoxy-4-(4-methyl-imidazol-1-yl)-phenyl]-[4-(3,4,5-trifluoro-benzyl)-pyrimidin-2-yl]-amine

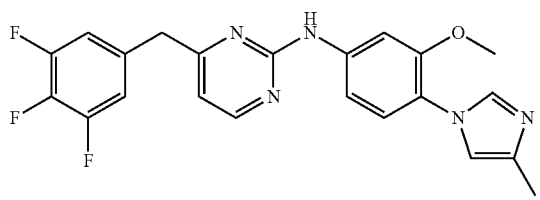 [SMILES: COc1cc(Nc2nccc(Cc3cc(F)c(F)c(F)c3)n2)ccc1-n1cnc(C)c1]

a) 2,4-Dichloro-6-(3,4,5-trifluoro-benzyl)-pyrimidine

To a suspension of magnesium (0.24 g, 10.0 mmol) in diethyl ether (15 mL) 3,4,5-trifluorobenzylbromide (1.69 g, 9.0 mmol) was added drop wise. The reaction was started with little iodine and heated to reflux for 2 h. To a solution of 2,4,6-trichloropyrimidine (2.32 g, 10.0 mmol) in tetrahydrofuran (90 mL) was added the above prepared Grignard solution at −78° C. under an atmosphere of nitrogen. The reaction was continued as described in example 1d) to yield the title compound (0.39 g, 15%) as a pale-yellow solid. $^1$H NMR (DMSO-D$_6$, 300 MHz): δ (ppm)=7.74 (s, 1H), 7.32 (m, 2H), 4.14 (s, 2H).

b) 2-Chloro-4-(3,4,5-trifluoro-benzyl)-pyrimidine

The title compound was prepared from 2,4-dichloro-6-(3,4,5-trifluoro-benzyl)-pyrimidine in analogous manner as described in example 1d). It was obtained in 54% yield as a yellow oil.

MS ISN (m/e): 257.0/258.9 (100/30) [(M−H)$^-$].

$^1$H NMR (DMSO-D$_6$, 300 MHz): δ (ppm)=8.69 (d, 1H), 7.47 (d, 1H), 7.31 (m, 2H), 4.14 (s, 2H).

c) [3-Methoxy-4-(4-methyl-imidazol-1-yl)-phenyl]-[4-(3,4,5-trifluoro-benzyl)-pyrimidin-2-yl]-amine The title compound was prepared in analogous manner as described in example 1e) from 3-methoxy-4-(4-methyl-imidazol-1-yl)-phenylamine and 4-(3,4,5-trifluoro-benzyl)-2-chloro-pyrimidine. It was obtained as a pale-brown solid in 54% yield.

MS ISP (m/e): 426.2 (100) [(M+H)$^+$].

$^1$H NMR (DMSO-D$_6$, 300 MHz): δ (ppm)=9.77 (s, 1H), 8.45 (d, 1H), 7.76 (s, 1H), 7.65 (s, 1H), 7.40 (d, 1H), 7.32 (t, 2H), 7.19 (d, 1H), 7.02 (s, 1H), 6.81 (d, 1H), 4.02 (s, 2H), 3.76 (s, 3H), 2.14 (s, 3H).

Example 3

[4-(3-Chloro-benzyl)-pyrimidin-2-yl]-[3-methoxy-4-(4-methyl-imidazol-1-yl)-phenyl]-amine

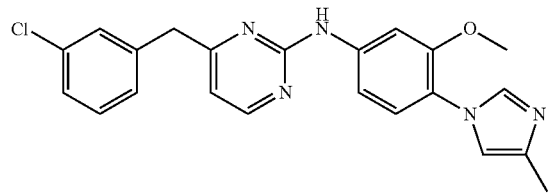 [SMILES: COc1cc(Nc2nccc(Cc3cccc(Cl)c3)n2)ccc1-n1cnc(C)c1]

a) 2,4-Dichloro-6-(3-chloro-benzyl)-pyrimidine

The title compound was prepared in analogous manner as described in example 2a) from 3-chloro-benzylbromide and 2,4,6-trichloropyrimidine. It was obtained as a pale-yellow oil in 26% yield.

$^1$H NMR (DMSO-D$_6$, 300 MHz): δ (ppm)=7.77 (s, 1H), 7.27-7.43 (m, 4H), 4.14 (s, 2H).

b) 2-Chloro-4-(3-chloro-benzyl)-pyrimidine

The title compound was prepared in analogous manner as described in example 1d) from 2,4-dichloro-6-(3-chloro-benzyl)-pyrimidine. It was obtained in 31% yield as a yellow oil.
$^1$H NMR (DMSO-D$_6$, 300 MHz): δ (ppm)=8.68 (d, 1H), 7.49 (d, 1H), 7.26-7.42 (m, 4H), 4.14 (s, 2H).

c) [4-(3-Chloro-benzyl)-pyrimidin-2-yl]-[3-methoxy-4-(4-methyl-imidazol-1-yl)-phenyl]-amine The title compound was prepared in analogous manner as described in example 1e) from 3-methoxy-4-(4-methyl-imidazol-1-yl)-phenylamine and 2-chloro-4-(3-chloro-benzyl)-pyrimidine. It was obtained as a yellow solid in 55% yield.

MS ISP (m/e): 406.3/408.3 (100/29) [(M+H)$^+$].

$^1$H NMR (DMSO-D$_6$, 300 MHz): δ (ppm)=9.78 (s, 1H), 8.43 (d, 1H), 7.79 (s, 1H), 7.65 (s, 1H), 7.27-7.42 (m, 5H), 7.18 (d, 1H), 7.02 (s, 1H), 6.83 (d, 1H), 4.02 (s, 2H), 3.74 (s, 3H), 2.14 (s, 3H).

Example 4

[3-Methoxy-4-(4-methyl-imidazol-1-yl)-phenyl]-[4-(1-phenyl-cyclohexyl)-pyrimidin-2-yl]-amine

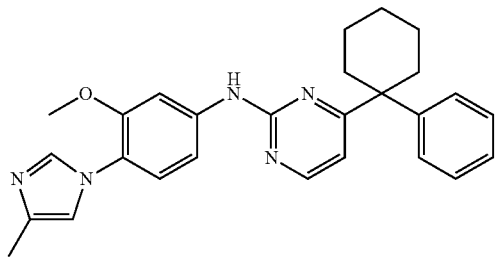 [SMILES: COc1cc(Nc2nccc(C3(c4ccccc4)CCCCC3)n2)ccc1-n1cnc(C)c1]

a) 3-Dimethylamino-1-(1-phenyl-cyclohexyl)-propenone

Acetyl-1-phenylcyclohexane (101 mg, 0.5 mmol) was heated in dimethyl formamide dimethyl acetate (0.8 mL) for 16 h to 110° C. under an atmosphere of nitrogen. The reaction was evaporated to dryness under reduced pressure and was twice evaporated with toluene to yield the crude title compound (126 mg, 98%) as a yellow semi-solid which was used without further purification in the next step.

MS ISP (m/e): 331.4 (79) [(M+H)$^+$], 275.1 (100) [(M-isobutene+H)$^+$].

b) N-[3-Methoxy-4-(4-methyl-imidazol-1-yl)-phenyl]-guanidine dinitrate

To a solution of 3-methoxy-4-(4-methyl-imidazol-1-yl)-phenylamine (5.08 g, 25.0 mmol) in ethanol (25 mL) was added at 20° C. cyanamide (3.15 g, 75 mmol) dissolved in water (3.2 mL) and then 37% aqueous hydrochloric acid solution (4.9 g, 50 mmol). The solution was heated for 3 h to reflux. Additional cyanamide (2.1 g) in water (2.1 mL) and 37% aq hydrochloric acid solution (2.8 mL) were added and the mixture was heated to reflux for another 2 h. At 20° C. 65% aqueous nitric acid (3.5 mL, 50 mmol) was added. The reaction was stirred for 30 minute at 20° C. and the formed precipitate was filtered off, washed with ethanol and diethyl ether. (Caution: the filtrate may contain the ethyl ester of nitric acid). The solid was dried under reduced pressure at 20° C. to yield the title compound (5.42 g, 58%) as a white solid.

MS ISP (m/e): 246.1 (100) [(M+H)$^+$].

$^1$H NMR (DMSO-D$_6$, 300 MHz): δ (ppm)=10.17 (s, 1H), 9.34 (s, 1H), 8.40 (br s, 2H), 7.67 (br s, 4H), 7.63 (d, 1H), 7.21 (s, 1H), 6.99 (d, 1H), 3.88 (s, 3H), 2.35 (s, 3H).

c) [3-Methoxy-4-(4-methyl-imidazol-1-yl)-phenyl]-[4-(1-phenyl-cyclohexyl)-pyrimidin-2-yl]-amine N-[3-methoxy-4-(4-methyl-imidazol-1-yl)-phenyl]guanidine dinitrate (74 mg, 0.20 mmol), crude 3-dimethylamino-1-(1-phenyl-yclohexyl)-propenone (124 mg, 0.48 mmol) and triethylamine (41 mg, 0.40 mmol) in ethanol (2 mL) were heated to reflux under an atmosphere of nitrogen for 16 h. The reaction was transferred with 1-methyl-2-pyrrolidone (3 mL) into a microwave tube and additional triethylamine (41 mg) was added. The reaction was heated to 200° C. for 30 min, which yields only traces of product. Therefore the reaction was heated to 250° C. in the microwave oven, but decomposition of the starting material occurred. The reaction was poured onto water, extracted twice with diethyl ether. The combined organic layers were washed with water and brine, dried over sodium sulfate, filtered and the solvent was removed under reduced pressure. The residue was purified by column chromatography on silica gel using dichloromethane/methanol (19:1 v/v) as eluent to yield the title compound (6 mg, 7%) as a pale-brown solid.

MS ISP (m/e): 440.3 [(M+H)$^+$].

$^1$H NMR (CDCl$_3$, 300 MHz): δ (ppm)=8.27 (d, 1H), 7.79 (s, 1H), 7.64 (s, 1H), 7.15-7.39 (m, 6H), 7.03 (d, 1H), 6.88 (s, 1H), 6.62 (d, 1H), 3.86 (s, 3H), 2.55 (m, 2H), 2.30 (s, 3H), 2.40 (m, 2H), 1.20-1.70 (m, 6H).

Example 5

[3-Methoxy-4-(4-methyl-imidazol-1-yl)-phenyl]-[5-methyl-4-(1-phenyl-ethyl)-pyrimidin-2-yl]-amine

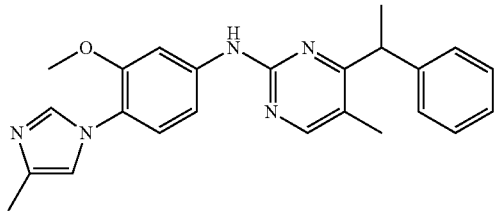 [SMILES: COc1cc(Nc2ncc(C)c(C(C)c3ccccc3)n2)ccc1-n1cnc(C)c1]

a) 1-Dimethylamino-2-methyl-4-phenyl-pent-1-en-3-one

A mixture of 2-phenyl-3-pentanone (106 mg, 0.54 mmol) and of tert.-butoxy-bis(dimethylamino)methane (146 mg, 0.75 mmol, 90%) was stirred at 110° C. for 16 h. The reaction was evaporated to dryness, treated twice with toluene and the solvent was evaporated under reduced pressure to give the crude title compound (138 mg, 97%) as a dark brown solid which was used directly in the next step without further purification.

$^1$H NMR (CDCl$_3$, 300 MHz): δ (ppm)=7.15-7.31 (m, 6H), 4.21 (q, 1H), 3.00 (s, 6H), 1.94 (s, 3H), 1.41 (d, 3H).

b) [3-Methoxy-4-(4-methyl-imidazol-1-yl)-phenyl]-[5-methyl-4-(1-phenyl-ethyl)-pyrimidin-2-yl]-amine The title compound was prepared in analogous manner described in example 4c) from N-[3-methoxy-4-(4-methyl-imidazol-1-yl)-phenyl]-guanidine dinitrate, 1-dimethylamino-2-methyl-4-phenyl-pent-1-en-3-one and triethylamine using 1-methyl-2-pyrrolidinone as the solvent. The reaction was performed in a microwave at 200° C. for 30 min. The title compound was isolated as a pale-yellow solid in 39% yield.

MS ISP (m/e): 400.3 (100) [(M+H)$^+$].

$^1$H NMR (DMSO-D$_6$, 300 MHz): δ (ppm)=9.64 (s, 1H), 8.22 (s, 1H), 7.90 (s, 1H), 7.66 (s, 1H), 7.42 (d, 1H), 7.15-7.32 (m, 6H), 7.03 (s, 1H), 4.38 (q, 1H), 3.78 (s, 3H), 2.14 (s, 3H), 2.07 (s, 3H), 1.63 (d, 3H).

Example 6

[3-Methoxy-4-(4-methyl-imidazol-1-yl)-phenyl]-{4-[1-(3-methoxy-phenyl)-1-methyl-ethyl]-pyrimidin-2-yl}-amine

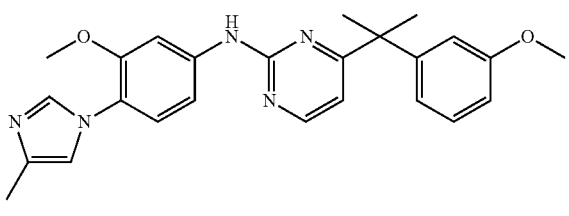

a) 1-Dimethylamino-4-(3-methoxy-phenyl)-4-methyl-pent-1-en-3-one

The title compound was prepared from 3-(3-methoxy-phenyl)-3-methyl-butan-2-one in analogous manner as described in example 5a) as a yellow viscous oil in 99% yield and was used without further purification in the next step.

MS ISP (m/e): 248.2 (100) [(M+H)$^+$].

$^1$H NMR (CDCl$_3$, 300 MHz): δ (ppm)=7.54 (d, 1H), 7.21 (t, 1H), 6.91 (d, 1H), 6.88 (s, 1H), 6.73 (d, 1H), 4.75 (d, 1H), 3.80 (s, 3H), 2.50-3.15 (br s, 6H), 1.48 (s, 3H).

b) [3-Methoxy-4-(4-methyl-imidazol-1-yl)-phenyl]-{4-[1-(3-methoxy-phenyl)-1-methyl-ethyl]-pyrimidin-2-yl}-amine The title compound was prepared in analogous manner as described in example 4c) from N-[3-methoxy-4-(4-methyl-imidazol-1-yl)-phenyl]guanidine dinitrate, 1-dimethylamino-4-(3-methoxy-phenyl)-4-methyl-pent-1-en-3-one and triethylamine using 1-methyl-pyrrolidinone as the solvent. The reaction was performed in a microwave at 200° C. for 2.5 h. The title compound was isolated as a brown viscous oil in 44% yield.

MS ISP (m/e): 430.3 (100) [(M+H)$^+$].

$^1$H NMR (DMSO-D$_6$, 300 MHz): δ (ppm)=9.74 (s, 1H), 8.41 (d, 1H), 7.85 (s, 1H), 7.64 (s, 1H), 7.29 (d, 1H), 7.23 (t, 1H), 7.19 (d, 1H), 7.02 (s, 1H), 6.80-6.82 (m, 3H), 6.73 (d, 1H), 3.71 (s, 6H), 2.14 (s, 3H), 1.68 (s, 6H).

Example 7

{4-[1-(4-Chloro-phenyl)-cyclopropyl]-pyrimidin-2-yl}-[3-methoxy-4-(4-methyl-imidazol-1-yl)-phenyl]-amine

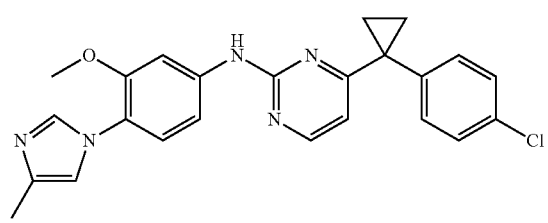 [SMILES: COc1cc(Nc2nccc(C3(c4ccc(Cl)cc4)CC3)n2)ccc1-n1cnc(C)c1]

a) 1-[1-(4-Chloro-phenyl)-cyclopropyl]-ethanone

To a solution of 1-(4-chlorophenyl)-1-cyclopropanecarbonitrile (181 mg, 1.0 mmol) in toluene (5 mL) was added drop wise at 20° C. under an atmosphere of nitrogen a 3 M solution of methylmagnesium chloride in tetrahydrofuran (0.5 mL, 1.5 mmol). The reaction was heated for 16 h to 80° C. In an ice bath 6 N aqueous hydrochloric acid solution (1.08 mL) was added carefully and the reaction was heated to reflux for 2 h. The reaction was diluted with toluene, extracted once with water, once with brine, dried over sodium sulfate, filtered and the solvent was evaporated under reduced pressure. The residue was purified by column chromatography on silica gel using heptane/ethyl acetate (9:1 v/v) as eluent to yield the title compound (67 mg, 34%) as a yellow oil.

$^1$H NMR (CDCl$_3$, 300 MHz): δ (ppm)=7.31 (m, 4H), 2.00 (s, 3H), 1.61 (q, 2H), 1.15 (q, 2H).

b) 1-[1-(4-Chloro-phenyl)-cyclopropyl]-3-dimethylamino-propenone

The title compound was prepared from 1-[1-(4-chloro-phenyl)-cyclopropyl]-ethanone in analogous manner as described in example 5a) as a pale-yellow viscous oil in 99% yield and was used without further purification in the next step.

$^1$H NMR (CDCl$_3$, 300 MHz): δ (ppm)=7.52 (d, 1H), 7.26-7.33 (m, 4H), 6.73 (d, 1H), 4.71 (d, 1H), 3.00 (br s, 3H), 2.65 (br s, 3H), 1.59 (m, 2H), 1.00 (m, 2H).

c) {4-[1-(4-Chloro-phenyl)-cyclopropyl]-pyrimidin-2-yl}-[3-methoxy-4-(4-methyl-imidazol-1-yl)-phenyl]-amine The title compound was prepared in analogous manner as described in example 4c) from N-[3-methoxy-4-(4-methyl-imidazol-1-yl)-phenyl]-guanidine dinitrate, 1-[1-(4-chloro-phenyl)-cyclopropyl]-3-dimethylamino-propenone and triethylamine using 1-methyl-2-pyrrolidine as the solvent. The reaction was performed in a microwave at 200° C. for 2.5 h. The title compound was isolated as a brown viscous oil in 22% yield.

MS ISP (m/e): 432.3/434.3 (100/39) [(M+H)$^+$].

$^1$H NMR (DMSO-D$_6$, 300 MHz): δ (ppm)=9.73 (s, 1H), 8.25 (d, 1H), 7.84 (s, 1H), 7.66 (s, 1H), 7.47 (d, 2H), 7.43 (d, 2H), 7.26 (d, 1H), 7.20 (d, 1H), 7.04 (s, 1H), 6.18 (d, 1H), 3.82 (s, 3H), 2.14 (s, 3H), 1.75 (m, 2H), 1.38 (m, 1H).

Example 8

(4-Chloro-6-methyl-pyrimidin-2-yl)-[3-methoxy-4-(4-methyl-imidazol-1-yl)-phenyl]-amine

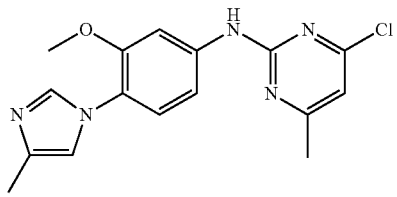 [SMILES: COc1cc(Nc2nc(C)cc(Cl)n2)ccc1-n1cnc(C)c1]

a) 2-[3-Methoxy-4-(4-methyl-imidazol-1-yl)-phenylamino]-6-methyl-pyrimidin-4-ol To a solution of sodium ethoxide (724 mg, 13 mmol) in methanol (60 mL) was added at 20° C. under an atmosphere of nitrogen N-[3-methoxy-4-(4-methyl-imidazol-1-yl)-phenyl]-guanidine dinitrate (2.10 g, 5.7 mmol) and ethyl acetoacetate (2.43 g, 18.7 mmol). The reaction was heated to reflux for 40 h. After cooling it was poured onto water and set to pH 7 with 1N aqueous hydrochloric acid solution. The precipitate was filtered off, washed with water and diethyl ether, and dried in high vacuum for 16 h at 45° C. to yield the title compound (146 g, 83%) as a white solid.

MS ISP (m/e): 312.2 (100) [(M+H)$^+$].

$^1$H NMR (DMSO-D$_6$, 300 MHz): δ (ppm)=7.83 (br s, 1H), 7.67 (s, 1H), 7.25 (s, 2H), 7.04 (s, 1H), 5.77 (s, 1H), 3.80 (s, 3H), 2.17 (s, 3H), 2.14 (s, 3H).

b) (4-Chloro-6-methyl-pyrimidin-2-yl)-[3-methoxy-4-(4-methyl-imidazol-1-yl)-phenyl]-amine A solution of 2-[3-methoxy-4-(4-methyl-imidazol-1-yl)-phenylamino]-6-methyl-pyrimidin-4-ol (1.45 g, 46.6 mmol) in phosphorous oxychloride (4.7 mL) was heated to reflux for 2 h. The excess of phosphorous oxychloride was evaporated under reduce pressure and the residue was treated carefully with ice and then, under ice cooling, with 25% aqueous ammonia. The precipitate formed was filtered off, washed with water and then with diethyl ether and dried to give the title compound (1.53 g, 100%) as a pale-brown solid.

MS ISP (m/e): 330.1/332.2 (100/25) [(M+H)$^+$].

$^1$H NMR (DMSO-D$_6$, 300 MHz): δ (ppm)=10.16 (s, 1H), 7.81 (s, 1H), 7.67 (s, 1H), 7.36 (d, 1H), 7.27 (d, 1H), 7.05 (s, 1H), 6.95 (s, 1H), 3.80 (s, 3H), 2.40 (s, 3H), 2.14 (s, 3H).

Example 9

[3-Methoxy-4-(4-methyl-imidazol-1-yl)-phenyl]-[4-methyl-6-(3,4,5-trifluoro-phenoxy)-pyrimidin-2-yl]-amine

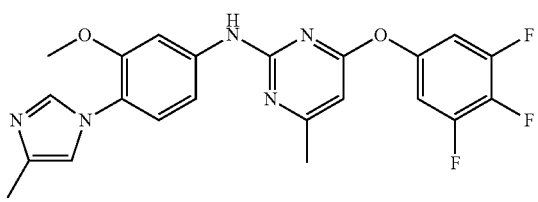 [SMILES: COc1cc(Nc2nc(C)cc(Oc3cc(F)c(F)c(F)c3)n2)ccc1-n1cnc(C)c1]

To a solution of 3,4,5-trifluorophenol (33 mg, 0.22 mmol) in 1-methyl-2-pyrrolidone (2 mL) was added at 20° C. under an atmosphere of nitrogen a 55% dispersion of sodium hydride in oil (10 mg, 0.22 mmol). The reaction was stirred for 30 min and then, (4-chloro-6-methyl-pyrimidin-2-yl)-[3-methoxy-4-(4-methyl-imidazol-1-yl)-phenyl]-amine (66 mg, 0.2 mmol) was added. The mixture was heated in a microwave oven to 200° C. for 30 min and then poured onto 1 N aqueous sodium hydroxide solution. The mixture was stirred for 15 min, and the precipitate formed was filtered off, washed with water and dried to yield the title compound (72 mg, 8%) as a pale-brown solid.

MS ISP (m/e): 442.2 (100) [(M+H)$^+$].

$^1$H NMR (DMSO-D$_6$, 300 MHz): δ (ppm)=9.74 (s, 1H), 7.63 (s, 1H), 7.60 (s, 1H), 7.46 (dd, 2H), 7.25 (d, 1H), 7.11 (d, 1H), 7.00 (s, 1H), 6.46 (s, 1H), 3.64 (s, 3H), 2.38 (s, 3H), 2.14 (s, 3H).

Example 10

[4-(2,6-Dichloro-phenoxy)-pyrimidin-2-yl]-[3-methoxy-4-(4-methyl-imidazol-1-yl)-phenyl]-amine

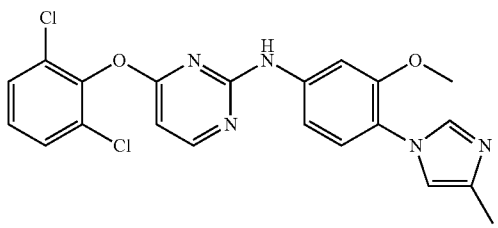 [SMILES: COc1cc(Nc2nccc(Oc3c(Cl)cccc3Cl)n2)ccc1-n1cnc(C)c1]

a) 4-Chloro-6-(2,6-dichloro-phenoxy)-pyrimidine 4,6-Dichloropyrimidine (149 mg, 1.0 mmol), 2,6-dichlorophenol (179 mg, 1.1 mmol), potassium carbonate (166 mg, 1.2 mmol), and sodium iodide (7.5 mg, 0.05 mmol) were stirred in acetonitrile (3 mL) at 20° C. under an atmosphere of nitrogen for 64 h. The reaction was poured onto 1N aqueous sodium hydroxide solution and extracted twice with diethyl ether. The combined organic layers were washed with brine, dried over sodium sulfate, filtered and the solvent was evaporated under reduced pressure to give the title compound (195 mg, 71%) as a white solid.

MS EI (m/e): 274.9/276.9/278.9 (100/95/50) [M+].

$^1$H NMR (DMSO-D$_6$, 300 MHz): δ (ppm)=8.69 (s, 1H), 7.78 (s, 1H), 7.66 (d, 2H), 7.42 (dd, 1H).

b) [4-(2,6-Dichloro-phenoxy)-pyrimidin-2-yl]-[3-methoxy-4-(4-methyl-imidazol-1-yl)-phenyl]-amine The title compound was prepared in analogous manner as described in example 1e) from 3-methoxy-4-(4-methyl-imidazol-1-yl)-phenylamine and 4-chloro-6-(2,6-dichloro-phenoxy)-pyrimidine. It was obtained as a yellow solid in 29% yield.

MS ISP (m/e): 442.1/444.1 (100/60) [(M+H)+].

$^1$H NMR (DMSO-D$_6$, 300 MHz): δ (ppm)=9.79 (s, 1H), 8.48 (d, 1H), 7.66 (d, 2H), 7.61 (s, 1H), 7.42 (dd, 1H), 7.31 (s, 1H), 7.11 (d, 1H), 6.99 (s, 1H), 6.96 (d, 1H), 6.71 (d, 1H), 3.64 (s, 3H), 2.13 (s, 3H).

Example 11

[4-(3,4-Difluoro-phenoxy)-6-methyl-pyrimidin-2-yl]-[3-methoxy-4-(4-methyl-imidazol-1-yl)-phenyl]-amine

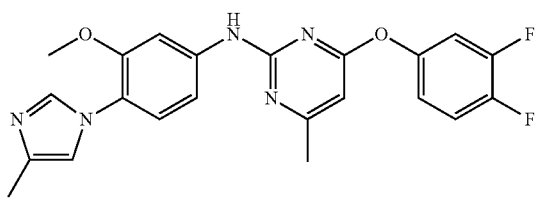 [SMILES: COc1cc(Nc2nc(C)cc(Oc3ccc(F)c(F)c3)n2)ccc1-n1cnc(C)c1]

The title compound was prepared in analogous manners as described in example 9) from 3,4-difluorophenol and (4-chloro-6-methyl-pyrimidin-2-yl)-[3-methoxy-4-(4-methyl-imidazol-1-yl)-phenyl]-amine. It was obtained in 81% yield as a pale-brown solid.

MS ISP (m/e): 424.2 (100) [(M+H)+].

$^1$H NMR (DMSO-D$_6$, 300 MHz): δ (ppm)=9.73 (s, 1H), 7.50-7.62 (m, 4H), 7.23 (d, 1H), 7.14 (m, 1H), 7.08 (d, 1H), 6.99 (s, 1H), 6.43 (s, 1H), 3.60 (s, 3H), 2.37 (s, 3H), 2.13 (s, 3H).

Example 12

[4-(4-Chloro-phenoxy)-6-methyl-pyrimidin-2-yl]-[3-methoxy-4-(4-methyl-imidazol-1-yl)-phenyl]-amine

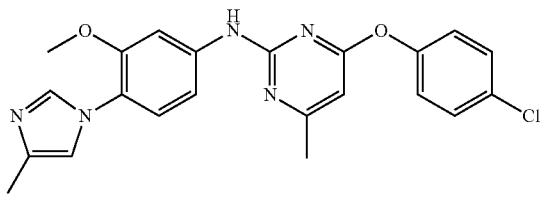 [SMILES: COc1cc(Nc2nc(C)cc(Oc3ccc(Cl)cc3)n2)ccc1-n1cnc(C)c1]

The title compound was prepared in analogous manners as described in example 9) from 4-chlorophenol and (4-chloro-6-methyl-pyrimidin-2-yl)-[3-methoxy-4-(4-methyl-imidazol-1-yl)-phenyl]-amine. It was obtained in 73% yield as a pale-brown solid.

MS ISP (m/e): 422.1/424.2 (100/35) [(M+H)+].

$^1$H NMR (DMSO-D$_6$, 300 MHz): δ (ppm)=9.72 (s, 1H), 7.61 (s, 1H), 7.58 (s, 1H), 7.52 (d, 2H), 7.28 (d, 2H), 7.18 (d, 1H), 7.07 (d, 1H), 6.99 (s, 1H), 6.43 (s, 1H), 3.54 (s, 3H), 2.37 (s, 3H), 2.13 (s, 3H).

Example 13

[4-(4-Dichloro-phenoxy)-pyrimidin-2-yl]-[3-methoxy-4-(4-methyl-imidazol-1-yl)-phenyl]-amine

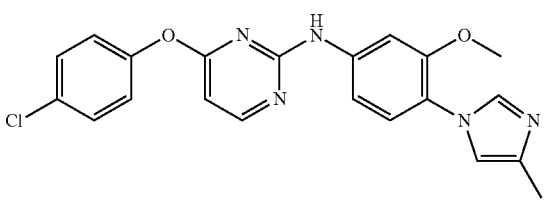 [SMILES: COc1cc(Nc2nccc(Oc3ccc(Cl)cc3)n2)ccc1-n1cnc(C)c1]

The title compound was prepared in analogous manner as described in example 1e) from 3-methoxy-4-(4-methyl-imidazol-1-yl)-phenylamine and 2-chloro-4-(4-chloro-phenoxy)-pyrimidine. It was obtained as a yellow solid in 58% yield.

MS ISP (m/e): 408.3/410.2 (100/34) [(M+H)+].

$^1$H NMR (DMSO-D$_6$, 300 MHz): δ (ppm)=9.74 (s, 1H), 8.42 (d, 1H), 7.62 (s, 1H), 7.53 (d, 2H), 7.48 (s, 1H), 7.31 (d, 2H), 7.23 (d, 1H), 7.07 (d, 1H), 6.99 (s, 1H), 6.54 (d, 1H), 3.56 (s, 3H), 2.13 (s, 3H).

Example 14

3-{2-[3-Methoxy-4-(4-methyl-imidazol-1-yl)-phenylamino]-6-methyl-pyrimidin-4-yloxy}-benzonitrile

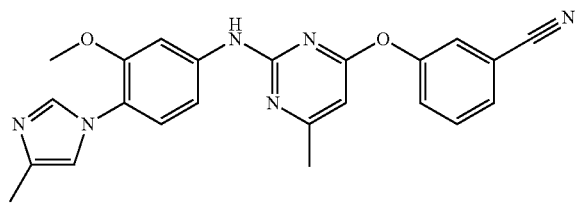 [SMILES: COc1cc(Nc2nc(C)cc(Oc3cccc(C#N)c3)n2)ccc1-n1cnc(C)c1]

The title compound was prepared in analogous manners as described in example 9) from 3-hydroxy-benzonitrile and (4-chloro-6-methyl-pyrimidin-2-yl)-[3-methoxy-4-(4-methyl-imidazol-1-yl)-phenyl]-amine. It was obtained in 75% yield as a pale-brown solid. MS ISP (m/e): 413.4 (100) [(M+H)$^+$].

$^1$H NMR (DMSO-D$_6$, 300 MHz): δ (ppm)=9.74 (s, 1H), 7.86 (s, 1H), 7.78 (d, 1H), 7.61-7.71 (m, 3H), 7.51 (br s, 1H), 7.17 (br d, 1H), 7.05 (d, 1H), 6.99 (s, 1H), 6.49 (s, 1H), 3.56 (s, 3H), 2.38 (s, 3H), 2.13 (s, 3H).

Example 15

[3-Methoxy-4-(4-methyl-imidazol-1-yl)-phenyl]-[4-methyl-6-(pyridin-3-yloxy)-pyrimidin-2-yl]-amine

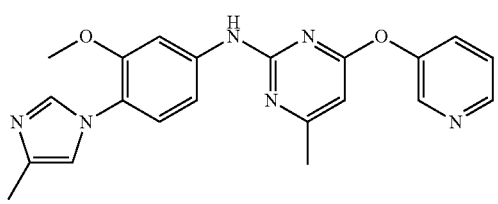 [SMILES: COc1cc(Nc2nc(C)cc(Oc3cccnc3)n2)ccc1-n1cnc(C)c1]

The title compound was prepared in analogous manners as described in example 9 from 3-hydroxy-pyridine and (4-chloro-6-methyl-pyrimidin-2-yl)-[3-methoxy-4-(4-methyl-imidazol-1-yl)-phenyl]-amine. It was obtained in 53% yield as a pale-yellow solid after purification by column chromatography on silica gel using dichloromethane/methanol (19:1 v/v) as eluent.

MS ISP (m/e): 389.3 (100) [(M+H)$^+$].

$^1$H NMR (DMSO-D$_6$, 300 MHz): δ (ppm)=9.72 (s, 1H), 8.54 (d, 1H), 8.48 (dd, 1H), 7.73 (dd, 1H), 7.48 (s, 1H), 7.49-7.55 (m, 2H), 7.17 (br d, 1H), 7.07 (d, 1H), 6.98 (s, 1H), 6.48 (s, 1H), 3.53 (s, 3H), 2.39 (s, 3H), 2.13 (s, 3H).

Example 16

[3-Methoxy-4-(4-methyl-imidazol-1-yl)-phenyl]-[4-methyl-6-(2-trifluoromethyl-phenoxy)-pyrimidin-2-yl]-amine

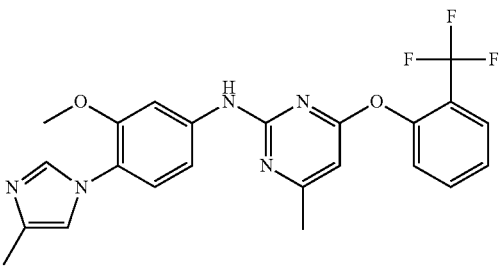 [SMILES: COc1cc(Nc2nc(C)cc(Oc3ccccc3C(F)(F)F)n2)ccc1-n1cnc(C)c1]

The title compound was prepared in analogous manners as described in example 9 from 2-trifluoromethyl-phenol and (4-chloro-6-methyl-pyrimidin-2-yl)-[3-methoxy-4-(4-methyl-imidazol-1-yl)-phenyl]-amine. The reaction was heated for 3.5 h to 200° C. in a microwave oven. Several times the phenol (overall 4.4 equivalents) and additional sodium hydride had to be added in order to obtain complete conversion. The title compound was obtained, after purification by column chromatography on silica gel using dichloromethane/methanol (19:1 v/v) as eluent, as a white solid in 15% yield.

MS ISP (m/e): 456.2 (100) [(M+H)$^+$].

$^1$H NMR (DMSO-D$_6$, 300 MHz): δ (ppm)=9.75 (s, 1H), 8.82 (m, 2H), 7.60 (s, 1H), 7.51 (m, 3H), 7.12 (br d, 1H), 7.01 (d, 1H), 6.96 (s, 1H), 6.53 (s, 1H), 3.53 (s, 3H), 2.39 (s, 3H), 2.13 (s, 3H).

Example 17

[3-Methoxy-4-(4-methyl-imidazol-1-yl)-phenyl]-[4-methyl-6-(3-trifluoromethoxy-phenoxy)-pyrimidin-2-yl]-amine

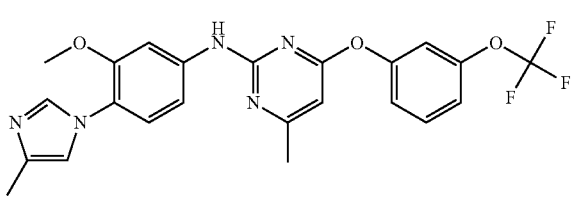 [SMILES: COc1cc(Nc2nc(C)cc(Oc3cccc(OC(F)(F)F)c3)n2)ccc1-n1cnc(C)c1]

The title compound was prepared in analogous manners as described in example 9 from 3-trifluoromethoxy-phenol and (4-chloro-6-methyl-pyrimidin-2-yl)-[3-methoxy-4-(4-methyl-imidazol-1-yl)-phenyl]-amine. It was obtained in 95% yield as a pale-brown solid. MS ISP (m/e): 472.0 (100) [(M+H)$^+$].

$^1$H NMR (DMSO-D$_6$, 300 MHz): δ (ppm)=9.77 (s, 1H), 751-7.63 (m, 3H), 7.28-7.36 (m, 3H), 7.18 (br d, 1H), 7.3 (d, 1H), 6.96 (s, 1H), 6.48 (s, 1H), 3.52 (s, 3H), 2.38 (s, 3H), 2.12 (s, 3H).

Example 18

[3-Methoxy-4-(4-methyl-imidazol-1-yl)-phenyl]-[4-methyl-6-(3-trifluoromethyl-phenoxy)-pyrimidin-2-yl]-amine

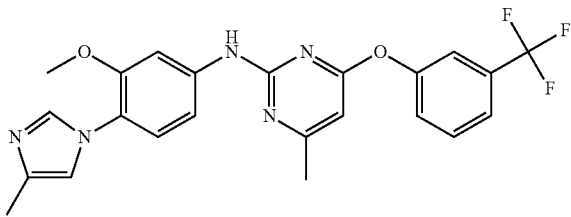 [SMILES: COc1cc(Nc2nc(C)cc(Oc3cccc(C(F)(F)F)c3)n2)ccc1-n1cnc(C)c1]

The title compound was prepared in analogous manners as described in example 9 from 3-trifluoromethyl-phenol and (4-chloro-6-methyl-pyrimidin-2-yl)-[3-methoxy-4-(4-methyl-imidazol-1-yl)-phenyl]-amine. It was obtained in 62% yield as a pale-yellow viscous oil.
MS ISP (m/e): 456.2 (100) [(M+H)$^+$].
$^1$H NMR (DMSO-D$_6$, 300 MHz): δ (ppm)=9.74 (s, 1H), 7.66-7.72 (m, 3H), 7.59 (s, 1H), 7.58 (d, 1H), 7.51 (br s, 1H), 7.13 (br d, 1H), 7.01 (d, 1H), 6.96 (s, 1H), 6.49 (s, 1H), 3.50 (s, 3H), 2.39 (s, 3H), 2.13 (s, 3H).

Example 19

[3-Methoxy-4-(4-methyl-imidazol-1-yl)-phenyl]-[4-methyl-6-(3,3,4,4,4-pentafluoro-butoxy)-pyrimidin-2-yl]-amine

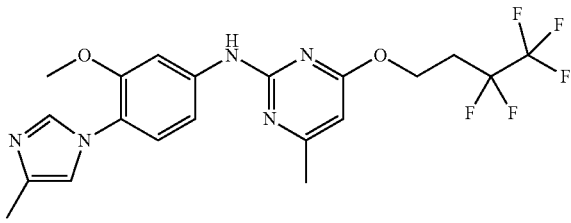 [SMILES: COc1cc(Nc2nc(C)cc(OCCC(F)(F)C(F)(F)F)n2)ccc1-n1cnc(C)c1]

Sodium (6.9 mg, 0.3 mmol) was dissolved under stirring and heating under an atmosphere of argon in 3,3,4,4,4-pentafluorobutan-1-ol (676 mg, 4.0 mmol). To this solution (4-chloro-6-methyl-pyrimidin-2-yl)-[3-methoxy-4-(4-methyl-imidazol-1-yl)-phenyl]-amine (66 mg, 0.20 mmol) was added and the reaction mixture was stirred for 16 h at 20° C. and then heated to 100° C. for 4 h. The reaction mixture was poured onto water and was acidified with 1N aqueous hydrochloric acid solution. It was extracted twice with diethyl ether. The aqueous layer was set to basic pH with 1N aqueous sodium hydroxide solution and extracted three times with diethyl ether. The combined organic layers were washed with brine, dried over sodium sulfate and evaporated under reduced pressure. The residue was purified by column chromatography on silica gel using dichloromethane/methanol (19:1 v/v) as eluent to yield the title compound (59 mg, 64%) as a pale-yellow solid.
MS ISP (m/e): 458.1 (100) [(M+H)$^+$].
$^1$H NMR (DMSO-D$_6$, 300 MHz): δ (ppm)=9.71 (s, 1H), 7.89 (s, 1H), 7.65 (s, 1H), 7.33 (d, 1H), 7.20 (d, 1H), 7.02 (s, 1H), 6.23 (s, 1H), 4.63 (t, 2H), 3.79 (s, 3H), 2.80 (tt, 2H), 2.31 (s, 3H), 2.14 (s, 3H).

Example 20

{4-[1-(4-Chloro-phenyl)-1-methyl-ethyl]-5-methyl-pyrimidin-2-yl}-[3-methoxy-4-(4-methyl-imidazol-1-yl)-phenyl]-amine

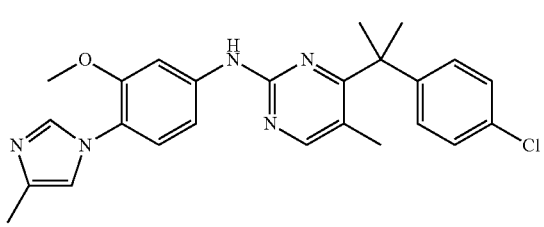 [SMILES: COc1cc(Nc2ncc(C)c(C(C)(C)c3ccc(Cl)cc3)n2)ccc1-n1cnc(C)c1]

a) 3-(4-Chlorophenyl)-3-methyl-2-pentanone

To a solution of 2-(4-chlorophenyl)-2-methylpropionitrile (243 mg, 1.4 mmol) in benzene (1.4 mL) was added slowly at 50° C. under an atmosphere of nitrogen and with stirring to a 2.8 M solution of ethylmagnesium chloride in tetrahydrofuran (1.45 ml, 4.1 mmol). The reaction mixture was heated to reflux for 2 h, and thereafter, cooled and poured onto 10% aqueous ammonium chloride solution (4 mL). The organic layer was separated and treated with 2 N aqueous hydrochloric acid solution (1 mL). The reaction was heated to reflux for 1 h. After cooling the reaction mixture was diluted with water and extracted twice with benzene. The organic layer was washed with brine, dried over sodium sulfate and evaporated under reduced pressure. The residue was purified by column chromatography on silica gel using heptane/ethyl acetate (9:1 v/v) as eluent to give the title compound (64 mg, 20%) as a pale-yellow oil.
$^1$H NMR (DMSO-D$_6$, 300 MHz): δ (ppm)=7.41 (d, 2H), 7.27 (d, 2H), 2.25 (q, 2H), 1.41 (s, 6H), 0.83 (t, 3H).

b) 4-(4-Chloro-phenyl)-1-dimethylamino-2,4-dimethyl-pent-1-en-3-one

The title compound was prepared from 3-(4-chlorophenyl)-3-methyl-2-pentanone in analogous manner as described in example 5a) as a brown viscous oil in 97% yield and was used without further purification in the next step.
$^1$H NMR (CDCl$_3$, 300 MHz): δ (ppm)=7.27 (d, 2H), 7.17 (d, 2H), 6.81 (s, 1H), 2.83 (s, 6H), 1.79 (s, 3H), 1.47 (s, 6H).

c) {4-[1-(4-Chloro-phenyl)-1-methyl-ethyl]-5-methyl-pyrimidin-2-yl}-[3-methoxy-4-(4-methyl-imidazol-1-yl)-phenyl]-amine The title compound was prepared in analogous manner as described in example 4c) from N-[3-methoxy-4-(4-methyl-imidazol-1-yl)-phenyl]guanidine dinitrate, 4-(4-chloro-phenyl)-1-dimethylamino-2,4-dimethyl-pent-1-en-3-one and triethylamine using 1-methyl-2-pyrrolidone as the solvent. The reaction was performed in a microwave oven at 200° C. for 2.5 h. The title compound was isolated as a yellow solid in 52% yield.
MS ISP (m/e): 448.1/450.1 (100/34) [(M+H)$^+$].
$^1$H NMR (DMSO-D$_6$, 300 MHz): δ (ppm)=9.66 (s, 1H), 8.16 (s, 1H), 7.84 (s, 1H), 7.65 (s, 1H), 7.44 (d, 1H), 7.38 (d, 2H), 7.23 (d, 1H), 7.20 (d, 2H), 7.03 (s, 1H), 3.79 (s, 3H), 2.14 (s, 3H), 1.67 (s, 6H), 1.57 (s, 3H).

Example 21

{4-[1-(4-Chloro-phenyl)-1-methyl-ethyl]-pyrimidin-2-yl}-[3-methoxy-4-(4-methyl-imidazol-1-yl)-phenyl]-amine

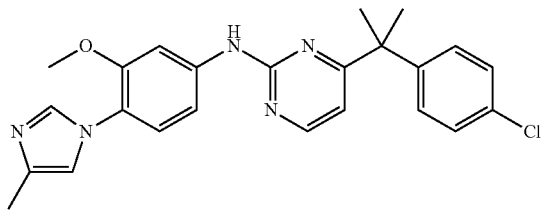 [SMILES: COc1cc(Nc2nccc(C(C)(C)c3ccc(Cl)cc3)n2)ccc1-n1cnc(C)c1]

a) 4-(4-Chloro-phenyl)-1-dimethylamino-4-methyl-pent-1-en-3-one

The title compound was prepared from 3-(4-chlorophenyl)-3-methyl-2-butanone in analogous manner as described in example 5a) as a pale-yellow solid in 73% yield and was used without further purification in the next step.

$^1$H NMR (CDCl$_3$, 300 MHz): δ (ppm)=7.55 (d, 1H), 7.26 (m, 4H), 4.70 (d, 1H), 3.00 (br s, 3H), 2.70 (br s, 3H), 1.47 (s, 6H).

b) {4-[1-(4-Chloro-phenyl)-1-methyl-ethyl]-pyrimidin-2-yl}-[3-methoxy-4-(4-methyl-imidazol-1-yl)-phenyl]-amine The title compound was prepared in analogous manner as described in example 4c) from N-[3-methoxy-4-(4-methyl-imidazol-1-yl)-phenyl]guanidine dinitrate and 4-(4-chloro-phenyl)-1-dimethylamino-4-methyl-pent-1-en-3-one, and triethylamine using 1-methyl-2-pyrrolidone as solvent. The reaction was performed in a microwave oven at 200° C. for 2 h. The title compound was isolated as a brown solid in 20% yield.

MS ISP (m/e): 434.3/436.1 (100/40) [(M+H)$^+$].

$^1$H NMR (CDCl$_3$, 300 MHz): δ (ppm)=8.31 (d, 1H), 7.72 (s, 1H), 7.63 (s, 1H), 7.27 (d, 2H), 7.21 (d, 1H), 7.15 (d, 1H), 7.01 (d, 1H), 6.87 (s, 1H), 6.57 (d, 1H), 3.77 (s, 3H), 2.30 (s, 3H), 1.71 (s, 6H).

Example 22

{4-[1-(4-Chloro-phenyl)-1-methyl-ethyl]-pyrimidin-2-yl}-[3-fluoro-4-(4-methyl-imidazol-1-yl)-phenyl]-amine

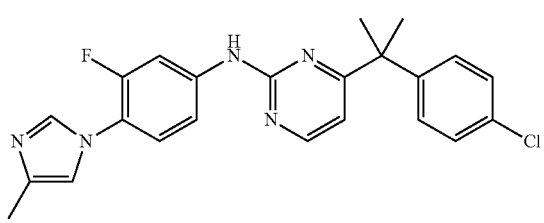 [SMILES: Cc1cn(-c2ccc(Nc3nccc(C(C)(C)c4ccc(Cl)cc4)n3)cc2F)cn1]

a) 1-(2-Fluoro-4-nitro-phenyl)-4-methyl-1H-imidazole 3,4-Difluoro-4-nitro-benzene (7.97 g (50 mmol), 4-methyl-1H-imidazole (4.51 g, 55 mmol) and N,N-diisopropylethylamine (16.16 g (125 mmol) were dissolved in acetonitrile (80 mL) and the reaction was heated to reflux for 24 h under an atmosphere of nitrogen. The solvent was evaporated under reduced pressure and the residue was crystallized from a mixture of ethyl acetate and heptane to yield the title compound (4.66 g, 42%) as a pale-yellow solid.

MS ISP (m/e): 222.1 (100) [(M+H)$^+$].

$^1$H NMR (DMSO-D$_6$, 300 MHz): δ (ppm)=8.42 (d, 1H), 8.21 (d, 1H), 8.11 (s, 1H), 7.95 (t, 1H), 7.43 (s, 1H), 2.19 (s, 3H).

b) 3-Fluoro-4-(4-methyl-imidazol-1-yl)-phenylamine 1-(2-Fluoro-4-nitro-phenyl)-4-methyl-1H-imidazole (4.66 g, 21.1 mmol) was dissolved in a mixture of methanol (25 mL) and tetrahydrofuran (100 mL). The solution was cooled to 0° C. under an atmosphere of nitrogen. Ammonium formate (6.64 g, 105 mmol) and 10% palladium on charcoal (0.24 g) was added and the mixture was stirred at 20° C. for 18 h. The mixture was filtered through celite and the celite was washed with methanol. The filtrate was evaporated under reduced pressure and the residue was partitioned between ethyl acetate and 10% aqueous sodium bicarbonate solution. The organic layer was separated, washed with brine, dried over sodium sulfate and evaporated under reduced pressure to yield the title compound (3.89 g, 97%) as a yellow solid.

$^1$H NMR (DMSO-D$_6$, 300 MHz): δ (ppm)=7.62 (s, 1H), 7.12 (t, 1H), 7.01 (s, 1H), 6.41-6.51 (m, 2H), 5.64 (br s, 2H), 2.13 (s, 3H).

c) N-[3-fluoro-4-(4-methyl-imidazol-1-yl)-phenyl]-guanidine nitrate

A suspension of 3-fluoro-4-(4-methyl-imidazol-1-yl)-phenylamine (500 mg, 2.62 mmol), of 50% aqueous cyanamide solution (249 mg, 2.96 mmol) and of 65% aqueous nitric acid (253 mg, 2.62 mmol) in ethanol (2.6 mL) was heated for 5 days to reflux under an atmosphere of nitrogen. Twice the same amounts of cyanamide and nitric acid were added to the reaction mixture after 2 and 4 days, respectively. The mixture was cooled and let stand at 20° C. for 1 d. The precipitated solid was filtered off (Caution: the filtrate may contain the ethyl ester of nitric acid) and washed with ethanol to yield the title compound (280 mg, 36%) as an off-white solid.

MS ISP (m/e): 234.1 (100) [(M+H)$^+$].

$^1$H NMR (DMSO-D$_6$, 300 MHz): δ (ppm)=9.82 (br s, 1H), 7.90 (s, 1H), 7.67 (t, 1H), 7.56 (s, 4H), 7.43 (d, 1H), 7.25 (s, 1H), 7.21 (d, 1H), 2.18 (s, 1H).

d) {4-[1-(4-Chloro-phenyl)-1-methyl-ethyl]-5-methyl-pyrimidin-2-yl}-[3-methoxy-4-(4-methyl-imidazol-1-yl)-phenyl]-amine The title compound was prepared in analogous manner as described in example 4c) from N-[3-methoxy-4-(4-methyl-imidazol-1-yl)-phenyl]guanidine dinitrate, 4-(4-chloro-phenyl)-1-dimethylamino-4-methyl-pent-1-en-3-one, and triethylamine using 1-methyl-2-pyrrolidone as solvent. The reaction was performed in a microwave at 200° C. for 2.5 h. The title compound was isolated as a yellow solid in 52% yield.

MS ISP (m/e): 448.1/450.1 (100/34) [(M+H)$^+$].

$^1$H NMR (DMSO-D$_6$, 300 MHz): δ (ppm)=9.66 (s, 1H), 8.16 (s, 1H), 7.84 (s, 1H), 7.65 (s, 1H), 7.44 (d, 1H), 7.38 (d, 2H), 7.23 (d, 1H), 7.20 (d, 2H), 7.03 (s, 1H), 3.79 (s, 3H), 2.14 (s, 3H), 1.67 (s, 6H), 1.57 (s, 3H).

Example 23

[3-Methoxy-4-(4-methyl-imidazol-1-yl)-phenyl]-{4-[1-methyl-1-(3,4,5-trifluoro-phenyl)-ethyl]-pyrimidin-2-yl}-amine

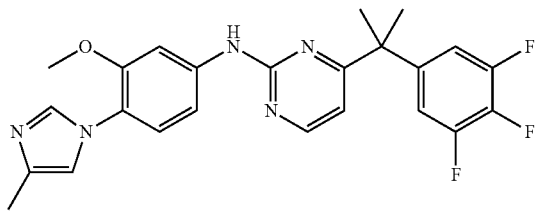 [SMILES: COc1cc(Nc2nccc(C(C)(C)c3cc(F)c(F)c(F)c3)n2)ccc1-n1cnc(C)c1]

a) 2-Methyl-2-(3,4,5-trifluoro-phenyl)-propionitrile

Potassium tert.-butoxide (3.44 g, 30 mmol) was dissolved in tetrahydrofuran (100 mL) and stirred under am atmosphere of nitrogen. (3,4,5-trifluorophenyl)-acetonitrile (2.12 g, 12 mmol) dissolved in tetrahydrofuran (10 mL) was added drop wise at 0° C. The solution turned orange and heat was evolved. Methyl iodide (1.88 mL, 30 mmol) dissolved in tetrahydrofuran (10 mL) was added drop wise. The solution turned pale brown and was stirred for 4 h at 20° C. The reaction was poured onto water and extracted twice with diethyl ether. The combined organic layers were washed with brine, dried over sodium sulfate, filtered and the solvent was evaporated and reduce pressure to yield the title compound (2.30 g, 96%) as a yellow solid.

$^1$H NMR (CDCl$_3$, 300 MHz): δ (ppm)=7.26 (m, 2H), 1.71 (s, 6H).

b) 3-Methyl-3-(3,4,5-trifluoro-phenyl)-butan-2-one

The title compound was prepared in analogous manner as described in example 20a) from 2-methyl-2-(3,4,5-trifluoro-phenyl)-propionitrile and 3 M methylmagnesium chloride solution in tetrahydrofuran in 42% yield as a pale-yellow oil.

$^1$H NMR (DMSO-D$_6$, 300 MHz): δ (ppm)=7.24 (m, 2H), 1.97 (s, 3H), 1.42 (s, 6H).

c) 1-Dimethylamino-4-methyl-4-(3,4,5-trifluoro-phenyl)-pent-1-en-3-one

The title compound was prepared crude in analogous manner as described in example 5a) from 3-methyl-3-(3,4,5-trifluoro-phenyl)-butan-2-one as a yellow oil and was used as crude material in the next step.

MS ISP (m/e): 272.2 (100) [(M+H)$^+$].

$^1$H NMR (CDCl$_3$, 300 MHz): δ (ppm)=7.58 (d, 1H), 6.93 (m, 2H), 4.70 (d, 1H), 3.04 (br s, 3H), 2.69 (br s, 3H), 1.44 (s, 6H).

d) [3-Methoxy-4-(4-methyl-imidazol-1-yl)-phenyl]-{4-[1-methyl-1-(3,4,5-trifluoro-phenyl)-ethyl]-pyrimidin-2-yl}-amine The title compound was prepared in analogous manner as described in example 4c) from N-[3-methoxy-4-(4-methyl-imidazol-1-yl)-phenyl]guanidine dinitrate and 1-dimethylamino-4-methyl-4-(3,4,5-trifluoro-phenyl)-pent-1-en-3-one as a pale-brown solid in 21% yield.

MS ISP (m/e): 454.2 (100) [(M+H)$^+$].

$^1$H NMR (DMSO-D$_6$, 300 MHz): δ (ppm)=9.77 (s, 1H), 8.44 (d, 1H), 7.78 (s, 1H), 7.65 (s, 1H), 7.32 (d, 1H), 7.17-7.28 (m, 4H), 7.02 (s, 1H), 6.75 (d, 1H), 3.74 (s, 3H), 2.14 (s, 3H), 1.69 (s, 6H).

Example 24

{4-Chloro-6-[1-(4-chloro-phenyl)-1-methyl-ethyl]-pyrimidin-2-yl}-[3-methoxy-4-(4-methyl-imidazol-1-yl)-phenyl]-amine

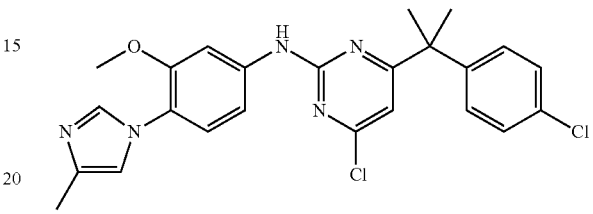

a) Ethyl 4-(4-chloro-phenyl)-4-methyl-3-oxo-pentanoate

To a solution of 3-(4-chlorophenyl)-3-methyl-2-butanone (197 mg, 1 mmol) in diethyl carbonate (1.32 g, 11 mmol) was added at 20° C. under an atmosphere of nitrogen portion wise a dispersion of 55% sodium hydride in mineral oil (91 mg, 2.1 mmol). The reaction turned yellow and was heated to 50° C. After the gas evolution stopped the reaction was stirred at 85° C. for 30 min. After cooling to 20° C. the reaction was poured onto ice-water (2 mL) and then acetic acid (0.14 mL) was added. The reaction was extracted twice with diethyl ether. The combined organic layers were washed with water and with brine, dried over sodium sulfate and evaporated under reduced pressure. The residue was purified by column chromatography on silica gel using heptene/ethyl acetate (9:1 v/v) as eluent to yield the title compound as a pale-yellow oil (79 mg, 29%).

$^1$H NMR (DMSO-D$_6$, 300 MHz): δ (ppm)=7.43 (d, 2H), 7.30 (d, 2H), 3.99 (q, 2H), 3.42 (s, 2H), 1.44 (s, 6H), 1.13 (t, 3H).

b) 6-[1-(4-Chloro-phenyl)-1-methyl-ethyl]-2-[3-methoxy-4-(4-methyl-imidazol-1-yl)-phenylamino]-pyrimidin-4-ol Sodium ethoxide (288 mg, 5.18 mmol) was dissolved in methanol (20 mL). At 20° C. under an atmosphere of nitrogen N-[3-methoxy-4-(4-methyl-imidazol-1-yl)-phenyl]guanidine dinitrate (835 mg, 2.25 mmol) and ethyl 4-(4-chloro-phenyl)-4-methyl-3-oxo-pentanoate (700 mg, 2.48 mmol) dissolved in methanol (2.5 mL) were added. The reaction was heated for 48 h to reflux. The solvent was evaporated under reduced pressure and the residue was taken up in water and acidified to pH 6 with 1 N aqueous hydrochloric acid solution. The mixture was extracted with dichloromethane and the organic layer was washed with brine, dried over sodium sulfate and evaporated under reduced pressure to afford a solid residue. The concentrated aqueous layer was extracted further with boiling tetrahydrofuran. The organic layer was concentrated and combined with the first residue. The crude material was purified by column chromatography on silica gel using dichloromethane/methanol (9:1 v/v) as eluent. The product fraction was stirred with diethyl ether for 15 min. The precipitate was collected by filtration to yield the title compound as an off-white solid (180 mg, 18%).

MS ISP (m/e): 450.1/452.0 (100/35) [(M+H)+].
1H NMR (DMSO-D6, 300 MHz): δ (ppm)=7.65-7.69 (m, 2H), 7.33 (dd, 4H), 7.20 (m, 1H), 6.93-7.03 (m, 2H), 5.84 (s, 1H), 3.58 (s, 3H), 2.13 (s, 3H), 1.58 (s, 6H).

c) {4-Chloro-6-[1-(4-chloro-phenyl)-1-methyl-ethyl]-pyrimidin-2-yl}-[3-methoxy-4-(4-methyl-imidazol-1-yl)-phenyl]-amine The title compound was prepared in analogous manner as described in example 8b) starting with 6-[1-(4-chloro-phenyl)-1-methyl-ethyl]-2-[3-methoxy-4-(4-methyl-imidazol-1-yl)-phenylamino]-pyrimidin-4-ol. The crude product was purified by column chromatography on silica gel using dichloromethane/methanol (19:1 v/v) as eluent to yield a pale-yellow foam (92 mg, 49%).
MS ISP (m/e): 368.0/470.1 (100/59) [(M+H)+].
1H NMR (DMSO-D6, 300 MHz): δ (ppm)=10.16 (s, 1H), 7.75 (s, 1H), 7.65 (s, 1H), 7.37 (dd, 4H), 7.26 (s, 2H), 7.03 (s, 1H), 6.86 (s, 1H), 3.69 (s, 3H), 2.14 (s, 3H), 1.69 (s, 6H).

Example 25

[3-Methoxy-4-(4-methyl-imidazol-1-yl)-phenyl]-(4-trifluoromethyl-pyrimidin-2-yl)-amine

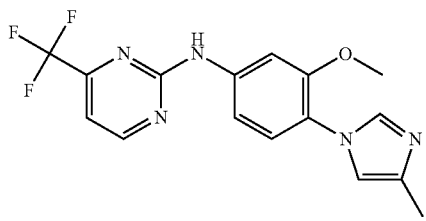 [SMILES: COc1cc(Nc2nccc(C(F)(F)F)n2)ccc1-n1cnc(C)c1]

The title compound was prepared in analogous manner as described in example 1e) from 3-methoxy-4-(4-methyl-imidazol-1-yl)-phenylamine and 2-chloro-4-trifluoromethyl-pyrimidine. The reaction was refluxed for 16 h. The title compound was obtained as a pale-yellow solid in 43% yield.
MS ISP (m/e): 350.3 (100) [(M+H)+].
1H NMR (DMSO-D6, 300 MHz): δ (ppm)=10.41 (s, 1H), 8.86 (d, 1H), 7.84 (s, 1H), 7.69 (s, 1H), 7.37 (d, 1H), 7.32 (d, 1H), 7.29 (d, 1H), 7.06 (s, 1H), 3.80 (s, 3H), 2.15 (s, 3H).

Example 26

2-[3-Methoxy-4-(4-methyl-imidazol-1-yl)-phenylamino]-4-trifluoromethyl-pyrimidine-5-carboxylic acid methyl ester

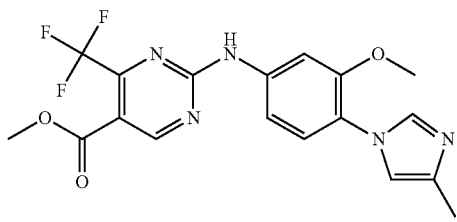

The title compound was prepared in analogous manner as described in example 1e) from 3-methoxy-4-(4-methyl-imidazol-1-yl)-phenylamine and methyl 2-chloro-4-trifluoromethyl-pyrimidine-5-carboxylate. The reaction was heated to reflux for 16 h. The title compound was obtained as a pale-yellow solid in 20% yield.

MS ISP (m/e): 408.2 (100) [(M+H)+].
1H NMR (DMSO-D6, 300 MHz): δ (ppm)=10.92 (s, 1H), 9.10 (d, 1H), 7.88 (br s, 1H), 7.72 (s, 1H), 7.35 (s, 2H), 7.08 (s, 1H), 3.87 (s, 3H), 3.81 (s, 3H), 2.15 (s, 3H).

Example 27

Methyl 2-[3-Methoxy-4-(4-methyl-imidazol-1-yl)-phenylamino]-6-methyl-pyrimidine-4-carboxylate

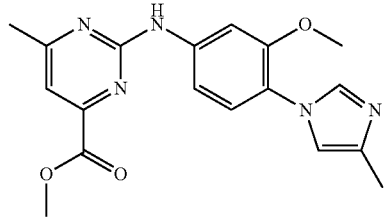

The title compound was prepared in analogous manner as described in example 1e) from 3-methoxy-4-(4-methyl-imidazol-1-yl)-phenylamine and methyl 2-chloro-6-methyl-pyrimidine-4-carboxylate. The reaction was heated to reflux for 16 h. The title compound was obtained as a pale-brown solid in 18% yield.
MS ISP (m/e): 354.2 (100) [(M+H)+].
1H NMR (DMSO-D6, 300 MHz): δ (ppm)=10.19 (s, 1H), 8.26 (br s, 1H), 7.67 (s, 1H), 7.34 (s, 1H), 7.30 (d, 1H), 7.24 (d, 1H), 7.04 (s, 1H), 3.90 (s, 3H), 3.84 (s, 3H), 2.14 (s, 3H).

Example 28

Ethyl 4-(4-chloro-phenyl)-2-[3-methoxy-4-(4-methyl-imidazol-1-yl)-phenylamino]-pyrimidine-5-carboxylate

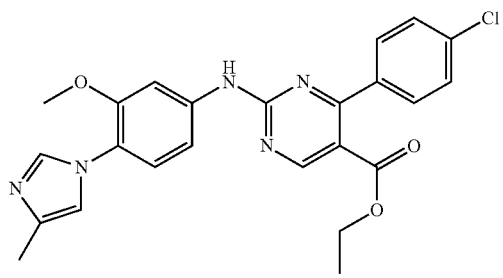 [SMILES: CCOC(=O)c1cnc(Nc2ccc(-n3cnc(C)c3)c(OC)c2)nc1-c1ccc(Cl)cc1]

a) Ethyl 3-dimethylamino-2-(4-chloromethyl-benzoyl)-acrylate

A mixture of ethyl 3-(4-chloro-phenyl)-3-oxo-propionate (227 mg, 1.0 mmol) and of tert.-butoxy-bis(dimethylamino)methane (271 mg, 1.4 mmol, 90%) was stirred at 110° C. for 2 h. The reaction was evaporated to dryness, treated twice with toluene and the solvent was evaporated under reduced pressure to give the crude title compound (292 mg, 99%) as a brown oil which was used directly in the next step without further purification.
MS ISP (m/e): 282.3 [(M+H)+].

b) Ethyl 4-(4-chloro-phenyl)-2-[3-methoxy-4-(4-methyl-imidazol-1-yl)-phenylamino]-pyrimidine-5-carboxylate A mixture of N-[3-methoxy-4-(4-methyl-imidazol-1-yl)-phenyl]-guanidine dinitrate (185 mg, 0.5 mmol), crude ethyl 3-dimethylamino-2-(4-chloro-benzoyl)-acrylate (292 mg, 1.0 mmol), and triethylamine (0.66 mL, 4.7 mmol) in ethanol (2 mL) was heated at reflux for 15 h. The mixture was cooled and diluted with ethyl acetate (50 mL). The solution was washed with sat. sodium carbonate solution (5 mL) and with brine (5 mL), dried over sodium sulfate and evaporated under reduced pressure. The residual material was purified by chromatography on silica gel using dichloromethane/0-20% methanol as eluent to give the title compound (157 mg, 68%) as a pale-yellow solid. Mp 216-218° C.

MS ISP (m/e): 464.1 [(M+H)+].

Example 29

[4-(4-Chloro-phenyl)-6-trifluoromethyl-pyrimidin-2-yl]-[3-methoxy-4-(4-methyl-imidazol-1-yl)-phenyl]-amine

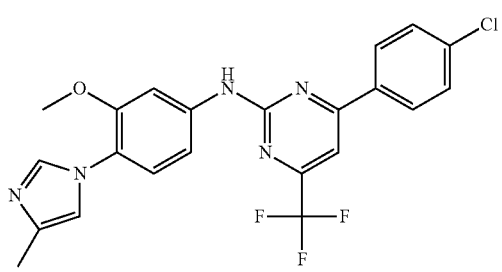 [SMILES: COc1cc(Nc2nc(-c3ccc(Cl)cc3)cc(C(F)(F)F)n2)ccc1-n1cnc(C)c1]

A mixture of 1-(4-chloro-phenyl)-4,4,4-trifluoro-butane-1,3-dione (50 mg, 0.2 mmol), N-[3-methoxy-4-(4-methyl-imidazol-1-yl)-phenyl]-guanidine dinitrate (74 mg, 0.2 mmol), and triethylamine (0.14 mL, 1.0 mmol) in ethanol (0.5 mL) was heated to 78° C. for 18 h. The mixture was cooled, diluted with ethyl acetate (30 mL), and then washed with sat. sodium carbonate solution (5 mL) and with brine (5 mL). The organic layer was dried over sodium sulfate and evaporated under reduced pressure. The residual material was purified by column chromatography on silica gel (5 g) using ethyl acetate/0-10% ethanol as eluent to give the title compound (10 mg, 11%) as light-yellow solid. Mp 202-204° C.

MS ISP (m/e): 460.0 [(M+H)+].

Example 30

[4-(4-Imidazol-1-yl-phenyl)-6-trifluoromethyl-pyrimidin-2-yl]-[3-methoxy-4-(4-methyl-imidazol-1-yl)-phenyl]-amine

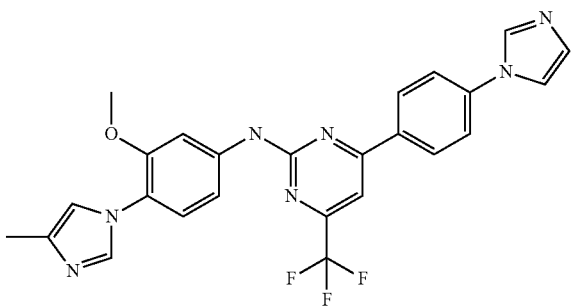 [SMILES: COc1cc(Nc2nc(-c3ccc(-n4ccnc4)cc3)cc(C(F)(F)F)n2)ccc1-n1cnc(C)c1]

The title compound was prepared from 4,4,4-trifluoro-1-(4-imidazol-1-yl-phenyl)-butane-1,3-dione (137 mg, 0.49 mmol) and N-[3-methoxy-4-(4-methyl-imidazol-1-yl)-phenyl]-guanidine dinitrate (180 mg, 0.49 mmol) using in analogous manner the procedure described in example 29). Obtained as a pale-yellow solid (19 mg, 8%). Mp 248-250° C.

MS ISP (m/e): 492.1 [(M+H)+].

Example 31

[3-Methoxy-4-(4-methyl-imidazol-1-yl)-phenyl]-[4-(4-pyrazol-1-yl-phenyl)-6-trifluoromethyl-pyrimidin-2-yl]-amine

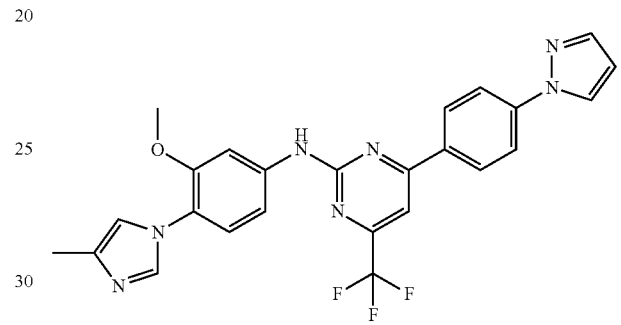

a) 4,4,4-Trifluoro-1-(4-pyrazol-1-yl-phenyl)-butane-1,3-dione

A 5.4 N solution of sodium methoxide in methanol (3.0 mL, 16.2 mmol) was added drop wise over 10 min to a solution of ethyl trifluoro-acetate (1.81 mL, 15.2 mmol) in 2-ethoxy-2-methyl-propane (20 mL) at 20° C. followed by the addition of a suspension of 1-(4-pyrazol-1-yl-phenyl)-ethanone (2.57 g, 13.8 mmol) in 2-ethoxy-2-methyl-propane (10 mL). The reaction mixture was stirred for 22 h at 20° C. and then poured onto ice-water (50 mL). The mixture was extracted with ethyl acetate and the organic layer was washed with brine, dried over sodium sulfate and evaporated under reduced pressure. The remaining solid was recrystallized from ethyl acetate/heptane to give the title compound (2.47 g, 63%) as off-white solid. Mp 96° C.

b) [3-Methoxy-4-(4-methyl-imidazol-1-yl)-phenyl]-[4-(4-pyrazol-1-yl-phenyl)-6-trifluoromethyl-pyrimidin-2-yl]-amine The title compound was prepared from 4,4,4-trifluoro-1-(4-pyrazol-1-yl-phenyl)-butane-1,3-dione (137 mg, 0.0.49 mmol) and N-[3-methoxy-4-(4-methyl-imidazol-1-yl)-phenyl]-guanidine dinitrate (180 mg, 0.49 mmol) using in analogous manner the procedure described in example 29). Obtained as a pale-yellow solid (25 mg, 10%). Mp 252-254° C.

MS ISP (m/e): 492.0 [(M+H)+].

Example 32

Ethyl 2-[3-methoxy-4-(4-methyl-imidazol-1-yl)-phenylamino]-4-(4-trifluoromethyl-phenyl)-pyrimidine-5-carboxylate

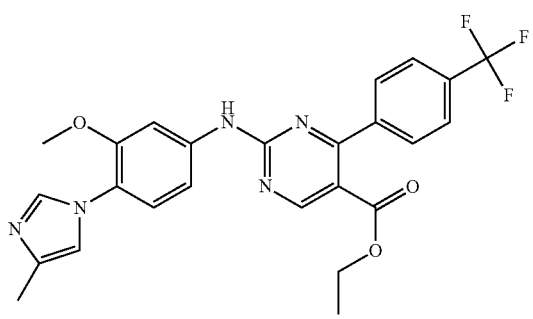 [SMILES: CCOC(=O)c1cnc(Nc2ccc(-n3cnc(C)c3)c(OC)c2)nc1-c1ccc(C(F)(F)F)cc1]

a) Ethyl 3-dimethylamino-2-(4-trifluoromethyl-benzoyl)-acrylate

Ethyl 3-oxo-3-(4-trifluoromethyl-phenyl)-propionate (130 mg, 0.5 mmol) was reacted with tert.-butoxy-bis-(dimethylamino)-methane using in analogous manner the procedure described in example 28a) to give crude title compound (151 mg) as a red oil which was used directly in the next step.
MS ISP (m/e): 316.3 [(M+H)$^+$].

b) Ethyl 2-[3-methoxy-4-(4-methyl-imidazol-1-yl)-phenylamino]-4-(4-trifluoromethyl-phenyl)-pyrimidine-5-carboxylate The title compound was prepared from ethyl 3-dimethylamino-2-(4-trifluoromethyl-benzoyl)-acrylate (151 mg, 0.48 mmol) and N-[3-methoxy-4-(4-methyl-imidazol-1-yl)-phenyl]-guanidine dinitrate (133 mg, 0.36 mmol) using in analogous manner the procedure described in example 28b). Obtained as a pale-yellow solid (14 mg, 6%).
MS ISP (m/e): 498.0 [(M+H)$^+$].

Example 33

Ethyl 4-(3-cyano-phenyl)-2-[3-methoxy-4-(4-methyl-imidazol-1-yl)-phenylamino]-pyrimidine-5-carboxylate

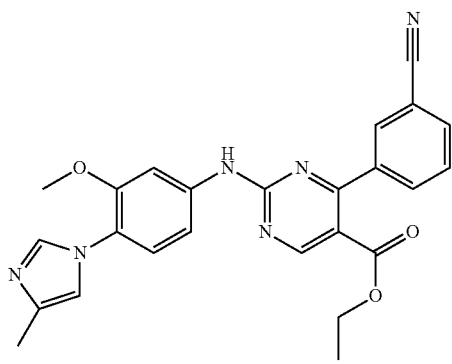 [SMILES: CCOC(=O)c1cnc(Nc2ccc(-n3cnc(C)c3)c(OC)c2)nc1-c1cccc(C#N)c1]

a) Ethyl 3-dimethylamino-2-(3-cyano-benzoyl)-acrylate

Ethyl 3-oxo-3-(3-cyano-phenyl)-propionate (109 mg, 0.5 mmol) was reacted with tert.-butoxy-bis-(dimethylamino)-methane using in analogous manner the procedure described in example 28a) to give crude title compound (85 mg) as a yellow oil which was used directly in the next step.

b) Ethyl 4-(3-cyano-phenyl)-2-[3-methoxy-4-(4-methyl-imidazol-1-yl)-phenylamino]-pyrimidine-5-carboxylate The title compound was prepared from ethyl 3-dimethylamino-2-(3-cyano-benzoyl)-acrylate (85 mg, 0.31 mmol) and N-[3-methoxy-4-(4-methyl-imidazol-1-yl)-phenyl]-guanidine dinitrate (116 mg, 0.31 mmol) using in analogous manner the procedure described in example 28b). Obtained as a pale-yellow solid (41 mg, 29%). Mp 195-197° C.
MS ISP (m/e): 455.1 [(M+H)$^+$].

Example 34

Ethyl {2-[3-methoxy-4-(4-methyl-imidazol-1-yl)-phenylamino]-5-phenyl-pyrimidin-4-yl}-phenyl-acetate

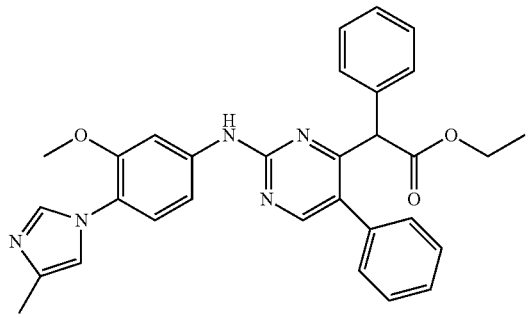 [SMILES: CCOC(=O)C(c1ccccc1)c1nc(Nc2ccc(-n3cnc(C)c3)c(OC)c2)ncc1-c1ccccc1]

a) Ethyl-5-dimethylamino-3-oxo-2,4-diphenyl-pent-4-enoate

Ethyl 3-oxo-2,4-diphenyl-butyrate (76 mg, 0.3 mmol) was reacted with tert.-butoxy-bis-(dimethylamino)-methane using in analogous manner the procedure described in example 28a) to give crude title compound (102 mg) as a red oil which was used directly in the next step.
MS ISP (m/e): 338.4 [(M+H)$^+$].

b) Ethyl {2-[3-methoxy-4-(4-methyl-imidazol-1-yl)-phenylamino]-5-phenyl-pyrimidin-4-yl}-phenyl-acetate The title compound was prepared from ethyl-5-dimethylamino-3-oxo-2,4-diphenyl-pent-4-enoate (102 mg, 0.3 mmol) and N-[3-methoxy-4-(4-methyl-imidazol-1-yl)-phenyl]-guanidine dinitrate (83 mg, 0.22 mmol) using in analogous manner the procedure described in example 28b). Obtained as a light-brown solid (5 mg, 3%). Mp 84-86° C.
MS ISP (m/e): 520.0 [(M+H)$^+$].

Example 35

Ethyl 4-(4-chloro-phenyl)-2-[3-fluoro-4-(4-methyl-imidazol-1-yl)-phenylamino]-pyrimidine-5-carboxylate

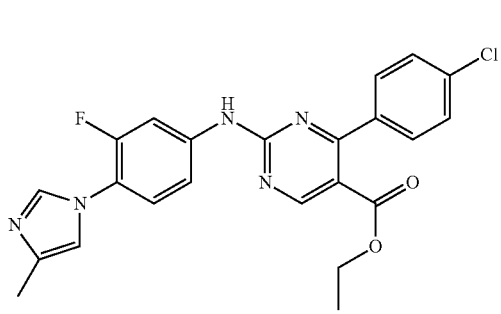 [SMILES: CCOC(=O)c1cnc(Nc2ccc(-n3cnc(C)c3)c(F)c2)nc1-c1ccc(Cl)cc1]

The title compound was prepared from crude ethyl 3-dimethylamino-2-(4-chloro-benzoyl)-acrylate (89 mg, 0.3 mmol) and N-[3-fluoro-4-(4-methyl-imidazol-1-yl)-phenyl]-guanidine dinitrate (80 mg, 0.22 mmol) using in analogous manner the procedure described in example 28b). Obtained as a pale-yellow solid (28 mg, 28%). Mp 232-234° C.

MS ISP (m/e): 452.1 [(M+H)$^+$].

Example 36

Ethyl 4-(4-bromo-2-chloro-phenyl)-2-[3-methoxy-4-(4-methyl-imidazol-1-yl)-phenylamino]-pyrimidine-5-carboxylate

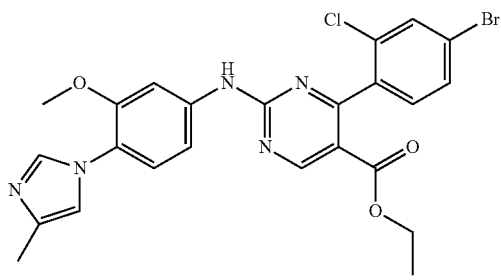 [SMILES: CCOC(=O)c1cnc(Nc2ccc(-n3cnc(C)c3)c(OC)c2)nc1-c1ccc(Br)cc1Cl]

The title compound was prepared from crude ethyl 2-(4-bromo-2-chloro-benzoyl)-3-dimethylamino-acrylate (50 mg, 0.14 mmol) and N-[3-methoxy-4-(4-methyl-imidazol-1-yl)-phenyl]-guanidine dinitrate (43 mg, 0.12 mmol) using in analogous manner the procedure described in example 28b). Obtained as a yellow solid (50 mg) in 28% yield.

MS ISP (m/e): 544.1/542.1/546.0/545.1/543.1 (100/85/39/30/26) [(M+H)$^+$].

$^1$H NMR (CDCl$_3$, 300 MHz): δ (ppm)=7.74 (br s, 1H), 7.65 (s, 1H), 7.61 (d, 1H), 7.51 (d, 2H), 7.24 (d, 1H), 7.19 (d, 1H), 7.08 (d, 1H), 6.88 (s, 1H), 4.19 (q, 2H), 3.82 (s, 3H), 2.29 (s, 3H), 1.14 (t, 3H).

Example 37

[4-(4-Chloro-phenyl)-pyrimidin-2-yl]-[3-methoxy-4-(4-methyl-imidazol-1-yl)-phenyl]-amine

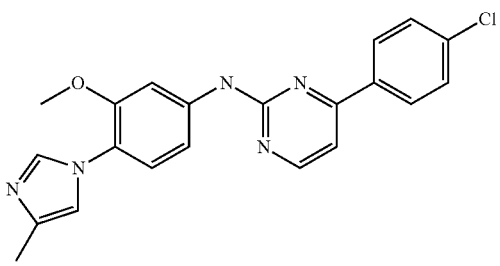 [SMILES: COc1cc(Nc2nccc(-c3ccc(Cl)cc3)n2)ccc1-n1cnc(C)c1]

a) 1-(4-Chloro-phenyl)-3-dimethylamino-propenone 1-(4-Chloro-phenyl)-ethanone (49 mg, 0.3 mmol) was reacted with tert.-butoxy-bis-(dimethylamino)-methane using in analogous manner the procedure described in example 28a) to give crude title compound (87 mg) as a yellow solid which was used directly in the next step.

MS ISP (m/e): 210.1 [(M+H)$^+$].

b) [4-(4-Chloro-phenyl)-pyrimidin-2-yl-3-methoxy-4-(4-methyl-imidazol-1-yl)-phenyl]-amine The title compound was prepared from crude 1-(4-chloro-phenyl)-3-dimethylamino-propenone (87 mg, 0.3 mmol) and N-[3-methoxy-4-(4-methyl-imidazol-1-yl)-phenyl]-guanidine dinitrate (83 mg, 0.22 mmol) using in analogous manner the procedure described in example 28b). Obtained as a pale-yellow solid (29 mg, 33%). Mp 202-204° C.

MS ISP (m/e): 392.1 [(M+H)$^+$].

Example 38

[3-Methoxy-4-(4-methyl-imidazol-1-yl)-phenyl]-[4-(4-trifluoromethyl-phenyl)-pyrimidin-2-yl]-amine

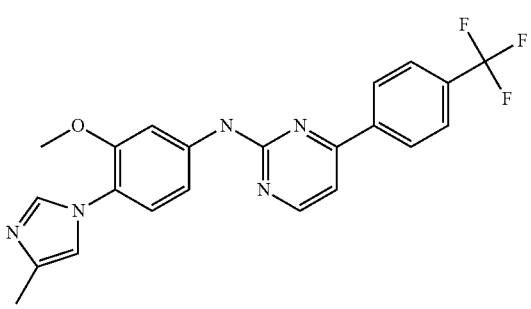 [SMILES: COc1cc(Nc2nccc(-c3ccc(C(F)(F)F)cc3)n2)ccc1-n1cnc(C)c1]

a) 1-(4-Trifluoromethyl-phenyl)-3-dimethylamino-propenone 4-(Trifluoromethyl)-acetophenone (58 mg, 0.3 mmol) was reacted with tert.-butoxy-bis-(dimethylamino)-methane using in analogous manner the procedure described in example 28a) to give crude title compound (81 mg) as a yellow solid which was used directly in the next step.

MS ISP (m/e): 244.4 [(M+H)+].

b) [3-Methoxy-4-(4-methyl-imidazol-1-yl)-phenyl]-[4-(4-trifluoromethyl-phenyl)-pyrimidin-2-yl]-amine The title compound was prepared from crude 1-(4-trifluoromethyl-phenyl)-3-dimethylamino-propenone (81 mg, 0.3 mmol) and N-[3-methoxy-4-(4-methyl-imidazol-1-yl)-phenyl]-guanidine dinitrate (83 mg, 0.22 mmol) using in analogous manner the procedure described in example 28b). Obtained as a pale-yellow solid (25 mg, 27%).

MS ISP (m/e): 426.1 [(M+H)+].

Example 39

[3-Methoxy-4-(4-methyl-imidazol-1-yl)-phenyl]-(4-pyridin-3-yl-pyrimidin-2-yl)-amine

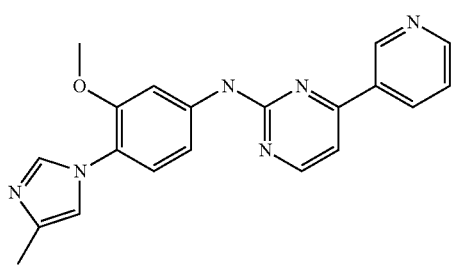 [SMILES: COc1cc(Nc2nccc(-c3cccnc3)n2)ccc1-n1cnc(C)c1]

a) 3-Dimethylamino-1-pyridin-3-yl-propenone

Pyridin-3-yl-ethanone (62 mg, 0.5 mmol) was reacted with tert.-butoxy-bis-(dimethylamino)-methane using in analogous manner the procedure described in example 28a) to give crude title compound (90 mg) as a yellow solid which was used directly in the next step.

MS ISP (m/e): 177.1 [(M+H)+].

b) [3-Methoxy-4-(4-methyl-imidazol-1-yl)-phenyl]-(4-pyridin-3-yl-pyrimidin-2-yl)-amine A mixture of N-[3-methoxy-4-(4-methyl-imidazol-1-yl)-phenyl]-guanidine dinitrate (185 mg, 0.37 mmol), crude 3-dimethylamino-1-pyridin-3-yl-propenone (90 mg, 0.5 mmol) and triethylamine (0.35 mL, 2.5 mmol) in ethanol (1 mL) was heated in a sealed tube in a microwave oven to 160° C. for 0.5 h. The mixture was cooled, diluted with ethyl acetate (30 mL), and then washed with sat. sodium carbonate solution (5 mL) and with brine (5 mL). The organic layer was dried over sodium sulfate and evaporated under reduced pressure. The residual material was purified by chromatography on silica gel using dichloromethane/0-20% methanol as eluent to give the title compound (62 mg, 47%) as a pale-yellow solid. Mp 204-206° C.

MS ISP (m/e): 359.4 [(M+H)+].

Example 40

[4-(4-Chloro-phenyl)-6-trifluoromethyl-pyrimidin-2-yl]-[3-fluoro-4-(4-methyl-imidazol-1-yl)-phenyl]-amine

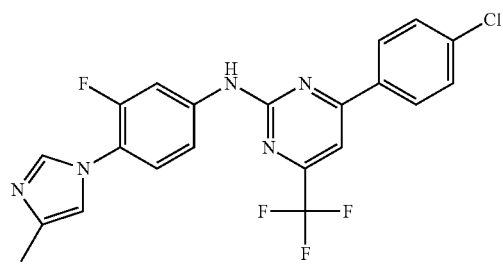

The title compound was prepared from 1-(4-chloro-phenyl)-4,4,4-trifluoro-butane-1,3-dione (125 mg, 0.5 mmol) and N-[3-fluoro-4-(4-methyl-imidazol-1-yl)-phenyl]-guanidine dinitrate (180 mg, 0.5 mmol) using in analogous manner the procedure described in example 29). Obtained as a pale-yellow solid (18 mg, 8%). Mp 248-250° C.

MS ISP (m/e): 447.6 [(M+H)+].

Example 41

Ethyl 2-[3-Fluoro-4-(4-methyl-imidazol-1-yl)-phenylamino]-4-(4-fluoromethyl-phenyl)-pyrimidine-5-carboxylate

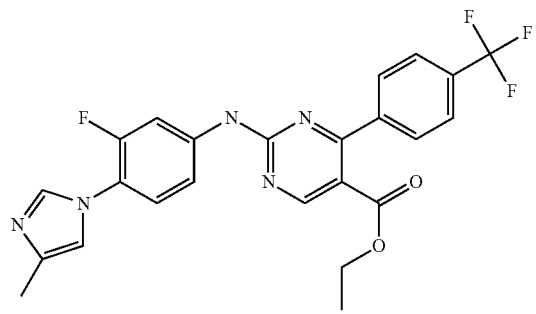 [SMILES: CCOC(=O)c1cnc(Nc2ccc(-n3cnc(C)c3)c(F)c2)nc1-c1ccc(C(F)(F)F)cc1]

The title compound was prepared from crude ethyl 3-dimethylamino-2-(4-trifluoromethyl-benzoyl)-acrylate (142 mg, 0.45 mmol) and N-[3-fluoro-4-(4-methyl-imidazol-1-yl)-phenyl]-guanidine dinitrate (121 mg, 0.34 mmol) using in analogous manner the procedure described in example 28b). Obtained as a pale-yellow solid (128 mg, 78%). Mp 219-221° C.

MS ISP (m/e): 486.4 [(M+H)+].

Example 42

[3-Fluoro-4-(4-methyl-imidazol-1-yl)-phenyl]-[4-(4-trifluoromethyl-phenyl)-pyrimidin-2-yl]-amine

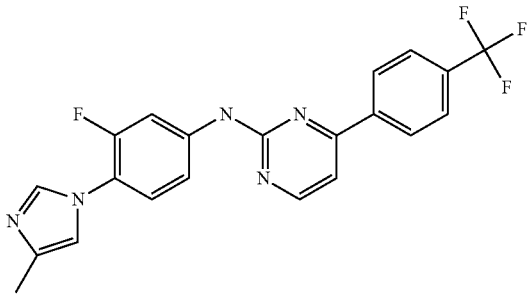 [SMILES: Cc1cn(-c2ccc(Nc3nccc(-c4ccc(C(F)(F)F)cc4)n3)cc2F)cn1]

The title compound was prepared from crude 1-(4-trifluoromethyl-phenyl)-3-dimethylamino-propenone (114 mg, 0.47 mmol) and N-[3-fluoro-4-(4-methyl-imidazol-1-yl)-phenyl]-guanidine dinitrate (126 mg, 0.35 mmol) using in analogous manner the procedure described in example 39b). Obtained as a pale-yellow solid (99 mg, 68%). Mp 196-197° C.

MS ISP (m/e): 414.1 [(M+H)$^+$].

Example 43

(4-Benzyl-6-methyl-pyrimidin-2-yl)-[3-methoxy-4-(4-methyl-imidazol-1-yl)-phenyl]-amine

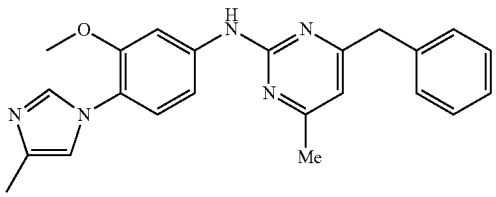 [SMILES: COc1cc(Nc2nc(C)cc(Cc3ccccc3)n2)ccc1-n1cnc(C)c1]

a) 4-Benzyl-2-chloro-6-methyl-pyrimidine

4-Benzyl-2,6-dichloro-pyrimidine (2.5 g, 10.5 mmol) was dissolved in tetrahydrofuran (40 mL) under an atmosphere of nitrogen and subsequently treated with dimethylzinc (2M in toluene, 5.76 mL) and tetrakis(triphenylphosphine)palladium(0) (245 mg). After stirring for 18 h at ambient temperature, ethyl acetate and water were added, the phases separated and the aqueous layer was extracted twice with ethyl acetate. The combined organic phases were dried over magnesium sulfate and evaporated under reduced pressure. Column chromatography on silica gel using heptane/ethyl acetate 9:1 v/v) as eluent afforded the title compound (1.89 g, 83%) as colorless oil.

NMR (CDCl$_3$, 300 MHz): δ (ppm)=7.35-7.24 (m, 5H), 6.84 (s, 1H), 4.06 (s, 2H), 2.44 (s, 3H).
MS ISP (m/e): 219.3 (100) [(M+H)$^+$].

b) (4-Benzyl-6-methyl-pyrimidin-2-yl)-[3-methoxy-4-(4-methyl-imidazol-1-yl)-phenyl]-amine Palladium(II)acetate (3.3 mg) and 2-(dicyclohexylphosphino)-biphenyl (11 mg) were stirred in dioxane (1.5 mL) while nitrogen was bubbled through the solution. In a second flask, a mixture of 4-benzyl-2-chloro-6-methyl-pyrimidine (80 mg), 3-methoxy-4-(4-methyl-imidazol-1-yl)-phenylamine (75 mg), and potassium carbonate (1.03 g) in dioxane (2 mL) was degassed with nitrogen, and subsequently, the above described catalyst solution was added. The reaction mixture was heated in a microwave oven at 200° C. for 30 min. The suspension was filtered, insoluble material was washed with ethyl acetate, and the combined solutions are concentrated under reduced pressure. The residual material was purified by chromatography on silica gel using dichloromethane/methanol 19:1 v/v) as eluent to afford the title compound (93 mg, 66%) as a colorless wax.

$^1$H NMR (CDCl$_3$, 300 MHz): δ (ppm)=7.84 (d, 1H), 7.62 (d, 1H), 7.33-7.26 (m, 5H), 7.13 (m, 2H), 7.00 (m, 1H), 6.86 (s, 1H), 6.50 (s, 1H), 3.97 (s, 2H), 3.78 (s, 3H), 2.37 (s, 3H), 2.30 (s, 3H);
MS ISP (m/e): 386.4 (100) [(M+H)$^+$].

Example 44

[3-Fluoro-4-(4-methyl-imidazol-1-yl)-phenyl]-{4-[1-methyl-1-(3,4,5-trifluoro-phenyl)-ethyl]-pyrimidin-2-yl}-amine

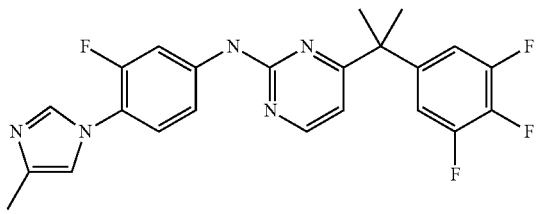 [SMILES: Cc1cn(-c2ccc(Nc3nccc(C(C)(C)c4cc(F)c(F)c(F)c4)n3)cc2F)cn1]

The title compound was prepared in analogous manner as described in example 5b) from N-[3-fluoro-4-(4-methyl-imidazol-1-yl)-phenyl]-guanidine dinitrate (81 mg, 0.30 mmol) and 1-dimethylamino-4-methyl-4-(3,4,5-trifluoro-phenyl)-pent-1-en-3-one (98 mg, 0.36 mmol) as a light yellow solid (74 mg) in 56% yield.

MS ISP (m/e): 442.2 (100) [(M+H)$^+$].
$^1$H NMR (DMSO-D$_6$, 300 MHz): δ (ppm)=10.0 (s, 1H), 8.48 (d, 1H), 7.78 (s, 1H), 7.86 (d, 1H), 7.78 (s, 1H), 7.44 (m, 2H), 7.27 (dd, 2H), 7.15 (s, 1H), 6.87 (d, 1H), 2.16 (s, 3H), 1.68 (s, 6H).

Example 45

[4-(4-Chloro-phenyl)-5-pyridin-4-yl-pyrimidin-2-yl]-[3-methoxy-4-(4-methyl-imidazol-1-yl)-phenyl]-amine

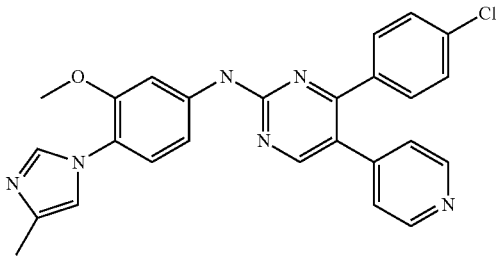 [SMILES: COc1cc(Nc2ncc(-c3ccncc3)c(-c3ccc(Cl)cc3)n2)ccc1-n1cnc(C)c1]

a) 1-(4-Chloro-phenyl)-3-dimethylamino-2-pyridin-4-yl-propenone 1-(4-Chloro-phenyl)-2-pyridin-4-yl-ethanone (116 mg, 0.5 mmol) was reacted with tert.-butoxy-bis-(dimethylamino)-methane using in analogous manner the procedure described in example 28a) to give crude title compound (165 mg) as a yellow oil which was used directly in the next step. MS ISP (m/e): 287.0 [(M+H)$^+$].

b) [4-(4-Chloro-phenyl)-5-pyridin-4-yl-pyrimidin-2-yl]-[3-methoxy-4-(4-methyl-imidazol-1-yl)-phenyl]-amine The title compound was prepared from crude 1-(4-chloro-phenyl)-3-dimethylamino-2-pyridin-4-yl-propenone (165 mg, ca 0.5 mmol) and N-[3-methoxy-4-(4-methyl-imidazol-1-yl)-phenyl]-guanidine dinitrate (138 mg, 0.37 mmol) using in analogous manner the procedure described in example 39b). Obtained as yellow solid (9 mg, 5%).

MS ISP (m/e): 469.4 [(M+H)$^+$].

$^1$H NMR (CDCl$_3$, 300 MHz): δ (ppm)=8.58 (d, 1H), 8.49 (s, 1H), 7.85 (s, 1H), 7.65 (s, 1H), 7.42 (s, 1H), 7.41 and 7.30 (2 d, 4H), 7.18 (d, 1H), 7.12 (s, 1H), 7.11 (d, 2H), 6.89 (s, 1H), 3.86 (s, 3H), 2.31 (s, 3H).

Example 46

(4-Ethoxy-6-methyl-pyrimidin-2-yl)-[3-methoxy-4-(4-methyl-imidazol-1-yl)-phenyl]-amine

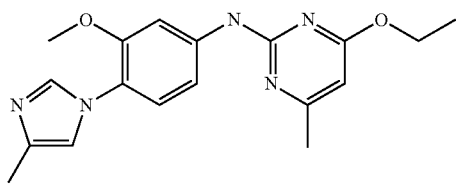 [SMILES: CCOc1cc(C)nc(Nc2ccc(-n3cnc(C)c3)c(OC)c2)n1]

A mixture of (4-chloro-6-methyl-pyrimidin-2-yl)-[3-methoxy-4-(4-methyl-imidazol-1-yl)-phenyl]-amine (165 mg, 0.5 mmol) and sodium ethoxide (54 mg, 0.75 mmol) in ethanol (3 ml) was heated for 30 min to 160° C. in a microwave oven. The reaction mixture was concentrated under reduced pressure and the residue was partitioned between ethyl acetate and water. The organic layer was washed with brine, dried over sodium sulfate and evaporated under reduced pressure. The residue was stirred with diethyl ether for 30 min to yield the title compound as a brown solid (139 mg, 82%).

MS ISP (m/e): 340.1 [(M+H)$^+$];

$^1$H NMR (CDCl$_3$, 300 MHz): δ (ppm)=7.77 (s, 1H), 7.62 (s, 1H), 7.15 (d, 1H), 7.06 (s, 1H), 7.01 (d, 2H), 6.87 (s, 1H), 6.10 (s, 1H), 4.41 (q, 2H), 3.86 (s, 3H), 2.35 (s, 3H), 2.30 (s, 3H), 1.40 (t, 3H).

Example 47

N-4-(2,2,3,3,4,4,4-Heptafluoro-butyl)-N2-[3-methoxy-4-(4-methyl-imidazol-1-yl)-phenyl]-6-methyl-pyrimidine-2,4-diamine

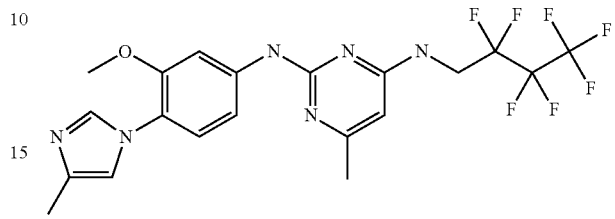

A mixture of (4-chloro-6-methyl-pyrimidin-2-yl)-[3-methoxy-4-(4-methyl-imidazol-1-yl)-phenyl]-amine (66 mg, 0.20 mmol) and 1H,1H-heptafluorobutylamine (119 mg, 0.60 mmol) in 1-methyl-2-pyrrolidone (2 mL) was heated for 1 h to 200° C. in a microwave oven. The reaction mixture was poured onto 1 N aqueous sodium hydroxide solution and the mixture was extracted with diethyl ether. The organic layer was washed with water and with brine, dried over sodium sulfate and evaporated under reduced pressure. The residue was purified by column chromatography on silica gel using dichloromethane/methanol (9:1 v/v) as eluent to yield the title compound as a brown solid (15 mg, 13%).

MS ISP (m/e): 493.1 [(M+H)$^+$].

$^1$H NMR (CDCl$_3$, 300 MHz): δ (ppm)=7.62 (s, 1H), 7.54 (s, 1H), 7.14 (s, 2H), 6.96 (s, 1H), 6.87 (s, 1H), 5.90 (s, 1H), 4.79 (br t, 1H), 4.32-4.16 (m, 2H), 3.84 (s, 3H), 2.30 (s, 6H).

Example 48

(4-Benzyl-pyrimidin-2-yl)-[3-fluoro-4-(4-methyl-imidazol-1-yl)-phenyl]-amine

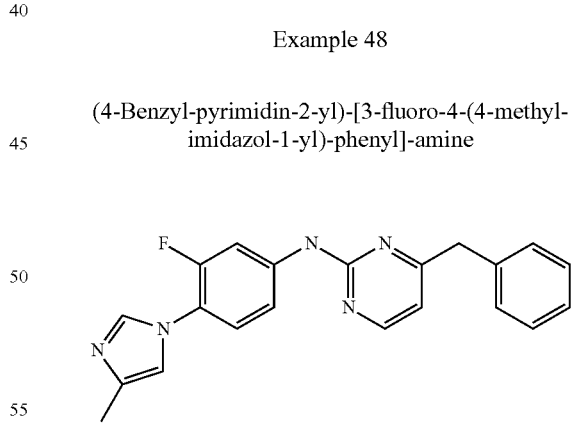

The title compound was prepared from 3-fluoro-4-(4-methyl-imidazol-1-yl)-phenylamine (94 mg, 0.49 mmol) and 4-benzyl-2-chloro-pyrimidine (100 mg, 0.49 mmol) in analogous manner to the procedure described in example 1e). Obtained as a pale-yellow solid (50 mg, 29%).

MS ISP (m/e): 360.3 [(M+H)$^+$].

$^1$H NMR (CDCl$_3$, 300 MHz): δ (ppm)=8.33 (d, 1H), 7.94 (dd, 1H), 7.66 (s, 1H), 7.28 (m, 8H), 6.92 (s, 1H), 6.65 (d, 1H), 4.025 (s, 2H), 2.30 (s, 3H).

Example 49

(4-Benzyl-6-methyl-pyrimidin-2-yl)-[3-fluoro-4-(2-methyl-imidazol-1-yl)-phenyl]-amine

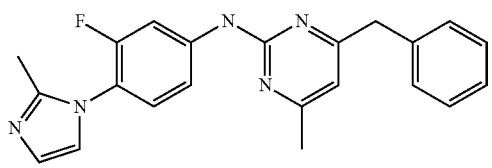 [SMILES: Cc1cc(Cc2ccccc2)nc(Nc2ccc(-n3ccnc3C)c(F)c2)n1]

The title compound was prepared from 3-fluoro-4-(2-methyl-imidazol-1-yl)-phenylamine (87 mg, 0.46 mmol) and 4-benzyl-2-chloro-6-methyl-pyrimidine (100 mg, 0.46 mmol) in analogous manner to the procedure described in example 1e). Obtained as a light yellow oil (140 mg, 82%).

MS ISP (m/e): 374.4 [(M+H)$^+$].

$^1$H NMR (CDCl$_3$, 300 MHz): δ (ppm)=8.00 (dd, 1H), 7.30 (m, 5H), 7.18 (m, 3H), 7.05 (s, 1H), 6.94 (s, 1H), 3.99 (s, 2H), 2.39 (s, 3H), 2.30 (s, 3H).

Example 50

(4-Benzyl-6-methyl-pyrimidin-2-yl)-(3-fluoro-4-imidazol-1-yl-phenyl)-amine

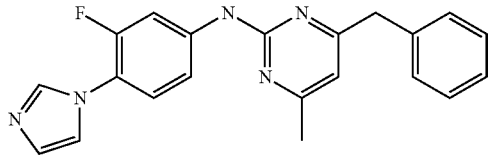 [SMILES: Cc1cc(Cc2ccccc2)nc(Nc2ccc(-n3ccnc3)c(F)c2)n1]

The title compound was prepared from 3-fluoro-4-imidazol-1-yl-phenylamine (81 mg, 0.46 mmol) and 4-benzyl-2-chloro-6-methyl-pyrimidine (100 mg, 0.46 mmol) in analogous manner to the procedure described in example 1e). Obtained as a light yellow wax (40 mg, 24%).

MS ISP (m/e): 360.4 [(M+H)$^+$].

$^1$H NMR (CDCl$_3$, 300 MHz): δ (ppm)=8.01 (dd, 1H), 7.76 (s, 1H), 7.27 (m, 10H), 6.54 (s, 1H), 3.99 (s, 2H), 2.39 (s, 3H).

Example 51

(4-Benzyl-6-methyl-pyrimidin-2-yl)-(3-fluoro-4-[1,2,4]triazol-1-yl-phenyl)-amine

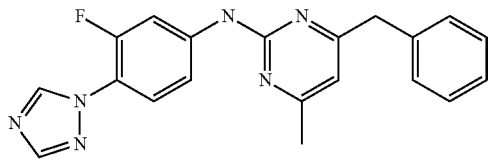 [SMILES: Cc1cc(Cc2ccccc2)nc(Nc2ccc(-n3cncn3)c(F)c2)n1]

The title compound was prepared from 3-fluoro-4-[1,2,4]triazol-1-yl-phenylamine (81.4 mg, 0.46 mmol) and 4-benzyl-2-chloro-6-methyl-pyrimidine (100 mg, 0.46 mmol) in analogous manner to the procedure described in example 1e). Obtained as a light yellow wax (98 mg, 60%).

MS ISP (m/e): 361.0 [(M+H)$^+$].

$^1$H NMR (CDCl$_3$, 300 MHz): δ (ppm)=8.57 (d, 1H), 8.11 (s, 1H), 8.11 (dd, 1H), 7.69 (dd, 1H), 7.31 (m, 5H), 7.20 (m, 2H), 6.55 (s, 1H), 3.99 (s, 2H), 2.39 (s, 3H).

Example 52

(4-Benzyl-6-methyl-pyrimidin-2-yl)-(3-methoxy-4-thiazol-5-yl-phenyl)-amine

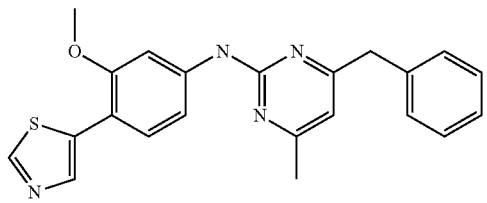 [SMILES: COc1cc(Nc2nc(C)cc(Cc3ccccc3)n2)ccc1-c1cncs1]

a) 5-(2-Methoxy-4-nitro-phenyl)-thiazole

In a microwave vial, a mixture of 2-bromo-5-nitroanisole (300 mg, 1.27 mmol), potassium acetate (188 mg, 1.90 mmol) and tetrakis(triphenylphosphine)palladium(0) (74 mg, 0.634 mmol) in 4 ml dimethyl acetamide was flushed with argon. Thiazole (459 uL, 6.34 mmol) was added, the tube was sealed, and the mixture was heated for 1 h to 160° C. in a microwave oven. The mixture was diluted with ethyl acetate and water, the layers were separated and the aqueous layer was extracted with ethyl acetate. The organic phase was dried over magnesium sulfate and evaporated under reduced pressure. The residual material was subjected to column chromatography on silica gel using heptane/ethyl acetate (7:3) as eluent to afford the title compound as yellow solid (177 mg, 59%). Mp 125-128° C.

MS ISP (m/e): 237.1 [(M+H)$^+$].

$^1$H NMR (CDCl$_3$, 400 MHz): δ (ppm)=8.91 (s, 1H), 8.44 (s, 1H), 7.93 (d, 1H), 7.87 (d, 1H), 7.81 (d, 1H), 4.08 (s, 3H),%). $^{13}$C NMR (CDCl$_3$, 100 MHz): δ (ppm)=155.5, 154.7, 148.0, 143.1, 132.0, 128.7, 126.9, 116.42, 106.7, 56.3.

b) 3-Methoxy-4-thiazol-5-yl-phenylamine

A suspension of 5-(2-methoxy-4-nitro-phenyl)-thiazole (160 mg, 0.68 mmol and stannous dichloride (655 mg, 3.39 mmol) in ethanol (10 mL) was stirred at reflux temperature for 75 min. The yellow solution was evaporated under reduced pressure and the residue was dissolved in ethyl acetate. This solution is washed successively with 2N aqueous sodium hydroxide and with brine, dried over magnesium sulfate and evaporated under reduced pressure. The residual material was triturated with dichloromethane, insoluble material was filtered off, and the filtrate was evaporated under reduced pressure to afford the title compound (128 mg, 92%) as orange oil.

MS ISP (m/e): 206.9 [(M+H)$^+$].

$^1$H NMR (CDCl$_3$, 300 MHz): δ (ppm)=8.68 (s, 1H), 8.11 (s, 1H), 7.40 (d, 1H), 6.31-6.36 (m, 2H), 3.89 (s, b, 5H).

c) (4-Benzyl-6-methyl-pyrimidin-2-yl)-(3-methoxy-4-thiazol-5-yl-phenyl)-amine The title compound was prepared from 3-methoxy-4-thiazol-5-yl-phenylamine (118 mg, 0.57 mmol) and 4-benzyl-2- chloro-6-methyl-pyrimidine (125 mg, 0.57 mmol) in analogous manner to the procedure described in example 1e). Obtained as a colorless wax (70 mg, 32%).

MS ISP (m/e): 389.4 [(M+H)⁺].

¹H NMR (CDCl₃, 300 MHz): δ (ppm)=8.72 (s, 1H), 8.20 (s, 1H), 7.86 (d, 1H), 7.53 (d, 1H), 7.29-7.34 (m, 5H), 7.16 (s, 1H), 7.01 (dd, 1H), 6.49 (s, 1H), 3.98 (s, 2H), 3.89 (s, 3H), 2.37 (s, 3H).

Example 53

(4-Benzyl-6-methyl-pyrimidin-2-yl)-(3-fluoro-4-[1,3,4]oxadiazol-2-yl-phenyl)-amine

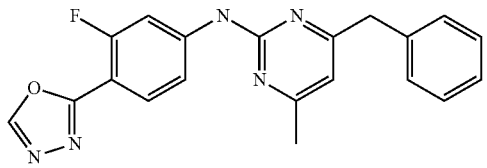 [SMILES: Cc1cc(Cc2ccccc2)nc(Nc2ccc(-c3nnco3)c(F)c2)n1]

a) Methyl 4-(4-benzyl-6-methyl-pyrimidin-2-ylamino)-2-fluoro-benzoate

The title compound was prepared from methyl 4-amino-2-fluoro-benzoate (480 mg, 2.84 mmol) and 4-benzyl-2-chloro-6-methyl-pyrimidine (620 mg, 2.84 mmol) in the same manner as described for example 1e). Obtained as white solid (840 mg, 84%). Mp 148-151° C.

MS ISP (m/e): 352.4 [(M+H)⁺].

¹H NMR (CDCl₃, 300 MHz): δ (ppm)=7.90 (dd, 1H), 7.85 (d, 1H), 7.31 (m, 6H), 7.12 (d, 1H), 6.55 (s, 1H), 3.99 (s, 2H), 3.91 (s, 3H), 2.39 (s, 3H).

b) 4-(4-Benzyl-6-methyl-pyrimidin-2-ylamino)-2-fluoro-benzoic acid hydrazide

A mixture of methyl 4-(4-benzyl-6-methyl-pyrimidin-2-ylamino)-2-fluoro-benzoate (420 mg, 1.20 mmol) and hydrazine monohydrate (1.4 mL, 28.8 mmol) in ethanol (9 mL) was stirred at 90° C. for 6 h. After cooling to 20° C., a white precipitate was formed which was isolated by filtration to afford the title compound (345 mg, 82%) as white solid. Mp 191-193° C.

MS ISP (m/e): 352.4 [(M+H)⁺].

¹H NMR (DMSO-d6, 300 MHz): δ (ppm)=10.0 (s, 1H), 9.25 (s broad, 1H), 7.88 (d, 1H), 7.48 (d, 2H) 7.33 (m, 3H), 7.25 (m, 2H), 6.75 (s, 1H), 4.47 (d, 2H), 3.97 (s, 2H), 2.35 (s, 3H).

c) (4-Benzyl-6-methyl-pyrimidin-2-yl)-(3-fluoro-[1,3,4]oxadiazol-2-yl-phenyl)-amine A suspension of 4-(4-benzyl-6-methyl-pyrimidin-2-ylamino)-2-fluoro-benzoic acid hydrazide (98 mg, 0.28 mmol) in trimethyl orthoformate (2.0 ml, 17.9 mmol) was heated in a microwave oven for 2 h to 200° C. followed by 5.5 h at 230° C. The mixture was evaporated under reduced pressure and the residue was purified by column chromatography on silica gel using dichloromethane/methanol (95:5 v/v) as eluent to afford the title compound (60 mg, 60%) as a light yellow solid. Mp 153-15.6° C.

MS ISP (m/e): 362.3 [(M+H)⁺].

¹H NMR (CDCl₃, 300 MHz): δ (ppm)=8.48 (s, 1H), 8.06 (dd, 1H), 7.96 (dd, 1H), 7.29 (m, 6H), 6.58 (s, 1H), 4.01 (s, 2H), 2.40 (s, 3H).

Example 54

Ethyl 4-(2-chloro-4-fluoro-phenyl)-2-[3-methoxy-4-(4-methyl-imidazol-1-yl)-phenylamino]-pyrimidine-5-carboxylate

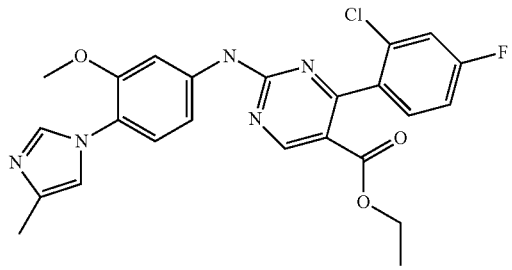 [SMILES: CCOC(=O)c1cnc(Nc2ccc(-n3cnc(C)c3)c(OC)c2)nc1-c1ccc(F)cc1Cl]

a) 1-(4-Chloro-phenyl)-3-dimethylamino-propenone

Ethyl 3-(2-chloro-4-fluoro-phenyl)-3-oxo-propionate (42 mg, 0.17 mmol) was reacted with tert.-butoxy-bis-(dimethylamino)-methane using in analogous manner the procedure described in example 28a) to give crude title compound (51 mg) as a white solid which was used directly in the next step. Mp 100-101° C.

b) Ethyl 4-(2-chloro-4-fluoro-phenyl)-2-[3-methoxy-4-(4-methyl-imidazol-1-yl)-phenylamino]-pyrimidine-5-carboxylate The title compound was prepared from crude ethyl 2-(2-chloro-4-fluoro-benzoyl)-3-dimethylamino-acrylate (50 mg, 0.17 mmol) and N-[3-methoxy-4-(4-methyl-imidazol-1-yl)-phenyl]-guanidine dinitrate (51 mg, 0.14 mmol) using in analogous manner the procedure described in example 28b). Obtained as a yellow solid (14 mg, 21%).

MS ISP (m/e): 482.2/484.2/483.1 (100/39/27)[(M+H)⁺].

¹H NMR (CDCl₃, 300 MHz): δ (ppm)=7.73 (s, 2H), 7.65 (s, 1H), 7.62 (d, 1H), 7.52 (d, 2H), 7.24 (s, 1H), 7.20 (d, 1H), 7.08 (d, 1H), 6.88 (s, 1H), 4.19 (q, 2H), 3.82 (s, 3H), 2.30 (s, 3H), 1.15 (s, 3H).

Example 55

4-(4-Chloro-phenyl)-2-[3-methoxy-4-(4-methyl-imidazol-1-yl)-phenylamino]-pyrimidine-5-carbonitrile

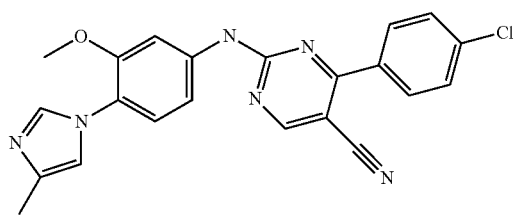 [SMILES: COc1cc(Nc2ncc(C#N)c(-c3ccc(Cl)cc3)n2)ccc1-n1cnc(C)c1]

The title compound was prepared from crude 2-(4-chlorobenzoyl)-3-dimethylamino-acrylonitrile (50 mg, 0.21 mmol) and N-[3-methoxy-4-(4-methyl-imidazol-1-yl)-phenyl]-guanidine dinitrate (66 mg, 0.18 mmol) using in analogous manner the procedure described in example 28b). Obtained as a pale-yellow solid (10 mg, 14%).

$^1$H NMR (CDCl$_3$, 300 MHz): δ (ppm)=8.75 (s, 2H), 8.05 (s, 1H), 7.97 (s, 1H), 7.70 (d, 2H), 7.40 (d, 2H), 7.24 (d, 1H), 7.15 (d, 1H), 6.90 (s, 1H), 3.86 (s, 3H), 2.31 (s, 3H);

Example 56

[3-Methoxy-4-(4-methyl-imidazol-1-yl)-phenyl]-[4-methyl-5-(3-methyl-[1,2,4]oxadiazol-5-yl)-pyrimidin-2-yl]-amine

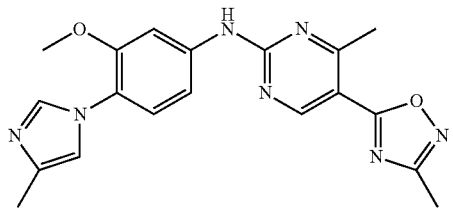 [SMILES: COc1cc(Nc2ncc(-c3nc(C)no3)c(C)n2)ccc1-n1cnc(C)c1]

a) 4-Dimethylamino-3-(3-methyl-[1,2,4]oxadiazol-5-yl)-but-3-en-2-one 1-(3-Methyl-[1,2,4]oxadiazol-5-yl)-propan-2-one (224 mg, 1.6 mmol) was reacted with tert.-butoxy-bis-(dimethylamino)-methane using in analogous manner the procedure described in example 28a) to give crude title compound (313 mg) as a yellow oil which was used directly in the next step.

MS ISP (m/e): 196.1 [(M+H)$^+$].

b) [3-Methoxy-4-(4-methyl-imidazol-1-yl)-phenyl]-[4-methyl-5-(3-methyl-[1,2,4]oxadiazol-5-yl)-pyrimidin-2-yl]-amine The title compound was prepared from crude 4-dimethylamino-3-(3-methyl-[1,2,4]oxadiazol-5-yl)-but-3-en-2-one (313 mg, 1.6 mmol) and N-[3-methoxy-4-(4-methyl-imidazol-1-yl)-phenyl]-guanidine dinitrate (297 mg, 0.8 mmol) using in analogous manner the procedure described in example 39b). Obtained as a pale-yellow solid (142 mg, 47%).

$^1$H NMR (CDCl$_3$, 300 MHz): δ (ppm)=9.08 (s, 1H), 7.77 (s, 1H), 7.66 (s, 1H), 7.48 (s, 1H), 7.22 (d, 1H), 7.13 (dd, 1H), 6.90 (s, 1H), 3.90 (s, 3H), 2.86 (s, 3H), 2.49 (s, 3H), 2.31 (s, 3H); MS ISP (m/e): 378.5 [(M+H)$^+$].

Example 57

[3-Methoxy-4-(4-methyl-imidazol-1-yl)-phenyl]-{4-[1-(5-methyl-[1,3,4]oxadiazol-2-yl)-cyclopropyl]-pyrimidin-2-yl}-amine

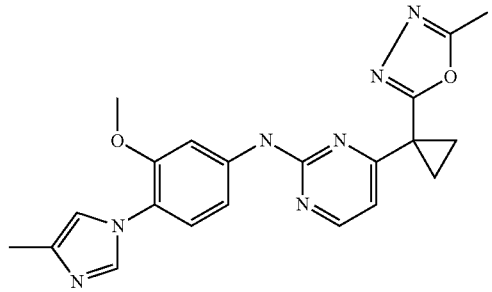

a) 1-[1-(5-Methyl-[1,3,4]oxadiazol-2-yl)-cyclopropyl]-ethanone

A mixture of 1-(5-methyl-[1,3,4]oxadiazol-2-yl)-propan-2-one (312 mg, 2.2 mmol), 1,2-dibromo-ethane (0.25 mL, 2.85 mmol), and potassium carbonate (770 mg, 5.6 mmol) in acetone (5 mL) was stirred at 60° C. for 16 h. Insoluble material was filtered off and the filtrate was diluted with ethyl acetate (30 mL). The solution was washed with water and brine, dried over sodium sulfate, and evaporated under reduced pressure. The residual material was purified by chromatography on silica gel using heptane/0-100% ethyl acetate as eluent to afford the title compound (75 mg, 20%) as pale-yellow oil.

MS ISP (m/e): 167.3 [(M+H)$^+$].

b) 3-Dimethylamino-1-[1-(5-methyl-[1,3,4]oxadiazol-2-yl)-cyclopropyl]-propenone 1-[1-(5-Methyl-[1,3,4]oxadiazol-2-yl)-cyclopropyl]-ethanone_(75 mg, 0.45 mmol) was reacted with tert.-butoxy-bis-(dimethylamino)-methane using in analogous manner the procedure described in example 28a) to give crude title compound (118 mg) as a yellow oil which was used directly in the next step.

MS ISP (m/e): 222.3 [(M+H)$^+$].

c) [3-Methoxy-4-(4-methyl-imidazol-1-yl)-phenyl]-{4-[1-(5-methyl-[1,3,4]oxadiazol-2-yl)-cyclopropyl]-pyrimidin-2-yl}-amine The title compound was prepared from crude 3-dimethylamino-1-[1-(5-methyl-[1,3,4]oxadiazol-2-yl)-cyclopropyl]-propenone (118 mg, ca. 0.45 mmol) and N-[3-methoxy-4-(4-methyl-imidazol-1-yl)-phenyl]-guanidine dinitrate (149 mg, 0.4 mmol) using in analogous manner the procedure described in example 39b). Obtained as a pale-yellow solid (31 mg, 17%).

$^1$H NMR (CDCl$_3$, 300 MHz): δ (ppm)=8.34 (d, 1H), 7.64 (s, 1H), 7.60 (d, 1H), 7.21 (s, 1H), 7.17 (d, 1H), 7.02 (dd, 1H), 6.95 (d, 1H), 6.88 (s, 1H), 3.87 (s, 3H), 2.56 (s, 3H), 2.30 (s, 3H), 1.94 (m, 2H), 1.76 (m, 2H); MS ISP (m/e): 404.5 [(M+H)$^+$].

Example 58

[3-Methoxy-4-(4-methyl-imidazol-1-yl)-phenyl]-{4-[1-methyl-1-(3-methyl-[1,2,4]oxadiazol-5-yl)-ethyl]-pyrimidin-2-yl}-amine

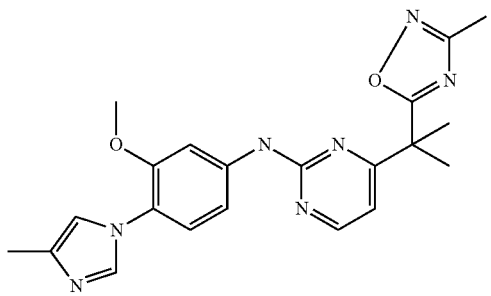

a) 3-Methyl-3-(3-methyl-[1,2,4]oxadiazol-5-yl)-butan-2-one

Methyl iodide (0.375 ml, 6 mmol) was added to a mixture of 1-(3-methyl-[1,2,4]oxadiazol-5-yl)-propan-2-one (0.84 g, 6 mmol) and potassium carbonate (4.15 g, 30 mmol) in acetonitrile (8 mL), and the mixture was stirred at 20° C. for 12 h. Insoluble material was filtered off and the filtrate was diluted with dichloromethane. The solution was washed with 1 N hydrochloric acid and with brine, dried over sodium sulfate, and evaporated under reduced pressure. The residual oil was subjected to column chromatography on silica gel. Heptane/ 0-20% ethyl acetate eluted successively the title compound 3-methyl-3-(3-methyl-[1,2,4]oxadiazol-5-yl)-butan-2-one (181 mg, 18%), obtained as colorless oil, Rf 0.4 (SiO$_2$, ethyl acetate/heptane 1:1), MS ISP (m/e): 169.1 [(M+H)$^+$]; 3-(3-Methyl-[1,2,4]oxadiazol-5-yl)-butan-2-one (296 mg, 3 2%), obtained as colorless oil, Rf 0.2 (SiO$_2$, ethyl acetate/heptane 1:1), MS ISP (m/e): 155.1 [(M+H)$^+$]; and 3-hydroxy-3-(3-methyl-[1,2,4]oxadiazol-5-yl)-butan-2-one (204 mg, 20%), obtained as colorless oil, Rf 0.1 (SiO$_2$, ethyl acetate/heptane 1:1), MS ISP (m/e): 171.1 [(M+H)$^+$].

b) 1-Dimethylamino-4-methyl-4-(3-methyl-[1,2,4]oxadiazol-5-yl)-pent-1-en-3-one 3-Methyl-3-(3-methyl-[1,2,4]oxadiazol-5-yl)-butan-2-one (101 mg, 0.6 mmol) was reacted with tert.-butoxy-bis-(dimethylamino)-methane using in analogous manner the procedure described in example 28a) to give crude title compound (140 mg) as a yellow oil which was used directly in the next step.

MS ISP (m/e): 224.4 [(M+H)$^+$].

c) [3-Methoxy-4-(4-methyl-imidazol-1-yl)-phenyl]-{4-[1-methyl-1-(3-methyl-[1,2,4]oxadiazol-5-yl)-ethyl]-pyrimidin-2-yl}-amine The title compound was prepared from crude 1-dimethylamino-4-methyl-4-(3-methyl-[1,2,4]oxadiazol-5-yl)-pent-1-en-3-one (140 mg, 0.6 mmol) and N-[3-methoxy-4-(4-methyl-imidazol-1-yl)-phenyl]-guanidine dinitrate (186 mg, 0.5 mmol) using in analogous manner the procedure described in example 39b). Obtained as a pale-yellow solid (31 mg, 13%).

$^1$H NMR (CDCl$_3$, 300 MHz): δ (ppm)=8.42 (d, 1H), 7.64 (s, 1H), 7.48 (br s, 1H), 7.15 (d, 1H), 7.02 (dd, 1H), 6.87 (s, 1H), 6.73 (d, 1H), 3.87 (s, 3H), 2.41 (s, 3H), 2.30 (s, 3H), 1.85 (s, 6H);

MS ISP (m/e): 406.1 [(M+H)$^+$].

As a by-product 2-{2-[3-methoxy-4-(4-methyl-imidazol-1-yl)-phenylamino]-pyrimidin-4-yl}-isobutyramide (20 mg, 9%) was obtained (see example 60)

Example 59

1-{2-[3-Methoxy-4-(4-methyl-imidazol-1-yl)-phenylamino]-pyrimidin-4-yl}-1-(3-methyl-[1,2,4]oxadiazol-5-yl)-ethanol

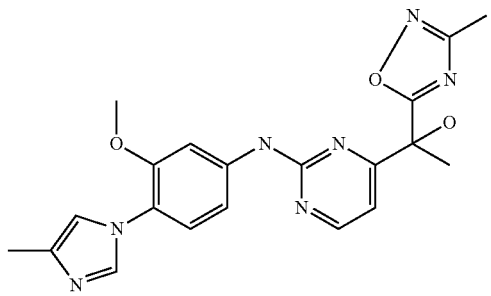

a) 1-Dimethylamino-4-hydroxy-4-(3-methyl-[1,2,4]oxadiazol-5-yl)-pent-1-en-3-one 3-Hydroxy-3-(3-methyl-[1,2,4]oxadiazol-5-yl)-butan-2-one (see example 58a) (102 mg, 0.6 mmol) was reacted with tert.-butoxy-bis-(dimethylamino)-methane using in analogous manner the procedure described in example 28a) to give crude title compound (138 mg) as a yellow oil which was used directly in the next step.

MS ISP (m/e): 226.3 [(M+H)$^+$].

b) 1-{2-[3-Methoxy-4-(4-methyl-imidazol-1-yl)-phenylamino]-pyrimidin-4-yl}-1-(3-methyl-[1,2,4]oxadiazol-5-yl)-ethanol The title compound was prepared from crude 1-dimethylamino-4-methyl-4-(3-methyl-[1,2,4]oxadiazol-5-yl)-pent-1-en-3-one (138 mg, 0.6 mmol) and N-[3-methoxy-4-(4-methyl-imidazol-1-yl)-phenyl]-guanidine dinitrate (185 mg, 0.5 mmol) using in analogous manner the procedure described in example 39b). Obtained as a pale-yellow solid (32 mg, 16%);

$^1$H NMR (CDCl$_3$, 300 MHz): δ (ppm)=8.51 (d, 1H), 7.59 (s, 1H), 7.66 (s, 1H), 7.46 (s, 1H), 7.19 (d, 1H), 7.05 (d, 1H), 7.03 (dd, 1H), 6.88 (s, 1H), 3.88 (s, 3H), 2.40 (s, 3H), 2.30 (s, 3H), 2.03 (s, 3H); MS ISP (m/e): 408.1 [(M+H)$^+$].

Example 60

2-{2-[3-Methoxy-4-(4-methyl-imidazol-1-yl)-phenylamino]-pyrimidin-4-yl}-isobutyramide

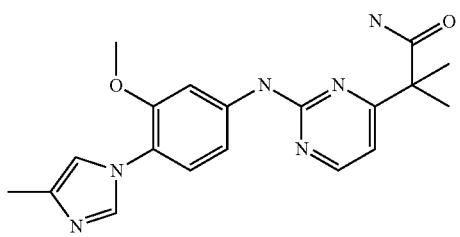 [SMILES: COc1cc(Nc2nccc(C(C)(C)C(N)=O)n2)ccc1-n1cnc(C)c1]

The title compound was isolated as a by-product in the preparation of example 58 (see example 58c)). Obtained as a pale-yellow solid.

MS ISP (m/e): 367.1 [(M+H)$^+$].

$^1$H NMR (CDCl$_3$, 300 MHz): δ (ppm)=8.45 (d, 1H), 7.70 (s, 1H), 7.64 (s, 1H), 7.40 (s, 1H), 7.19 (d, 1H), 7.08 (dd, 1H), 6.89 (d, 1H), 6.88 (s, 1H), 6.16 and 5.44 (2 br s, 2H), 3.88 (s, 3H), 2.30 (s, 3H), 1.65 (s, 6H).

Example 61

[4-(4-Chloro-phenyl)-5-(4-methoxy-benzyl)-pyrimidin-2-yl]-[3-methoxy-4-(4-methyl-imidazol-1-yl)-phenyl]-amine

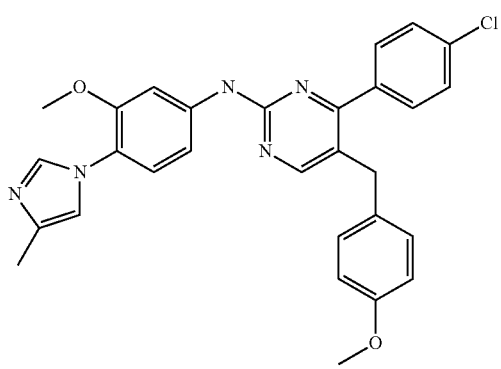 [SMILES: COc1ccc(Cc2cnc(Nc3ccc(-n4cnc(C)c4)c(OC)c3)nc2-c2ccc(Cl)cc2)cc1]

a) 1-(4-Chloro-phenyl)-3-dimethylamino-2-(4-methoxy-benzyl)-propenone 1-(4-Chloro-phenyl)-3-(4-methoxy-phenyl)-propan-1-one (137 mg, 0.5 mmol) was reacted with tert.-butoxy-bis-(dimethylamino)-methane using in analogous manner the procedure described in example 28a) to give crude title compound (172 mg) as a yellow solid which was used directly in the next step.

MS ISP (m/e): 330.4 [(M+H)$^+$].

b) 4-(4-Chloro-phenyl)-5-(4-methoxy-benzyl)-pyrimidin-2-yl]-[3-methoxy-4-(4-methyl-imidazol-1-yl)-phenyl]-amine The title compound was prepared from crude 1-(4-chloro-phenyl)-3-dimethylamino-2-(4-methoxy-benzyl)-propenone (172 mg, 0.5 mmol) and N-[3-methoxy-4-(4-methyl-imidazol-1-yl)-phenyl]-guanidine dinitrate (137 mg, 0.37 mmol) using in analogous manner the procedure described in example 39b). Obtained as an off-white solid (38 mg, 20%).

MS ISP (m/e): 512.3 [(M+H)$^+$].

$^1$H NMR (CDCl$_3$, 300 MHz): δ (ppm)=8.32 (s, 1H), 7.84 (s, 1H), 7.62 (s, 1H), 7.49 and 7.41 (2 d, 4H), 7.16 (d, 1H), 7.02 (dd, 1H), 6.95 (d, 2H), 6.87 (s, 1H), 6.82 (d, 2H), 3.91 (s, 2H), 3.81 (s, 3H), 3.79 (s, 3H), 2.29 (s, 3H).

Example 62

(6-Benzyl-2-chloro-pyrimidin-4-yl)-[3-methoxy-4-(4-methyl-imidazol-1-yl)-phenyl]-amine

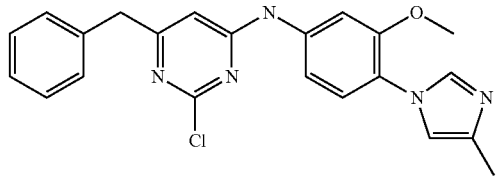 [SMILES: COc1cc(Nc2cc(Cc3ccccc3)nc(Cl)n2)ccc1-n1cnc(C)c1]

Palladium acetate (2.7 mg, 0.012 mmol) and 2-(dicyclohexylphosphino)-biphenyl (8.5 mg, 0.024 mmol) were dissolved under an atmosphere of nitrogen under stirring in dioxane (1 mL). After 10 min stirring this solution was added to a suspension of 3-methoxy-4-(4-methyl-imidazol-1-yl)-phenylamine (61 mg, 0.3 mmol), 4-benzyl-2,6-dichloropyrimidine (71.7 mg, 0.3 mmol) and potassium carbonate (829 mg, 6 mmol) in dioxane (1.7 mL). The reaction was heated to reflux for 16 h. After cooling to 20° C. the reaction was poured onto water and the mixture was extracted with ethyl acetate. The organic layer was washed with brine, dried over sodium sulfate, and the solvent was evaporated under reduced pressure. The residue was purified by column chromatography on silica gel using dichloromethane/methanol (19:1 v/v) as eluent to yield the title compound (9.0 mg, 24%) as a yellow solid.

MS ISP (m/e): 406.3/408.3 (100/50) [(M+H)$^+$].

$^1$H NMR (CDCl$_3$, 300 MHz): δ (ppm)=7.63 (s, 1H), 7.20-7.33 (m, 5H), 7.18 (d, 1H), 7.00 (s, 1H), 6.87 (s, 1H), 6.82 (d, 1H), 6.30 (s, 1H), 3.99 (s, 2H), 3.77 (s, 3H), 2.29 (s, 3H).

Example 63

[6-(4-Chloro-phenoxy)-pyrimidin-4-yl]-[3-methoxy-4-(4-methyl-imidazol-1-yl)-phenyl]-amine

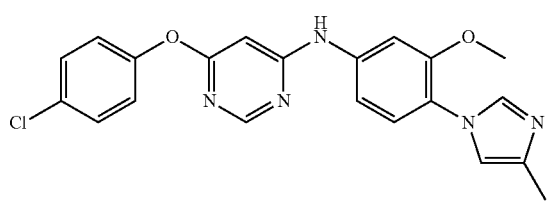 [SMILES: COc1cc(Nc2cc(Oc3ccc(Cl)cc3)ncn2)ccc1-n1cnc(C)c1]

a) 4-Chloro-6-(4-chloro-phenoxy)-pyrimidine 4,6-Dichloropyrimidine (149 mg, 1 mmol), 4-chlorophenol (135 mg, 1.05 mmol), potassium carbonate (166 mg, 1.2 mmol) and sodium iodide (7.5 mg, 0.05 mmol) were stirred in acetonitrile (3 mL) at 20° C. under an atmosphere of nitrogen for 16 h. The reaction was poured onto 1 N aqueous sodium hydroxide solution and the mixture was extracted with diethyl ether. The organic layer was washed with brine, dried over sodium sulfate, and the solvent was evaporated under reduced pressure. The title compound (224 mg, 93%) was obtained as a pale-yellow solid.

MS EI (m/e): 240.1/242.0 (100/55) [M+].

$^1$H NMR (DMSO-D$_6$, 300 MHz): δ (ppm)=8.06 (s, 1H), 7.53 (d, 2H), 7.45 (s, 1H), 7.31 (d, 2H).

b) [6-(4-Chloro-phenoxy)-pyrimidin-4-yl]-[3-methoxy-4-(4-methyl-imidazol-1-yl)-phenyl]-amine The title compound was prepared from 4-chloro-6-(4-chloro-phenoxy)-pyrimidine and 3-methoxy-4-(4-methyl-imidazol-1-yl)-phenylamine in analogous manner as described in example 62 by heating the reaction mixture in a microwave oven at 200° C. for 2.5 h. Obtained as a yellow solid in 18% yield.

MS ISP (m/e): 408.3/410.2 (100/34) [(M+H)+].

$^1$H NMR (DMSO-D$_6$, 300 MHz): δ (ppm)=9.79 (s, 1H), 8.40 (s, 1H), 7.68 (s, 1H), 7.51-7.54 (m, 3H), 7.25-7.32 (m, 3H), 7.05 (s, 1H), 6.19 (s, 1H), 3.80 (s, 3H), 2.14 (s, 3H).

Example 64

{6-[1-(4-Chloro-phenyl)-cyclobutyl]-2-methyl-pyrimidin-4-yl}-[3-methoxy-4-(4-methyl-imidazol-1-yl)-phenyl]-amine

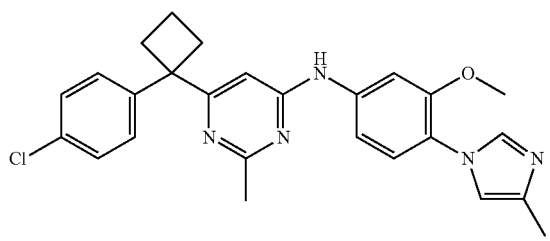 [SMILES: COc1cc(Nc2cc(C3(c4ccc(Cl)cc4)CCC3)nc(C)n2)ccc1-n1cnc(C)c1]

a) Methyl 3-[1-(4-chlorophenyl)cyclobutyl]-3-oxopropionate

Sodium hydride (1.86 g of a 60% dispersion in mineral oil, 46.5 mmol) was added to a solution of 1-[1-(4-chlorophenyl)cyclobutyl]ethanone (4.18 g, 20.0 mmol) and of dimethyl carbonate (8.4 mL, 99.6 mmol) in of dioxane (20 mL). After the reaction mixture had been refluxed for 4 h, it was chilled in an ice-water bath and treated drop wise with 1 M aqueous sodium hydrogen sulfate solution (50 mL). The mixture containing now a thick precipitate was then partitioned between diethyl ether and water. The organic phase was washed with sat. sodium hydrogen carbonate solution and with brine, dried over magnesium sulfate, and evaporated under reduced pressure. The residual material was purified by chromatography on silica gel using heptane/0-10% ethyl acetate as eluent to afford the title compound (4.45 g, 79%) as pale-yellow oil.

b) 6-[1-(4-Chlorophenyl)cyclobutyl]-2-methylpyrimidin-4-ol

To a solution of acetamidine hydrochloride (0.617 g, 6.53 mmol) in methanol (10 mL) was added potassium tert.-butoxide (0.80 g, 6.54 mmol) followed by methyl 3-[1-(4-chlorophenyl)cyclobutyl]-3-oxopropionate (1.34 g, 5.02 mmol). The mixture was stirred at 20° C. for 16 h, then refluxed for 2 h. The reaction mixture was cooled, diluted with water, made alkaline by the addition of 10 mL of 10% aqueous sodium hydroxide solution, and then washed with diethyl ether. The aqueous phase was acidified with concentrated hydrochloric acid, and then extracted with diethyl ether. This ether extract was washed with brine, dried over magnesium sulfate, and concentrated under reduced pressure to give the title compound (1.04 g, 75%) as a solid foam. Mp 130-140° C.

MS ISP (m/e): 275 [(M+H)+].

c) 4-Chloro-6-[1-(4-chlorophenyl)cyclobutyl]-2-methylpyrimidine

To 6-[1-(4-chlorophenyl)cyclobutyl]-2-methylpyrimidin-4-ol (1.00 g, 3.65 mmol) was added phosphorous oxychloride (10 mL) and the mixture was refluxed for 1.5 h. After cooling to 20° C., the reaction mixture was poured into ice/water (55 mL). After the addition of dichloromethane, the mixture was neutralized with 32% aqueous sodium hydroxide solution. The layers were separated and the organic layer was washed with 0.1 N sodium hydroxide solution and with water, dried over magnesium sulfate, and evaporated under reduced pressure. The residual material was purified by chromatography on silica gel using dichloromethane/methanol (95:5 v/v) as eluent to afford the title compound (0.91 g, 85%) as an off-white solid. Mp 96-98° C.

MS ISP (m/e): 293 [(M+H)+].

d) {6-[1-(4-Chloro-phenyl)-cyclobutyl]-2-methyl-pyrimidin-4-yl}-[3-methoxy-4-(4-methyl-imidazol-1-yl)-phenyl]-amine The title compound was prepared in analogous manner as described in example 62 from 4-chloro-6-[1-(4-chloro-phenyl)-cyclobutyl]-2-methyl-pyrimidine and 3-methoxy-4-(4-methyl-imidazol-1-yl)-phenylamine Obtained as a pale-yellow solid in 81% yield after column chromatography of the crude product on silica gel using dichloromethane/methanol (19:1 v/v) as eluent.

MS ISP (m/e): 460.3/462.2 (100/44) [(M+H)+].

$^1$H NMR (DMSO-D$_6$, 300 MHz): δ (ppm)=9.57 (s, 1H), 7.75 (s, 1H), 7.66 (s, 1H), 7.40 (d, 2H), 7.35 (d, 2H), 7.24 (s, 2H), 6.36 (s, 1H), 3.79 (s, 3H), 2.78-2.99 (m, 2H), 2.50-2.62 (m, 2H), 2.14 (s, 3H), 1.79-1.99 (m, 2H).

Example 65

(2-Benzyl-6-chloro-pyrimidin-4-yl)-[3-methoxy-4-(4-methyl-imidazol-1-yl)-phenyl]-amine

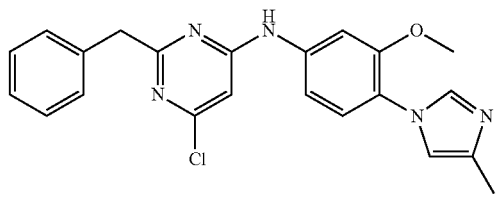 [SMILES: COc1cc(Nc2cc(Cl)nc(Cc3ccccc3)n2)ccc1-n1cnc(C)c1]

The title compound was prepared in analogous manner as described in example 62 from 2-benzyl-4,6-dichloro-pyrimidine and 3-methoxy-4-(4-methyl-imidazol-1-yl)-phenylamine. Obtained as yellow solid in 48% yield after column chromatography of the crude product on silica gel using dichloromethane/methanol (98:2 and then 95:5 v/v) as eluent.

MS ISP (m/e): 406.3/408.4 (100/26) [(M+H)⁺].

¹H NMR (DMSO-D₆, 300 MHz): δ (ppm)=10.01 (s, 1H), 7.68 (s, 1H), 7.64 (s, 1H), 7.32 (d, 4H), 7.18-7.28 (m, 2H), 7.17 (d, 1H), 7.05 (s, 1H), 6.69 (s, 1H), 4.06 (s, 2H), 3.72 (s, 3H), 2.14 (s, 3H).

Example 66

Methyl 2-Chloro-6-[3-methoxy-4-(4-methyl-imidazol-1-yl)-phenylamino]-isonicotinate

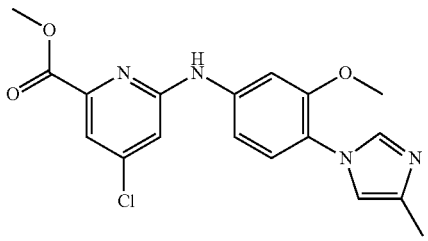 [SMILES: COC(=O)c1cc(Cl)cc(Nc2ccc(-n3cnc(C)c3)c(OC)c2)n1]

The title compound was prepared in analogous manner as described in example 1e) from methyl-2,6-dichloroisonicotinate (64 mg, 0.3 mmol) and 3-methoxy-4-(4-methyl-imidazol-1-yl)-phenylamine (61 mg, 0.3 mmol). The reaction mixture was heated for 16 h to reflux. Obtained as a yellow solid (40 mg, 36%) after column chromatography of the crude product on silica gel using dichloromethane/methanol (19:1 v/v) as eluent.

MS ISP (m/e): 373.2/375.2 (100/42) [(M+H)⁺].

¹H NMR (DMSO-D₆, 300 MHz): δ (ppm)=9.94 (s, 1H), 7.69 (s, 1H), 7.64 (s, 1H), 7.36 (s, 1H), 7.31 (d, 1H), 7.28 (d, 1H), 7.16 (s, 1H), 7.06 (s, 1H), 3.90 (s, 3H), 3.82 (s, 3H), 2.15 (s, 3H).

Example 67

[3-Methoxy-4-(4-methyl-imidazol-1-yl)-phenyl]-(6-methyl-4-trifluoromethyl-pyridin-2-yl)-amine

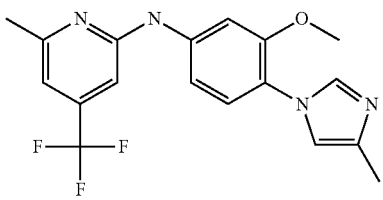

The title compound was prepared in analogous manner as described in example 1e) from 2-chlor-6-methyl-4-(trifluormethyl)pyridine (59 mg, 0.3 mmol) and 3-methoxy-4-(4-methyl-imidazol-1-yl)-phenylamine (61 mg, 0.3 mmol). The reaction was heated for 16 h to reflux. Obtained as a pale-yellow solid (75 mg 69%) after column chromatography of the crude reaction product on silica gel using dichloromethane/methanol (19:1 v/v) as eluent.

MS ISP (m/e): 363.3 (100) [(M+H)⁺].

¹H NMR (DMSO-D₆, 300 MHz): δ (ppm)=9.63 (s, 1H), 7.88 (s, 1H), 7.66 (s, 1H), 7.25 (s, 2H), 7.04 (s, 1H), 6.96 (s, 1H), 6.93 (s, 1H), 3.82 (s, 3H), 2.14 (s, 3H).

Example 68

{2-Chloro-6-[3-methoxy-4-(4-methyl-imidazol-1-yl)-phenylamino]-pyridin-4-yl}-methanol

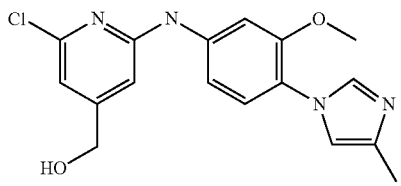 [SMILES: COc1cc(Nc2cc(CO)cc(Cl)n2)ccc1-n1cnc(C)c1]

The title compound was prepared in analogous manner as described in example 1e) from 2,6-dichloropyridin-4-methanol (53 mg, 0.3 mmol) and 3-methoxy-4-(4-methyl-imidazol-1-yl)-phenylamine (61 mg, 0.3 mmol). The reaction was heated for 16 h to reflux. Obtained as a pale-yellow solid (25 mg, 24%) after column chromatography on silica gel using dichloromethane/methanol (9:1 v/v) as eluent.

MS ISP (m/e): 345.2/347.1 (100/39) [(M+H)⁺].

¹H NMR (DMSO-D₆, 300 MHz): δ (ppm)=9.57 (s, 1H), 7.66 (s, 1H), 7.64 (s, 1H), 7.25 (s, 2H), 7.03 (s, 1H), 6.83 (s, 1H), 6.76 (s, 1H), 5.48 (t, 1H), 4.47 (d, 2H), 3.80 (s, 3H), 2.14 (s, 3H).

Example 69

[6-(4-Chloro-phenoxy)-pyridin-2-yl]-[3-methoxy-4-(4-methyl-imidazol-1-yl)-phenyl]-amine

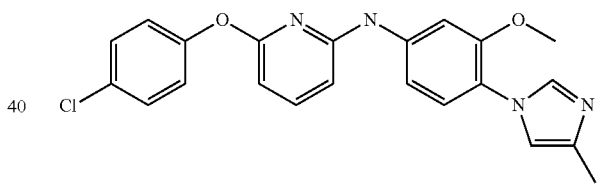

a) 2-Chloro-6-(4-chloro-phenoxy)-pyrimidine

The title compound was prepared in analogous manner as described in example 10a) from 4,6-dichloropyrimidin (149 mg, 1.0 mmol) and 4-chlorophenol (129 mg, 1.05 mmol). Obtained as a pale-yellow solid (224 mg, 93%).

MS EI (m/e): 240.1/242.0 (100/55) [M⁺].

¹H NMR (DMSO-D₆, 300 MHz): δ (ppm)=8.66 (s, 1H), 7.53 (d, 2H), 7.45 (s, 1H), 7.31 (d, 2H).

b) [6-(4-Chloro-phenoxy)-pyridin-2-yl]-[3-methoxy-4-(4-methyl-imidazol-1-yl)-phenyl]-amine The title compound was prepared in analogous manner as described in example 1e) from 3-methoxy-4-(4-methyl-imidazol-1-yl)-phenylamine (61 mg, 0.3 mmol) and 4-chloro-6-(4-chloro-phenoxy)-pyrimidine (90 mg, 0.3 mmol). The reaction was heated in a microwave oven to 200° C. for 1 h. Obtained as a yellow solid (48 mg, 39%) after chromatography of the crude reaction product on silica gel using dichloromethane/methanol (9:1 v/v) as eluent.

MS ISP (m/e): 407.2/409.3 (100/31) [(M+H)⁺].

¹H NMR (DMSO-D₆, 300 MHz): δ (ppm)=9.37 (s, 1H), 7.67 (m, 2H), 7.58 (s, 1H), 7.48 (d, 2H), 7.33 (s, 1H), 7.17 (d, 2H), 6.97 (s, 2H), 6.61 (d, 1H), 6.44 (d, 1H), 3.42 (s, 3H), 2.13 (s, 3H).

Example 70

N-[3-Methoxy-4-(4-methyl-imidazol-1-yl)-phenyl]-N'-phenyl-pyridine-2,6-diamine

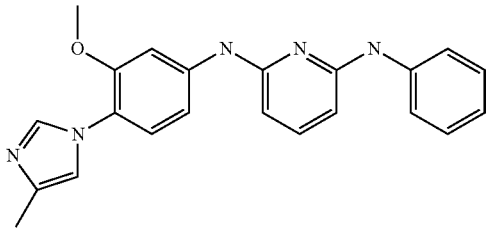 [SMILES: COc1cc(Nc2cccc(Nc3ccccc3)n2)ccc1-n1cnc(C)c1]

a) (6-Chloro-pyridin-2-yl)-phenyl-amine

A mixture of palladium(II)acetate (303 mg; 1.35 mmol) and rac-2,2'-bis(diphenylphosphino)-1,1'-binaphthyl (842 mg; 1.35 mmol) in toluene (10 mL) was stirred under argon for 10 min at 20° C., and then added to a mixture of 2,6-dichloroaniline (2.0 g; 13.5 mmol), aniline (1.51 g; 16.2 mmol), and potassium carbonate (37.4 g; 270 mmol) in 140 ml toluene. The reaction mixture was heated to reflux for 16 h. The resulting suspension was cooled, filtered, and the filtrate was concentrated under reduced pressure. Column chromatography of the residue on silica gel using heptane/ethyl acetate (4:1 v/v) as eluent gave the title compound (1.5 g, 54%) as an orange oil.

MS ISP (m/e): 205.1 (100)/207.1 (30) [(M+H)⁺].

¹H NMR (CDCl₃, 300 MHz): δ (ppm)=7.50-7.25 (m, 5H), 7.13 (t, 1H), 6.74 (dd, 2H), 6.58 (s broad, 1H).

b) N-[3-Methoxy-4-(4-methyl-imidazol-1-yl)-phenyl]-N'-phenyl-pyridine-2,6-diamine A mixture of palladium(II)acetate (4 mg; 0.02 mmol) and (2-biphenyl) dicyclohexylphosphine (14 mg; 0.04 mmol) in dioxane (5 mL) was stirred under argon for 10 min at 20° C. (6-Chloro-pyridin-2-yl)-phenyl-amine (100 mg; 0.5 mmol), 3-methoxy-4-(4-methyl-imidazol-1-yl)-phenylamine (99 mg; 0.5 mmol), and potassium carbonate (1.35 g; 10 mmol) were added and the mixture was refluxed under argon for 3 h. After quenching the reaction by addition of water, the mixture was extracted with ethyl acetate. The organic phase was dried over sodium sulfate, concentrated under reduced pressure. The crude product was purified by column chromatography on silica gel using dichloromethane/0-20% methanol as eluent to give the title compound (42 mg, 23%) as a light yellow solid.

MS ISP (m/e): 372.2 (100) [(M+H)⁺].

NMR (DMSO-D₆, 300 MHz): δ (ppm)=9.06 (br s, 1H), 8.85 (br s, 1H), 7.65 (d, 1H), 7.55 (d, 2H), 7.47 (d, 1H), 7.41 (t, 1H), 7.23 (t, 3H), 7.14 (d, 1H), 7.02 (s, 1H), 6.87 (t, 1H), 6.27 (dd, 2H), 3.56 (s, 3H), 2.14 (s, 3H).

Example 71

(5-Benzyl-4H-[1,2,4]triazol-3-yl)-[3-methoxy-4-(4-methyl-imidazol-1-yl)-phenyl]-amine

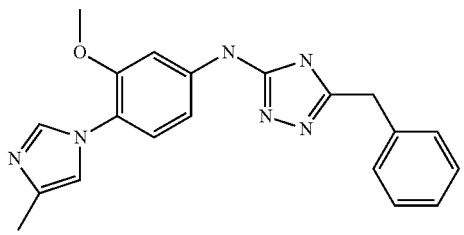 [SMILES: COc1cc(Nc2nnc(Cc3ccccc3)[nH]2)ccc1-n1cnc(C)c1]

a) 1-(4-Isothiocyanato-2-methoxy-phenyl)-4-methyl-1H-imidazole

A solution of 3-methoxy-4-(4-methyl-imidazol-1-yl)-phenylamine (203 mg, 1 mmol) and of 1,1'-thiocarbonyldi-2(1H)-pyridone (263 mg, 1.1 mmol) in dichloromethane (10 mL) was stirred at 20° C. for 16 h to yield an orange solution. The solution was concentrated under reduced pressure to ¼ of its volume and subjected to column chromatography on silica gel using dichloromethane/methanol (95:5 v/v) as eluent to yield the title compound (230 mg, 94%) as a yellow oil which solidified on standing.

MS ISP (m/e): 246.3 (100) [(M+H)⁺].

¹H NMR (CDCl₃, 300 MHz): δ (ppm)=7.67 (s, 1H), 7.21 (d, 1H), 6.91-6.86 (m, 3H), 3.86 (s, 3H), 2.29 (s, 3H).

b) [3-Methoxy-4-(4-methyl-imidazol-1-yl)-phenyl]-thiourea 1-(4-Isothiocyanato-2-methoxy-phenyl)-4-methyl-1H-imidazole (227 mg, 0.93 mmol) was dissolved in tetrahydrofuran (2.3 mL). At 0° C. under stirring ammonia gas was bubbled through the solution for 5 min. A solid precipitated. The suspension was stirred at 20° C. for 16 h. The solvent was evaporated under reduced pressure and the residue was stirred with diethyl ether for 30 min. The solid was filtered off and dried to yield the title compound (170 mg, 70%) as a pale-yellow solid.

MS ISP (m/e): 263.3 (100) [(M+H)⁺].

¹H NMR (DMSO-D₆, 300 MHz): δ (ppm)=9.84 (s, 1H), 7.90-7.20 (br s, 2H), 7.71 (s, 1H), 7.46 (s, 1H), 7.28 (d, 1H), 7.07 (s, 1H), 7.03 (d, 1H), 3.79 (s, 3H), 2.15 (s, 3H).

c) (5-Benzyl-4H-[1,2,4]triazol-3-yl)-[3-methoxy-4-(4-methyl-imidazol-1-yl)-phenyl]-amine A solution of [3-methoxy-4-(4-methyl-imidazol-1-yl)-phenyl]-thiourea (400 mg, 1.52 mmol) in acetone (25 ml) was treated with iodomethane (0.14 ml, 2.29 mmol) and stirred at 20° C. for 16 h. The reaction mixture was concentrated and the crude S-methyl-isothiourea redissolved in ethanol (25 ml). Phenylacetic acid hydrazide (252 mg, 1.52 mmol) was added and the mixture was refluxed for 16 h under argon. After cooling to 20° C., 2 N sodium hydroxide solution (5 ml) was added and the mixture was refluxed for 2 h. After cooling to 20° C., the mixture was brought to pH 7 by careful addition of 1 N aqueous hydrochloric acid and then extracted with ethyl acetate. The organic phase was dried over sodium sulfate and evaporation under reduced pressure to afford a sticky semisolid which was triturared in diethyl ether (3 mL). Filtration yielded the title compound (146 mg, 27%) as greyish solid.

MS ISP (m/e): 361.5 (100) [(M+H)+].

$^1$H NMR (DMSO-D$_6$, 300 MHz): δ (ppm)=13.5 (br s, 1H), 9.31 (br s, 1H), 7.59 (s, 1H), 7.50 (s, 1H), 7.40-7.20 (m, 5H), 7.12 (qa, 2H), 6.97 (s, 1H), 4.00 (s, 2H), 3.74 (s, 3H), 2.13 (s, 3H).

Example 72

[5-(4-Chloro-benzyl)-4H-[1,2,4]triazol-3-yl]-[3-methoxy-4-(4-methyl-imidazol-1-yl)-phenyl]-amine

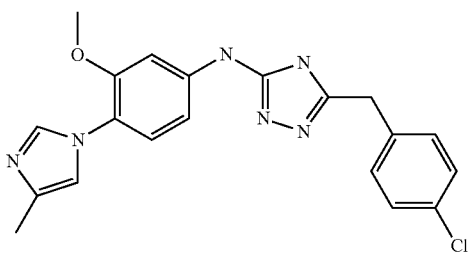 [SMILES: COc1cc(Nc2nnc(Cc3ccc(Cl)cc3)[nH]2)ccc1-n1cnc(C)c1]

The title compound was prepared in analogy to example 71c) starting with [3-methoxy-4-(4-methyl-imidazol-1-yl)-phenyl]-thiourea (150 mg, 0.57 mmol) and (4-chloro-phenyl)-acetic acid hydrazide (116 mg, 0.57 mmol). Obtained as a brownish solid (36 mg, 16%) after chromatography of the crude reaction product on amino-modified silica gel (Merck HPTLC Silica Gel 60 NH2F254S) using ethyl acetate as eluent.

MS ISN (m/e): 393.3 (100) [(M−H)−].

$^1$H NMR (DMSO-D$_6$, 300 MHz): δ (ppm)=13.2 (very br s, 1H), 9.50 (br s, 1H), 7.59 (s, 1H), 7.50 (s, 1H), 7.40-7.30 (qa, 4H), 7.20-7.10 (m, 2H), 6.97 (s, 1H), 3.99 (s, 2H), 3.73 (s, 3H), 2.13 (s, 3H).

Example 73

[5-(4-Fluoro-benzyl)-4H-[1,2,4]triazol-3-yl]-[3-methoxy-4-(4-methyl-imidazol-1-yl)-phenyl]-amine

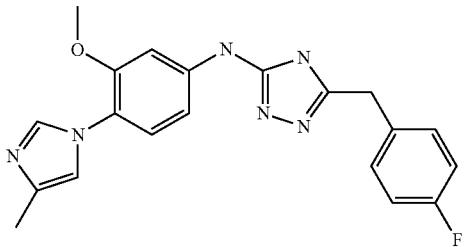 [SMILES: COc1cc(Nc2nnc(Cc3ccc(F)cc3)[nH]2)ccc1-n1cnc(C)c1]

The title compound was prepared in analogy to example 71c) starting with [3-methoxy-4-(4-methyl-imidazol-1-yl)-phenyl]-thiourea (200 mg, 0.76 mmol) and (4-fluoro-phenyl)-acetic acid hydrazide (141 mg, 0.76 mmol). Obtained as a greyish solid (21 mg, 7%).

MS ISP (m/e): 379.3 (100) [(M+H)+].

$^1$H NMR (DMSO-D$_6$, 300 MHz): δ (ppm)=13.1 (br s, 1H), 9.32 (br s, 1H), 7.59 (s, 1H), 7.49 (s, 1H), 7.40-7.30 (m, 2H), 7.20-7.10 (m, 3H), 6.98 (s, 1H), 4.00 (s, 2H), 3.74 (s, 3H), 2.13 (s, 3H).

Example 74

[5-(4-Fluoro-phenyl)-4H-[1,2,4]triazol-3-yl]-[3-methoxy-4-(4-methyl-imidazol-1-yl)-phenyl]-amine

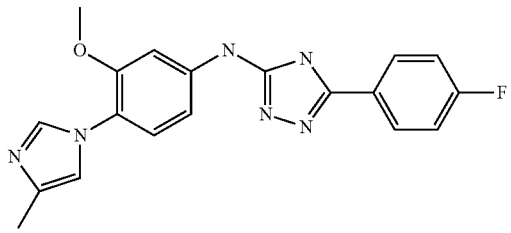 [SMILES: COc1cc(Nc2nnc(-c3ccc(F)cc3)[nH]2)ccc1-n1cnc(C)c1]

The title compound was prepared in analogy to example 71c) starting with [3-methoxy-4-(4-methyl-imidazol-1-yl)-phenyl]-thiourea (250 mg, 0.95 mmol) and 4-fluoro-benzohydrazide (162 mg, 0.95 mmol). Obtained as a brownish solid (41 mg, 12%).

MS ISP (m/e): 365.1 (100) [(M+H)+].

$^1$H NMR (DMSO-D$_6$, 300 MHz): δ (ppm)=13.85 (br s, 1H), 9.56 (br s, 1H), 8.01 (t, 2H), 7.63 (s, 2H), 7.50-7.25 (m, 2H), 7.19 (br s, 2H), 7.01 (s, 1H), 3.81 (s, 3H), 2.14 (s, 3H).

Example 75

[3-Methoxy-4-(4-methyl-imidazol-1-yl)-phenyl]-(4-methoxy-6-methyl-pyrimidin-2-yl)-amine

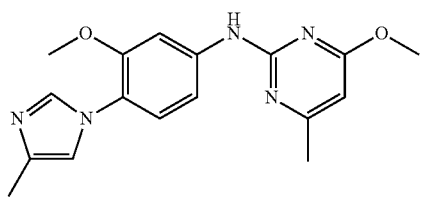

A mixture of (4-chloro-6-methyl-pyrimidin-2-yl)-[3-methoxy-4-(4-methyl-imidazol-1-yl)-phenyl]-amine (99 mg, 0.3 mmol) and sodium methoxide (25 mg, 0.45 mmol) in methanol (3 mL) was heated for 30 min to 160° C. in a microwave oven. The reaction mixture was concentrated under reduced pressure and the residue was partitioned between ethyl acetate and water. The aqueous layer was extracted twice with ethyl acetate. The combined organic layers were washed with brine, dried over sodium sulfate and evaporated under reduced pressure. The residue was purified by reversed preparative HPLC using acetonitril/water (0.1% formic acid) to yield the title compound as a yellow solid (30 mg, 31%). MS ISP (m/e): 326.2 (100) [(M+H)+].

$^1$H NMR (CDCl$_3$, 300 MHz): δ (ppm)=7.80 (s, 1H), 7.62 (s, 1H), 7.15 (d, 1H), 7.11 (s, 1H), 7.02 (d, 1H), 6.87 (s, 1H), 6.12 (s, 1H), 3.97 (s, 3H), 3.86 (s, 3H), 2.35 (s, 3H), 2.30 (s, 3H).

Example 76

(4-Isopropoxy-6-methyl-pyrimidin-2-yl)-[3-methoxy-4-(4-methyl-imidazol-1-yl)-phenyl]-amine

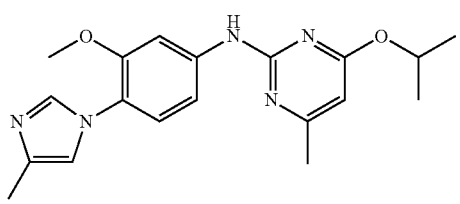 [SMILES: COc1cc(Nc2nc(C)cc(OC(C)C)n2)ccc1-n1cnc(C)c1]

Sodium (10 mg, 0.45 mmol) was dissolved under heating and stirring under an atmosphere of nitrogen in isopropanol (1 mL). (4-Chloro-6-methyl-pyrimidin-2-yl)-[3-methoxy-4-(4-methyl-imidazol-1-yl)-phenyl]-amine (99 mg, 0.3 mmol) was added and the suspension was heated to reflux over night. The solvent was evaporated under reduced pressure and the residue was taken up in water and extracted twice with diethyl ether. The combined organic layers were washed with brine, dried over sodium sulfate, filtered and evaporated under reduced pressure to dryness. The residue was purified by column chromatography on silica gel using dichloromethane/methanol (19:1 v/v) as eluent. The fraction containing the product was purified by reversed preparative HPLC using acetonitril/water (0.1% formic acid) to yield the title compound as an off-white solid (25 mg, 24%). MS ISP (m/e): 354.2 (100) [(M+H)$^+$]. $^1$H NMR (CDCl$_3$, 300 MHz): δ (ppm)=7.73 (s, 1H), 7.63 (s, 1H), 7.18 (d, 1H), 7.04 (s, 1H), 7.03 (d, 1H), 6.87 (s, 1H), 6.06 (s, 1H), 5.36 (sept, 1H), 3.86 (s, 3H), 2.33 (s, 3H), 2.30 (s, 3H), 1.38 (s, 3H), 1.36 (s, 3H).

Example 77

[4-(2-Methoxy-ethoxy)-6-methyl-pyrimidin-2-yl]-[3-methoxy-4-(4-methyl-imidazol-1-yl)-phenyl]-amine

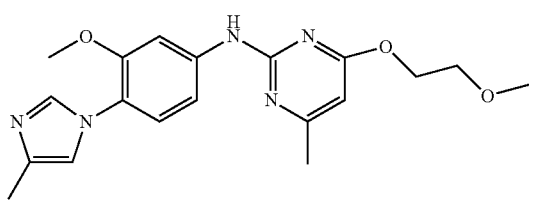

Sodium (10 mg, 0.45 mmol) was dissolved under an atmosphere of nitrogen in 2-methoxyethanol (0.95 mL). (4-Chloro-6-methyl-pyrimidin-2-yl)-[3-methoxy-4-(4-methyl-imidazol-1-yl)-phenyl]-amine (99 mg, 0.3 mmol) was added and the suspension was heated to 100° C. for 2 hours. The solvent was evaporated under reduced pressure and the residue was taken up in water and extracted twice with diethyl ether. The combined organic layers were washed with brine, dried over sodium sulfate, filtered and evaporated under reduced pressure to dryness. The residue was purified by column chromatography on silica gel using dichloromethane/methanol (19:1 v/v) as eluent to yield the title compound as a yellow solid (41 mg, 37%). MS ISP (m/e): 370.2 (100) [(M+H)$^+$]. $^1$H NMR (CDCl$_3$, 300 MHz): δ (ppm)=7.74 (s, 1H), 7.63 (s, 1H), 7.18 (d, 1H), 7.05 (s, 1H), 7.03 (d, 1H), 6.87 (s, 1H), 6.18 (s, 1H), 4.51 (dd, 2H), 3.86 (s, 3H), 3.73 (dd, 2H), 3.45 (s, 3H), 2.35 (s, 3H), 2.30 (s, 3H).

Example 78

[4-(2-Dimethylamino-ethoxy)-6-methyl-pyrimidin-2-yl]-[3-methoxy-4-(4-methyl-imidazol-1-yl)-phenyl]-amine

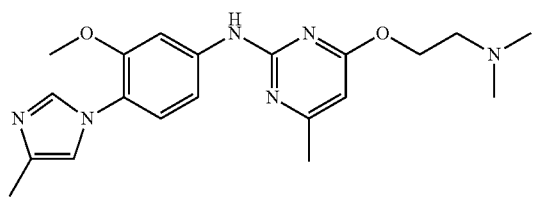

Sodium (10 mg, 0.45 mmol) was dissolved under an atmosphere of nitrogen in 2-dimethylaminoethanol (0.92 mL). (4-Chloro-6-methyl-pyrimidin-2-yl)-[3-methoxy-4-(4-methyl-imidazol-1-yl)-phenyl]-amine (99 mg, 0.3 mmol) was added and the suspension was heated to 100° C. for 2 hours. The solvent was evaporated under reduced pressure and the residue was taken up in water and extracted twice with diethyl ether. The combined organic layers were washed with brine, dried over sodium sulfate, filtered and evaporated under reduced pressure to dryness. The residue was purified by column chromatography on silica gel using dichloromethane/methanol/saturated aqueous ammonia solution (19:1:0.2 v/v/v) as eluent to yield the title compound as a brown viscous oil (37 mg, 33%). MS ISP (m/e): 383.2 (100) [(M+H)$^+$]. $^1$H NMR (CDCl$_3$, 300 MHz): δ (ppm)=7.74 (s, 1H), 7.62 (s, 1H), 7.15 (d, 1H), 7.07 (s, 1H), 7.05 (d, 1H), 6.87 (s, 1H), 6.16 (s, 1H), 4.45 (t, 2H), 3.86 (s, 3H), 2.71 (t, 2H), 2.36 (s, 3H), 2.34 (s, 6H), 2.30 (s, 3H).

Example 79

[3-Methoxy-4-(4-methyl-imidazol-1-yl)-phenyl]-[4-methyl-6-(tetrahydro-pyran-4-yloxy)-pyrimidin-2-yl]-amine

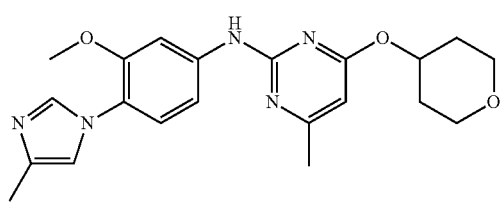 [SMILES: COc1cc(Nc2nc(C)cc(OC3CCOCC3)n2)ccc1-n1cnc(C)c1]

Sodium (10 mg, 0.45 mmol) was dissolved under stirring and heating (100° C. for 3 hours) under an atmosphere of nitrogen in tetrahydro-4H-pyran-4-ol (0.99 mL). (4-Chloro-6-methyl-pyrimidin-2-yl)-[3-methoxy-4-(4-methyl-imidazol-1-yl)-phenyl]-amine (99 mg, 0.3 mmol) was added and the suspension was heated to 100° C. for 2 hours. The solvent was evaporated under reduced pressure and the residue was taken up in water and extracted twice with diethyl ether. The combined organic layers were washed with brine, dried over sodium sulfate, filtered and evaporated under reduced pressure to dryness. The residue was purified by reversed preparative HPLC using acetonitril/water (0.1% formic acid) to yield the title compound as a white solid (13 mg, 11%). MS ISP (m/e): 396.2 (100) [(M+H)+]. 1H NMR (CDCl3, 300 MHz): δ (ppm)=7.65 (s, 1H), 7.62 (s, 1H), 7.17 (d, 1H), 7.15 (s, 1H), 7.13 (d, 1H), 6.87 (s, 1H), 6.12 (s, 1H), 5.30 (m, 1H), 3.98 (m, 2H), 3.86 (s, 3H), 3.62 (m, 2H), 2.36 (s, 3H), 2.31 (s, 3H), 2.04 (m, 2H), 1.84 (m, 2H).

Example 80

(4-Cyclopentyloxy-6-methyl-pyrimidin-2-yl)-[3-methoxy-4-(4-methyl-imidazol-1-yl)-phenyl]-amine

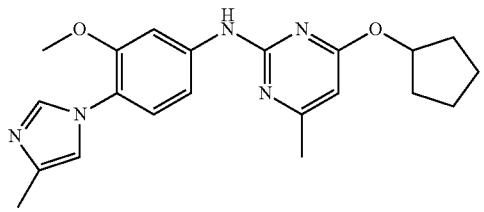 [SMILES: COc1cc(Nc2nc(C)cc(OC3CCCC3)n2)ccc1-n1cnc(C)c1]

a) 2-Chloro-4-cyclopentyloxy-6-methyl-pyrimidine and 4-chloro-2-cyclopentyloxy-6-methyl-pyrimidine To a solution of cyclopentanol (86 mg, 1.0 mmol) in tetrahydrofurane (6 mL) was added at under an atmosphere of nitrogen potassium tert.-butylate (126 mg, 1.1 mmol). 2,4-Dichloro-6-methylpyrimidine (166 mg, 1.0 mmol) was added to this solution and the reaction was stirred at for 3 hours. The solvent was evaporated under reduced pressure and the residue was taken up in water and extracted twice with diethyl ether. The combined organic layers were washed with brine, dried over sodium sulfate, filtered and evaporated under reduced pressure to dryness. The residue was purified by column chromatography on silica gel using heptane/ethyl acetate (9:1 v/v) as eluent to yield the title compound as a colorless oil as a 1:1 mixture of regioisomers (116 mg, 55%). MS ISP (m/e): 213.1/215.5 (14/3) [(M+H)+], 145.0/147.0 (100/41) [(M-cyclopentene+H)+]. 1H NMR (CDCl3, 300 MHz): δ (ppm)=6.81 (s, 1H), 6.42 (s, 1H), 5.45 (m, 2H), 2.42 (s, 3H), 2.40 (s, 3H), 1.58-2.04 (m, 16H).

b) (4-Cyclopentyloxy-6-methyl-pyrimidin-2-yl)-[3-methoxy-4-(4-methyl-imidazol-1-yl)-phenyl]-amine Palladium acetate (7.1 mg, 0.03 mmol) and 2-(dicyclohexylphosphino)biphenyl (23.1 mg, 0.64 mmol) were dissolved in dioxane (3.6 mL) and stirred for 10 minutes at. Sodium tert.-butylate (59 mg, 0.6 mmol), 3-methoxy-4-(4-methyl-imidazol-1-yl)-phenylamine (81 mg, 0.4 mmol) and 1:1 mixture of 2-chloro-4-cyclopentyloxy-6-methyl-pyrimidine and 4-chloro-2-cyclopentyloxy-6-methyl-pyrimidine (94 mg, 0.44 mmol) were added and the reaction was heated to 200° C. for 30 minutes in a microwave oven. The solvent was evaporated under reduced pressure and the residue was taken up in water and extracted twice with ethyl acetate. The combined organic layers were washed with brine, dried over sodium sulfate, filtered and evaporated under reduced pressure to dryness. The residue was purified by column chromatography on silica gel using methylenechloride/methanol (19:1 v/v) as eluent to yield the title compound as a white solid (56 mg, 37%). MS ISP (m/e): 380.1 (100) [(M+H)+]. 1H NMR (CDCl3, 300 MHz): δ (ppm)=7.70 (s, 1H), 7.62 (s, 1H), 7.15 (d, 1H), 7.07 (d, 1H), 7.05 (s, 1H), 6.87 (s, 1H), 6.06 (s, 1H), 5.30 (m, 1H), 3.85 (s, 3H), 2.33 (s, 3H), 2.30 (s, 3H), 1.75-2.00 (m, 6H), 1.60-1.68 (m, 2H).

Example 81

[4-(4-Fluoro-phenoxy)-6-methyl-pyrimidin-2-yl]-[3-methoxy-4-(4-methyl-imidazol-1-yl)-phenyl]-amine

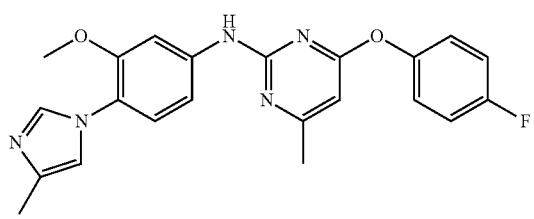 [SMILES: COc1cc(Nc2nc(C)cc(Oc3ccc(F)cc3)n2)ccc1-n1cnc(C)c1]

2-Chloro-4-(4-fluoro-phenoxy)-6-methyl-pyrimidine

4-Fluorophenol (103 mg, 0.92 mmol) and potassium-tert-butylate (113 mg, 1.0 mmol) were dissolved in 7 mL of tetrahydrofurane. 2,4-dichloro-6-methylpyrimidine (150 mg, 0.92 mmol) was added and the mixture stirred at 20° C. overnight. Water was added and the mixture extracted with diethyl ether. Chromatography of the crude reaction product on silica gel using a heptane/ethyl acetate as an eluent gave the title compound (150 mg, 68%) as a slightly yellow solid. 1H NMR (CDCl3, 300 MHz): δ (ppm)=7.50-7.40 (m, 2H), 7.28 (t, 1H), 7.14 (d, 2H), 6.57 (s, 1H), 2.47 (s, 3H).

b) [4-(4-Fluoro-phenoxy)-6-methyl-pyrimidin-2-yl]-[3-methoxy-4-(4-methyl-imidazol-1-yl)-phenyl]-amine Palladium acetate (7 mg, 0.03 mmol) and 2-(dicyclohexylphosphino)biphenyl (22 mg, 0.06 mmol) were dissolved in 2.5 mL of dioxane and stirred at 20° C. under argon for 10 minutes. Sodium tert-butylate (57 mg, 0.59 mmol) was added, followed by 3-methoxy-4-(4-methyl-imidazol-1-yl)-phenylamine (80 mg, 0.39 mmol) and 2-chloro-4-(4-fluoro-phenoxy)-6-methyl-pyrimidine (115 mg, 0.48 mmol). The resulting mixture was heated in the microwave oven for 20 minutes at 200° C. Dichloromethane was added, insoluble material filtered off and the resulting solution purified by chromatography on silica gel using ethyl acetate as a solvent. The title compound was isolated as a yellow solid (50 mg, 31%). MS ISP (m/e): 406.3 (100) [(M+H)+]. 1H NMR (CDCl3, 300 MHz): δ (ppm)=7.58 (d, 1H), 7.46 (d, 1H), 7.17 (s, 1H), 7.15-7.05 (m, 4H), 7.04 (d, 1H), 6.91 (dxd, 1H), 6.80 (s, 1H), 6.23 (s, 1H), 3.62 (s, 1H), 2.40 (s, 3H), 2.28 (s, 3H).

Example 82

[4-(4-tert-Butyl-phenoxy)-6-methyl-pyrimidin-2-yl]-[3-methoxy-4-(4-methyl-imidazol-1-yl)-phenyl]-amine

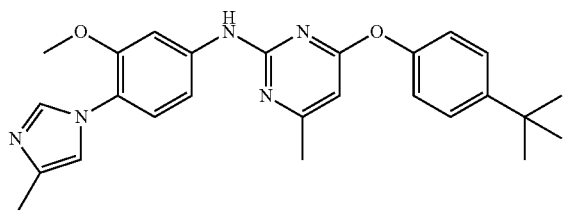 [SMILES: COc1cc(Nc2nc(C)cc(Oc3ccc(C(C)(C)C)cc3)n2)ccc1-n1cnc(C)c1]

a) 4-(4-tert-Butyl-phenoxy)-2-chloro-6-methyl-pyrimidine

Prepared in analogy to example 81a) from 4-t-butylphenol and 2,4-dichloro-6-methylpyrimidine in a yield of 51%. $^1$H NMR (CDCl$_3$, 300 MHz): δ (ppm)=7.44 (d, 2H), 7.07 (d, 2H), 6.54 (s, 1H), 2.45 (s, 3H), 1.35 (s, 9H).

b) [4-(4-tert-Butyl-phenoxy)-6-methyl-pyrimidin-2-yl]-[3-methoxy-4-(4-methyl-imidazol-1-yl)-phenyl]-amine Prepared in analogy to example 81b) from 3-methoxy-4-(4-methyl-imidazol-1-yl)-phenylamine and 4-(4-tert-butyl-phenoxy)-2-chloro-6-methyl-pyrimidine in a yield of 39%. MS ISP (m/e): 444.3 (100) [(M+H)$^+$]. $^1$H NMR (CDCl$_3$, 300 MHz): δ (ppm)=7.58 d, 1H), 7.55 (d, 1H), 7.42 (d, 2H), 7.18 (s, 1H), 7.08 (d, 2H), 7.03 (d, 1H), 6.91 (dxd, 1H), 6.82 (s, 1H), 6.21 (s, 1H), 3.59 (s, 3H), 2.39 (s, 3H), 2.28 (s, 3H), 1.35 (s, 9H).

Example 83

[3-Methoxy-4-(4-methyl-imidazol-1-yl)-phenyl]-[4-methyl-6-(4-trifluoromethyl-phenoxy)-pyrimidin-2-yl]-amine

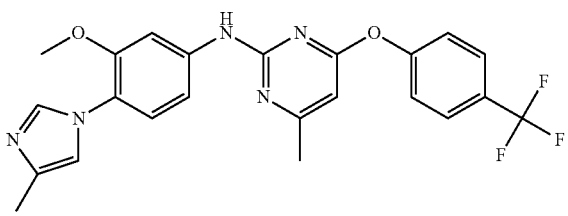 [SMILES: COc1cc(Nc2nc(C)cc(Oc3ccc(C(F)(F)F)cc3)n2)ccc1-n1cnc(C)c1]

a) 2-Chloro-4-methyl-6-(4-trifluoromethoxy-phenoxy)-pyrimidine

Prepared in analogy to example 81a) from 4-trifluoromethylphenol and 2,4-dichloro-6-methylpyrimidine in a yield of 56%. $^1$H NMR (CDCl$_3$, 300 MHz): δ (ppm)=7.70 (d, 2H), 7.28 (d, 2H), 6.70 (s, 1H), 2.52 (s, 3H).

b) [3-Methoxy-4-(4-methyl-imidazol-1-yl)-phenyl]-[4-methyl-6-(4-trifluoromethyl-phenoxy)-pyrimidin-2-yl]-amine Prepared in analogy to example 81b) from 3-methoxy-4-(4-methyl-imidazol-1-yl)-phenylamine and 2-chloro-4-methyl-6-(4-trifluoromethoxy-phenoxy)-pyrimidine in a yield of 29%. MS ISP (m/e): 456.2 (100) [(M+H)$^+$]. $^1$H NMR (CDCl$_3$, 300 MHz): δ (ppm)=7.70 (d, 2H), 7.58 (d, 1H), 7.46 (s broad, 1H), 7.30 (d, 2H), 7.05 (s broad, 1H), 7.03 (d, 1H), 7.37 (dxd, 1H), 6.82 (s, 1H), 6.32 (s, 1H), 3.55 (s, 3H), 2.43 (s, 3H), 2.28 (s, 3H).

Example 84

[3-Methoxy-4-(4-methyl-imidazol-1-yl)-phenyl]-[4-methyl-6-(4-trifluoromethoxy-phenoxy)-pyrimidin-2-yl]-amine

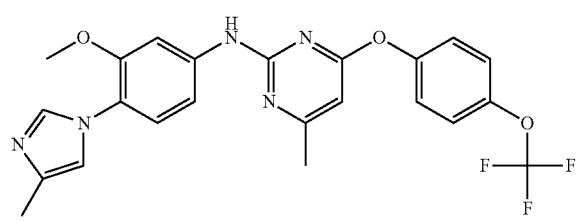 [SMILES: COc1cc(Nc2nc(C)cc(Oc3ccc(OC(F)(F)F)cc3)n2)ccc1-n1cnc(C)c1]

a) 2-Chloro-4-methyl-6-(4-trifluoromethoxy-phenoxy)-pyrimidine

Prepared in analogy to example 81a) from 4-trifluoromethoxyphenol and 2,4-dichloro-6-methylpyrimidine in a yield of 60%. $^1$H NMR (CDCl$_3$, 300 MHz): δ (ppm)=7.28 (d, 2H), 7.18 (d, 2H), 6.65 (s, 1H), 2.50 (s, 3H).

b) [3-Methoxy-4-(4-methyl-imidazol-1-yl)-phenyl]-[4-methyl-6-(4-trifluoromethoxy-phenoxy)-pyrimidin-2-yl]-amine Prepared in analogy to example 81b) from 3-methoxy-4-(4-methyl-imidazol-1-yl)-phenylamine and 2-chloro-4-methyl-6-(4-trifluoromethoxy-phenoxy)-pyrimidine in a yield of 13%. MS ISP (m/e): 472.1 (100) [(M+H)$^+$]. $^1$H NMR (CDCl$_3$, 300 MHz): δ (ppm)=7.44 (s, 1H), 7.35-7.15 (m, 5H), 7.01 (s, 2H), 6.86 (s, 1H), 6.30 (s, 1H), 3.63 (s, 3H), 2.43 (s, 3H), 2.39 (s, 3H).

Example 85

(4,6-Dimethoxy-pyrimidin-2-yl)-[3-methoxy-4-(4-methyl-imidazol-1-yl)-phenyl]-amine

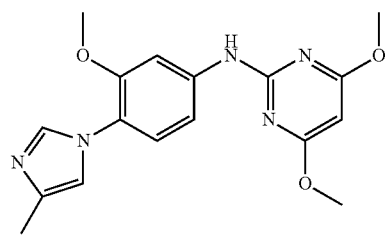 [SMILES: COc1cc(OC)nc(Nc2ccc(-n3cnc(C)c3)c(OC)c2)n1]

Prepared in analogy to example 81b) from 3-methoxy-4-(4-methyl-imidazol-1-yl)-phenylamine and 2-chloro-4,6-dimethoxypyrimidine, using potassium carbonate as a base. The title compound was isolated in a yield of 52%. MS ISP (m/e): 342.1 (100) [(M+H)$^+$]. $^1$H NMR (CDCl$_3$, 300 MHz): δ (ppm)=7.70-7.55 (m broad, 2H), 7.35-7.20 (m broad, 3H), 7.04 (s broad, 1H), 3.92 (s broad, 6H), 3.81 (s broad, 3H), 2.14 (s broad, 3H).

Example 86

[4-(4-Pentafluorothio-phenoxy)-6-methyl-pyrimidin-2-yl]-[3-methoxy-4-(4-methyl-imidazol-1-yl)-phenyl]-amine

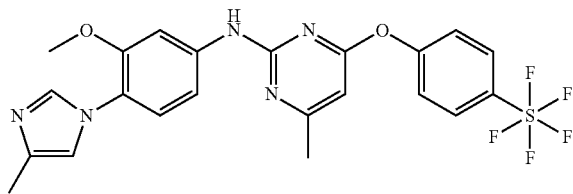 [SMILES: COc1cc(Nc2nc(C)cc(Oc3ccc(S(F)(F)(F)(F)F)cc3)n2)ccc1-n1cnc(C)c1]

a) 2-Chloro-4-methyl-6-(4-pentafluorothio-phenoxy)-pyrimidine

Prepared in analogy to example 81a) from 4-pentafluorothiophenol and 2,4-dichloro-6-methylpyrimidine in a yield of 55%. $^1$H NMR (CDCl$_3$, 300 MHz): δ (ppm)=7.83 (d, 2H), 7.26 (d, 2H), 6.73 (s, 1H), 2.53 (s, 3H).

b) [4-(4-Pentafluorothio-phenoxy)-6-methyl-pyrimidin-2-yl]-[3-methoxy-4-(4-methyl-imidazol-1-yl)-phenyl]-amine Prepared in analogy to example 81b) from 3-methoxy-4-(4-methyl-imidazol-1-yl)-phenylamine and 2-chloro-4-methyl-6-(4-pentafluorothio-phenoxy)-pyrimidine in a yield of 23%. MS ISP (m/e): 514.2 (100) [(M+H)$^+$]. $^1$H NMR (CDCl$_3$, 300 MHz): δ (ppm)=7.82 (d, 2H), 7.58 (d, 1H), 7.40 (s, 1H), 7.30-7.20 (m, 2H), 7.06 (s, 1H), 7.03 (s, 1H), 6.87 (dxd, 1H), 6.83 (s, 1H), 6.33 (s, 1H), 3.57 (s, 3H), 2.44 (s, 3H), 2.29 (s, 3H).

Example 87

[3-Methoxy-4-(4-methyl-imidazol-1-yl)-phenyl]-[4-methyl-6-(oxetan-3-yloxy)-pyrimidin-2-yl]-amine

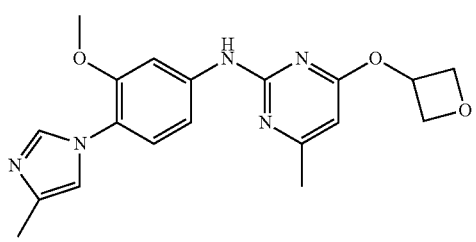 [SMILES: COc1cc(Nc2nc(C)cc(OC3COC3)n2)ccc1-n1cnc(C)c1]

a) 2-Chloro-4-methyl-6-(oxetan-3-yloxy)-pyrimidine

A solution of oxetan-3-ol (173 mg, 2.34 mmol) in 5 mL of tetrahydrofurane was treated with potassium tert-butylate (288 mg, 2.57 mmol) and stirred for 10 minutes at 20° C. 2,4-Dichloro-6-methylpyrimidine (381 mg, 2.34 mmol) was added and the resulting mixture stirred for 2 hours at 20° C. Addition of water and extraction with ethyl acetate, followed by chromatography on silica gel using heptane/ethyl acetate 7:3 v/v as a solvent gave the title compound as a yellowish foam (206 mg, 44%). MS ISP (m/e): 201.2 (33) [(M+H)$^+$].

b) [3-Methoxy-4-(4-methyl-imidazol-1-yl)-phenyl]-[4-methyl-6-(oxetan-3-yloxy)-pyrimidin-2-yl]-amine Prepared in analogy to example 81b) from 3-methoxy-4-(4-methyl-imidazol-1-yl)-phenylamine and 2-chloro-4-methyl-6-(oxetan-3-yloxy)-pyrimidine, using potassium carbonate as a base. The title compound was isolated in a yield of 27%. MS ISP (m/e): 368.1 (100) [(M+H)$^+$]. $^1$H NMR (CDCl$_3$, 300 MHz): δ (ppm)=9.62 (s broad, 1H), 7.67 (d, 2H), 7.41 (dxd, 1H), 7.26 (d, 1H), 7.04 (s, 1H), 6.28 (s, 1H), 5.65 (m, 1H), 4.90 (t, 2H), 4.58 (m, 2H), 3.81 (s, 3H), 2.31 (s, 3H), 2.14 (s, 3H).

Example 88

2-{6-Ethoxy-2-[3-methoxy-4-(4-methyl-imidazol-1-yl)-phenylamino]-pyrimidin-4-yl}-propan-2-ol

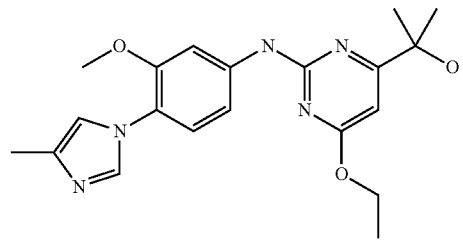 [SMILES: CCOc1cc(C(C)(C)O)nc(Nc2ccc(-n3cnc(C)c3)c(OC)c2)n1]

a) Ethyl 2-chloro-6-ethoxy-pyrimidine-4-carboxylate

A mixture of methyl 2,4-dichloropyrimidine-6-carboxylate (2.07 g, 10.0 mmol) and potassium tert.-butoxide (1.12 g, 10.0 mmol) in ethanol (50 mL) was stirred for 4 h at 60° C. The mixture was cooled to, insoluble material was removed by filtration, and the filtrate was evaporated under reduced pressure. The oily residue was partitioned between ethyl acetate and brine, and the organic layer was dried over sodium sulfate and evaporated under reduced pressure to give crude title compound (0.98 g, 43%) as colorless oil. MS ISP (m/e): 231.1 [(M+H)$^+$].

b) 2-(2-Chloro-6-ethoxy-pyrimidin-4-yl)-propan-2-ol

To a solution of ethyl 2-chloro-6-ethoxy-pyrimidine-4-carboxylate (460 mg, 2.0 mmol) in tetrahydrofurane (5 mL) was added at 0° C. over 2 min a 3 M solution of methylmagnesiumchloride in tetrahydrofurane (1.67 mL, 5.0 mmol). The reaction mixture was stirred at 0° C. for 15 min followed by 1.5 h at 20° C. The mixture was poured on saturated sodium carbonate solution (10 mL) and the product was extracted with ethyl acetate (40 mL). The organic layer was washed with brine (20 mL), dried over sodium sulfate and evaporated under reduced pressure. The residual material was purified by chromatography on silica gel using heptane/0-15% ethyl acetate as eluent to afford the title compound (223 mg, 53%) as colorless oil. MS ISP (m/e): 217.2 [(M+H)⁺]. ¹H NMR (CDCl₃, 300 MHz): δ (ppm)=6.72 (s, 1H), 4.52 (q, 2H), 3.35 (s, 1H), 1.57 (s, 6H), 1.43 (t, 3H).

c) 2-{6-Ethoxy-2-[3-methoxy-4-(4-methyl-imidazol-1-yl)-phenylamino]-pyrimidin-4-yl}-propan-2-ol A solution of 3-methoxy-4-(4-methyl-imidazol-1-yl)-phenylamine (102 mg, 0.5 mmol), 2-(2-chloro-6-ethoxy-pyrimidin-4-yl)-propan-2-ol (108 mg, 0.5 mmol) and 1 N aqueous hydrochloric acid (0.025 mL) in ethanol (0.8 mL) was heated in a sealed tube in a microwave oven to 170° C. for 45 min. The mixture was cooled, diluted with ethyl acetate (50 mL), and then washed with water (20 mL) and brine (20 mL). The organic layer was dried over sodium sulfate and evaporated under reduced pressure. The residual material was purified by chromatography on silica gel using dichloromethane/0-10% ethanol as eluent to give the title compound (20 mg, 10%) as yellow foam. MS ISP (m/e): 384.3 [(M+H)⁺].)⁺]. ¹H NMR (CDCl₃, 300 MHz): δ (ppm)=8.20, 7.78, 7.75 and 7.63 (4 d, 4×2H), 7.31 (s, 2H), 7.16 (s, 1H), 3.93 (s, 1H), 2.53 (s, 3H), 1.61 (s, 6H).

Example 89

N4-Cyclohexyl-N2-[3-methoxy-4-(4-methyl-imidazol-1-yl)-phenyl]-6-methyl-pyrimidine-2,4-diamine

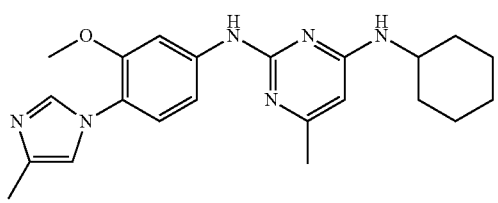 [SMILES: COc1cc(Nc2nc(C)cc(NC3CCCCC3)n2)ccc1-n1cnc(C)c1]

A solution of (4-chloro-6-methyl-pyrimidin-2-yl)-[3-methoxy-4-(4-methyl-imidazol-1-yl)-phenyl]-amine (66 mg, 0.2 mmol) and cyclohexylamine (60 mg, 0.6 mmol) in N-methylpyrroldione (2 mL) was heated for 30 min to 200° C. in a microwave oven. Additional cyclohexylamine (60 mg, 0.6 mmol) was added and the reaction was heated for 30 min to 200° C. in a microwave oven. The reaction mixture was poured onto water and the precipitate was filtered off, washed with water, dissolved in 1N aqueous sodium hydroxide solution and extracted twice with diethyl ether. The combined organic layers were washed with water, once with brine, dried over sodium sulfate, filtered and the solvent was evaporated under reduced pressure to yield the title compound as a light brown solid (64 mg, 82%). MS ISP (m/e): 393.4 (100) [(M+H)⁺]. ¹H NMR (CDCl₃, 300 MHz): δ (ppm)=7.60 (br s, 2H), 7.13 (s, 2H), 6.92 (br s, 1H), 6.86 (s, 1H), 5.75 (s, 1H), 4.61 (m, 1H), 3.85 (s, 3H), 3.69 (m, 1H), 2.30 (s, 3H), 2.26 (s, 3H), 2.05 (br d, 2H), 1.60-1.82 (m, 4H), 1.18-1.45 (m, 4H).

Example 90

N4-(3-Chloro-phenyl)-N2-[3-methoxy-4-(4-methyl-imidazol-1-yl)-phenyl]-6-methyl-pyrimidine-2,4-diamine

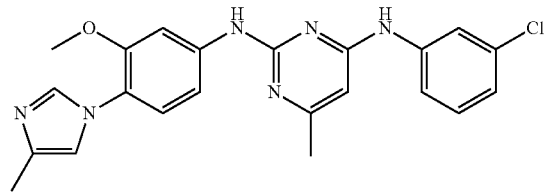 [SMILES: COc1cc(Nc2nc(C)cc(Nc3cccc(Cl)c3)n2)ccc1-n1cnc(C)c1]

Palladium acetate (5.4 mg, 0.024 mmol) and 2-(dicyclohexylphosphino)biphenyl (17.0 mg, 0.048 mmol) were dissolved in dioxane (2.7 mL) and stirred for 10 minutes at 20° C. Sodium tert.-butylate (44 mg, 0.45 mmol), 3-methoxy-4-(4-methyl-imidazol-1-yl)-phenylamine (99 mg, 0.3 mmol) and 3-chloroaniline (43 mg, 0.33 mmol) were added and the reaction was heated to 200° C. for 30 minutes in a microwave oven. The solvent was evaporated under reduced pressure and the residue was taken up in water and extracted twice with ethyl acetate. The combined organic layers were washed with brine, dried over sodium sulfate, filtered and evaporated under reduced pressure to dryness. The residue was purified by column chromatography on silica gel using methylenechloride/methanol (19:1 v/v) as eluent to yield the title compound as a yellow solid (34 mg, 27%). MS ISP (m/e): 421.2 (100) [(M+H)⁺]. ¹H NMR (DMSO-D₆, 300 MHz): δ (ppm)=9.47 (s, 1H), 9.41 (s, 1H), 7.88 (s, 1H), 7.18-7.68 (m, 10H), 7.02 (m, 2H), 3.70 (s, 3H), 2.26 (s, 3H), 2.14 (s, 3H).

Example 91

N4-(4-Chloro-phenyl)-N2-[3-methoxy-4-(4-methyl-imidazol-1-yl)-phenyl]-6-methyl-pyrimidine-2,4-diamine

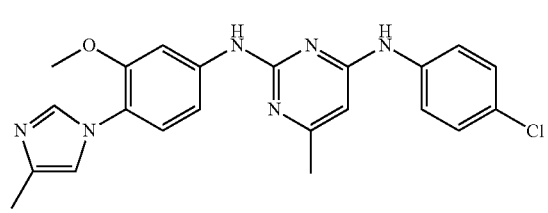 [SMILES: COc1cc(Nc2nc(C)cc(Nc3ccc(Cl)cc3)n2)ccc1-n1cnc(C)c1]

The title compound was prepared from 3-methoxy-4-(4-methyl-imidazol-1-yl)-phenylamine (99 mg, 0.3 mmol) and 4-chloroaniline (43 mg, 0.33 mmol) in analogous manner as described in example 90. It was obtained in 30% yield as a light yellow solid. MS ISP (m/e): 421.1/423.2 (100/30) [(M+H)⁺]. ¹H NMR (DMSO-D₆, 300 MHz): δ (ppm)=9.43 (s, 1H), 9.36 (s, 1H), 7.74 (m, 3H), 7.66 (s, 1H), 7.43 (d, 1H), 7.34 (d, 2H), 7.04 (s, 1H), 6.14 (s, 1H), 3.70 (s, 3H), 2.25 (s, 3H), 2.15 (s, 3H).

Example 92

N4,N4-Diethyl-N2-[3-methoxy-4-(4-methyl-imidazol-1-yl)-phenyl]-6-methyl-pyrimidine-2,4-diamine

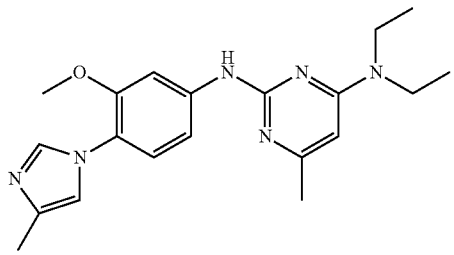 [SMILES: CCN(CC)c1cc(C)nc(Nc2ccc(-n3cnc(C)c3)c(OC)c2)n1]

a) (2-Chloro-6-methyl-pyrimidin-4-yl)-diethyl-amine

To a solution of 2,4-dichloro-6-methylpyrimidine (166 mg, 1.0 mmol) in tetrahydrofurane (5 mL) was added at 20° C. under stirring diethyl amine (88 mg, 1.2 mmol) and the reaction was stirred for 3 hours at 20° C. Additional diethylamine (44 mg, 0.6 mmol) were added and the reaction was stirred at 20° C. over night. The solvent was evaporated under reduced pressure and the residue was taken up in water and extracted twice with diethyl ether. The combined organic layers were washed with brine, dried over sodium sulfate, filtered and evaporated under reduced pressure to dryness. The residue was purified by column chromatography on silica gel using heptane/ethyl acetate (9:1 to 7:3 v/v) as eluent to yield the title compound (90 mg, 45%) as a yellow viscous. $^1$H NMR (CDCl$_3$, 300 MHz): δ (ppm)=6.11 (s, 1H), 3.49 (br s, 4H), 2.33 (s, 3H), 1.19 (t, 6H).

b) N4,N4-Diethyl-N2-[3-methoxy-4-(4-methyl-imidazol-1-yl)-phenyl]-6-methyl-pyrimidine-2,4-diamine The title compound was prepared from 3-methoxy-4-(4-methyl-imidazol-1-yl)-phenylamine (67 mg, 0.33 mmol) and (2-chloro-6-methyl-pyrimidin-4-yl)-diethyl-amine (67 mg, 0.33 mmol) in analogous manner as described in example 90. It was obtained in 65% yield as a light yellow viscous oil. MS ISP (m/e): 367.2 (100) [(M+H)$^+$]. $^1$H NMR (DMSO-D$_6$, 300 MHz): δ (ppm)=9.15 (s, 1H), 7.88 (s, 1H), 7.63 (s, 1H), 7.32 (d, 1H), 7.16 (d, 1H), 7.01 (s, 1H), 6.00 (s, 1H), 3.78 (s, 3H), 3.51 (br q, 4H), 2.20 (s, 3H), 2.14 (s, 3H), 1.13 (t, 6H).

Example 93

N4-Isobutyl-N2-[3-methoxy-4-(4-methyl-imidazol-1-yl)-phenyl]-6-methyl-pyrimidine-2,4-diamine

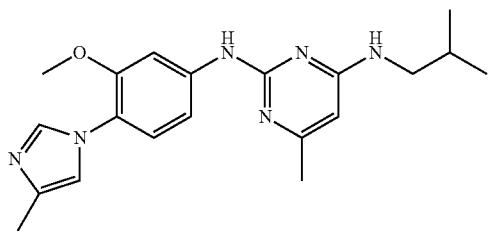 [SMILES: COc1cc(Nc2nc(C)cc(NCC(C)C)n2)ccc1-n1cnc(C)c1]

a) (2-Chloro-6-methyl-pyrimidin-4-yl)-isobutyl-amine

To a solution of 2,4-dichloro-6-methylpyrimidine (998 mg, 6.0 mmol) in tetrahydrofurane (30 mL) was added at 0° C. under stirring isobutylamine (895 mg, 12.0 mmol) and the reaction was stirred for 6 hours at 0° C. and for 2 hours at 20° C. The solvent was evaporated under reduced pressure and the residue was taken up in 1N aqueous sodium hydroxide solution and extracted twice with diethyl ether. The combined organic layers were washed with brine, dried over sodium sulfate, filtered and evaporated under reduced pressure to dryness. The residue was purified by column chromatography on silica gel using heptane/ethyl acetate (9:1 to 7:3 v/v) as eluent to yield the title compound (655 mg, 55%) as white crystals. MS ISP (m/e): 200.2/202.2 (100/32) [(M+H)$^+$]. $^1$H NMR (DMSO-D$_6$, 300 MHz, rotamers): δ (ppm)=7.75 (br s, 1H), 6.25 (br s, 1H), 2.90-3.12 (br m, 2H), 2.12-2.22 (br s, 3H), 1.79 (sept, 1H), 0.88 (d, 6H).

b) N4-Isobutyl-N2-[3-methoxy-4-(4-methyl-imidazol-1-yl)-phenyl]-6-methyl-pyrimidine-2,4-diamine The title compound was prepared from 3-methoxy-4-(4-methyl-imidazol-1-yl)-phenylamine (61 mg, 0.30 mmol) and (2-chloro-6-methyl-pyrimidin-4-yl)-isobutyl-amine (66 mg, 0.33 mmol) in analogous manner as described in example 90. It was obtained in 89% yield as a yellow solid. MS ISP (m/e): 367.2 (100) [(M+H)$^+$]. $^1$H NMR (DMSO-D$_6$, 300 MHz): δ (ppm)=9.12 (s, 1H), 7.97 (s, 1H), 7.63 (s, 1H), 7.34 (d, 1H), 7.13 (d, 1H), 7.10 (br s, 1H), 7.01 (s, 1H), 5.87 (s, 1H), 3.78 (s, 3H), 3.16 (br s, 2H), 2.13 (s, 3H), 1.74 (sept, 1H), 0.91 (d, 6H).

Example 94

1-{2-[3-Methoxy-4-(4-methyl-imidazol-1-yl)-phenylamino]-6-methyl-pyrimidin-4-yl}-piperidin-4-ol

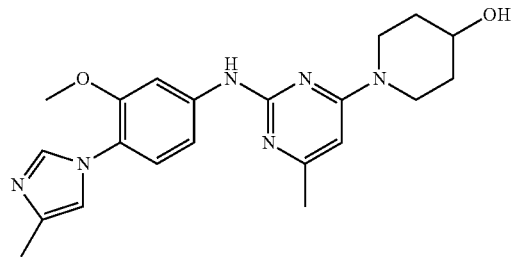 [SMILES: COc1cc(Nc2nc(C)cc(N3CCC(O)CC3)n2)ccc1-n1cnc(C)c1]

a) 1-(2-Chloro-6-methyl-pyrimidin-4-yl)-piperidin-4-ol

To a solution of 2,4-dichloro-6-methylpyrimidine (998 mg, 6.0 mmol) in tetrahydrofurane (30 mL) was added under stirring N,N-diisopropyl ethyl amine (853 mg, 6.6 mmol) and 4-hydroxypiperidine (681 mg, 6.6 mmol) and the reaction was stirred over night at 20° C. The solvent was evaporated under reduced pressure and the residue was taken up in water and extracted twice with diethyl ether. The combined organic layers were washed with brine, dried over sodium sulfate, filtered and evaporated under reduced pressure to dryness. The residue was purified by column chromatography on silica gel using heptane/ethyl acetate (1:1 v/v) as eluent to yield the title compound (779 mg, 57%) as white crystals. MS ISP (m/e): 228.2/230.2 (100/35) [(M+H)$^+$]. $^1$H NMR (DMSO- D$_6$, 300 MHz): δ (ppm)=6.73 (s, 1H), 4.78 (d, 1H), 3.95 (br m, 2H), 3.75 (m, 1H), 3.25 (m, 2H), 2.22 (s, 3H), 1.75 (m, 2H), 1.33 (m, 2H).

b) 1-{2-[3-Methoxy-4-(4-methyl-imidazol-1-yl)-phenylamino]-6-methyl-pyrimidin-4-yl}-piperidin-4-ol The title compound was prepared from 3-methoxy-4-(4-methyl-imidazol-1-yl)-phenylamine (41 mg, 0.20 mmol) and 1-(2-chloro-6-methyl-pyrimidin-4-yl)-piperidin-4-ol (50 mg, 0.22 mmol) in analogous manner as described in example 90. It was obtained in 82% yield as a light brown solid. MS ISP (m/e): 395.2 (100) [(M+H)$^+$]; $^1$H NMR (DMSO-D$_6$, 300 MHz): δ (ppm)=9.23 (s, 1H), 7.96 (s, 1H), 7.63 (s, 1H), 7.18 (m, 2H), 7.01 (s, 1H), 6.22 (s, 1H), 4.75 (d, 1H), 4.03 (br m, 2H), 3.78 (s, 3H), 3.75 (m, 1H), 3.23 (m, 2H), 2.20 (s, 3H), 2.14 (s, 3H), 1.76 (m, 2H), 1.32 (m, 2H).

Example 95

[3-Methoxy-4-(4-methyl-imidazol-1-yl)-phenyl]-(4-methyl-6-pyrrolidin-1-yl-pyrimidin-2-yl)-amine

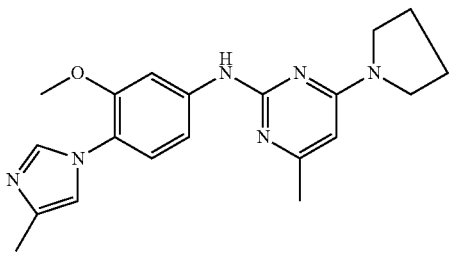 [SMILES: COc1cc(Nc2nc(C)cc(N3CCCC3)n2)ccc1-n1cnc(C)c1]

a) 2-Chloro-4-methyl-6-pyrrolidin-1-yl-pyrimidine

To a solution of 2,4-dichloro-6-methylpyrimidine (998 mg, 6.0 mmol) in tetrahydrofurane (30 mL) was added under stirring N,N-diisopropyl ethyl amine (853 mg, 6.6 mmol) and pyrrolidine (469 mg, 6.6 mmol) and the reaction was stirred over night at 20° C. The solvent was evaporated under reduced pressure and the residue was taken up in water and extracted twice with ethyl acetate. The combined organic layers were washed with brine, dried over sodium sulfate, filtered and evaporated under reduced pressure to dryness. The residue was purified by column chromatography on silica gel using heptane/ethyl acetate (9:1 to 7:3 v/v) as eluent to yield the title compound (694 mg, 58%) as white crystals. MS ISP (m/e): 198.1/200.1 (100/40) [(M+H)$^+$]. $^1$H NMR (DMSO-D$_6$, 300 MHz): δ (ppm)=6.35 (s, 1H), 3.44 (m, 2H), 3.30 (m, 2H), 2.29 (s, 3H), 1.94 (m, 4H).

In addition 4-chloro-2-methyl-6-pyrrolidin-1-yl-pyrimidine (89 mg, 8%) was obtained as colorless oil. MS ISP (m/e): 198.1/200.1 (100/39) [(M+H)$^+$]. $^1$H NMR (DMSO-D$_6$, 300 MHz): δ (ppm)=6.58 (s, 1H), 3.45 (m, 4H), 2.26 (s, 3H), 1.90 (m, 4H).

b) [3-Methoxy-4-(4-methyl-imidazol-1-yl)-phenyl]-(4-methyl-6-pyrrolidin-1-yl-pyrimidin-2-yl)-amine The title compound was prepared from 3-methoxy-4-(4-methyl-imidazol-1-yl)-phenylamine (61 mg, 0.30 mmol) and 2-chloro-4-methyl-6-pyrrolidin-1-yl-pyrimidine (65 mg, 0.33 mmol) in analogous manner as described in example 90. It was obtained in 91% yield as a light brown solid. MS ISP (m/e): 365.2 (100) [(M+H)$^+$]. $^1$H NMR (DMSO-D$_6$, 300 MHz): δ (ppm)=9.21 (s, 1H), 8.10 (s, 1H), 7.62 (s, 1H), 7.27 (d, 1H), 7.15 (d, 1H), 7.00 (s, 1H), 5.86 (s, 1H), 3.79 (s, 3H), 3.45 (br m, 4H), 2.19 (s, 3H), 2.14 (s, 3H), 1.94 (br m, 4H).

Example 96

[3-Methoxy-4-(4-methyl-imidazol-1-yl)-phenyl]-(4-methyl-6-morpholin-4-yl-pyrimidin-2-yl)-amine

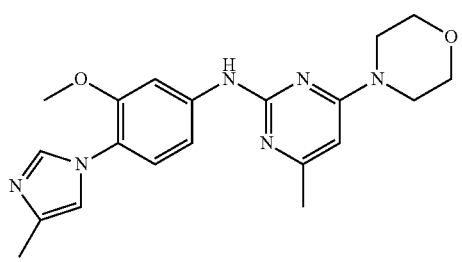 [SMILES: COc1cc(Nc2nc(C)cc(N3CCOCC3)n2)ccc1-n1cnc(C)c1]

a) 4-(2-Chloro-6-methyl-pyrimidin-4-yl)-morpholine

To a solution of 2,4-dichloro-6-methylpyrimidine (998 mg, 6.0 mmol) in tetrahydrofurane (30 mL) was added at 0° C. under stirring N,N-diisopropyl ethyl amine (853 mg, 6.6 mmol) and morpholine (627 mg, 6.6 mmol) and the reaction was stirred over night at 20° C. The solvent was evaporated under reduced pressure and the residue was taken up in water and extracted twice with ethyl acetate. The combined organic layers were washed with brine, dried over sodium sulfate, filtered and evaporated under reduced pressure to dryness. The residue was purified by column chromatography on silica gel using heptane/ethyl acetate (7:3 v/v) as eluent to yield the title compound (893 mg, 70%) as white crystals. MS ISP (m/e): 214.1/216.2 (100/34) [(M+H)$^+$]. $^1$H NMR (DMSO-D$_6$, 300 MHz): δ (ppm)=6.73 (s, 1H), 3.65 (m, 4H), 3.58 (m, 2H), 2.25 (s, 3H).

In addition 4-(2-chloro-6-methyl-pyrimidin-4-yl)-morpholine (304 mg, 24%) was obtained as white crystals. MS ISP (m/e): 214.2/216.2 (100/39) [(M+H)$^+$]. $^1$H NMR (DMSO-D$_6$, 300 MHz): δ (ppm)=6.68 (s, 1H), 3.65 (m, 8H), 2.28 (s, 3H).

b) [3-Methoxy-4-(4-methyl-imidazol-1-yl)-phenyl]-(4-methyl-6-morpholin-4-yl-pyrimidin-2-yl)-amine The title compound was prepared from 3-methoxy-4-(4-methyl-imidazol-1-yl)-phenylamine (61 mg, 0.30 mmol) and 4-(2-chloro-6-methyl-pyrimidin-4-yl)-morpholine (71 mg, 0.33 mmol) in analogous manner as described in example 90. The crude product was purified by stirring with diethyl ether. It was obtained in 87% yield as a light brown solid. MS ISP (m/e): 381.3 (100) [(M+H)$^+$]. $^1$H NMR (DMSO-D$_6$, 300 MHz): δ (ppm)=9.27 (s, 1H), 7.90 (s, 1H), 7.63 (s, 1H), 7.23 (d, 1H), 7.16 (d, 1H), 7.01 (s, 1H), 6.21 (s, 1H), 3.77 (s, 3H), 3.68 (m, 4H), 3.57 (m, 4H), 2.22 (s, 3H), 2.14 (s, 3H).

Example 97

[3-Methoxy-4-(4-methyl-imidazol-1-yl)-phenyl]-(4-methyl-6-piperidin-1-yl-pyrimidin-2-yl)-amine

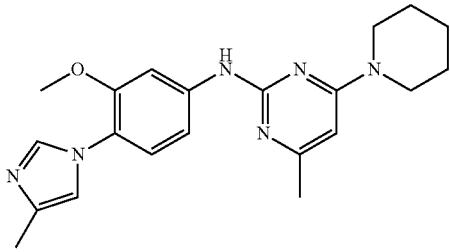 [SMILES: COc1cc(Nc2nc(C)cc(N3CCCCC3)n2)ccc1-n1cnc(C)c1]

a) 2-Chloro-4-methyl-6-piperidin-1-yl-pyrimidine

To a solution of 2,4-dichloro-6-methylpyrimidine (998 mg, 6.0 mmol) in tetrahydrofurane (30 mL) was added under stirring N,N-diisopropyl ethyl amine (853 mg, 6.6 mmol) and piperidine (613 mg, 6.6 mmol) and the reaction was stirred over night at 20° C. The solvent was evaporated under reduced pressure and the residue was taken up in water and extracted twice with ethyl acetate. The combined organic layers were washed with brine, dried over sodium sulfate, filtered and evaporated under reduced pressure to dryness. The residue was purified by column chromatography on silica gel using heptane/ethyl acetate (9:1 to 7:3 v/v) as eluent to yield the title compound (678 mg, 53%) as light yellow crystals. MS ISP (m/e): 212.1/214.3 (100/40) [(M+H)$^+$]. $^1$H NMR (DMSO-D$_6$, 300 MHz): δ (ppm)=6.70 (s, 1H), 3.58 (m, 4H), 2.22 (s, 3H), 1.61 (m, 2H), 1.51 (m, 4H).

In addition 4-chloro-2-methyl-6-piperidin-1-yl-pyrimidine (220 mg, 17%) was obtained as colorless oil. MS ISP (m/e): 212.1/214.1 (100/73) [(M+H)$^+$]. $^1$H NMR (DMSO-D$_6$, 300 MHz): δ (ppm)=6.57 (s, 1H), 3.70 (m, 4H), 2.23 (s, 3H), 1.61 (m, 2H), 1.50 (m, 4H).

b) [3-Methoxy-4-(4-methyl-imidazol-1-yl)-phenyl]-(4-methyl-6-piperidin-1-yl-pyrimidin-2-yl)-amine The title compound was prepared from 3-methoxy-4-(4-methyl-imidazol-1-yl)-phenylamine (61 mg, 0.30 mmol) and 2-chloro-4-methyl-6-piperidin-1-yl-pyrimidine (70 mg, 0.33 mmol) in analogous manner as described in example 90. The crude product was purified by stirring with diethyl ether. It was obtained in 78% yield as a light brown solid. MS ISP (m/e): 379.3 (100) [(M+H)$^+$]. $^1$H NMR (DMSO-D$_6$, 300 MHz): δ (ppm)=9.21 (s, 1H), 7.97 (s, 1H), 7.63 (s, 1H), 7.19 (d, 1H), 7.15 (d, 1H), 7.01 (s, 1H), 6.19 (s, 1H), 3.77 (s, 3H), 3.62 (m, 4H), 2.20 (s, 3H), 2.14 (s, 3H), 1.63 (m, 2H), 1.53 (m, 4H).

Example 98

[4-(1,1-Dioxo-6-thiomorpholin-4-yl)-6-methyl-pyrimidin-2-yl]-[3-methoxy-4-(4-methyl-imidazol-1-yl)-phenyl]-amine

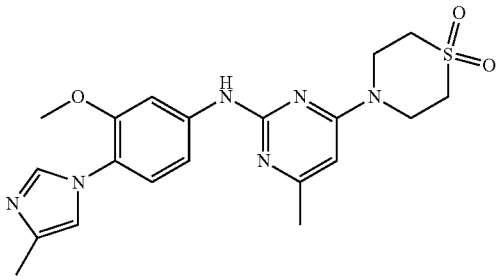 [SMILES: COc1cc(Nc2nc(C)cc(N3CCS(=O)(=O)CC3)n2)ccc1-n1cnc(C)c1]

a) 4-(2-Chloro-6-methyl-pyrimidin-4-yl)-thiomorpholine 1,1-dioxide

A mixture of 2,4-dichloro-6-methylpyrimidine (579 mg, 3.55 mmol), thiomorpholine-1,1-dioxide (480 mg, 3.55 mmol) and triethylamine (0.99 mL, 7.10 mmol) in 7 mL isopropanol was refluxed overnight. Water was added and the mixture of the regioisomers were extracted with ethyl acetate. Chromatography on on Si—NH$_2$ gel (Isolute) using cyclohexane/ethyl acetate(gradient 30 to 60% ethyl acetate) gave the title compound as a colourless solid (364 mg, 39%). MS ISP (m/e): 201.2 (33) [(M+H)$^+$]. $^1$H NMR (CDCl$_3$, 300 MHz): δ (ppm)=6.39 (s, 1H), 4.20 (t broad, 4H), 3.08 (t broad, 4H), 2.41 (s, 3H).

b) [4-(1,1-Dioxo-6-thiomorpholin-4-yl)-6-methyl-pyrimidin-2-yl]-[3-methoxy-4-(4-methyl-imidazol-1-yl)-phenyl]-amine Prepared in analogy to example 81b) from 3-methoxy-4-(4-methyl-imidazol-1-yl)-phenylamine and 4-(2-chloro-6-methyl-pyrimidin-4-yl)-thiomorpholine 1,1-dioxide, using potassium carbonate as a base. The title compound was isolated as a slightly yellow solid in a yield of 82%. MS ISP (m/e): 429.3 (100) [(M+H)$^+$]. $^1$H NMR (CDCl$_3$, 300 MHz): δ (ppm)=7.62 (s, 1H), 7.58 (d, 1H), 7.16 (d, 1H), 7.04 (dxd, 1H), 6.99 (s, 1H), 6.87 (s, 1H), 6.07 (s, 1H), 4.18 (t broad, 4H), 3.84 (s, 3H), 3.09 (t broad, 4H), 2.35 (s, 3H), 2.26 (s, 3H).

Example 99

({2-[3-Methoxy-4-(4-methyl-imidazol-1-yl)-phenylamino]-6-methyl-pyrimidin-4-yl}-methyl-amino)-acetic acid tert-butyl ester

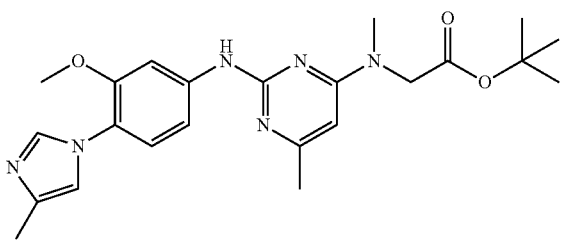 [SMILES: COc1cc(Nc2nc(C)cc(N(C)CC(=O)OC(C)(C)C)n2)ccc1-n1cnc(C)c1]

a) [(2-Chloro-6-methyl-pyrimidin-4-yl)-methyl-amino]-acetic acid tert-butyl ester Prepared in analogy to example 98a), using 2,4-dichloro-6-methylpyrimidine and sarcosine tert-butyl ester hydrochloride. The title compound was isolated as a slightly yellow oil in a yield of 52%. MS ISP (m/e): 272.2 & 274.0 (25 & 10) [(M+H)$^+$]. $^1$H NMR (CDCl$_3$, 300 MHz): δ (ppm)=6.23 (s broad, 1H), 4.21 (s broad, 2H), 3.10 (s broad, 3H), 2.36 (s, 3H), 1.46 (s, 9H).

b) ({2-[3-Methoxy-4-(4-methyl-imidazol-1-yl)-phenylamino]-6-methyl-pyrimidin-4-yl}-methyl-amino)-acetic acid tert-butyl ester Prepared in analogy to example 81b) from 3-methoxy-4-(4-methyl-imidazol-1-yl)-phenylamine and [(2-chloro-6-methyl-pyrimidin-4-yl)-methyl-amino]acetic acid tert-butyl ester, using potassium carbonate as a base. The title compound was isolated as a slightly yellow foam in a yield of 79%. MS ISP (m/e): 439.3 (100) [(M+H)$^+$]. $^1$H NMR (CDCl$_3$, 300 MHz): δ (ppm)=7.65 (s broad, 1H), 7.60 (d, 1H), 7.12 (d, 1H), 7.05-6.95 (m, 2H), 6.85 (s, 1H), 5.94 (s, 1H), 3.87 (s, 3H), 3.12 (s broad, 3H), 2.30 (s, 3H), 2.29 (s, 3H), 1.39 (s, 9H).

Example 100

1-({2-[3-Methoxy-4-(4-methyl-imidazol-1-yl)-phenylamino]-6-methyl-pyrimidin-4-yl}-methyl-amino)-2-methyl-propan-2-ol

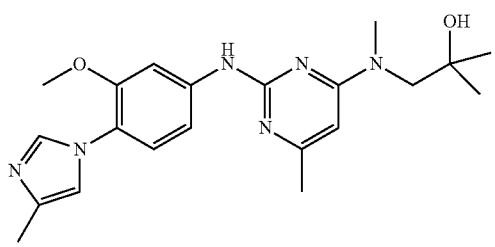 [SMILES: COc1cc(Nc2nc(C)cc(N(C)CC(C)(C)O)n2)ccc1-n1cnc(C)c1]

a) [(2-Chloro-6-methyl-pyrimidin-4-yl)-methyl-amino]acetic acid benzyl ester Prepared in analogy to example 98a), using 2,4-dichloro-6-methylpyrimidine and sarcosine-benzylester hydrochloride. The title compound was isolated as a slightly yellow oil in a yield of 62%. MS ISP (m/e): 306.1 & 308.2 (100 & 38) [(M+H)$^+$]. $^1$H NMR (CDCl$_3$, 300 MHz): δ (ppm)=7.40-7.35 (m, 5H), 6.23 (s broad, 1H), 5.19 (s, 2H), 4.39 (s broad, 2H), 3.11 (s broad, 3H), 2.36 (s, 3H).

b) ({2-[3-Methoxy-4-(4-methyl-imidazol-1-yl)-phenylamino]-6-methyl-pyrimidin-4-yl}-methyl-amino)-acetic acid benzyl ester Prepared in analogy to example 81b) from 3-methoxy-4-(4-methyl-imidazol-1-yl)-phenylamine and [(2-chloro-6-methyl-pyrimidin-4-yl)-methyl-amino]acetic acid benzyl ester, using potassium carbonate as a base. The title compound was isolated as a colorless solid in a yield of 56%. MS ISP (m/e): 473.3 (100) [(M+H)$^+$]. $^1$H NMR (CDCl$_3$, 300 MHz): δ (ppm)=7.58 (s, 1H), 7.54 (s broad, 1H), 7.35-7.20 (m, 4H), 7.10-6.95 (m, 2H), 6.89 (s broad, 1H), 6.82 (s, 1H), 5.95 (s, 1H), 5.16 (s, 2H), 4.39 (s broad, 2H), 3.80 (s, 3H), 3.14 (s, 3H), 2.31 (s, 3H), 2.30 (s, 3H).

c) 1-({2-[3-Methoxy-4-(4-methyl-imidazol-1-yl)-phenylamino]-6-methyl-pyrimidin-4-yl}-methyl-amino)-2-methyl-propan-2-ol A solution of ({2-[3-methoxy-4-(4-methyl-imidazol-1-yl)-phenylamino]-6-methyl-pyrimidin-4-yl}-methyl-amino)-acetic acid benzyl ester (32 mg, 0.07 mmol) in 2 mL of tetrahydrofurane was cooled in an ice-bath and treated with a 3 molar solution of methyl magnesium chloride in tetrahydrofurane (0.15 mL, 1.5 mmol). The mixture was stirred for 10 minutes in the ice-bath and for additional 2 hours at 20° C. Hydrolysis and extraction with ethyl acetate gave the title compound as a yellowish sticky gum (27 mg, 100%). MS ISP (m/e): 397.3 (100) [(M+H)$^+$]. $^1$H NMR (CDCl$_3$, 300 MHz): δ (ppm)=7.62 (s, 1H), 7.52 (s, 1H), 7.37 (d, 1H), 7.30-7.10 (m, 2H), 6.86 (s, 1H), 5.98 (s, 1H), 3.834 (s, 3H), 3.62 (s, 2H), 3.19 (s, 3H), 2.33 (s, 3H), 2.29 (s, 3H), 1.25 (s, 6H).

Example 101

2-{2-[3-Methoxy-4-(4-methyl-imidazol-1-yl)-phenylamino]-pyrimidin-4-ylamino}-ethanol

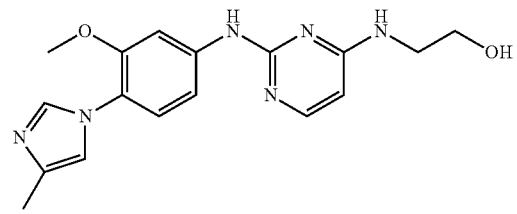 [SMILES: COc1cc(Nc2nccc(NCCO)n2)ccc1-n1cnc(C)c1]

a) 2-(2-Chloro-pyrimidin-4-ylamino)-ethanol

Prepared in analogy to example 98a), using 2,4-dichloropyrimidine and ethanolamine. The title compound was isolated as a colorless solid in a yield of 16%. MS ISP (m/e): 174.3 & 172.1 (100 & 40) [(M+H)$^+$]. $^1$H NMR (DMSO-D$_6$, 300 MHz): δ (ppm)=7.90 (s broad, 1H), 7.84 (d, 1H), 6.48 (d, 1H), 4.77 (t, 1H), 3.52 (qa, 2H), 3.26 (qa broad, 2H).

b) 2-{2-[3-Methoxy-4-(4-methyl-imidazol-1-yl)-phenylamino]-pyrimidin-4-ylamino}-ethanol Prepared in analogy to example 81b) from 3-methoxy-4-(4-methyl-imidazol-1-yl)-phenylamine and 2-(2-chloro-pyrimidin-4-ylamino)-ethanol, using potassium carbonate as a base. The title compound was isolated as a slightly orange solid in a yield of 23%. MS ISP (m/e): 341.2 (100) [(M+H)$^+$]. $^1$H NMR (DMSO-D$_6$, 300 MHz): δ (ppm)=9.14 (s, 1H), 7.91 (s broad, 1H), 7.82 (d broad, 1H), 7.63 (s, 1H), 7.33 (d broad, 1H), 7.25 (s broad, 1H), 7.15 (d, 1H), 7.01 (s, 1H), 6.00 (d, 1H), 4.74 (t, 1H), 3.78 (s, 3H), 3.55 (qa, 2H), 3.50-3.35 (m, 2H), 2.14 (s, 3H).

Example 102

2-{2-[3-Methoxy-4-(4-methyl-imidazol-1-yl)-phenylamino]-pyrimidin-4-ylamino}-2-methyl-propan-1-ol

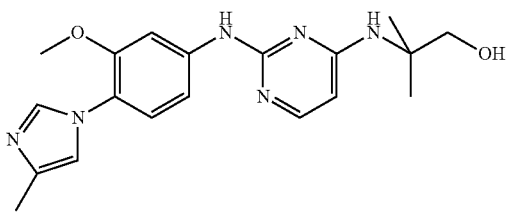 [SMILES: COc1cc(Nc2nccc(NC(C)(C)CO)n2)ccc1-n1cnc(C)c1]

a) 2-(2-Chloro-pyrimidin-4-ylamino)-2-methyl-propan-1-ol

Prepared in analogy to example 98a), using 2,4-dichloropyrimidine and 2-amino-2-methylpropan-1-ol. The title compound was isolated as a yellowish solid in a yield of 19%. MS ISP (m/e): 200.3 (100) [(M+H)$^+$]. $^1$H NMR (DMSO-D$_6$, 300 MHz): δ (ppm)=7.84 (d, 1H), 7.49 (s, 1H), 6.50 (d, 1H), 4.85 (s, 1H), 3.53 (d, 2H), 1.29 (s, 6H).

b) 2-{2-[3-Methoxy-4-(4-methyl-imidazol-1-yl)-phenylamino]-pyrimidin-4-ylamino}-2-methyl-propan-1-ol Prepared in analogy to example 81b) from 3-methoxy-4-(4-methyl-imidazol-1-yl)-phenylamine and 2-(2-chloro-pyrimidin-4-ylamino)-2-methyl-propan-1-ol, using potassium carbonate as a base. The title compound was isolated as a slightly orange solid in a yield of 62%. MS ISP (m/e): 369.2 (100) [(M+H)$^+$]. $^1$H NMR (DMSO-D$_6$, 300 MHz): δ (ppm)=7.91 (d, 1H), 7.62 (d, 1H), 7.43 (d, 1H), 7.20-7.10 (m, 2H), 6.87 (s, 1H), 6.79 (s, 1H), 5.88 (d, 1H), 4.74 (s, 1H), 3.84 (s, 3H), 3.69 (s, 2H), 2.29 (s, 3H), 1.42 (s, 6H).

Example 103

[4-(4-Methanesulfonyl-piperazin-1-yl)-6-methyl-pyrimidin-2-yl]-[3-methoxy-4-(4-methyl-imidazol-1-yl)-phenyl]-amine

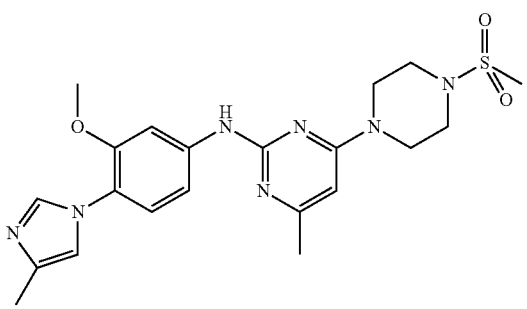 [SMILES: COc1cc(Nc2nc(C)cc(N3CCN(S(C)(=O)=O)CC3)n2)ccc1-n1cnc(C)c1]

a) 4-Chloro-2-(4-methanesulfonyl-piperazin-1-yl)-6-methyl-pyrimidine

Prepared in analogy to example 98a), using 2,4-dichloro-6-methylpyrimidine and 1-methanesulfonyl-piperazine. The title compound was isolated as a yellow solid in a yield of 41%. MS ISP (m/e): 291.1 (100) [(M+H)$^+$]. $^1$H NMR (DMSO-D$_6$, 300 MHz): δ (ppm)=6.81 (s, 1H), 3.80-3.70 (m, 4H), 3.20-3.15 (m, 4H), 2.90 (s, 3H), 2.26 (s, 3H).

b) [4-(4-Methanesulfonyl-piperazin-1-yl)-6-methyl-pyrimidin-2-yl]-[3-methoxy-4-(4-methyl-imidazol-1-yl)-phenyl]-amine Prepared in analogy to example 81b) from 3-methoxy-4-(4-methyl-imidazol-1-yl)-phenylamine and 4-chloro-2-(4-methanesulfonyl-piperazin-1-yl)-6-methyl-pyrimidine. The title compound was isolated as a yellowish solid in a yield of 4%. MS ISP (m/e): 458.3 (100) [(M+H)$^+$]. $^1$H NMR (DMSO-D$_6$, 300 MHz): δ (ppm)=9.32 (s, 1H), 7.90 (s, 1H), 7.63 (d, 1H), 7.24 (d, 1H), 7.18 (d, 1H), 7.01 (s, 1H), 6.28 (s, 1H), 3.78 (s, 3H), 3.80-3.70 (m, 4H), 3.19 (t, 4H), 2.91 (s, 3H), 2.23 (s, 3H), 2.14 (s, 3H).

Example 104

2-({2-[3-Methoxy-4-(4-methyl-imidazol-1-yl)-phenylamino]-6-methyl-pyrimidin-4-yl}-methyl-amino)-ethanol

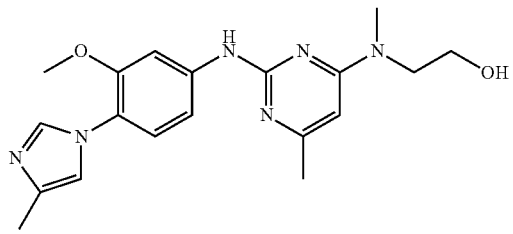 [SMILES: COc1cc(Nc2nc(C)cc(N(C)CCO)n2)ccc1-n1cnc(C)c1]

a) 2-[(2-Chloro-6-methyl-pyrimidin-4-yl)-methyl-amino]-ethanol

Prepared in analogy to example 98a), using 2,4-dichloro-6-methylpyrimidine and 2-(methylamino)ethanol. The title compound was isolated as a yellowish oil in a yield of 61%. MS ISP (m/e): 202.2 (100) [(M+H)$^+$]. $^1$H NMR (CDCl$_3$, 300 MHz): δ (ppm)=6.22 (s, 1H), 3.86 (t, 2H), 3.70-3.60 (m, 2H), 3.11 (s, 3H), 2.70 (s very broad, 1H), 2.34 (s, 3H).

b) 2-({2-[3-Methoxy-4-(4-methyl-imidazol-1-yl)-phenylamino]-6-methyl-pyrimidin-4-yl}-methyl-amino)-ethanol Prepared in analogy to example 81b) from 3-methoxy-4-(4-methyl-imidazol-1-yl)-phenylamine and 2-[(2-chloro-6-methyl-pyrimidin-4-yl)-methyl-amino]ethanol. The title compound was isolated as a colorless solid in a yield of 57%. MS ISP (m/e): 369.2 (100) [(M+H)$^+$]. $^1$H NMR (CDCl$_3$, 300 MHz): δ (ppm)=7.70 (d, 1H), 7.60 (s, 1H), 7.11 (d, 1H), 7.05-6.90 (m, 2H), 6.85 (s, 1H), 5.92 (s, 1H), 3.95-3.80 (m, 2H), 3.84 (s, 3H), 3.80-3.70 (m, 2H), 3.12 (s, 3H), 2.31 (s, 3H), 2.29 (s, 3H).

Example 105

2-{2-[3-Methoxy-4-(4-methyl-imidazol-1-yl)-phenylamino]-6-piperidin-1-yl-pyrimidin-4-yl}-propan-2-ol

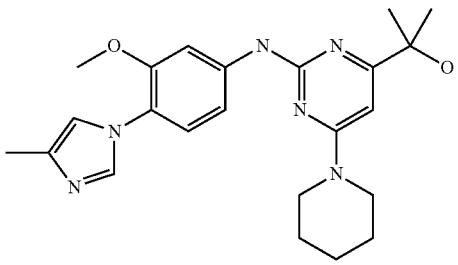 [SMILES: COc1cc(Nc2nc(N3CCCCC3)cc(C(C)(C)O)n2)ccc1-n1cnc(C)c1]

a) 2-(2-Chloro-6-piperidin-1-yl-pyrimidin-4-yl)-propan-2-ol

Using in analogous manner the procedure described in example 88b), but replacing ethyl 2-chloro-6-ethoxy-pyrimidine-4-carboxylate by methyl 2-chloro-6-piperidin-1-yl-pyrimidine-4-carboxylate (511 mg, 2.0 mmol), the title compound was obtained as light yellow solid (144 mg, 26%). MS ISP (m/e): 256.2 [(M+H)⁺]. ¹H NMR (CDCl₃, 300 MHz): δ (ppm)=6.47 (s, 1H), 3.64 (m, 4H), 3.44 (s, 1H), 1.63 (m, 6H), 1.50 (s, 6H).

b) 2-{2-[3-Methoxy-4-(4-methyl-imidazol-1-yl)-phenylamino]-6-piperidin-1-yl-pyrimidin-4-yl}-propan-2-ol Using in analogous manner the procedure described in example 88c), but replacing 2-(2-chloro-6-ethoxy-pyrimidin-4-yl)-propan-2-ol by 2-(2-chloro-6-piperidin-1-yl-pyrimidin-4-yl)-propan-2-ol (26 mg, 0.1 mmol), the title compound was obtained as light yellow foam (5 mg, 12%). MS ISP (m/e): 423.3 [(M+H)⁺]. ¹H NMR (CDCl₃, 300 MHz): δ (ppm)=7.67 (d, 1H), 7.64 (s, 1H), 7.18 (d, 1H), 7.11 (s, 1H), 7.02 (dd, 1H), 6.88 (s, 1H), 6.27 (s, 1H), 4.43 (q, 2H), 4.10 (br s, 1H), 2.30 (s, 3H), 1.51 (s, 6H), 1.42 (t, 3H).

Example 106

2-{2-[3-Methoxy-4-(4-methyl-imidazol-1-yl)-phenylamino]-6-pyrrolidin-1-yl-pyrimidin-4-yl}-propan-2-ol

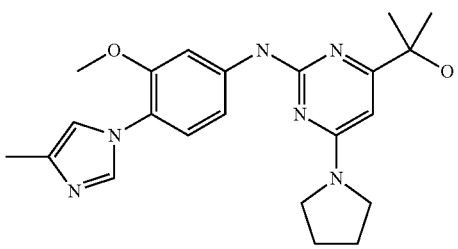 [SMILES: COc1cc(Nc2nc(N3CCCC3)cc(C(C)(C)O)n2)ccc1-n1cnc(C)c1]

a) Methyl 2-chloro-6-pyrrolidin-1-yl-pyrimidine-4-carboxylate

A mixture of methyl 2,4-dichloropyrimidine-6-carboxylate (1.66 g, 8.0 mmol), pyrrolidine (0.66 mL, 8 mmol) and sodium carbonate (1.54 g, 14.0 mmol) in methanol (8 mL) was stirred for 1 h at 20° C. The mixture was partitioned between ethyl acetate and water, and the organic layer was subsequently washed with brine, dried over sodium sulfate and evaporated under reduced pressure to give crude title compound (0.78 g, 40%) as light yellow solid. MS ISP (m/e): 242.2 [(M+H)⁺].

b) 2-(2-Chloro-6-pyrrolidin-1-yl-pyrimidin-4-yl)-propan-2-ol

Using in analogous manner the procedure described in example 88b), but replacing ethyl 2-chloro-6-ethoxy-pyrimidine-4-carboxylate by methyl 2-chloro-6-pyrrolidin-1-yl-pyrimidine-4-carboxylate (773 mg, 3.2 mmol), the title compound was obtained as light yellow solid (584 mg, 76%). MS ISP (m/e): 242.2 [(M+H)⁺]. ¹H NMR (CDCl₃, 300 MHz): δ (ppm)=6.24 (s, 1H), 3.64 (m, 2H), 3.56 (s, 1H), 3.37 (m, 2H), 2.04 (m, 4H), 1.50 (s, 6H).

c) 2-{2-[3-Methoxy-4-(4-methyl-imidazol-1-yl)-phenylamino]-6-pyrrolidin-1-yl-pyrimidin-4-yl}-propan-2-ol Using in analogous manner the procedure described in example 88c), but replacing 2-(2-chloro-6-ethoxy-pyrimidin-4-yl)-propan-2-ol by 2-(2-chloro-6-pyrrolidin-1-yl-pyrimidin-4-yl)-propan-2-ol (120 mg, 0.5 mmol), the title compound was obtained as light yellow foam (16 mg, 8%). MS ISP (m/e): 409.3 [(M+H)⁺]. ¹H NMR (CDCl₃, 300 MHz): δ (ppm)=7.82 (d, 1H), 7.62 (s, 1H), 7.14 (d, 1H), 7.02 (dd, 1H), 6.98 (s, 1H), 6.87 (s, 1H), 5.86 (s, 1H), 4.46 (br s, 1H), 3.86 (s, 3H), 3.3-3.8 (m, 4H), 2.30 (s, 3H), 2.05 (m, 4H), 1.57 (s, 6H).

Example 107

1-{2-[3-Methoxy-4-(4-methyl-imidazol-1-yl)-phenylamino]-pyrimidin-4-yl}-piperidin-4-ol

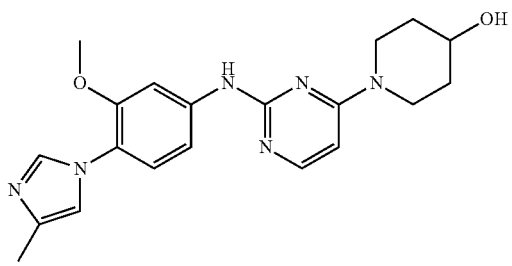 [SMILES: COc1cc(Nc2nccc(N3CCC(O)CC3)n2)ccc1-n1cnc(C)c1]

The title compound was prepared from 1-(2-chloropyrimidin-4-yl)-4-piperidinol (120 mg, 0.534 mmol) and 3-methoxy-4-(4-methyl-imidazol-1-yl)-phenylamine (109 mg, 0534 mmol) using in analogous manner the procedure described in example 43b). Obtained after trituration in dichloromethane/methanol (19:1 v/v) as a white solid (117 mg, 57%). MS ISP (m/e): 381.1 [(M+¹⁻¹)⁺]. ¹H NMR (DMSO-D₆, 300 MHz): δ (ppm)=9.24 (s, 1H), 7.97 (d, 1H), 7.84 (d, 1H), 7.63 (s, 1H), 7.26 (dd, 1H), 7.18 (d, 1H), 7.03 (s, 1H), 6.31 (d, 1H), 4.77 (d, 1H), 4.07 (m broad, 2H), 3.78 (s, 3H), 3.77 (m, 1H), 3.25 (m broad, 2H), 2.14 (s, 3H), 1.78 (m broad, 2H), 1.36 (m broad, 2H). Mp 197-200° C.

Example 108

[4-Butyl-6-(4-chloro-phenyl)-pyrimidin-2-yl]-[3-methoxy-4-(4-methyl-imidazol-1-yl)-phenyl]-amine

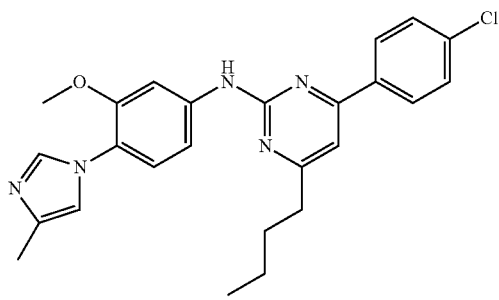 [SMILES: CCCCc1cc(-c2ccc(Cl)cc2)nc(Nc2ccc(-n3cnc(C)c3)c(OC)c2)n1]

A suspension of N-[3-Methoxy-4-(4-methyl-imidazol-1-yl)-phenyl]-guanidine dinitrate (153 mg, 0.41 mmol), 1-(4-chloro-phenyl)-hept-2-yn-1-one (100 mg, 0.45 mmol, CAS 105363-17-5) and sodium methanolat (120 mg, 1.24 mmol) in acetonitrile (2.0 mL) was heated two times to 120° C. for 30 minutes in a microwave oven. Water was added and the reaction was extracted twice with ethyl acetate. The combined organic layers were dried over sodium sulfate, filtered and the solvent was evaporated. The residue was purified by column chromatography on silica gel using dichloromethane/methanol (9:1 v/v) as eluent to yield the title compound as a yellow solid (30 mg, 16%). MS ISP (m/e): 448.3/450.1 (100/37) [(M+H)$^+$]. $^1$H NMR (CDCl$_3$, 300 MHz): δ (ppm)=8.04 (d, 2H), 7.98 (s, 1H), 7.64 (s, 1H), 7.46 (d, 2H), 7.29 (s, 1H), 7.18 (d, 1H), 7.04 (d, 1H), 6.89 (s, 1H), 3.89 (s, 3H), 2.74 (t, 2H), 2.31 (, 3H), 1.79 (m, 2H), 1.43 (m, 2H), 0.98 (t, 3H).

Example 109

[3-Methoxy-4-(4-methyl-imidazol-1-yl)-phenyl]-(4-phenyl-pyrimidin-2-yl)-amine

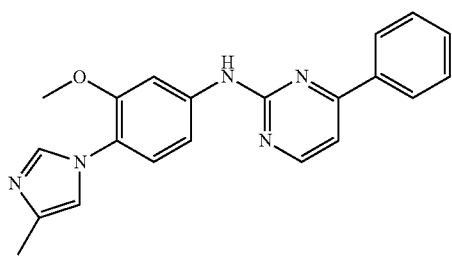

A solution of N-[3-methoxy-4-(4-methyl-imidazol-1-yl)-phenyl]-guanidine dinitrate (249 mg, 0.67 mmol), 3-(dimethylamino)-1-phenyl-2-propen-1-one (141 mg, 0.80 mmol, CAS 1131-80-2) and triethyl amine (187 uL. 1.34 mmol) in ethanol (4 mL) was heated to 160° C. for 1 hour in a microwave oven. The solvent was evaporated under reduced pressure and the residue purified by column chromatography on silica using methylenechloride and dichloromethane/methanol (19:1 v/v) as eluent to yield the title compound a a yellow solid (67 mg, 28%). MS ISP (m/e): 358.2 (100) [(M+H)$^+$]. $^1$H NMR (DMSO-D$_6$, 300 MHz): δ (ppm)=9.90 (s, 1H), 8.60 (s, 1H), 8.20 (br s, 2H), 7.99 (s, 1H), 7.68 (s, 1H), 7.43-7.56 (m, 5H), 7.26 (t, 1H), 7.06 (s, 1H), 3.84 (s, 3H), 2.15 (s, 3H).

Example 110

[5-(3,4-Dichloro-phenyl)-4-methyl-pyrimidin-2-yl]-[3-methoxy-4-(4-methyl-imidazol-1-yl)-phenyl]-amine

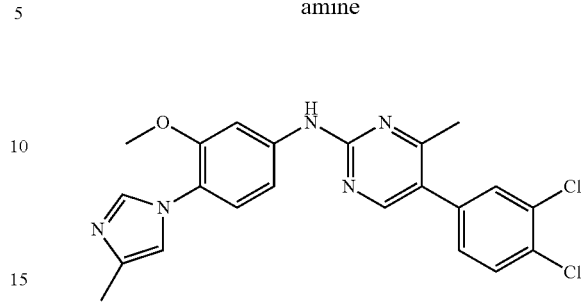

a) (E/Z)-3-(3,4-Dichloro-phenyl)-4-dimethylamino-but-3-en-2-one

A mixture of 1-(3,4-dichlorophenyl)propan-2-one (1.0 g, 4.93 mmol) and N,N-dimethylformamide dimethyl acetal (1.64 mL, 12.3 mmol) was heated overnight at 130° C. The resulting solution was concentrated, treated with diethyl ether and filtered to yield the crude title product as a brownish solid. MS ISP (m/e): 258.0 & 260.1 (100 & 68) [(M+H)$^+$].

b) [5-(3,4-Dichloro-phenyl)-4-methyl-pyrimidin-2-yl]-[3-methoxy-4-(4-methyl-imidazol-1-yl)-phenyl]-amine A solution of N-[3-methoxy-4-(4-methyl-imidazol-1-yl)-phenyl]-guanidine dinitrate (100 mg, 0.27 mmol; see Example 4b), (E/Z)-3-(3,4-dichloro-phenyl)-4-dimethylamino-but-3-en-2-one (156 mg, 0.60 mmol) and triethylamine (0.19 mL, 1.34 mmol) in 5 mL of ethanol was refluxed for 28 hours. The mixture was diluted with water, extracted with ethyl acetate and the product purified by chromatography on silica gel using ethyl acetate as a solvent. The product was isolated as a yellow solid (3 mg, 3%). MS ISP (m/e): 440.1 (100) [(M+H)$^+$]. $^1$H NMR (CDCl$_3$, 300 MHz): δ (ppm)=9.65 (s very broad, 1H), 8.38 (s, 1H), 8.20 (s, 1H), 7.50-6.90 (m, 5H), 6.92 (s, 1H), 3.85 (s, 3H), 2.40 (s, 3H), 2.38 (s, 3H).

Example 111

[3-Methoxy-4-(4-methyl-imidazol-1-yl)-phenyl]-(4-thiazol-2-yl-pyrimidin-2-yl)-amine

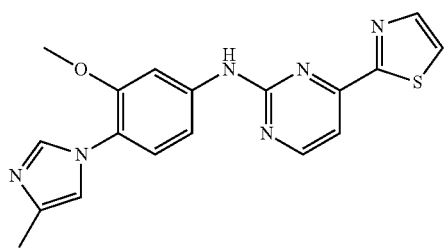 [SMILES: COc1cc(Nc2nccc(-c3nccs3)n2)ccc1-n1cnc(C)c1]

a) (E/Z)-3-Dimethylamino-1-thiazol-2-yl-propenone

A mixture of 2-acetylthiazole (145 mg, 1.14 mmol) and tert-butoxy-bis(dimethylamino)methane (0.33 mL, 1.59 mmol) was heated for 2 hours at 130° C. The mixture was concentrated in vacuo to give the crude title compound (160 mg; 93%) as a brownish gum. MS ISP (m/e): 183.0 (100).

b) [3-Methoxy-4-(4-methyl-imidazol-1-yl)-phenyl]-(4-thiazol-2-yl-pyrimidin-2-yl)-amine A solution of N-[3-methoxy-4-(4-methyl-imidazol-1-yl)-phenyl]-guanidine dinitrate (75 mg, 0.22 mmol; see Example 4b), (E/Z)-3-dimethylamino-1-thiazol-2-yl-propenone (160 mg, 0.88 mmol) and triethylamine (0.12 mL, 0.87 mmol) in 5 mL of ethanol was heated in the microwave oven for 1.5 hours at 100° C. The mixture was diluted with water, extracted with ethyl acetate and the product purified by chromatography on silica gel using a mixture of heptane/ethyl acetate 2:8 v/v as a solvent. The product was isolated as a yellow solid (10 mg, 12%).
MS ISP (m/e): 365.1 (100) [(M+H)$^+$]. $^1$H NMR (CDCl$_3$, 300 MHz): δ (ppm)=8.59 (d; 1H), 8.02 (d, 1H), 7.84 (d, 1H), 7.77 (s, 1H), 7.62 (d, 1H), 7.57 (d, 1H), 7.35 (s, 1H), 7.22 (d, 1H), 7.10 (dxd; 1H), 6.91 (s, 1H), 3.97 (s, 3H), 2.34 (s, 3H).

Example 112

5-(4,6-Dimethyl-pyrimidin-2-ylamino)-2-(4-methyl-imidazol-1-yl)-benzonitrile

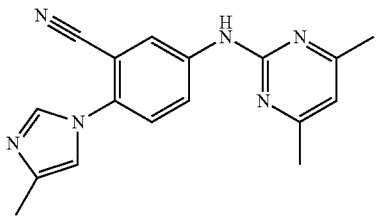 [SMILES: Cc1cn(-c2ccc(Nc3nc(C)cc(C)n3)cc2C#N)cn1]

a) 5-Bromo-2-(4-methyl-imidazol-1-yl)-benzonitrile

This compound was prepared from 5-bromo-2-fluorobenzonitrile and 4-methylimidazole, as described in US2006/0004013.

b) 5-(4,6-Dimethyl-pyrimidin-2-ylamino)-2-(4-methyl-imidazol-1-yl)-benzonitrile

A mixture of 5-bromo-2-(4-methyl-imidazol-1-yl)-benzonitrile (200 mg, 0.76 mmol), 2-amino-4,6-dimethyl-pyrimidine (141 mg, 1.14 mmol), sodium phenoxide (266 mg, 2.29 mmol), tris(dibenzylideneacetone)dipalladium chloroform complex (21 mg, 0.02 mmol) and 4,5-bis(diphenylphosphino)-9,9-dimethylxanthene=xanthphos (26 mg, 0.04 mmol) in 5 mL of dioxane was heated to 80° C. under argon for 2 hours. The mixture was diluted with water, extracted with ethyl acetate and the product purified by by chromatography on silica gel using dichloromethane/methanol 9:1 v/v as an eluent. The title compound was obtained as a colorless solid (144 mg, 62%). MS ISP (m/e): 305.1 (100) [(M+H)$^+$]. $^1$H NMR (DMSO-D$_6$, 300 MHz): 8 (ppm)=10.08 (s, 1H), 8.44 (s, 1H), 8.15 (d, 1H), 7.89 (s, 1H), 7.55 (d, 1H), 7.25 (s, 1H), 6.76 (s, 1H), 2.36 (s, 6H), 2.18 (s, 3H).

Example 113

5-[4-(4-Chloro-phenyl)-pyrimidin-2-ylamino]-2-(4-methyl-imidazol-1-yl)-benzonitrile

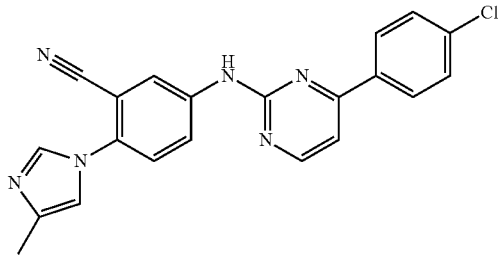 [SMILES: Cc1cn(-c2ccc(Nc3nccc(-c4ccc(Cl)cc4)n3)cc2C#N)cn1]

Prepared in analogy to example 112b) from 5-bromo-2-(4-methyl-imidazol-1-yl)-benzonitrile and 4-(4-chloro-phenyl)-pyrimidin-2-ylamine. The title compound was obtained as a colorless solid (Yield=35%). MS ISP (m/e): 387.2 (100) [(M+H)$^+$]. $^1$H NMR (DMSO-D$_6$, 300 MHz): δ (ppm)=10.31 (s, 1H), 8.69 (d, 1H), 8.47 (s, 1H), 8.25-8.15 (m, 3H), 7.97 (s, 1H), 7.55-7.50 (m, 3H), 7.57 (d, 1H), 7.29 (s, 1H), 2.20 (s, 3H).

Examples 114-138

Using in analogous manner the procedure described in example 28a), 1-(4-trifluoromethyl-phenyl)-propan, 1-(4-trifluoromethyl-phenyl)-butan-1-one, 1-(3,4,5-trifluoro-phenyl)-ethanone, 1-(2,5-dichloro-phenyl)-ethanone, 1-(3,4-dichloro-phenyl)-ethanone, 1-(2,4-dichloro-phenyl)-ethanone, 1-(4-chloro-3-methyl-phenyl)-ethanone, 1-(4-chloro-phenyl)-pentan-1-one, 1-(4-chloro-phenyl)-2-methoxy-ethanone, 1-(3,5-dimethyl-pyrazin-2-yl)-ethanone, 3-methyl-butan-2-one, 3,3-dimethyl-butan-2-one, 1-methoxy-propan-2-one, acetic acid 2-oxo-propyl ester, 3-hydroxy-butan-2-one, 3-hydroxy-3-methyl-butan-2-one, 1-cyclopentyl-propan-2-one, 1-cyclopropyl-ethanone, 1-cyclopentyl-ethanone, 1-cyclohexyl-propan-1-one, ethyl 3-oxo-4-phenyl-butyrate, ethyl 7-methyl-3-oxo-oct-6-enoate, 6-methyl-1-phenyl-hept-5-en-2-one, ethyl 2-oxo-propionate, and 6-acetyl-4H-benzo[1,4]oxazin-3-one, were reacted with tert.-butoxy-bis-(dimethylamino)-methane, respectively, and the resulting products were subsequently reacted with N-[3-methoxy-4-(4-methyl-imidazol-1-yl)-phenyl]-guanidine dinitrate operating in analogous manner as described in example 39b) to afford the following compounds:

Example 114

[3-Methoxy-4-(4-methyl-imidazol-1-yl)-phenyl]-[5-methyl-4-(4-trifluoromethyl-phenyl)-pyrimidin-2-yl]-amine

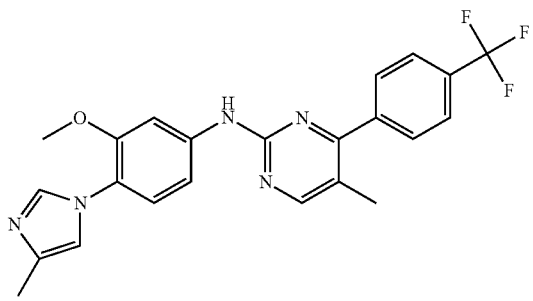 [SMILES: COc1cc(Nc2ncc(C)c(-c3ccc(C(F)(F)F)cc3)n2)ccc1-n1cnc(C)c1]

Obtained in 42% yield as light yellow solid. MS ISP (m/e): 440.3 [(M+H)⁺]. $^1$H NMR (CDCl$_3$, 300 MHz): δ (ppm)=8.40 (s, 1H), 7.74-7.80 (m, 5H), 7.62 (s, 1H), 7.23 (s, 1H), 7.17 (d, 1H), 7.06 (dd, 1H), 6.87 (s, 1H), 3.82 (s, 3H), 2.30 (s, 3H), 2.29 (s, 3H).

Example 115

[5-Ethyl-4-(4-trifluoromethyl-phenyl)-pyrimidin-2-yl]-[3-methoxy-4-(4-methyl-imidazol-1-yl)-phenyl]-amine

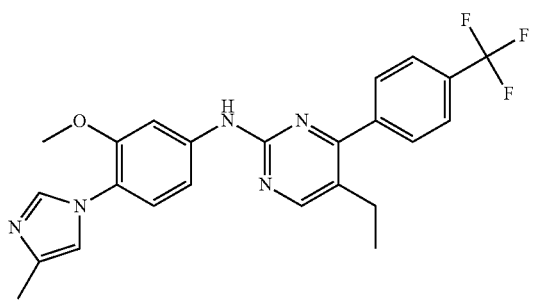 [SMILES: CCc1cnc(Nc2ccc(-n3cnc(C)c3)c(OC)c2)nc1-c1ccc(C(F)(F)F)cc1]

Obtained in 53% yield as light yellow solid. MS ISP (m/e): 454.3 [(M+H)⁺]. $^1$H NMR (CDCl$_3$, 300 MHz): δ (ppm)=8.45 (s, 1H), 7.77 (d, 1H), 7.75 and 7.70 (2 d, 2×2H), 7.62 (s, 1H), 7.22 (s, 1H), 7.16 (d, 1H), 7.05 (dd, 1H), 6.86 (s, 1H), 3.81 (s, 3H), 2.64 (q, 2H), 2.30 (s, 3H), 1.65 (t, 3H).

Example 116

[3-Methoxy-4-(4-methyl-imidazol-1-yl)-phenyl]-[4-(3,4,5-trifluoro-phenyl)-pyrimidin-2-yl]-amine

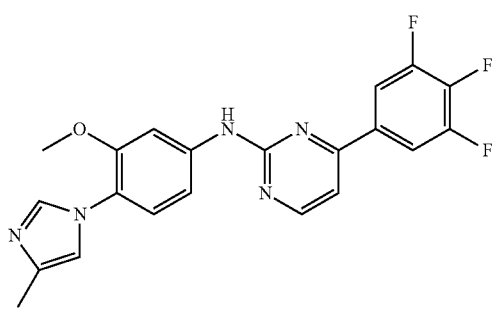 [SMILES: COc1cc(Nc2nccc(-c3cc(F)c(F)c(F)c3)n2)ccc1-n1cnc(C)c1]

Obtained in 7% yield as yellow solid. MS ISP (m/e): 412.2 [(M+H)⁺]. $^1$H NMR (CDCl$_3$, 300 MHz): δ (ppm)=8.55 (d, 1H), 7.78 (d, 1H), 7.73-7.78 (m, 2H), 7.66 (s, 1H), 7.32 (s, 1H), 7.22 (s, 1H), 7.12 (d, 1H), 7.09 (dd, 1H), 6.90 (s, 1H), 3.91 (s, 3H), 2.31 (s, 3H).

Example 117

[4-(2,5-Dichloro-phenyl)-pyrimidin-2-yl]-[3-methoxy-4-(4-methyl-imidazol-1-yl)-phenyl]-amine

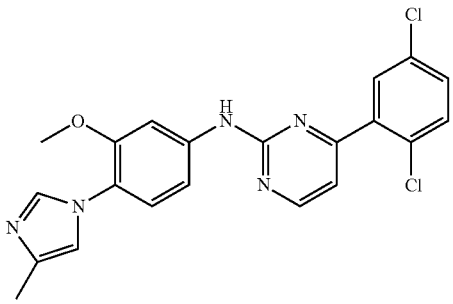 [SMILES: COc1cc(Nc2nccc(-c3cc(Cl)ccc3Cl)n2)ccc1-n1cnc(C)c1]

Obtained in 36% yield as light yellow solid. MS ISP (m/e): 426.1 [(M+H)⁺]. $^1$H NMR (CDCl$_3$, 300 MHz): δ (ppm)=8.55 (d, 1H), 7.92 (d, 1H), 7.73 (d, 1H), 7.63 (s, 1H), 7.45 (d, 1H), 7.37 (dd, 1H), 7.35 (s, 1H), 7.21 (d, 1H), 7.19 (d, 1H), 7.00 (dd, 1H), 6.88 (s, 1H), 3.81 (s, 3H), 2.30 (s, 3H).

Example 118

[4-(3,4-Dichloro-phenyl)-pyrimidin-2-yl]-[3-methoxy-4-(4-methyl-imidazol-1-yl)-phenyl]-amine

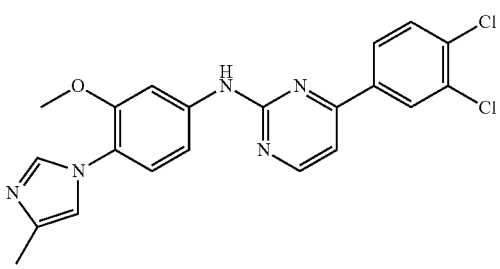 [SMILES: COc1cc(Nc2nccc(-c3ccc(Cl)c(Cl)c3)n2)ccc1-n1cnc(C)c1]

Obtained in 18% yield as light yellow solid. MS ISP (m/e): 426.1 [(M+H)⁺]. $^1$H NMR (CDCl$_3$, 300 MHz): δ (ppm)=8.53 (d, 1H), 8.27 (d, 1H), 7.90 (d, 1H), 7.87 (dd, 1H), 7.66 (s, 1H), 7.58 (d, 1H), 7.33 (s, 1H), 7.21 (d, 1H), 7.18 (d, 1H), 7.03 (dd, 1H), 6.90 (s, 1H), 3.93 (s, 3H), 2.31 (s, 3H).

Example 119

[4-(2,4-Dichloro-phenyl)-pyrimidin-2-yl]-[3-methoxy-4-(4-methyl-imidazol-1-yl)-phenyl]-amine

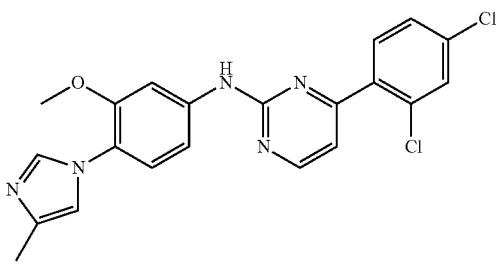 [SMILES: COc1cc(Nc2nccc(-c3ccc(Cl)cc3Cl)n2)ccc1-n1cnc(C)c1]

Obtained in 24% yield as light yellow solid. MS ISP (m/e): 426.0 [(M+H)⁺]. $^1$H NMR (CDCl$_3$, 300 MHz): δ (ppm)=8.53 (d, 1H), 7.79 (d, 1H), 7.64 (s, 1H), 7.63 (s, 1H), 7.54 (s, 1H), 7.38 (dd, 1H), 7.31 (s, 1H), 7.18 (d, 1H), 7.16 (d, 1H), 7.08 (dd, 1H), 6.88 (s, 1H), 3.84 (s, 3H), 2.30 (s, 3H).

Example 120

[4-(4-Chloro-3-methyl-phenyl)-pyrimidin-2-yl]-[3-methoxy-4-(4-methyl-imidazol-1-yl)-phenyl]-amine

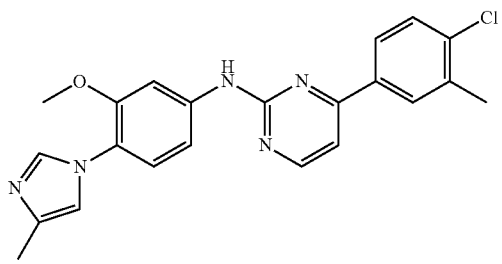 [SMILES: COc1cc(Nc2nccc(-c3ccc(Cl)c(C)c3)n2)ccc1-n1cnc(C)c1]

Obtained in 15% yield as light yellow solid. MS ISP (m/e): 406.3 [(M+H)+]. $^1$H NMR (CDCl$_3$, 300 MHz): δ (ppm)=8.50 (d, 1H), 7.97 (d, 1H), 7.86 (d, 1H), 7.84 (dd, 1H), 7.65 (s, 1H), 7.46 (d, 1H), 7.30 (s, 1H), 7.20 (d, 1H), 7.18 (d, 1H), 7.08 (dd, 1H), 6.89 (s, 1H), 3.90 (s, 3H), 2.47 (s, 3H), 2.31 (s, 3H).

Example 121

[4-(4-Chloro-phenyl)-5-propyl-pyrimidin-2-yl]-[3-methoxy-4-(4-methyl-imidazol-1-yl)-phenyl]-amine

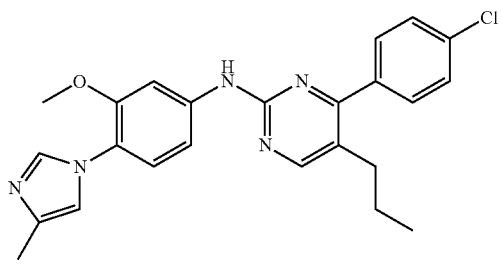 [SMILES: CCCc1cnc(Nc2ccc(-n3cnc(C)c3)c(OC)c2)nc1-c1ccc(Cl)cc1]

Obtained in 25% yield as off-white solid. MS ISP (m/e): 434.3 [(M+H)+]. $^1$H NMR (CDCl$_3$, 300 MHz): δ (ppm)=8.38 (s, 1H), 7.82 (d, 1H), 7.62 (s, 1H), 7.53 and 7.46 (2 d, 2×2H), 7.21 (s, 1H), 7.16 (d, 1H), 7.02 (dd, 1H), 6.86 (s, 1H), 3.81 (s, 3H), 2.59 (t, 2H), 2.30 (s, 3H), 1.59 (m, 2H), 0.86 (t, 3H).

Example 122

[3-Methoxy-4-(4-methyl-imidazol-1-yl)-phenyl]-(5-methoxy-4-phenyl-pyrimidin-2-yl)-amine

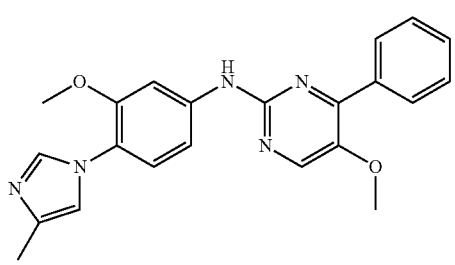 [SMILES: COc1cc(Nc2ncc(OC)c(-c3ccccc3)n2)ccc1-n1cnc(C)c1]

Obtained in 23% yield as light yellow solid. MS ISP (m/e): 388.3 [(M+H)+]. $^1$H NMR (CDCl$_3$, 300 MHz): δ (ppm)=8.27 (s, 1H), 8.12 (m, 3H), 7.86 (d, 1H), 7.62 (s, 1H), 7.48 (m, 3H), 7.17 (d, 1H), 7.15 (s, 1H), 7.02 (dd, 1H), 6.87 (s, 1H), 3.91 (s, 3H), 3.86 (s, 3H), 2.30 (s, 3H).

Example 123

[4-(3,5-Dimethyl-pyrazin-2-yl)-pyrimidin-2-yl]-[3-methoxy-4-(4-methyl-imidazol-1-yl)-phenyl]-amine

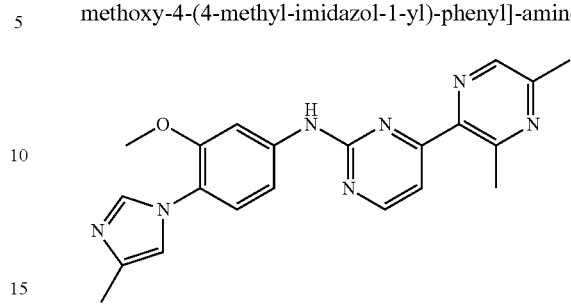

Obtained in 22% yield as light yellow solid. MS ISP (m/e): 388.3 [(M+H)+].)+]. $^1$H NMR (CDCl$_3$, 300 MHz): δ (ppm)=8.61 (d, 1H), 8.45 (s, 1H), 7.63 (m, 2H), 7.34 (d, 1H), 7.15-7.20 (m, 2H), 6.88 (s, 1H), 6.80 (dd, 1H), 3.85 (s, 3H), 2.80 (s, 3H), 2.61 (s, 3H), 2.30 (s, 3H).

Example 124

(4-Isopropyl-pyrimidin-2-yl)-[3-methoxy-4-(4-methyl-imidazol-1-yl)-phenyl]-amine

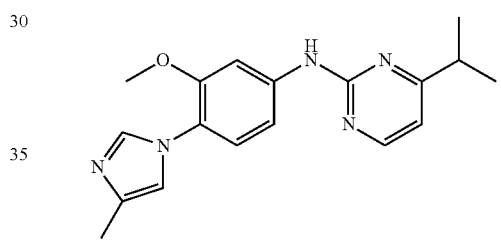

Obtained in 42% yield as yellow oil. MS ISP (m/e): 324.3 [(M+H)+]. $^1$H NMR (CDCl$_3$, 300 MHz): δ (ppm)=8.33 (d, 1H), 7.88 (d, 1H), 7.63 (s, 1H), 7.18 (s, 1H), 7.16 (d, 1H), 7.02 (dd, 1H), 6.88 (s, 1H), 6.68 (d, 1H), 3.88 (s, 3H), 2.92 (m, 1H), 2.30 (s, 3H), 1.32 (d, 6H).

Example 125

(4-tert-Butyl-pyrimidin-2-yl)-[3-methoxy-4-(4-methyl-imidazol-1-yl)-phenyl]-amine

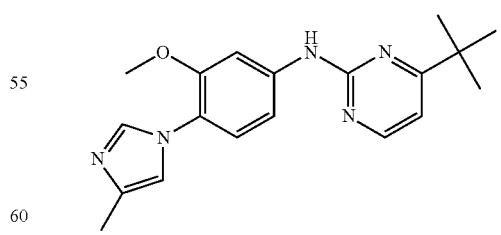

Obtained in 30% yield as light yellow solid. MS ISP (m/e): 338.3 [(M+H)+]. $^1$H NMR (CDCl$_3$, 300 MHz): δ (ppm)=8.38 (d, 1H), 8.40 (d, 1H), 7.63 (s, 1H), 7.18 (s, 1H), 7.17 (d, 1H), 7.02 (dd, 1H), 6.88 (s, 1H), 6.82 (d, 1H), 3.89 (s, 3H), 2.30 (s, 3H), 1.37 (s, 9H).

Example 126

[3-Methoxy-4-(4-methyl-imidazol-1-yl)-phenyl]-(4-methoxymethyl-pyrimidin-2-yl)-amine

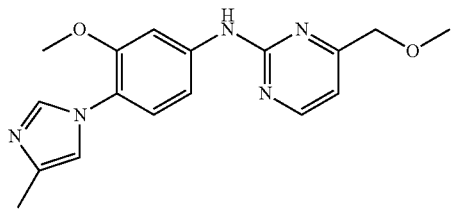 [SMILES: COCc1ccnc(Nc2ccc(-n3cnc(C)c3)c(OC)c2)n1]

Obtained in 29% yield as light yellow solid. MS ISP (m/e): 326.2 [(M+H)+]. $^1$H NMR (CDCl$_3$, 300 MHz): δ (ppm)=8.45 (d, 1H), 7.71 (d, 1H), 7.63 (s, 1H), 7.21 (s, 1H), 7.17 (d, 1H), 7.07 (dd, 1H), 6.92 (d, 1H), 6.87 (s, 1H), 4.46 (s, 2H), 3.87 (s, 3H), 3.51 (s, 3H), 2.30 (s, 3H).

Example 127

Acetic acid 2-[3-methoxy-4-(4-methyl-imidazol-1-yl)-phenylamino]-pyrimidin-4-ylmethyl ester

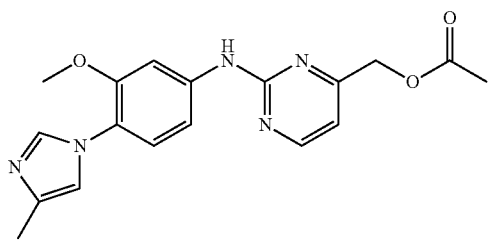 [SMILES: COc1cc(Nc2nccc(COC(C)=O)n2)ccc1-n1cnc(C)c1]

Obtained in 11% yield as off-white solid. MS ISP (m/e): 354.2 [(M+H)+]. $^1$H NMR (CDCl$_3$, 300 MHz): δ (ppm)=8.45 (d, 1H), 7.66 (d, 1H), 7.63 (s, 1H), 7.23 (s, 1H), 7.17 (d, 1H), 7.11 (dd, 1H), 6.88 (s, 1H), 6.80 (d, 1H), 5.10 (s, 2H), 3.87 (s, 3H), 2.30 (s, 3H), 2.21 (s, 3H).

Example 128

1-{2-[3-Methoxy-4-(4-methyl-imidazol-1-yl)-phenylamino]-pyrimidin-4-yl}-ethanol

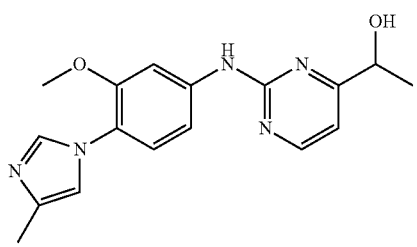 [SMILES: COc1cc(Nc2nccc(C(C)O)n2)ccc1-n1cnc(C)c1]

Obtained in 22% yield as light yellow solid. MS ISP (m/e): 326.2 [(M+H)+]. $^1$H NMR (CDCl$_3$, 300 MHz): δ (ppm)=8.43 (d, 1H), 7.64 (m, 2H), 7.24 (s, 1H), 7.19 (d, 1H), 7.09 (dd, 1H), 6.88 (s, 1H), 6.80 (d, 1H), 4.78 (q, 1H), 3.87 (s, 3H), 2.30 (s, 3H), 1.52 (d, 3H).

Example 129

2-{2-[3-Methoxy-4-(4-methyl-imidazol-1-yl)-phenylamino]-pyrimidin-4-yl}-propan-2-ol

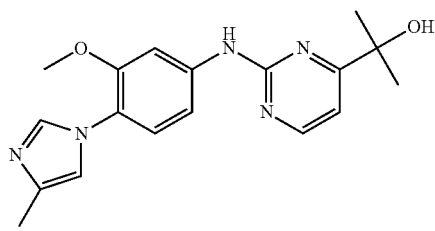 [SMILES: COc1cc(Nc2nccc(C(C)(C)O)n2)ccc1-n1cnc(C)c1]

Obtained in 23% yield as off-white solid. MS ISP (m/e): 340.2 [(M+H)+]. $^1$H NMR (CDCl$_3$, 300 MHz): δ (ppm)=8.44 (d, 1H), 7.64 (s, 1H), 7.63 (d, 1H), 7.22 (s, 1H), 7.19 (d, 1H), 7.07 (dd, 1H), 6.89 (s, 1H), 6.88 (d, 1H), 4.01 (s, 1H), 3.88 (s, 3H), 2.31 (s, 3H), 1.55 (s, 6H).

Example 130

(4-Cyclopentylmethyl-pyrimidin-2-yl)-[3-methoxy-4-(4-methyl-imidazol-1-yl)-phenyl]-amine

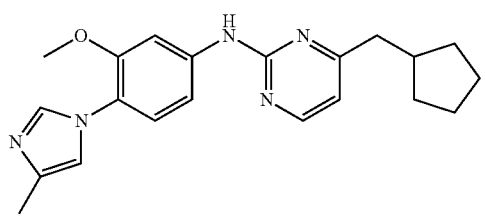 [SMILES: COc1cc(Nc2nccc(CC3CCCC3)n2)ccc1-n1cnc(C)c1]

Obtained in 15% yield as yellow oil. MS ISP (m/e): 364.2 [(M+H)+]. $^1$H NMR (CDCl$_3$, 300 MHz): δ (ppm)=8.32 (d, 1H), 7.80 (d, 1H), 7.63 (s, 1H), 7.18 (s, 1H), 7.17 (d, 1H), 7.05 (dd, 1H), 6.87 (s, 1H), 6.65 (d, 1H), 3.87 (s, 3H), 2.67 (d, 2H), 2.31 (s, 3H), 2.27-2.33 (m, 1H), 1.50-1.80 (m, 8H).

Example 131

(4-Cyclopropyl-pyrimidin-2-yl)-[3-methoxy-4-(4-methyl-imidazol-1-yl)-phenyl]-amine

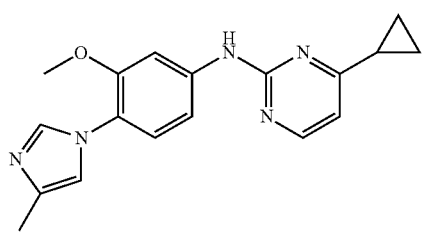 [SMILES: COc1cc(Nc2nccc(C3CC3)n2)ccc1-n1cnc(C)c1]

Obtained in 44% yield as light yellow solid. MS ISP (m/e): 322.2 [(M+H)+]. $^1$H NMR (CDCl$_3$, 300 MHz): δ (ppm)=8.22 (d, 1H), 7.81 (d, 1H), 7.62 (s, 1H), 7.15 (d, 1H), 7.10 (s, 1H), 6.94 (dd, 1H), 6.87 (s, 1H), 6.70 (d, 1H), 3.89 (s, 3H), 2.30 (s, 3H), 2.27-2.33 (m, 1H), 1.94 (m, 1H), 1.20 (m, 2H), 1.08 (m, 2H).

Example 132

(4-Cyclopentyl-pyrimidin-2-yl)-[3-methoxy-4-(4-methyl-imidazol-1-yl)-phenyl]-amine

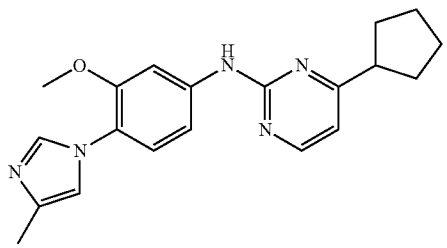 [SMILES: COc1cc(Nc2nccc(C3CCCC3)n2)ccc1-n1cnc(C)c1]

Obtained in 13% yield as light yellow solid. MS ISP (m/e): 350.4 [(M+H)+]. $^1$H NMR (CDCl$_3$, 300 MHz): δ (ppm)=8.30 (d, 1H), 7.82 (d, 1H), 7.63 (s, 1H), 7.17 (d, 1H), 7.15 (s, 1H), 7.03 (dd, 1H), 6.87 (s, 1H), 6.68 (d, 1H), 3.87 (s, 3H), 3.08 (m, 1H), 2.30 (s, 3H), 2.00-2.28 (m, 2H), 1.65-1.92 (m, 6H).

Example 133

(4-Cyclohexyl-5-methyl-pyrimidin-2-yl)-[3-methoxy-4-(4-methyl-imidazol-1-yl)-phenyl]-amine

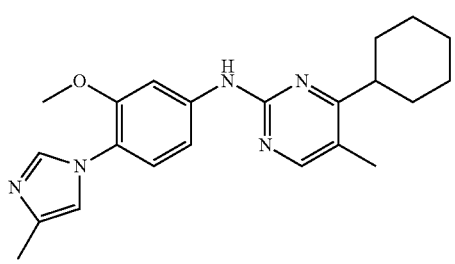 [SMILES: COc1cc(Nc2ncc(C)c(C3CCCCC3)n2)ccc1-n1cnc(C)c1]

Obtained in 38% yield as light yellow solid. MS ISP (m/e): 378.3 [(M+H)+]. $^1$H NMR (CDCl$_3$, 300 MHz): δ (ppm)=8.13 (s, 1H), 7.93 (d, 1H), 7.62 (s, 1H), 7.15 (d, 1H), 7.08 (s, 1H), 6.94 (dd, 1H), 6.87 (s, 1H), 3.90 (s, 3H), 2.78 (m, 1H), 2.30 (s, 3H), 2.20 (s, 3H), 1.60-1.95 (m, 8H), 1.3-1.5 (m, 2H).

Example 134

Ethyl 4-benzyl-2-[3-methoxy-4-(4-methyl-imidazol-1-yl)-phenylamino]-pyrimidine-5-carboxylate

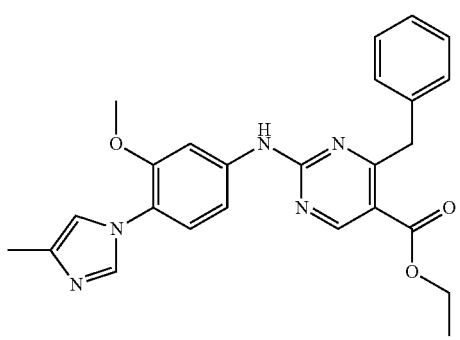 [SMILES: CCOC(=O)c1cnc(Nc2ccc(-n3cnc(C)c3)c(OC)c2)nc1Cc1ccccc1]

Obtained in 10% yield as light yellow solid. MS ISP (m/e): 444.3 [(M+H)+]. $^1$H NMR (CDCl$_3$, 300 MHz): δ (ppm)=8.99 (s, 1H), 7.63 (s, 1H), 7.59 (d, 1H), 7.42 (s, 1H), 7.20-7.35 (m, 5H), 7.13 (d, 1H), 7.06 (dd, 1H), 6.87 (s, 1H), 4.52 (s, 2H), 4.36 (q, 2H), 3.79 (s, 3H), 2.30 (s, 3H), 1.37 (t, 3H).

Example 135

Ethyl 2-[3-methoxy-4-(4-methyl-imidazol-1-yl)-phenylamino]-4-(4-methyl-pent-3-enyl)-pyrimidine-5-carboxylate

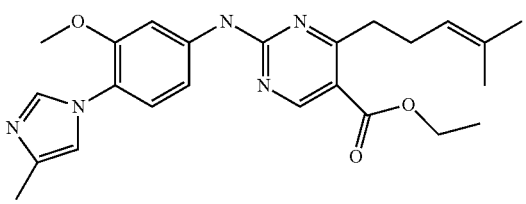 [SMILES: CCOC(=O)c1cnc(Nc2ccc(-n3cnc(C)c3)c(OC)c2)nc1CCC=C(C)C]

Obtained in 8% yield as light yellow solid. MS ISP (m/e): 436.2 [(M+H)+]. $^1$H NMR (CDCl$_3$, 300 MHz): δ (ppm)=8.95 (s, 1H), 7.82 (d, 1H), 7.65 (s, 1H), 7.42 (s, 1H), 7.20 (d, 1H), 7.10 (dd, 1H), 6.89 (s, 1H), 5.22 (t, 1H), 4.36 (q, 2H), 3.88 (s, 3H), 3.16 (m, 2H), 2.45 (m, 2H), 2.30 (s, 3H), 1.68 and 1.59 (2 s, 2×3H).

Example 136

[3-Methoxy-4-(4-methyl-imidazol-1-yl)-phenyl]-[4-(4-methyl-pent-3-enyl)-5-phenyl-pyrimidin-2-yl]-amine

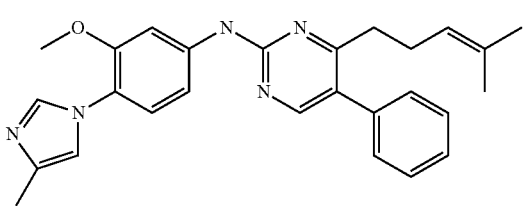 [SMILES: COc1cc(Nc2ncc(-c3ccccc3)c(CCC=C(C)C)n2)ccc1-n1cnc(C)c1]

Obtained in 17% yield as light yellow solid. $^1$H NMR (CDCl$_3$, 300 MHz): δ (ppm)=8.27 (s, 1H), 7.84 (d, 1H), 7.64 (s, 1H), 7.15-7.50 (m, 6H), 7.20 (d, 1H), 7.12 (dd, 1H), 6.87 (s, 1H), 5.06 (t, 1H), 3.88 (s, 3H), 2.72 (m, 2H), 2.40 (m, 2H), 2.31 (s, 3H), 1.63 and 1.49 (2 s, 2×3H).

Example 137

6-{2-[3-Methoxy-4-(4-methyl-imidazol-1-yl)-phenylamino]-pyrimidin-4-yl}-4H-benzo[1,4]oxazin-3-one

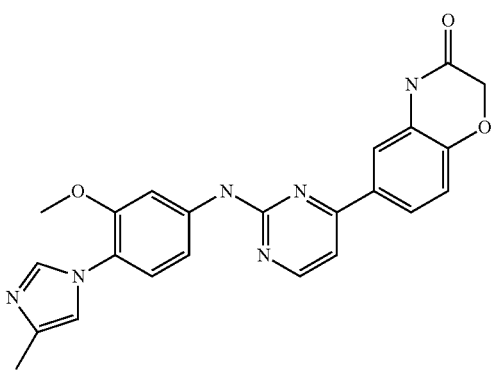 [SMILES: COc1cc(Nc2nccc(-c3ccc4c(c3)NC(=O)CO4)n2)ccc1-n1cnc(C)c1]

Obtained in 20% yield as white solid. MS ISP (m/e): 429.2 [(M+H)+]. $^1$H NMR (DMSO-D$_6$, 300 MHz): δ (ppm)=10.96 (s, 1H), 9.84 (s, 1H), 8.55 (d, 1H), 7.85 (d, 1H), 7.75 (dd, 1H), 7.74 (d, 1H), 7.68 (s, 1H), 7.33 (dd, 1H), 7.31 (s, 1H), 7.28 (d, 1H), 7.10 (d, 1H), 7.07 (s, 1H), 4.68 (s, 2H), 3.81 (s, 3H), 2.16 (s, 3H).

Example 138

Cyclopropyl-[2-[3-methoxy-4-(4-methyl-imidazol-1-yl)-phenylamino]-4-(4-trifluoromethyl-phenyl)-pyrimidin-5-yl]-acetonitrile

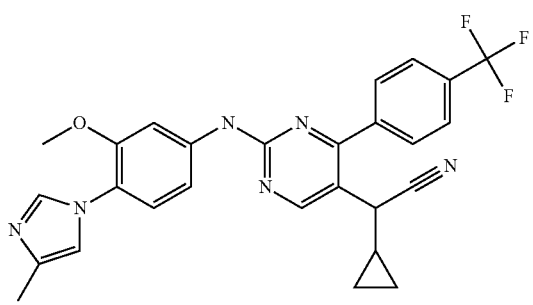 [SMILES: COc1cc(Nc2ncc(C(C#N)C3CC3)c(-c3ccc(C(F)(F)F)cc3)n2)ccc1-n1cnc(C)c1]

2-Cyclopropyl-4-oxo-4-(4-trifluoromethyl-phenyl)-butyronitrile

A solution of potassium cyanide (313 mg, 4.8 mmol) in water (1 mL) was added at to a solution of (E)-3-cyclopropyl-1-(4-trifluoromethyl-phenyl)-propenone (961 mg, 4.0 mmol) in a ethanol (8 mL) and acetic acid (0.26 mL). The reaction mixture was stirred at 20° C. for 6 days and then partitioned between ethyl acetate and saturated sodium hydrogencarbonate solution. The organic layer was washed with brine, dried over sodium sulfate, and evaporated under reduced pressure. The residual oil was subjected to column chromatography on silica gel using heptane/0-15% ethyl acetate to give the title compound as white solid (620 mg, 58%). Mp 91-93° C.

b) Cyclopropyl-[2-β-methoxy-4-(4-methyl-imidazol-1-yl)-phenylamino-1-4-(4-trifluoromethyl-phenyl)-pyrimidin-5-yl]-acetonitrile Using in analogous manner the procedure described in example 28a), 2-cyclopropyl-4-oxo-4-(4-trifluoromethyl-phenyl)-butyronitrile (170 mg, 0.5 mmol) was reacted with tert.-butoxy-bis-(dimethylamino)-methane, and the resulting product was subsequently reacted with N-[3-methoxy-4-(4-methyl-imidazol-1-yl)-phenyl]-guanidine dinitrate operating in analogous manner as described in example 39b) to give the title compound (46 mg, 24%). MS ISP (m/e): 505.3 [(M+H)$^+$]. $^1$H NMR (CDCl$_3$, 300 MHz): δ (ppm)=8.81 (s, 1H), 7.82 (d, 2H), 7.60-7.75 (m, 4H), 7.39 (s, 1H), 7.20 (d, 1H), 7.12 (dd, 1H), 6.87 (s, 1H), 3.82 (s, 3H), 3.74 (d, 1H), 2.30 (s, 3H), 1.20 (m, 1H), 0.55-0.90 (m, 4H).

Example 139

Ethyl 2-[3-methoxy-4-(4-methyl-imidazol-1-yl)-phenylamino]-pyrimidine-4-carboxylate

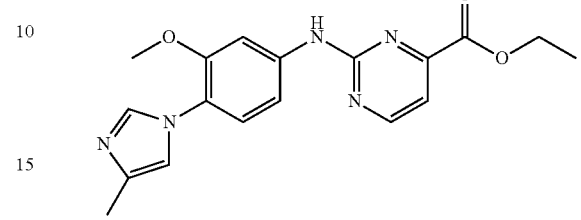

A mixture of N-[3-methoxy-4-(4-methyl-imidazol-1-yl)-phenyl]guanidine dinitrate (298 mg, 0.80 mmol), ethyl 4-dimethylamino-2-oxo-but-3-enoate (171 mg, 1.0 mmol) and potassium carbonate (69 mg, 0.5 mmol) in ethanol (2 mL) was heated in a sealed tube in a microwave oven to 170° C. for 0.5 h. The mixture was cooled, diluted with ethyl acetate (30 mL), and then washed with saturated sodium carbonate solution (10 mL) and with brine (10 mL). The organic layer was dried over sodium sulfate and evaporated under reduced pressure. The residual material was purified by chromatography on silica gel using dichloromethane/0-20% methanol as eluent to give the title compound (96 mg, 34%) as a pale-yellow solid. MS ISP (m/e): 354.2 [(M+H)$^+$]. $^1$H NMR (CDCl$_3$, 300 MHz): δ (ppm)=8.67 (d, 1H), 7.91 (d, 1H), 7.64 (s, 1H), 7.45 (s, 1H), 7.44 (d, 1H), 7.19 (d, 1H), 7.02 (dd, 1H), 6.88 (s, 1H), 4.47 (q, 2H), 3.91 (s, 3H), 2.30 (s, 3H), 1.44 (t, 3H).

Example 140

[4-(2-Chloro-phenyl)-pyrimidin-2-yl]-[3-methoxy-4-(4-methyl-imidazol-1-yl)-phenyl]-amine

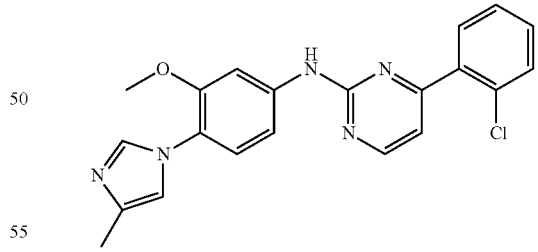

The title compound was prepared from N-[3-methoxy-4-(4-methyl-imidazol-1-yl)-phenyl]-guanidine dinitrate (149 mg, 0.4 mmol) and 1-(2-chloro-phenyl)-3-dimethylamino-propenone (105 mg, 0.5 mmol) using in analogous manner the procedure described in example 139. Obtained as a white solid (49 mg, 31%). MS ISP (m/e): 392.1 [(M+H)$^+$]. $^1$H NMR (CDCl$_3$, 300 MHz): δ (ppm)=8.53 (d, 1H), 7.85 (d, 1H), 7.68 (m, 1H), 7.63 (d, 1H), 7.51 (m, 1H), 7.40 (m, 2H), 7.34 (s, 1H), 7.17 (d, 1H), 7.16 (s, 1H), 7.06 (dd, 1H), 6.87 (s, 1H), 3.84 (s, 3H), 2.30 (s, 3H).

Example 141

Ethyl 2-[3-methoxy-4-(4-methyl-imidazol-1-yl)-phenylamino]-5-methyl-pyrimidine-4-carboxylate

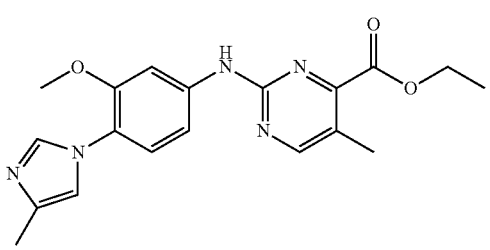 [SMILES: CCOC(=O)c1nc(Nc2ccc(-n3cnc(C)c3)c(OC)c2)ncc1C]

The title compound was prepared from N-[3-methoxy-4-(4-methyl-imidazol-1-yl)-phenyl]-guanidine dinitrate (298 mg, 0.8 mmol) and ethyl 4-dimethylamino-3-methyl-2-oxo-but-3-enoate (185 mg, 1.0 mmol) using in analogous manner the procedure described in example 139. Obtained as a white solid (30 mg, 8%). MS ISP (m/e): 368.2 [(M+H)$^+$]. $^1$H NMR (CDCl$_3$, 300 MHz): δ (ppm)=8.45 (s, 1H), 7.83 (d, 1H), 7.63 (s, 1H), 7.31 (s, 1H), 7.17 (d, 1H), 7.02 (dd, 1H), 6.87 (s, 1H), 4.46 (q, 2H), 3.89 (s, 3H), 2.41 (s, 3H), 2.30 (s, 3H), 1.44 (t, 3H).

Example 142

(4,5-Dimethyl-pyrimidin-2-yl)-[3-methoxy-4-(4-methyl-imidazol-1-yl)-phenyl]-amine

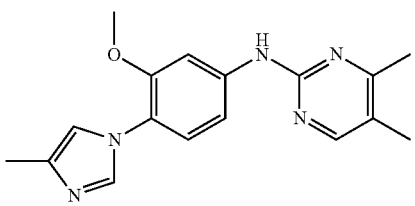

The title compound was prepared from N-[3-methoxy-4-(4-methyl-imidazol-1-yl)-phenyl]-guanidine dinitrate (149 mg, 0.4 mmol) and 1-(2-chloro-phenyl)-3-dimethylamino-propenone (64 mg, 0.5 mmol) using in analogous manner the procedure described in example 139. Obtained as a white solid (12 mg, 10%). MS ISP (m/e): 310.2 [(M+H)$^+$]. NMR (CDCl$_3$, 300 MHz): δ (ppm)=8.14 (s, 1H), 7.75 (d, 1H), 7.62 (s, 1H), 7.15 (d, 1H), 7.05 (m, 2H), 6.86 (s, 1H), 3.88 (s, 3H), 2.41 (s, 3H), 2.30 (s, 3H), 2.18 (s, 3H).

Example 143

(4-Ethyl-pyrimidin-2-yl)-[3-methoxy-4-(4-methyl-imidazol-1-yl)-phenyl]-amine

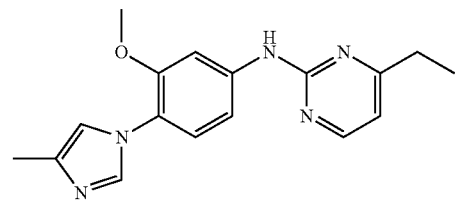 [SMILES: CCc1ccnc(Nc2ccc(-n3cnc(C)c3)c(OC)c2)n1]

The title compound was prepared from N-[3-methoxy-4-(4-methyl-imidazol-1-yl)-phenyl]-guanidine dinitrate (149 mg, 0.4 mmol) and 1-dimethylamino-pent-1-en-3-one (64 mg, 0.5 mmol) using in analogous manner the procedure described in example 139. Obtained as a white solid (18 mg, 16%). MS ISP (m/e): 310.2 [(M+H)$^+$]. NMR (CDCl$_3$, 300 MHz): δ (ppm)=8.33 (d, 1H), 7.81 (d, 1H), 7.63 (s, 1H), 7.25 (s, 1H), 7.15 (d, 1H), 7.07 (dd, 1H), 6.87 (s, 1H), 6.67 (d, 1H), 3.87 (s, 3H), 2.71 (q, 2H), 2.30 (s, 3H), 1.33 (t, 3H).

Example 144

(4-tert-Butyl-6-trifluoromethyl-pyrimidin-2-yl)-[3-methoxy-4-(4-methyl-imidazol-1-yl)-phenyl]-amine

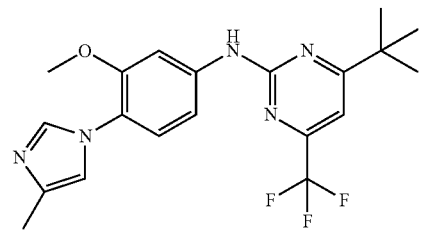 [SMILES: COc1cc(Nc2nc(C(C)(C)C)cc(C(F)(F)F)n2)ccc1-n1cnc(C)c1]

A mixture of N-[3-methoxy-4-(4-methyl-imidazol-1-yl)-phenyl]guanidine dinitrate (224 mg, 0.60 mmol), crude 3-dimethylamino-1-pyridin-3-yl-propenone (118 mg, 0.60 mmol) and triethylamine (0.50 mL, 3.60 mmol) in ethanol (1.5 mL) was heated in a sealed tube in a microwave oven to 170° C. for 0.5 h. The mixture was cooled, diluted with ethyl acetate (30 mL), and then washed with saturated sodium carbonate solution (5 mL) and with brine (5 mL). The organic layer was dried over sodium sulfate and evaporated under reduced pressure. The residual material was purified by chromatography on silica gel using dichloromethane/0-10% methanol as eluent to give the title compound (116 mg, 47%) as a white solid. MS ISP (m/e): 406.3 [(M+H)$^+$]. NMR (CDCl$_3$, 300 MHz): δ (ppm)=8.00 (d, 1H), 7.67 (s, 1H), 7.39 (s, 1H), 7.18 (d, 1H), 7.11 (s, 1H), 6.97 (dd, 1H), 6.90 (s, 1H), 3.89 (s, 3H), 2.30 (s, 3H), 1.39 (s, 9H).

Examples 145-150

Using in analogous manner the procedure described in example 144, heptane-3,5-dione, 6-methyl-heptane-2,4-dione, 1-phenyl-butane-1,3-dione, 4,4,4-trifluoro-1-pyrazin-2-yl-butane-1,3-dione, 4,4,4-trifluoro-1-furan-2-yl-butane-1,3-dione, and 2-benzoyl-cyclohexanone were reacted with N-[3-methoxy-4-(4-methyl-imidazol-1-yl)-phenyl]guanidine dinitrate, respectively, to afford the following compounds:

Example 145

(4-Isobutyl-6-methyl-pyrimidin-2-yl)-[3-methoxy-4-(4-methyl-imidazol-1-yl)-phenyl]-amine

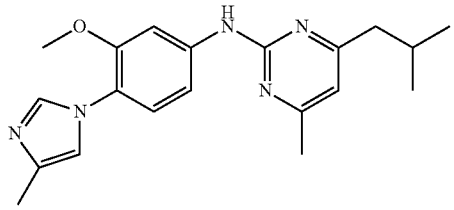 [SMILES: COc1cc(Nc2nc(C)cc(CC(C)C)n2)ccc1-n1cnc(C)c1]

Obtained in 12% yield as light yellow solid. MS ISP (m/e): 352.3 [(M+H)$^+$]. NMR (CDCl$_3$, 300 MHz): δ (ppm)=7.96 (d, 1H), 7.62 (s, 1H), 7.14 (d, 1H), 7.12 (s, 1H), 6.98 (dd, 1H), 6.87 (s, 1H), 6.51 (s, 1H), 3.87 (s, 3H), 2.49 (d, 2H), 2.40 (s, 3H), 2.30 (s, 3H), 1.25 (m, 1H), 0.97 (d, 6H).

Example 146

(4,6-Diethyl-pyrimidin-2-yl)-[3-methoxy-4-(4-methyl-imidazol-1-yl)-phenyl]-amine

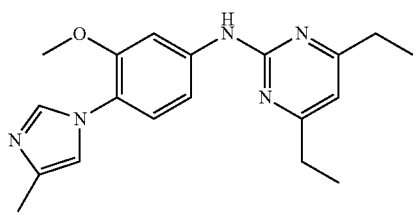 [SMILES: CCc1cc(CC)nc(Nc2ccc(-n3cnc(C)c3)c(OC)c2)n1]

Obtained in 18% yield as light yellow solid. MS ISP (m/e): 338.2 [(M+H)$^+$]. NMR (CDCl$_3$, 300 MHz): δ (ppm)=8.00 (d, 1H), 7.62 (s, 1H), 7.15 (d, 1H), 7.13 (s, 1H), 6.98 (dd, 1H), 6.87 (s, 1H), 6.55 (s, 1H), 3.88 (s, 3H), 2.68 (q, 2H), 2.30 (s, 3H), 1.32 (t, 3H).

Example 147

[3-Methoxy-4-(4-methyl-imidazol-1-yl)-phenyl]-(4-methyl-6-phenyl-pyrimidin-2-yl)-amine

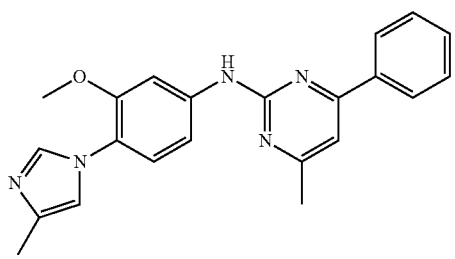 [SMILES: COc1cc(Nc2nc(C)cc(-c3ccccc3)n2)ccc1-n1cnc(C)c1]

Obtained in 11% yield as off-white solid. MS ISP (m/e): 372.2 [(M+H)$^+$]. NMR (CDCl$_3$, 300 MHz): δ (ppm)=8.09 (m, 2H), 8.02 (d, 1H), 7.64 (s, 1H), 7.18 (d, 1H), 7.12 (s, 1H), 7.05 (dd, 1H), 6.89 (s, 1H), 3.90 (s, 3H), 2.51 (s, 3H), 2.31 (s, 3H).

Example 148

[3-Methoxy-4-(4-methyl-imidazol-1-yl)-phenyl]-(4-pyrazin-2-yl-6-trifluoromethyl-pyrimidin-2-yl)-amine

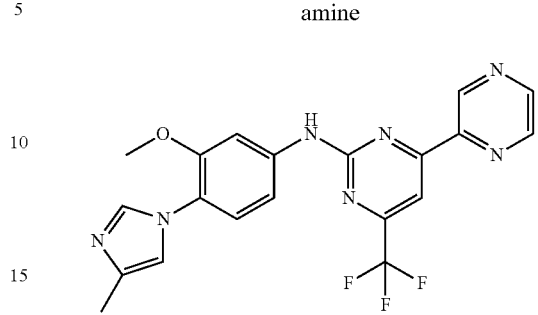

Obtained in 4% yield as light yellow solid. MS ISP (m/e): 428.2 [(M+H)$^+$]. NMR (CDCl$_3$, 300 MHz): δ (ppm)=9.68 (s, 1H), 8.77 and 8.73 (2 d, 2×1H), 8.14 (s, 1H), 7.92 (s, 1H), 7.64 (s, 1H), 7.24 (d, 1H), 7.09 (dd, 1H), 6.90 (s, 1H), 3.93 (s, 3H), 2.31 (s, 3H).

Example 149

(4-Furan-2-yl-6-trifluoromethyl-pyrimidin-2-yl)-[3-methoxy-4-(4-methyl-imidazol-1-yl)-phenyl]-amine

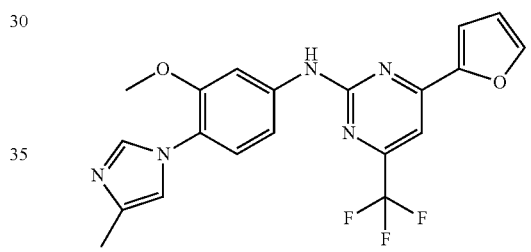

Obtained in 3% yield as light yellow solid. MS ISP (m/e): 416.3 [(M+H)$^+$]. NMR (CDCl$_3$, 300 MHz): δ (ppm)=8.00 (s, 1H), 7.66 (s, 2H), 7.45 (s, 1H), 7.41 (s, 1H), 7.31 (d, 1H), 7.20 (d, 1H), 6.99 (dd, 1H), 6.64 (m, 1H), 3.91 (s, 3H), 2.31 (s, 3H).

Example 150

[3-Methoxy-4-(4-methyl-imidazol-1-yl)-phenyl]-(4-phenyl-5,6,7,8-tetrahydro-quinazolin-2-yl)-amine

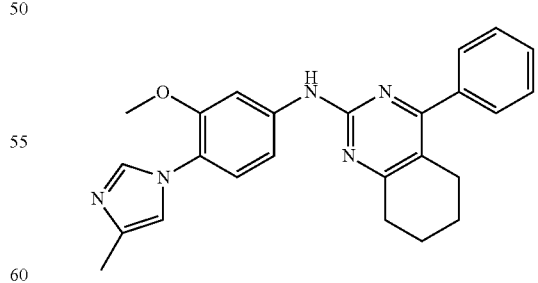

Obtained in 61% yield as light yellow solid. MS ISP (m/e): 412.3 [(M+H)$^+$]. NMR (CDCl$_3$, 300 MHz): δ (ppm)=8.04 (d, 1H), 7.62 (s, 1H), 7.61 (m, 2H), 7.46 (m, 3H), (s, 1H), 7.20 (s, 1H), 7.12 (d, 1H), 6.94 (dd, 1H), 6.86 (s, 1H), 3.81 (s, 3H), 2.88 and 2.70 (2 t, 2×2H), 2.30 (s, 3H), 1.91 and 1.76 (2 m, 2×2H).

Example 151

Ethyl 2-[3-methoxy-4-(4-methyl-imidazol-1-yl)-phenylamino]-6-methyl-pyrimidine-4-carboxylate

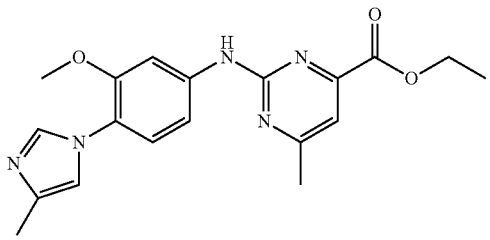

A mixture of N-[3-methoxy-4-(4-methyl-imidazol-1-yl)-phenyl]-guanidine dinitrate (371 mg, 1.0 mmol), ethyl 2,4-dioxo-pentanoate (158 mg, 1.0 mmol) and potassium carbonate (69 mg, 0.5 mmol) in ethanol (2 mL) was heated in a sealed tube in a microwave oven to 170° C. for 0.5 h. The mixture was cooled, diluted with ethyl acetate (50 mL), and then washed with water (20 mL) and with brine (20 mL). The organic layer was dried over sodium sulfate and evaporated under reduced pressure. The residual material was purified by chromatography on silica gel using dichloromethane/0-10% methanol as eluent to give the title compound (229 mg, 62%) as a yellow solid. MS ISP (m/e): 368.2 [(M+H)$^+$]. $^1$H NMR (CDCl$_3$, 300 MHz): δ (ppm)=8.04 (d, 1H), 7.64 (s, 1H), 7.40 (s, 1H), 7.34 (s, 1H), 7.17 (d, 1H), 6.98 (dd, 1H), 6.87 (s, 1H), 4.46 (q, 2H), 3.91 (s, 3H), 2.54 (s, 3H), 2.30 (s, 3H), 1.43 (t, 3H).

Examples 152-164

Using in analogous manner the procedure described in example 151, pentane-2,4-dione, 1,1,1,5,5,5-hexafluoro-pentane-2,4-dione, 2,6-dimethyl-heptane-3,5-dione, 1-(2-chloro-phenyl)-butane-1,3-dione, ethyl 2,4-dioxo-4-thiophen-2-yl-butyrate, ethyl 2,4-dioxo-hexanoate, ethyl 5-methyl-2,4-dioxo-hexanoate, ethyl 5,5-dimethyl-2,4-dioxo-hexanoate, ethyl 4-cyclopropyl-2,4-dioxo-butyrate, ethyl 2,4-dioxo-4-pyridin-2-yl-butyrate, ethyl 2,4-dioxo-4-(4-trifluoromethyl-phenyl)-butyrate, and ethyl 5-(4-chloro-phenyl)-2,4-dioxo-pentanoate were reacted with N-[3-methoxy-4-(4-methyl-imidazol-1-yl)-phenyl]-guanidine dinitrate, respectively, to afford the following compounds:

Example 152

(4,6-Dimethyl-pyrimidin-2-yl)-[3-methoxy-4-(4-methyl-imidazol-1-yl)-phenyl]-amine

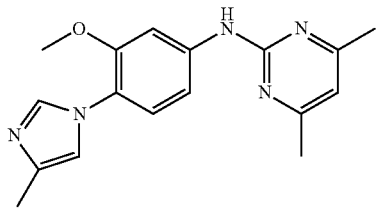 [SMILES: COc1cc(Nc2nc(C)cc(C)n2)ccc1-n1cnc(C)c1]

Obtained in 20% yield as off-white solid. MS ISP (m/e): 310.2 [(M+H)$^+$]. $^1$H NMR (CDCl$_3$, 300 MHz): δ (ppm)=7.89 (d, 1H), 7.62 (s, 1H), 7.15 (d, 1H), 7.12 (s, 1H), 7.03 (dd, 1H), 6.87 (s, 1H), 6.56 (s, 1H), 3.87 (s, 3H), 2.40 (s, 6H), 2.30 (s, 3H).

Example 153

(4,6-Bis-trifluoromethyl-pyrimidin-2-yl)-[3-methoxy-4-(4-methyl-imidazol-1-yl)-phenyl]-amine

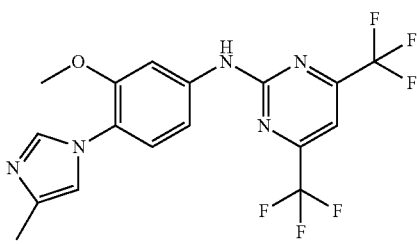 [SMILES: COc1cc(Nc2nc(C(F)(F)F)cc(C(F)(F)F)n2)ccc1-n1cnc(C)c1]

Obtained in 46% yield as yellow solid. MS ISP (m/e): 418.2 [(M+H)$^+$]. $^1$H NMR (CDCl$_3$, 300 MHz): δ (ppm) 7.93 (d, 1H), 7.77 (s, 1H), 7.67 (s, 1H), 7.35 (s, 1H), 7.23 (d, 1H), 6.97 (dd, 1H), 6.90 (s, 1H), 3.89 (s, 3H), 2.31 (s, 3H).

Example 154

(4-Isopropyl-6-trifluoromethyl-pyrimidin-2-yl)-[3-methoxy-4-(4-methyl-imidazol-1-yl)-phenyl]-amine

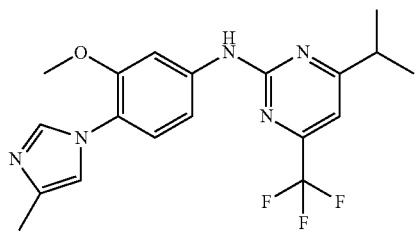 [SMILES: COc1cc(Nc2nc(C(C)C)cc(C(F)(F)F)n2)ccc1-n1cnc(C)c1]

Obtained in 52% yield as light yellow solid. MS ISP (m/e): 392.2 [(M+H)$^+$]. $^1$H NMR (CDCl$_3$, 300 MHz): δ (ppm)=8.00 (d, 1H), 7.64 (s, 1H), 7.40 (s, 1H), 7.18 (d, 1H), 6.97 (s, 1H), 6.94 (dd, 1H), 6.88 (s, 1H), 3.89 (s, 3H), 3.01 (m, 1H), 2.30 (s, 3H), 1.34 (d, 6H).

Example 155

(4,6-Diisopropyl-pyrimidin-2-yl)-[3-methoxy-4-(4-methyl-imidazol-1-yl)-phenyl]-amine

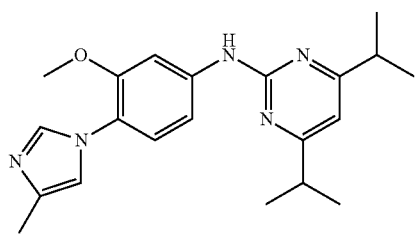 [SMILES: COc1cc(Nc2nc(C(C)C)cc(C(C)C)n2)ccc1-n1cnc(C)c1]

Obtained in 12% yield as off-white solid. MS ISP (m/e): 366.2 [(M+H)$^+$.)]$^+$. $^1$H NMR (CDCl$_3$, 300 MHz): δ (ppm)=8.10 (d, 1H), 7.63 (s, 1H), 7.15 (s, 1H), 7.14 (d, 1H), 6.94 (dd, 1H), 6.88 (s, 1H), 6.55 (s, 1H), 3.89 (s, 3H), 2.88 (m, 2H), 2.30 (s, 3H), 1.30 (d, 12H).

Example 156

[4-(2-Chloro-phenyl)-6-methyl-pyrimidin-2-yl]-[3-methoxy-4-(4-methyl-imidazol-1-yl)-phenyl]-amine

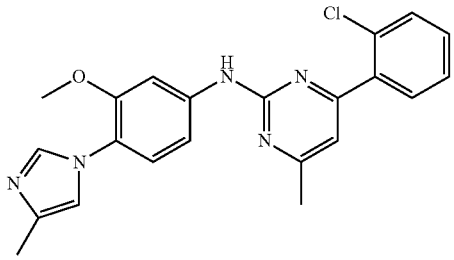 [SMILES: COc1cc(Nc2nc(C)cc(-c3ccccc3Cl)n2)ccc1-n1cnc(C)c1]

Obtained in 8% yield as light yellow solid. MS ISP (m/e): 406.3 [(M+H)$^+$]. $^1$H NMR (CDCl$_3$, 300 MHz): δ (ppm)=7.99 (d, 1H), 7.64 (m, 1H), 7.62 (s, 1H), 7.50 (m, 1H), 7.38 (m, 2H), 7.29 (s, 1H), 7.15 (d, 1H), 7.03 (s, 1H), 7.01 (dd, 1H), 6.86 (s, 1H), 3.89 (s, 3H), 2.52 (s, 3H), 2.30 (s, 3H).

Example 157

Ethyl 2-[3-methoxy-4-(4-methyl-imidazol-1-yl)-phenylamino]-6-thiophen-2-yl-pyrimidine-4-carboxylate

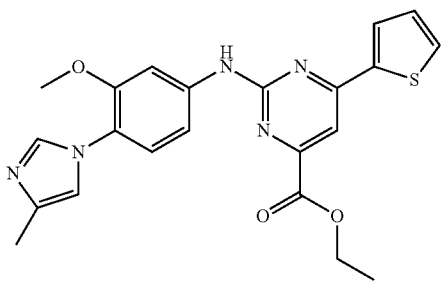 [SMILES: CCOC(=O)c1cc(-c2cccs2)nc(Nc2ccc(-n3cnc(C)c3)c(OC)c2)n1]

Obtained in 15% yield as light yellow solid. MS ISP (m/e): 436.1 [(M+H)$^+$]. $^1$H NMR (CDCl$_3$, 300 MHz): δ (ppm)=8.05 (d, 1H), 7.87 (d, 1H), 7.77 (s, 1H), 7.66 (s, 1H), 7.59 (d, 1H), 7.51 (s, 1H), 7.20 (s, 1H), 7.20 (d, 1H), 7.15 (d, 1H), 7.03 (s, 1H), 6.98 (dd, 1H), 6.90 (s, 1H), 4.51 (q, 2H), 3.99 (s, 3H), 2.31 (s, 3H), 1.47 (t, 3H).

Example 158

Ethyl 6-ethyl-2-[3-methoxy-4-(4-methyl-imidazol-1-yl)-phenylamino]-pyrimidine-4-carboxylate

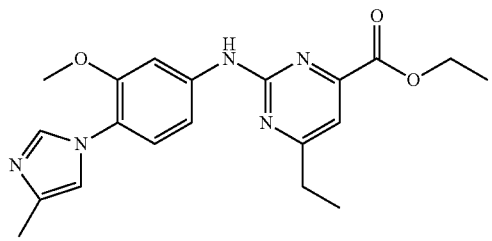 [SMILES: CCOC(=O)c1cc(CC)nc(Nc2ccc(-n3cnc(C)c3)c(OC)c2)n1]

Obtained in 38% yield as light yellow solid. MS ISP (m/e): 382.4 [(M+H)$^+$]. $^1$H NMR (CDCl$_3$, 300 MHz): δ (ppm)=8.06 (d, 1H), 7.63 (s, 1H), 7.43 (s, 1H), 7.35 (s, 1H), 7.17 (d, 1H), 6.96 (dd, 1H), 6.88 (s, 1H), 4.47 (q, 2H), 3.91 (s, 3H), 2.82 (q, 2H), 2.31 (s, 3H), 1.44 (t, 3H), 1.37 (t, 3H).

Example 159

Ethyl 6-Isopropyl-2-[3-methoxy-4-(4-methyl-imidazol-1-yl)-phenylamino]-pyrimidine-4-carboxylate

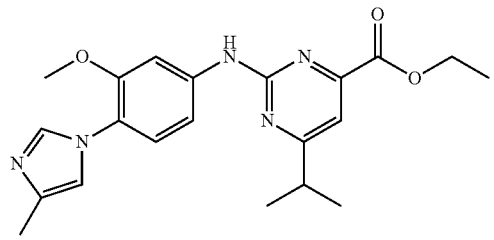

Obtained in 49% yield as light yellow solid. MS ISP (m/e): 396.2 [(M+H)$^+$]. $^1$H NMR (CDCl$_3$, 300 MHz): δ (ppm)=8.10 (d, 1H), 7.63 (s, 1H), 7.45 (s, 1H), 7.35 (s, 1H), 7.17 (d, 1H), 6.94 (dd, 1H), 6.88 (s, 1H), 4.47 (q, 2H), 3.91 (s, 3H), 3.03 (m, 1H), 2.30 (s, 3H), 1.44 (t, 3H), 1.35 (d, 6H).

Example 160

Ethyl 6-tert-butyl-2-[3-methoxy-4-(4-methyl-imidazol-1-yl)-phenylamino]-pyrimidine-4-carboxylate

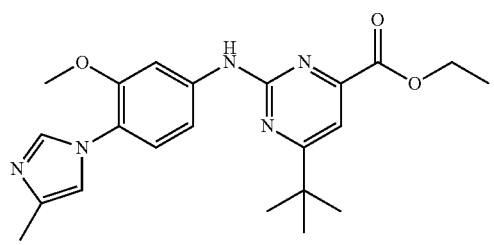 [SMILES: CCOC(=O)c1cc(C(C)(C)C)nc(Nc2ccc(-n3cnc(C)c3)c(OC)c2)n1]

Obtained in 24% yield as light yellow solid. MS ISP (m/e): 410.2 [(M+H)$^+$]. $^1$H NMR (CDCl$_3$, 300 MHz): δ (ppm)=8.05 (d, 1H), 7.63 (s, 1H), 7.49 (s, 1H), 7.47 (s, 1H), 7.17 (d, 1H), 6.95 (dd, 1H), 6.88 (s, 1H), 4.48 (q, 2H), 3.91 (s, 3H), 2.30 (s, 3H), 1.44 (t, 3H), 1.40 (s, 9H).

Example 161

Ethyl 6-cyclopropyl-2-[3-methoxy-4-(4-methyl-imidazol-1-yl)-phenylamino]-pyrimidine-4-carboxylate

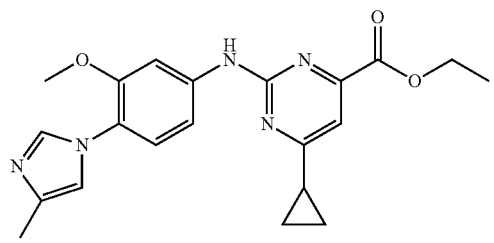 [SMILES: CCOC(=O)c1cc(C2CC2)nc(Nc2ccc(-n3cnc(C)c3)c(OC)c2)n1]

Obtained in 23% yield as light yellow solid. MS ISP (m/e): 394.2 [(M+H)⁺]. ¹H NMR (CDCl₃, 300 MHz): δ (ppm)=7.98 (d, 1H), 7.63 (s, 1H), 7.38 (s, 1H), 7.36 (s, 1H), 7.15 (d, 1H), 6.87 (m, 2H), 4.48 (q, 2H), 3.91 (s, 3H), 2.30 (s, 3H), 2.05 (m, 1H), 1.44 (t, 3H), 1.40 (s, 9H), 1.25 (m, 2H), 1.15 (m, 2H).

Example 162

Ethyl 2-[3-methoxy-4-(4-methyl-imidazol-1-yl)-phenylamino]-6-pyridin-2-yl-pyrimidine-4-carboxylate

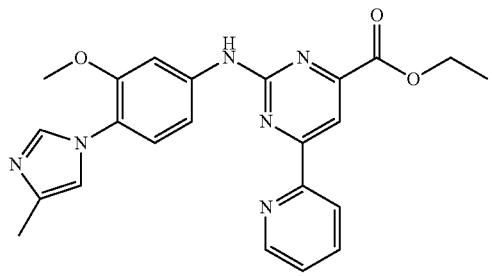 [SMILES: CCOC(=O)c1cc(-c2ccccn2)nc(Nc2ccc(-n3cnc(C)c3)c(OC)c2)n1]

Obtained in 14% yield as light yellow solid. MS ISP (m/e): 431.3 [(M+H)⁺]. ¹H NMR (CDCl₃, 300 MHz): δ (ppm)=8.78 (dd, 1H), 8.45 (s, 1H), 8.44 (d, 1H), 8.01 (d, 1H), 7.88 (td, 1H), 7.66 (s, 1H), 7.60 (s, 1H), 7.46 (dd, 1H), 7.22 (d, 1H), 7.08 (dd, 1H), 6.90 (s, 1H), 4.51 (q, 2H), 3.94 (s, 3H), 2.31 (s, 3H), 1.47 (t, 3H).

Example 163

Ethyl 2-[3-methoxy-4-(4-methyl-imidazol-1-yl)-phenylamino]-6-(4-trifluoromethyl-phenyl)-pyrimidine-4-carboxylate

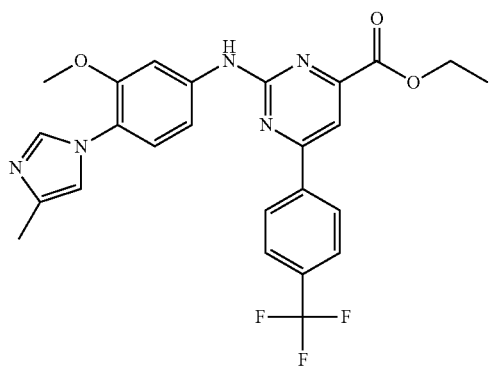 [SMILES: CCOC(=O)c1cc(-c2ccc(C(F)(F)F)cc2)nc(Nc2ccc(-n3cnc(C)c3)c(OC)c2)n1]

Obtained in 26% yield as light yellow solid. MS ISP (m/e): 498.2 [(M+H)⁺]. ¹H NMR (CDCl₃, 300 MHz): δ (ppm)=8.26 (d, 2H), 8.01 (d, 1H), 7.92 (s, 1H), 7.79 (d, 2H), 7.66 (s, 1H), 7.59 (s, 1H), 7.22 (d, 1H), 7.07 (dd, 1H), 6.90 (s, 1H), 4.52 (q, 2H), 3.93 (s, 3H), 2.31 (s, 3H), 1.47 (t, 3H).

Example 164

Ethyl 6-(4-chloro-benzyl)-2-[3-methoxy-4-(4-methyl-imidazol-1-yl)-phenylamino]-pyrimidine-4-carboxylate

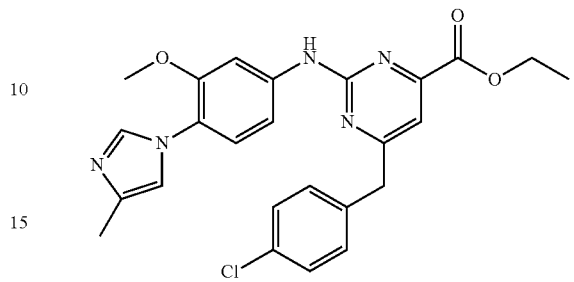

Obtained in 33% yield as light yellow solid. MS ISP (m/e): 478.1 [(M+H)⁺]. ¹H NMR (CDCl₃, 300 MHz): δ (ppm)=7.90 (s, 1H), 7.63 (s, 1H), 7.44 (s, 1H), 7.31 (d, 2H), 7.29 (s, 1H), 7.21 (d, 2H), 7.16 (d, 1H), 6.96 (dd, 1H), 6.87 (s, 1H), 4.45 (q, 2H), 3.83 (s, 3H), 2.30 (s, 3H), 1.42 (t, 3H).

Example 165

2-{2-[3-Methoxy-4-(4-methyl-imidazol-1-yl)-phenylamino]-6-methyl-pyrimidin-4-yl}-propan-2-ol

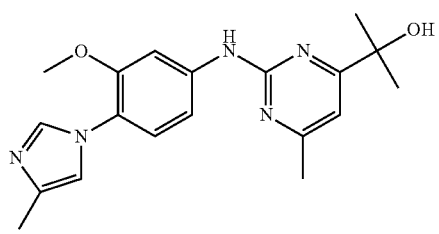 [SMILES: COc1cc(Nc2nc(C)cc(C(C)(C)O)n2)ccc1-n1cnc(C)c1]

To a solution of ethyl 2-[3-methoxy-4-(4-methyl-imidazol-1-yl)-phenylamino]-6-methyl-pyrimidine-4-carboxylate (184 mg, 0.5 mmol) in tetrahydrofurane (10 mL) was added at 0° C. over 2 min a 3 M solution of methylmagnesiumchloride in tetrahydrofurane (0.55 mL, 1.65 mmol). The reaction mixture was stirred at 0° C. for 15 min followed by 1 h at 20° C. The mixture was poured on saturated sodium carbonate solution (20 mL) and the product was extracted with ethyl acetate (40 mL). The organic layer was washed with brine (20 mL), dried over sodium sulfate and evaporated under reduced pressure. The residual material was crystallized from dichloromethane/heptane to give the title compound to give the title compound (105 mg, 59%) as an off-white solid. MS ISP (m/e): 354.3 [(M+H)⁺]. ¹H NMR (CDCl₃, 300 MHz): δ (ppm)=7.76 (d, 1H), 7.63 (s, 1H), 7.18 (d, 1H), 7.02 (dd, 1H), 6.88 (s, 1H), 6.75 (s, 1H), 4.04 (s, 1H), 3.88 (s, 3H), 2.47 (s, 3H), 2.30 (s, 3H), 1.53 (s, 6H).

Example 166-173

Using in analogous manner the procedure described in example 165, the products of examples 158, 159, 161, 160, 157, 141, 162, and 164 were reacted with methylmagnesiumchloride, respectively, to give, after purification of the crude products by crystallization from dichloromethane/heptane or by chromatography on silica gel using dichloro-methane/0-10% methanol as eluent, the following compounds:

Example 166

2-{6-Ethyl-2-[3-methoxy-4-(4-methyl-imidazol-1-O-phenylamino]-pyrimidin-4-yl}-propan-2-ol

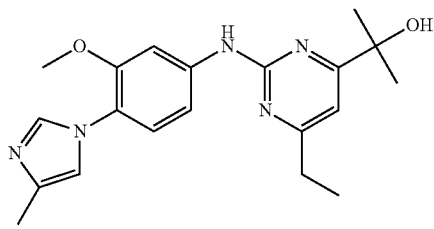 [SMILES: CCc1cc(C(C)(C)O)nc(Nc2ccc(-n3cnc(C)c3)c(OC)c2)n1]

Obtained in 35% yield as light yellow solid. MS ISP (m/e): 368.2 [(M+H)+]. ¹H NMR (CDCl₃, 300 MHz): δ (ppm)=7.84 (d, 1H), 7.63 (s, 1H), 7.21 (s, 1H), 7.17 (d, 1H), 7.00 (dd, 1H), 6.88 (s, 1H), 6.74 (s, 1H), 4.10 (s, 1H), 3.88 (s, 3H), 2.43 (q, 2H), 2.30 (s, 3H), 1.54 (s, 6H), 1.34 (t, 3H).

Example 167

2-{6-Isopropyl-2-[3-methoxy-4-(4-methyl-imidazol-1-yl)-phenylamino]-pyrimidin-4-yl}-propan-2-ol

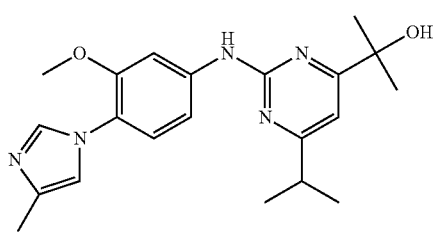 [SMILES: COc1cc(Nc2nc(C(C)C)cc(C(C)(C)O)n2)ccc1-n1cnc(C)c1]

Obtained in 49% yield as light yellow solid. MS ISP (m/e): 382.3 [(M+H)+]. ¹H NMR (CDCl₃, 300 MHz): δ (ppm)=7.91 (d, 1H), 7.64 (s, 1H), 7.19 (s, 1H), 7.17 (d, 1H), 6.98 (dd, 1H), 6.88 (s, 1H), 6.74 (s, 1H), 4.18 (s, 1H), 3.89 (s, 3H), 2.94 (m, 1H), 2.30 (s, 3H), 1.54 (s, 6H), 1.33 (d, 6H).

Example 168

2-{6-Cyclopropyl-2-[3-methoxy-4-(4-methyl-imidazol-1-yl)-phenylamino]-pyrimidin-4-yl}-propan-2-ol

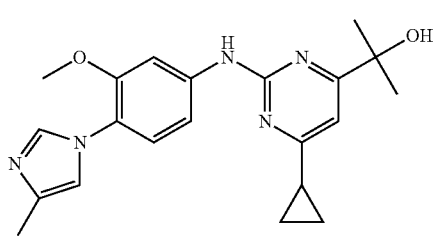 [SMILES: COc1cc(Nc2nc(C3CC3)cc(C(C)(C)O)n2)ccc1-n1cnc(C)c1]

Obtained in 31% yield as light white solid. MS ISP (m/e): 380.3 [(M+H)+]. ¹H NMR (CDCl₃, 300 MHz): δ (ppm)=7.84 (d, 1H), 7.65 (s, 1H), 7.16 (d, 1H), 7.12 (s, 1H), 6.90 (dd, 1H), 6.88 (s, 1H), 6.78 (s, 1H), 4.20 (s, 1H), 3.89 (s, 3H), 2.31 (s, 3H), 1.96 (m, 1H), 1.53 (s, 6H), 1.22 (m, 2H), 1.09 (m, 2H).

Example 169

2-{6-tert-Butyl-2-[3-methoxy-4-(4-methyl-imidazol-1-O-phenylamino]-pyrimidin-4-yl}-propan-2-ol

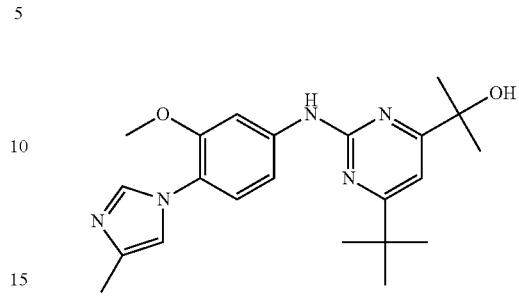

Obtained in 17% yield as light yellow solid. MS ISP (m/e): 396.3 [(M+H)+]. ¹H NMR (CDCl₃, 300 MHz): δ (ppm)=7.94 (d, 1H), 7.64 (s, 1H), 7.19 (s, 1H), 7.17 (d, 1H), 6.98 (dd, 1H), 6.89 (s, 1H), 6.87 (s, 1H), 4.17 (s, 1H), 3.89 (s, 3H), 2.30 (s, 3H), 1.54 (s, 6H), 1.38 (s, 9H).

Example 170

2-{2-[3-Methoxy-4-(4-methyl-imidazol-1-yl)-phenylamino]-6-thiophen-2-yl-pyrimidin-4-yl}-propan-2-ol

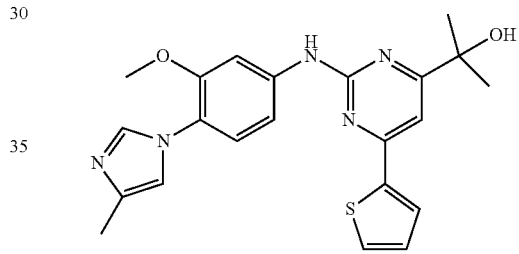

Obtained in 62% yield as light yellow solid. MS ISP (m/e): 422.2 [(M+H)+]. ¹H NMR (CDCl₃, 300 MHz): δ (ppm)=7.90 (d, 1H), 7.78 (d, 1H), 7.64 (s, 1H), 7.53 (d, 1H), 7.20 (d, 1H), 7.19 (s, 1H), 7.18 (m, 1H), 7.01 (dd, 1H), 6.90 (s, 1H), 4.00 (s, 1H), 3.96 (s, 3H), 2.31 (s, 3H), 1.58 (s, 6H).

Example 171

2-{2-[3-Methoxy-4-(4-methyl-imidazol-1-yl)-phenylamino]-5-methyl-pyrimidin-4-yl}-propan-2-ol

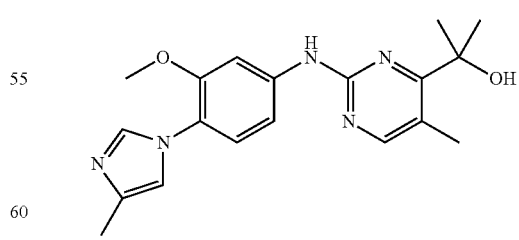

Obtained in 54% yield as light yellow solid. MS ISP (m/e): 354.3 [(M+H)+]. ¹H NMR (CDCl₃, 300 MHz): δ (ppm)=8.22 (s, 1H), 7.63 (s, 1H), 7.53 (d, 1H), 7.18 (s, 1H), 7.13 (s, 1H), 7.03 (dd, 1H), 6.87 (s, 1H), 5.30 (s, 1H), 3.87 (s, 3H), 2.37 (s, 3H), 2.31 (s, 3H), 1.59 (s, 6H).

Example 172

2-{2-[3-Methoxy-4-(4-methyl-imidazol-1-yl)-phenylamino]-6-pyridin-2-yl-pyrimidin-4-yl}-propan-2-ol

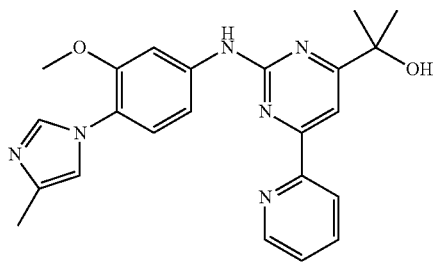 [SMILES: COc1cc(Nc2nc(-c3ccccn3)cc(C(C)(C)O)n2)ccc1-n1cnc(C)c1]

Obtained in 82% yield as light yellow solid. MS ISP (m/e): 417.3 [(M+H)+]. ¹H NMR (CDCl₃, 300 MHz): δ (ppm)=8.75 (dd, 1H), 8.44 (d, 1H), 7.94 (s, 1H), 7.87 (td, 1H), 7.77 (d, 1H), 7.66 (s, 1H), 7.43 (dd, 1H), 7.24 (d, 1H), 7.13 (dd, 1H), 6.91 (s, 1H), 4.29 (s, 1H), 3.91 (s, 3H), 2.31 (s, 3H), 1.63 (s, 6H).

Example 173

2-{6-(4-Chloro-benzyl)-2-[3-methoxy-4-(4-methyl-imidazol-1-yl)-phenylamino]-pyrimidin-4-yl}-propan-2-ol

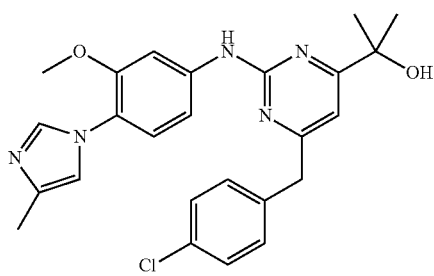 [SMILES: COc1cc(Nc2nc(Cc3ccc(Cl)cc3)cc(C(C)(C)O)n2)ccc1-n1cnc(C)c1]

Obtained in 47% yield as off-white solid. MS ISP (m/e): 464.2 [(M+H)+]. ¹H NMR (CDCl₃, 300 MHz): δ (ppm)=7.67 (d, 1H), 7.62 (s, 1H), 7.30 (d, 2H), 7.22 (d, 2H), 7.15 (d, 1H), 6.99 (dd, 1H), 6.88 (s, 1H), 6.73 (s, 1H), 3.99 (s, 2H), 3.94 (br s, 1H), 3.78 (s, 3H), 2.30 (s, 3H), 1.51 (s, 6H).

Example 174

2-[2-[3-Methoxy-4-(4-methyl-imidazol-1-yl)-phenylamino]-6-(4 fluoromethyl-phenyl)-pyrimidin-4-yl]-propan-2-ol

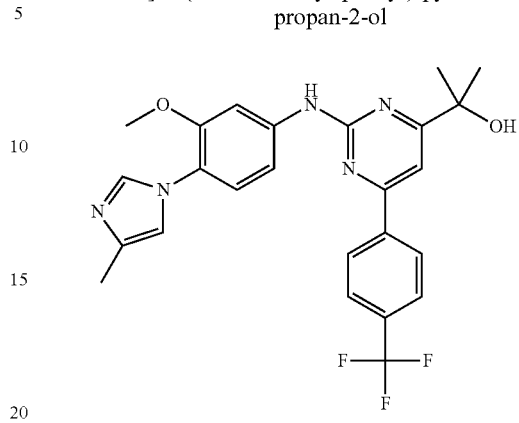

To a solution of ethyl 2-[3-methoxy-4-(4-methyl-imidazol-1-yl)-phenylamino]-6-(4-trifluoromethyl-phenyl)-pyrimidine-4-carboxylate (597 mg, 1.2 mmol) in tetrahydrofurane (25 mL) was added at 0° C. over 2 min a 3 M solution of methylmagnesiumchloride in tetrahydrofurane (1.68 mL, 5.04 mmol). The reaction mixture was stirred at 0° C. for 15 min followed by 1.5 h at 20° C. The mixture was poured on saturated sodium carbonate solution (20 mL) and the product was extracted with ethyl acetate (80 mL). The organic layer was washed with brine (20 mL), dried over sodium sulfate and evaporated under reduced pressure. The residual material was purified by chromatography on silica gel using dichloromethane/0-10% methanol as eluent. Following a more liopophilic by-product (54 mg, example 175) the title compound was eluted and crystallized from dichloromethane/diethyl ether to give a white solid (314 mg, 54%). MS ISP (m/e): 484.4 [(M+H)+]. ¹H NMR (CDCl₃, 300 MHz): δ (ppm)=8.21 (d, 2H), 7.82 (d, 1H), 7.77 (d, 2H), 7.66 (s, 1H), 7.36 (s, 2H), 7.22 (d, 1H), 7.10 (dd, 1H), 6.90 (s, 1H), 3.90 (s, 3H), 3.84 (br s, 1H), 2.31 (s, 3H), 1.56 (s, 6H).

Example 175

1-[2-[3-Methoxy-4-(4-methyl-imidazol-1-yl)-phenylamino]-6-(4-trifluoromethyl-phenyl)-pyrimidin-4-yl]-ethanone

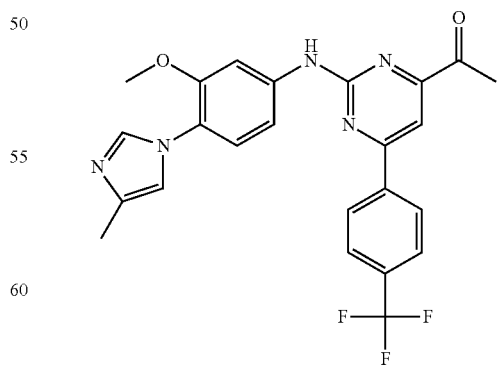

Obtained as by-product in the preparation of example 174 in 10% yield as light yellow solid. MS ISP (m/e): 468.3 [(M+H)+]. ¹H NMR (CDCl₃, 300 MHz): δ (ppm)=8.26 (d, 2H), 7.84 (s, 1H), 7.82 (d, 1H), 7.79 (d, 2H), 7.67 (s, 1H), 7.52 (s, 1H), 7.26 (m, 2H), 7.17 (dd, 1H), 6.91 (s, 1H), 3.92 (s, 3H), 2.76 (s, 3H), 2.32 (s, 3H).

Example 176

3-{2-[3-Methoxy-4-(4-methyl-imidazol-1-yl)-phenylamino]-pyrimidin-4-yl}-pentan-3-ol

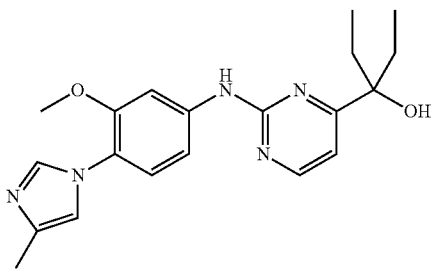 [SMILES: CCC(O)(CC)c1ccnc(Nc2ccc(-n3cnc(C)c3)c(OC)c2)n1]

To a solution of 2-[3-methoxy-4-(4-methyl-imidazol-1-yl)-phenylamino]-pyrimidine-4-carboxylic acid ethyl ester (46 mg, 0.13 mmol) in tetrahydrofurane (2.5 mL) was added at 0° C. over 1 min a 1 M solution of ethylmagnesiumbromide in tetrahydrofurane (0.43 mL, 0.43 mmol). The reaction mixture was stirred at 0° C. for 15 min followed by 1 h at 20° C. The mixture was poured on saturated sodium carbonate solution (5 mL) and the mixture was extracted with ethyl acetate (40 mL). The organic layer was washed with brine (20 mL), dried over sodium sulfate and evaporated under reduced pressure. The residual material was purified by chromatography on silica gel using dichloromethane/0-10% methanol as eluent to give the title compound (4 mg, 9%) as yellow oil. MS ISP (m/e): 368.2 [(M+H)$^+$]. $^1$H NMR (CDCl$_3$, 300 MHz): δ (ppm)=8.42 (d, 1H), 7.66 (d, 1H), 7.65 (s, 1H), 7.39 (s, 1H), 7.20 (d, 1H), 7.06 (dd, 1H), 6.89 (s, 1H), 6.79 (d, 1H), 4.32 (br s, 1H), 3.88 (s, 3H), 2.31 (s, 3H), 2.35 (m, 4H), 0.76 (t, 6H).

Example 177

1-{2-[3-Methoxy-4-(4-methyl-imidazol-1-yl)-phenylamino]-pyrimidin-4-yl

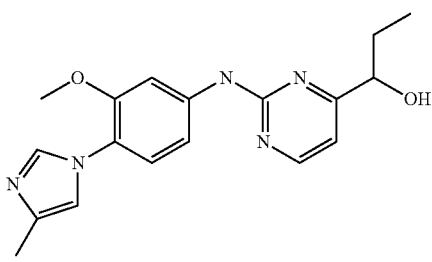 [SMILES: CCC(O)c1ccnc(Nc2ccc(-n3cnc(C)c3)c(OC)c2)n1]

Obtained as by-product in the preparation of example 177 in 3% yield as white solid. MS ISP (m/e): 340.2 [(M+H)$^+$]. $^1$H NMR (CDCl$_3$, 300 MHz): δ (ppm)=8.41 (d, 1H), 7.66 (s, 2H), 7.20 (s, 1H), 7.17 (d, 1H), 7.09 (dd, 1H), 6.88 (s, 1H), 6.78 (d, 1H), 4.60 (br t, 1H), 3.87 (s, 3H), 2.30 (s, 3H), 1.6-1.8 (m, 2H), 0.99 (t, 3H).

Example 178

Dicyclopropyl-{2-[3-methoxy-4-(4-methyl-imidazol-1-yl)-phenylamino]-pyrimidin-4-yl}-methanol

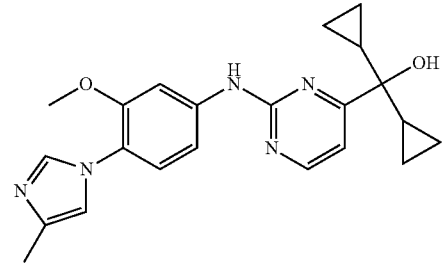 [SMILES: COc1cc(Nc2nccc(C(O)(C3CC3)C3CC3)n2)ccc1-n1cnc(C)c1]

To a solution of 2-[3-methoxy-4-(4-methyl-imidazol-1-yl)-phenylamino]-pyrimidine-4-carboxylic acid ethyl ester (46 mg, 0.13 mmol) in tetrahydrofurane (2.5 mL) was added at 0° C. over 1 min a 0.5 M solution of cyclopropylmagnesiumbromide in tetrahydrofurane (1.02 mL, 0.51 mmol). The reaction mixture was stirred at 0° C. for 15 min followed by 1.5 h at 20° C. The mixture was poured on saturated sodium carbonate solution (5 mL) and the mixture was extracted with ethyl acetate (40 mL). The organic layer was washed with brine (20 mL), dried over sodium sulfate and evaporated under reduced pressure. The residual material was purified by chromatography on silica gel using dichloromethane/0-10% methanol as eluent to give the title compound as light yellow foam (44 mg, 88%). MS ISP (m/e): 392.3 [(M+H)$^+$]. $^1$H NMR (CDCl$_3$, 300 MHz): δ (ppm)=8.45 (d, 1H), 7.64 (s, 1H), 7.56 (d, 1H), 7.23 (s, 1H), 7.19 (d, 1H), 7.08 (dd, 1H), 7.00 (d, 1H), 6.88 (s, 1H), 4.15 (s, 1H), 3.87 (s, 3H), 2.30 (s, 3H), 1.14 (m, 2H), 0.70, 0.50, 0.35, 0.25 (4 m, 4×2H).

Example 179

2-[2-[3-Methoxy-4-(4-methyl-imidazol-1-yl)-phenylamino]-6-(3,4,5-trifluoro-phenyl)-pyrimidin-4-yl]-propan-2-ol

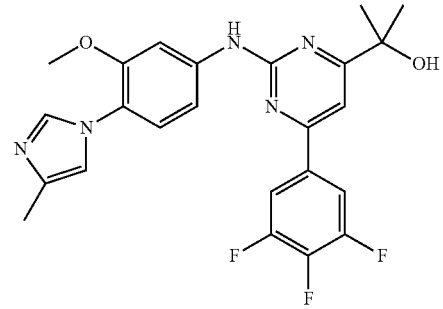 [SMILES: COc1cc(Nc2nc(-c3cc(F)c(F)c(F)c3)cc(C(C)(C)O)n2)ccc1-n1cnc(C)c1]

a) Ethyl 2,4-dioxo-4-(3,4,5-trifluoro-phenyl)-butyrate

Potassium tert.-butoxide (1.12 g, 10.0 mmol) was added to a solution of 1-(3,4,5-trifluoro-phenyl)-ethanone (1.74 g, 10.0 mmol) and diethyl oxalate (1.49 mL, 11.0 mmol) in diethyl ether (20 mL) cooled to 0° C. The heterogenous mixture was stirred for 15 min at 0° C. followed by 15 h at 20° C. The mixture was partitioned between 3 N hydrochloric acid (20 mL) and diethyl ether (50 mL). The organic layer was washed with brine (20 mL), dried over sodium sulfate and evaporated under reduced pressure and the residual oil was crystallized from diethyl ether/heptane to give the title compound as a white solid.

2-[2-[3-Methoxy-4-(4-methyl-imidazol-1-yl)-phenylamino]-6-(3,4,5-trifluoro-phenyl)-pyrimidin-4-yl]-propan-2-ol Ethyl 2,4-dioxo-4-(3,4,5-trifluoro-phenyl)-butyrate (274 mg, 1.0 mmol) was reacted with N-[3-methoxy-4-(4-methyl-imidazol-1-yl)-phenyl]-guanidine dinitrate (298 mg, 0.80 mmol) in analogous manner as described in example 139, and the resulting product was subjected in analogous manner to the procedure described in example 165 to give the title compound light yellow solid (35 mg, 9%). MS ISP (m/e): 470.4 [(M+H)+]. 1H NMR (CDCl3, 300 MHz): δ (ppm)=7.81 (m, 2H), 7.78 (d, 1H), 7.75 (s, 1H), 7.66 (s, 1H), 7.35 (s, 1H), 7.22 (d, 1H), 7.04 (dd, 1H), 6.90 (s, 1H), 3.91 (s, 3H), 3.76 (br s, 1H), 2.31 (s, 3H), 1.61 (s, 6H).

Example 180

2-{6-(2,4-Dichloro-phenyl)-2-[3-methoxy-4-(4-methyl-imidazol-1-yl)-phenylamino]-pyrimidin-4-yl}-propan-2-ol

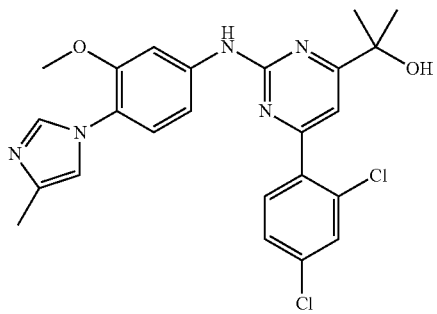 [SMILES: COc1cc(Nc2nc(-c3ccc(Cl)cc3Cl)cc(C(C)(C)O)n2)ccc1-n1cnc(C)c1]

Ethyl 3-(2,4-dichloro-phenyl)-3-oxo-propionate (145 mg, 0.5 mmol) was subjected in analogous manner to the procedure described in example 179b) to give the title compound as light yellow foam (42 mg, 22%). MS ISP (m/e): 484.3 [(M+H)+]. 1H NMR (CDCl3, 300 MHz): δ (ppm)=7.82 (d, 1H), 7.64 (d, 1H), 7.64 (s, 1H), 7.53 (d, 1H), 7.36 (dd, 1H), 7.33 (s, 1H), 7.23 (s, 1H), 7.18 (d, 1H), 7.04 (dd, 1H), 6.88 (s, 1H), 3.95 (br s, 1H), 3.84 (s, 3H), 2.30 (s, 3H), 1.59 (s, 6H).

Example 181

2-{6-(4-Chloro-phenyl)-2-[3-methoxy-4-(4-methyl-imidazol-1-yl)-phenylamino]-pyrimidin-4-yl}-propan-2-ol

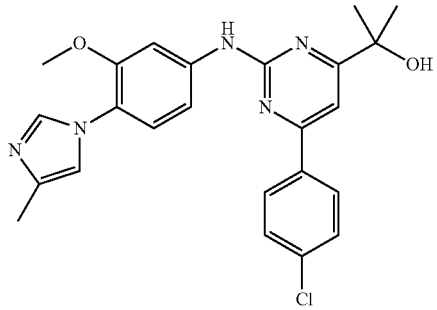 [SMILES: COc1cc(Nc2nc(-c3ccc(Cl)cc3)cc(C(C)(C)O)n2)ccc1-n1cnc(C)c1]

Ethyl 3-(4-chloro-phenyl)-3-oxo-propionate (127 mg, 0.5 mmol) was subjected in analogous manner to the procedure described in example 179b) to give the title compound as light yellow foam (42 mg, 13%). MS ISP (m/e): 450.2 [(M+H)+].) 1 1H NMR (CDCl3, 300 MHz): δ (ppm)=8.05 (d, 2H), 7.84 (d, 1H), 7.66 (s, 1H), 7.48 (d, 2H), 7.31 (s, 1H), 7.29 (s, 1H), 7.21 (d, 1H), 7.06 (dd, 1H), 6.89 (s, 1H), 3.94 (br s, 1H), 3.89 (s, 3H), 2.31 (s, 3H), 1.61 (s, 6H).

Example 182

2-{6-(2-Chloro-phenyl)-2-[3-methoxy-4-(4-methyl-imidazol-1-yl)-phenylamino]-pyrimidin-4-yl}-propan-2-ol

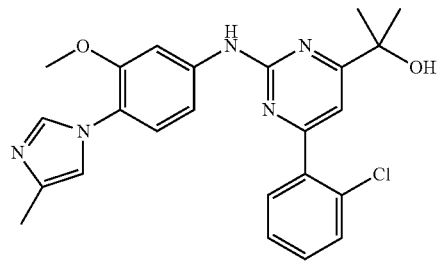 [SMILES: COc1cc(Nc2nc(-c3ccccc3Cl)cc(C(C)(C)O)n2)ccc1-n1cnc(C)c1]

Ethyl 3-(2-chloro-phenyl)-3-oxo-propionate (127 mg, 0.5 mmol) was subjected in analogous manner to the procedure described in example 179b) to give the title compound as light yellow foam (33 mg, 18%). MS ISP (m/e): 450.2 [(M+H)+]. 1H NMR (CDCl3, 300 MHz): δ (ppm)=7.88 (d, 1H), 7.66 (m, 1H), 7.64 (s, 1H), 7.52 (m, 1H), 7.41 (m, 2H), 7.34 (s, 1H), 7.25 (s, 1H), 7.18 (d, 1H), 7.04 (dd, 1H), 6.88 (s, 1H), 4.08 (br s, 1H), 3.84 (s, 3H), 2.30 (s, 3H), 1.60 (s, 6H).

Example 183

2-{2-[3-Methoxy-4-(4-methyl-imidazol-1-yl)-phenylamino]-5,6,7,8-tetrahydro-quinazolin-4-yl}-propan-2-ol

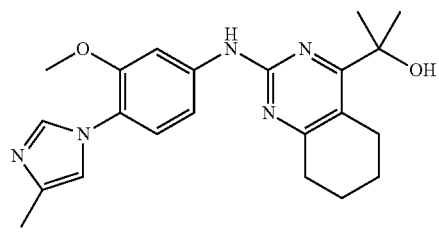 [SMILES: COc1cc(Nc2nc3c(c(C(C)(C)O)n2)CCCC3)ccc1-n1cnc(C)c1]

Ethyl oxo-(2-oxo-cyclohexyl)-acetate (198 mg, 1.0 mmol) was subjected in analogous manner to the procedure described in example 179b) to give the title compound as light yellow foam (15 mg, 5%). MS ISP (m/e): 394.2 [(M+H)+]. 1H NMR (CDCl3, 300 MHz): δ (ppm)=7.67 (d, 1H), 7.63 (s, 1H), 7.45 (s, 1H), 7.13 (d, 1H), 7.00 (dd, 1H), 6.88 (s, 1H), 3.87 (s, 3H), 2.75-2.95 (m, 4H), 2.30 (s, 3H), 1.75-1.95 (m, 4H), 1.58 (s, 6H).

Example 184

(4-Benzyl-6-methyl-pyrimidin-2-yl)-[3-fluoro-4-(4-methyl-imidazol-1-yl)-phenyl]-amine

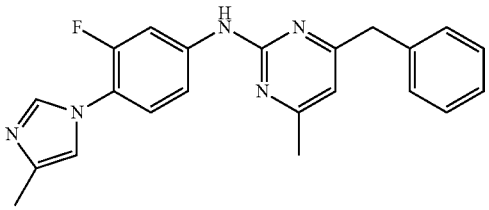 [SMILES: Cc1cn(-c2ccc(Nc3nc(C)cc(Cc4ccccc4)n3)cc2F)cn1]

The title compound was prepared from 4-benzyl-2-chloro-6-methyl-pyrimidine (100 mg, 0.46 mmol) and 3-fluoro-4-(4-methyl-imidazol-1-yl)-phenylamine (88 mg, 0.57 mmol) using in analogous manner the procedure described in example 43b). Column chromatography (15 g silica, dichloromethane+3.7% methanol v/v) afforded the title compound (148 mg, 86%) as a white solid. MS ISP (m/e): 374.4 [(M+H)$^+$]. $^1$H NMR (CDCl$_3$, 300 MHz): δ (ppm)=7.98 (dd, 1H), 7.65 (s, 1H), 7.26 (m, 8H), 6.92 (s, 1H), 6.53 (s, 1H), 3.98 (s, 2H), 2.38 8s, 3H), 2.31 (s, 3H). Mp 155-158° C.

Example 185

(6-Ethoxy-pyridin-2-yl)-[3-methoxy-4-(4-methyl-imidazol-1-yl)-phenyl]-amine

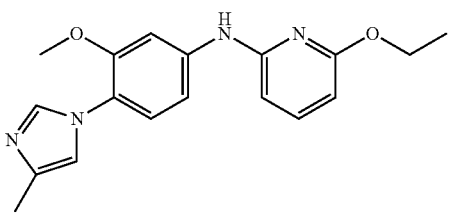 [SMILES: CCOc1cccc(Nc2ccc(-n3cnc(C)c3)c(OC)c2)n1]

A solution of (6-chloro-pyridin-2-yl)-[3-methoxy-4-(4-methyl-imidazol-1-yl)-phenyl]-amine (63 mg, 0.2 mmol) and 21% sodium ethanolate solution in ethanol (112 uL, 0.3 mmol) was heated to 200° C. for 30 minutes in a microwave oven. The same amount of sodium ethanolate solution was added and the reaction was again heated to 200° C. for 30 minutes in a microwave oven. Water was added and the reaction was extracted twice with ethyl acetate. The combined organic layers were washed with brine, dried over sodium sulfate, filtered and the solvent was evaporated under reduced pressure. The residue was purified by column chromatography on silica gel using dichloromethane/methanol (19:1 v/v) as eluent to yield the title compound as a light brown solid (25 mg, 39%). MS ISP (m/e): 325.2 (100) [(M+H)$^+$]. $^1$H NMR (CDCl$_3$, 300 MHz): δ (ppm)=7.64 (s, 1H), 7.45 (t, 1H), 7.34 (s, 1H), 7.15 (d, 1H), 6.92 (d, 1H), 6.87 (s, 1H), 6.50 (s, 1H), 6.37 (d, 1H), 6.24 (d, 1H), 4.35 (q, 2H), 3.83 (s, 3H), 2.30 (s, 3H), 1.41 (t, 3H).

Example 186

N-(4-Fluoro-phenyl)-N'-[3-methoxy-4-(4-methyl-imidazol-1-yl)-phenyl]-pyridine-2,6-diamine

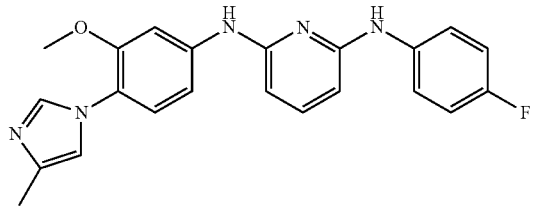 [SMILES: COc1cc(Nc2cccc(Nc3ccc(F)cc3)n2)ccc1-n1cnc(C)c1]

a) (6-Chloro-pyridin-2-yl)-[3-methoxy-4-(4-methyl-imidazol-1-yl)-phenyl]-amine Prepared in analogy to example 62 from 3-methoxy-4-(4-methyl-imidazol-1-yl)-phenylamine and 2,6-dichloropyridine. The title compound was obtained as a yellow solid (Yield=60%). MS ISP (m/e): 315.1 & 317.1 (100 & 37) [(M+H)$^+$]. $^1$H NMR (CDCl$_3$, 300 MHz): 8 (ppm)=7.63 (s, 1H), 7.48 (t, 1H), 7.37 (s, 1H), 7.18 (d, 1H), 6.95-6.80 (m, 2H), 6.82 (d, 1H), 6.72 (d, 1H), 6.64 (s, 1H), 3.86 (s, 3H), 2.30 (s, 3H).

b) N-(4-Fluoro-phenyl)-N'-[3-methoxy-4-(4-methyl-imidazol-1-yl)-phenyl]-pyridine-2,6-diamine Prepared in analogy to example 62 from 4-fluoroaniline and (6-chloro-pyridin-2-yl)-[3-methoxy-4-(4-methyl-imidazol-1-yl)-phenyl]-amine. The title compound was obtained as a colorless foam (Yield=17%). MS ISP (m/e): 390.4 (100) [(M+H)$^+$]. $^1$H NMR (DMSO-D$_6$, 300 MHz): δ (ppm)=9.02 (s, 1H), 8.83 (s, 1H), 7.64 (d, 1H), 7.60-7.50 (m, 2H), 7.45-7.35 (m, 2H), 7.24 (dxd, 1H), 7.15 (d, 1H), 7.07 (t, 1H), 7.02 (s, 1H), 6.24 (qa, 1H), 3.59 (s, 3H), 2.15 (s, 3H).

Example 187

N-[3-Methoxy-4-(4-methyl-imidazol-1-yl)-phenyl]-N'-(4-trifluoromethoxy-phenyl)-pyridine-2,6-diamine

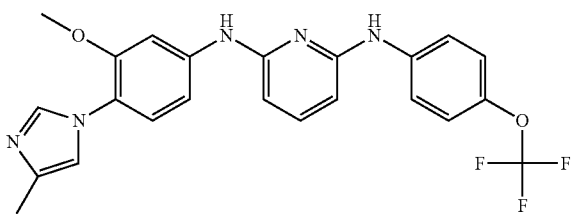 [SMILES: COc1cc(Nc2cccc(Nc3ccc(OC(F)(F)F)cc3)n2)ccc1-n1cnc(C)c1]

Prepared in analogy to example 62 from 4-(trifluoromethoxy)aniline and (6-chloro-pyridin-2-yl)-[3-methoxy-4-(4-methyl-imidazol-1-yl)-phenyl]-amine. The title compound was obtained as a brownish solid (Yield=10%). MS ISP (m/e): 456.3 (100) [(M+H)$^+$].

1H NMR (CDCl$_3$, 300 MHz): δ (ppm)=7.63 (s, 1H), 7.45-7.35 (m, 3H), 7.20-7.10 (m, 3H), 6.94 (dxd, 1H), 6.87 (s, 1H), 6.44 (s, 1H), 6.36 (s, 1H), 6.34 (dxd, 1H), 3.73 (s, 3H), 2.30 (s, 3H).

Example 188

N-[3-Methoxy-4-(4-methyl-imidazol-1-yl)-phenyl]-N'-(3-trifluoromethoxy-phenyl)-pyridine-2,6-diamine

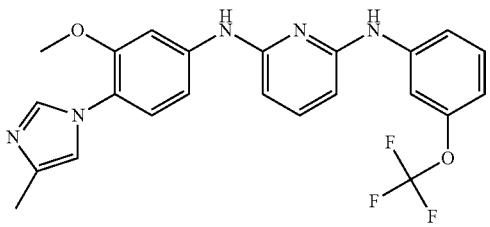 [SMILES: COc1cc(Nc2cccc(Nc3cccc(OC(F)(F)F)c3)n2)ccc1-n1cnc(C)c1]

Prepared in analogy to example 62 from 3-(trifluoromethoxy)aniline and (6-chloro-pyridin-2-yl)-[3-methoxy-4-(4-methyl-imidazol-1-yl)-phenyl]-amine. The title compound was obtained as a brownish solid (Yield=3%). MS ISP (m/e): 456.3 (100) [(M+H)+].

1H NMR (CDCl₃, 300 MHz): δ (ppm)=7.63 (s, 1H), 7.45-7.35 (m, 3H), 7.20-7.10 (m, 2H), 6.96 (dxd, 1H), 6.90-6.80 (m 2H), 6.43 (s, 1H), 6.42 (s, 1H), 6.35 (dxd, 1H), 3.74 (s, 3H), 2.30 (s, 3H).

Example 189

N-[3-Methoxy-4-(4-methyl-imidazol-1-yl)-phenyl]-N'-(4-pentafluorosulfanyl-phenyl)-pyridine-2,6-diamine

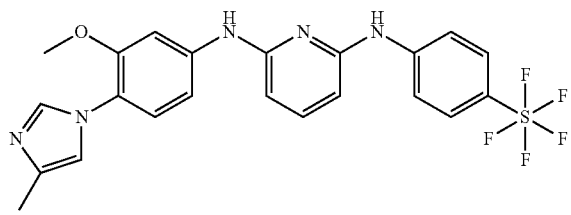 [SMILES: COc1cc(Nc2cccc(Nc3ccc(S(F)(F)(F)(F)F)cc3)n2)ccc1-n1cnc(C)c1]

Prepared in analogy to example 62 from 4-aminosulfurpentafluoride and (6-chloro-pyridin-2-yl)-[3-methoxy-4-(4-methyl-imidazol-1-yl)-phenyl]-amine. The title compound was obtained as a colorless solid (Yield=44%). MS ISP (m/e): 498.3 (100) [(M+H)+].

1H NMR (CDCl₃, 300 MHz): δ (ppm)=7.70-7.60 (m, 3H), 7.55-7.40 (m, 3H), 7.20-7.10 (m, 2H), 6.57 (s, 1H), 6.48 (s, 1H), 6.42 (d, 1H), 6.37 (d, 1H), 3.72 (s, 3H), 2.30 (s, 3H).

Example 190

N-[3-Methoxy-4-(4-methyl-imidazole-1-yl)-phenyl)] N'-(3-sulfurpentafluoride-phenyl)-pyridine-2,6-diamine

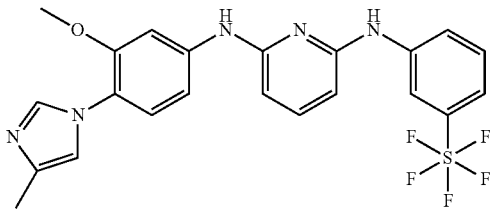 [SMILES: COc1cc(Nc2cccc(Nc3cccc(S(F)(F)(F)(F)F)c3)n2)ccc1-n1cnc(C)c1]

Prepared in analogy to example 62 from 3-aminosulfurpentafluoride and (6-chloro-pyridin-2-yl)-[3-methoxy-4-(4-methyl-imidazol-1-yl)-phenyl]-amine. The title compound was obtained as a slightly orange solid (Yield=30%). MS ISP (m/e): 498.1 (100) [(M+H)+]. ¹H NMR (CDCl₃, 300 MHz): δ (ppm)=7.84 (s, 1H), 7.63 (s, 1H), 7.60-7.50 (m, 1H), 7.44 (t, 1H), 7.40-7.30 (m, 2H), 7.20-7.10 (m, 2H), 6.95 (dxd, 1H), 6.87 (s, 1H), 6.45 (s, 1H), 6.43 (s, 1H), 6.39 (d, 1H), 6.30 (d, 1H), 3.71 (s, 3H), 3.30 (s, 3H).

Example 191

N-[3-Methoxy-4-(4-methyl-imidazol-1-yl)-phenyl]-N'-(3-trifluoromethyl-phenyl)-pyridine-2,6-diamine

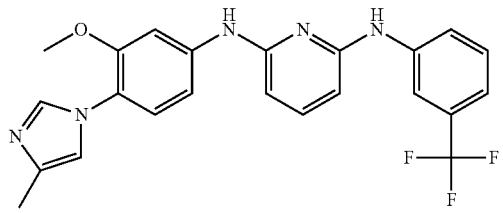 [SMILES: COc1cc(Nc2cccc(Nc3cccc(C(F)(F)F)c3)n2)ccc1-n1cnc(C)c1]

Prepared in analogy to example 62 from 3-trifluoromethylaniline and (6-chloro-pyridin-2-yl)-[3-methoxy-4-(4-methyl-imidazol-1-yl)-phenyl]-amine. The title compound was obtained as a brownish solid (Yield=48%). MS ISP (m/e): 440.3 (100) [(M+H)+]. ¹H NMR (DMSO-D₆, 300 MHz): δ (ppm)=9.24 (s, 1H), 9.13 (s, 1H), 7.93 (s, 1H), 7.82 (d, 1H), 7.65 (s, 1H), 7.55-7.40 (m, 2H), 7.36 (d, 1H), 7.25-7.10 (m, 3H), 7.00 (s, 1H), 6.32 (t, 2H), 3.54 (s, 3H), 2.15 (s, 3H).

Example 192

N-[3-Methoxy-4-(4-methyl-imidazol-1-yl)-phenyl]-N'-(4-trifluoromethyl-phenyl)-pyridine-2,6-diamine

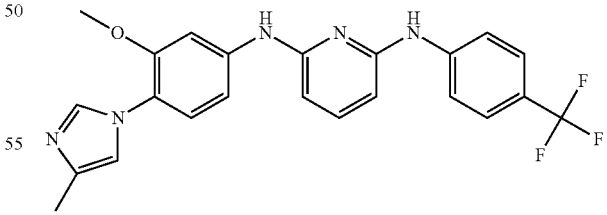

Prepared in analogy to example 62 from 4-trifluoromethylaniline and (6-chloro-pyridin-2-yl)-[3-methoxy-4-(4-methyl-imidazol-1-yl)-phenyl]-amine. The title compound was obtained as a brownish solid (Yield=18%). MS ISN (m/e): 438.4 (100) [(M−H)−]. ¹H NMR (CDCl₃, 300 MHz): δ (ppm)=7.64 (s, 1H), 7.60-7.45 (m, 4H), 7.44 (d, 1H), 7.20-7.10 (m, 2H), 6.95 (dxd, 1H), 6.88 (s, 1H), 6.52 (s, 1H), 6.46 (s, 1H), 6.39 (t, 2H), 3.73 (s, 3H), 2.31 (s, 3H).

Example 193

N-(3-Fluoro-phenyl)-N'-[3-methoxy-4-(4-methyl-imidazol-1-yl)-phenyl]-pyridine-2,6-diamine

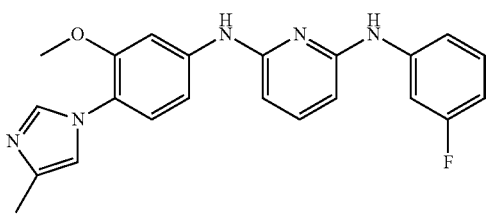 [SMILES: COc1cc(Nc2cccc(Nc3cccc(F)c3)n2)ccc1-n1cnc(C)c1]

Prepared in analogy to example 62 from 3-fluoroaniline and (6-chloro-pyridin-2-yl)-[3-methoxy-4-(4-methyl-imidazol-1-yl)-phenyl]-amine. The title compound was obtained as a brownish solid (Yield=24%). MS ISP (m/e): 390.3 (100) [(M+H)$^+$]. $^1$H NMR (DMSO-D$_6$, 300 MHz): δ (ppm)=9.10 (s very broad, 2H), 7.70-7.50 (m, 2H), 7.45 (t, 2H), 7.39 (s, 1H), 7.30-7.10 (m, 4H), 7.02 (s, 1H), 6.63 (t broad, 1H), 6.30 (t, 2H), 3.62 (s, 3H), 2.14 (s broad, 3H).

Example 194

N-[3-Methoxy-4-(4-methyl-imidazol-1-yl)-phenyl]-N'-methyl-N'-phenyl-pyridine-2,6-diamine

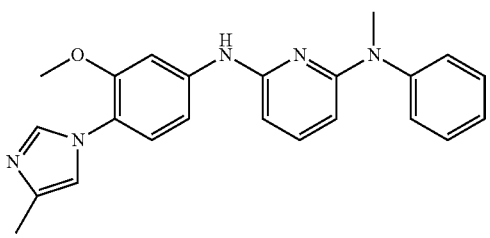 [SMILES: COc1cc(Nc2cccc(N(C)c3ccccc3)n2)ccc1-n1cnc(C)c1]

Prepared in analogy to example 62 from N-methylaniline and (6-chloro-pyridin-2-yl)-[3-methoxy-4-(4-methyl-imidazol-1-yl)-phenyl]-amine. The title compound was obtained as a brownish solid (Yield=16%). MS ISP (m/e): 386.2 (100) [(M+H)$^+$]. $^1$H NMR (DMSO-D$_6$, 300 MHz): δ (ppm)=9.06 (s, 1H), 7.68 (d, 1H), 7.61 (s, 1H), 7.50-7.35 (m, 3H), 7.35-7.15 (m, 4H), 7.09 (, 1H), 6.99 (s, 1H), 6.19 (d, 1H), 5.95 (d, 1H), 3.70 (s, 3H), 3.44 (s, 3H), 2.14 (s, 3H).

Example 195

N-Benzyl-N'-[3-methoxy-4-(4-methyl-imidazol-1-yl)-phenyl]-pyridine-2,6-diamine

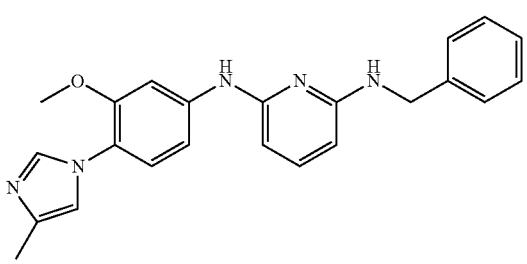 [SMILES: COc1cc(Nc2cccc(NCc3ccccc3)n2)ccc1-n1cnc(C)c1]

Prepared in analogy to example 62 from benzylamine and (6-chloro-pyridin-2-yl)-[3-methoxy-4-(4-methyl-imidazol-1-yl)-phenyl]-amine. The title compound was obtained as a brown solid (Yield=11%). MS ISP (m/e): 386.2 (100) [(M+H)$^+$]. $^1$H NMR (DMSO-D$_6$, 300 MHz): δ (ppm)=8.88 (s, 1H), 7.67 (d, 1H), 7.59 (d, 1H), 7.35-7.25 (m, 3H), 7.35-7.10 (m, 4H), 7.06 (d, 1H), 6.97 (d, 1H), 6.90 (t, 1H), 6.00 (d, 1H), 5.95 (d, 1H), 4.54 (d, 2H), 3.65 (s, 3H), 2.13 (s, 3H).

Example 196

N-[3-Methoxy-4-(4-methyl-imidazol-1-yl)-phenyl]-N'-(4-trifluoromethoxy-phenyl)-4-trifluoromethyl-pyridine-2,6-diamine

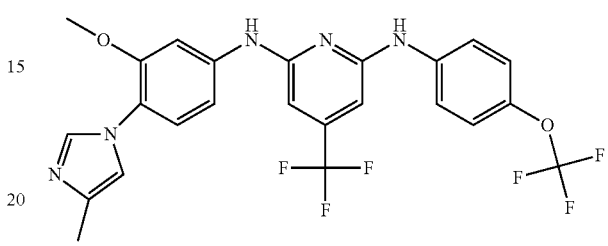

a) (6-Chloro-4-trifluoromethyl-pyridin-2-yl)-[3-methoxy-4-(4-methyl-imidazol-1-yl)-phenyl]-amine Prepared in analogy to example 62 from 3-methoxy-4-(4-methyl-imidazol-1-yl)-phenylamine and 2,6-dichloro-4-trifluoromethyl-pyridine. The title compound was obtained as a yellowish solid (Yield=30%). MS ISP (m/e): 383.1 (39) [(M+H)$^+$]. $^1$H NMR (CDCl$_3$, 300 MHz): δ (ppm)=7.67 (d, 1H), 7.39 (d, 1H), 7.23 (d, 1H), 7.11 (s, 1H), 6.99 (s, 1H), 6.965-6.85 (m, 3H), 3.87 (s, 3H), 2.31 (s, 3H).

b) N-[3-Methoxy-4-(4-methyl-imidazol-1-yl)-phenyl]-N'-(4-trifluoromethoxy-phenyl)-4-trifluoromethyl-pyridine-2,6-diamine Prepared in analogy to example 62 from 4-(trifluoromethoxy)aniline and (6-chloro-4-trifluoromethyl-pyridin-2-yl)-[3-methoxy-4-(4-methyl-imidazol-1-yl)-phenyl]-amine. The title compound was obtained as a yellowish solid (Yield=33%). MS ISP (m/e): 524.2 (100) [(M+H)$^+$]. $^1$H NMR (CDCl$_3$, 300 MHz): δ (ppm)=7.65 (d, 1H), 7.42 (d, 2H), 7.19 (d, 2H), 7.13 (d, 1H), 6.97 (dxd, 1H), 6.89 (s, 1H), 6.65 (s, 1H), 6.58 (s, 1H), 6.48 (s, 1H), 6.42 (s, 1H), 3.74 (s, 3H), 2.31 (s, 3H).

Example 197

N-[3-Methoxy-4-(4-methyl-imidazol-1-yl)-phenyl]-N'-(3-trifluoromethoxy-phenyl)-4-trifluoromethyl-pyridine-2,6-diamine

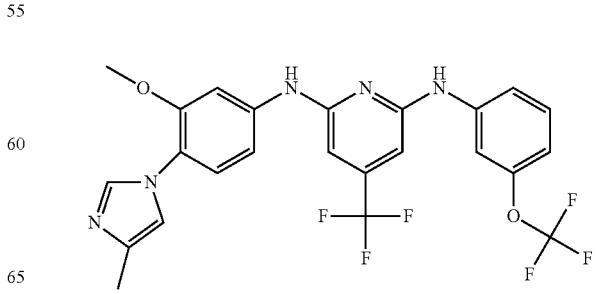

Prepared in analogy to example 62 from 3-(trifluoromethoxy)aniline and (6-chloro-4-trifluoromethyl-pyridin-2-yl)-[3-methoxy-4-(4-methyl-imidazol-1-yl)-phenyl]-amine. The title compound was obtained as a yellowish solid (Yield=63%). MS ISP (m/e): 524.3 (100) [(M+H)+]. 1H NMR (CDCl3, 300 MHz): δ (ppm)=7.65 (d, 1H), 7.42 (s broad, 1H), 7.35-7.25 (m, 2H), 7.19 (d, 1H), 7.12 (d, 1H), 7.00 (dxd, 1H), 6.95-6.85 (m, 2H), 6.77 (d, 1H), 6.50 (s, 1H), 6.46 (s, 1H), 3.73 (s, 3H), 2.30 (s, 3H).

Example 198

N-[3-Methoxy-4-(4-methyl-imidazol-1-yl)-phenyl]-4-trifluoromethyl-N'-(4-trifluoromethyl-phenyl)-pyridine-2,6-diamine

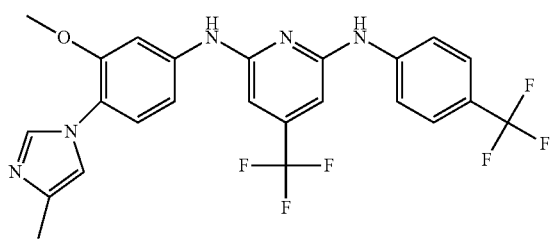 [SMILES: COc1cc(Nc2cc(C(F)(F)F)cc(Nc3ccc(C(F)(F)F)cc3)n2)ccc1-n1cnc(C)c1]

Prepared in analogy to example 62 from 4-trifluoromethylaniline and (6-chloro-4-trifluoromethyl-pyridin-2-yl)-[3-methoxy-4-(4-methyl-imidazol-1-yl)-phenyl]-amine. The title compound was obtained as a yellowish solid (Yield=61%). MS ISP (m/e): 508.2 (100) [(M+H)+]. 1H NMR (CDCl3, 300 MHz): δ (ppm)=7.65 (d, 1H), 7.65-7.45 (AA'BB'-System, 4H), 7.21 (d, 1H), 7.13 (d, 1H), 6.98 (dxd, 1H), 6.90 (s, 1H), 6.83 (s, 1H), 6.75 (s, 1H), 6.54 (s, 1H), 6.50 (s, 1H), 3.72 (s, 3H), 2.31 (s, 3H).

Example 199

N-[3-Methoxy-4-(4-methyl-imidazol-1-yl)-phenyl]-4-trifluoromethyl-N'-(3-trifluoromethyl-phenyl)-pyridine-2,6-diamine

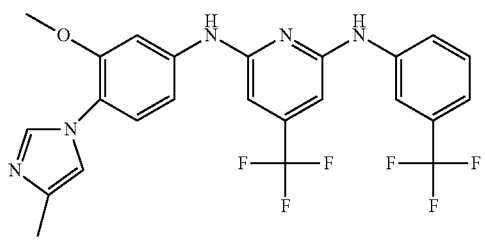 [SMILES: COc1cc(Nc2cc(C(F)(F)F)cc(Nc3cccc(C(F)(F)F)c3)n2)ccc1-n1cnc(C)c1]

Prepared in analogy to example 62 from 3-trifluoromethylaniline and (6-chloro-4-trifluoromethyl-pyridin-2-yl)-[3-methoxy-4-(4-methyl-imidazol-1-yl)-phenyl]-amine. The title compound was obtained as a yellowish solid (Yield=60%). MS ISP (m/e): 508.2 (100) [(M+H)+]. 1H NMR (CDCl3, 300 MHz): δ (ppm)=7.74 (s, 1H), 7.65 (d, 1H), 7.60 (d, 1H), 7.43 (t, 1H), 7.30 (d, 1H), 7.18 (d, 1H), 7.11 (d, 1H), 7.00 (dxd, 1H), 6.89 (s, 1H), 6.87 (s, 1H), 6.82 (s, 1H), 6.51 (s, 1H), 6.44 (s, 1H9, 3.70 (s, 3H), 3.31 (s, 3H).

Example 200

N-(4-Sulfurpentafluoride-phenyl)-N'-[3-methoxy-4-(4-methyl-imidazol-1-yl)-phenyl]-4-trifluoromethyl-pyridine-2,6-diamine

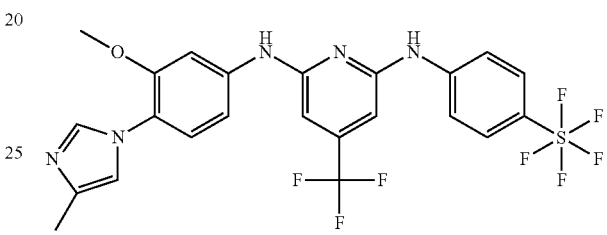

Prepared in analogy to example 62 from 4-aminosulfurpentafluoride and (6-chloro-4-trifluoromethyl-pyridin-2-yl)-[3-methoxy-4-(4-methyl-imidazol-1-yl)-phenyl]-amine. The title compound was obtained as a yellowish solid (Yield=43%). MS ISP (m/e): 566.2 (100) [(M+H)+]. 1H NMR (CDCl3, 300 MHz): δ (ppm)=7.69 (s, 1H), 7.66 (s, 2H), 7.52 (d, 2H), 7.20 (d, 1H), 7.13 (d, 1H), 7.10 (s, 1H), 6.97 (dxd, 1H), 6.90 (s, 1H), 6.87 (s, 1H), 6.56 (s, 1H), 6.51 (s, 1H), 3.71 (s, 3H), 2.31 (s, 3H).

Example 201

N,N'-Bis-[3-methoxy-4-(4-methyl-imidazol-1-yl)-phenyl]-4-trifluoromethyl-pyridine-2,6-diamine

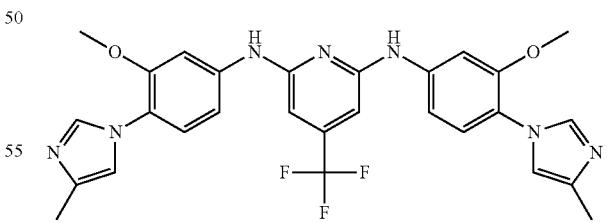

Prepared in analogy to example 62 from 3-methoxy-4-(4-methyl-imidazol-1-yl)-phenylamine and (6-chloro-4-trifluoromethyl-pyridin-2-yl)-[3-methoxy-4-(4-methyl-imidazol-1-yl)-phenyl]-amine. The title compound was obtained as a yellowish solid (Yield=18%). MS ISP (m/e): 550.4 (100) [(M+H)+]. 1H NMR (CDCl3, 300 MHz): δ (ppm)=7.63 (d, 2H), 7.24 (d, 2H), 7.15 (d, 2H), 6.88 (s, 2H), 6.66 (s, 2H), 6.50 (s, 2H), 3.73 (s, 6H), 2.30 (, 6H).

Example 202

[2-[3-Methoxy-4-(4-methyl-imidazol-1-yl)-phenylamino]-6-(4-trifluoromethoxy-phenylamino)-pyridin-4-yl]-methanol

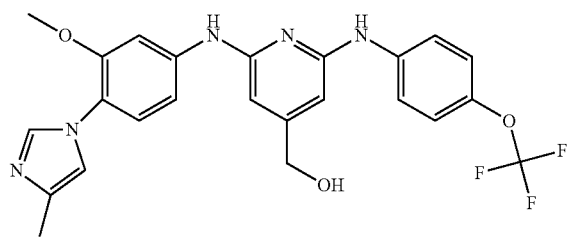 [SMILES: COc1cc(Nc2cc(CO)cc(Nc3ccc(OC(F)(F)F)cc3)n2)ccc1-n1cnc(C)c1]

a) 4-(tert-Butyl-dimethyl-silanyloxymethyl)-2,6-dichloro-pyridine

A solution of 2,6-dichloropyridine-4-methanol (150 mg, 0.84 mmol), tert-butyl-chloro-dimethyl-silane (152 mg, 1.01 mmol) and imidazol (143 mg, 2.01 mmol) in 1 mL of N,N-dimethylformamide was stirred overnight at 20° C. The reaction mixture was concentrated in the rotatory evaporator, water was added and the slurry extracted with ethyl acetate. Chromatography on amino-modified silica gel (Merck HPTLC Silica Gel 60 NH2F254S) using heptane/ethylacetate (gradient 0 to 50% ethyl acetate) gave the pure title compound as a colorless solid (160 mg, 65%). MS ISP (m/e): 292.1 & 294.0 (100 & 97) [(M+H)$^+$]. $^1$H NMR (CDCl$_3$, 300 MHz): δ (ppm)=7.21 (s, 2H), 4.70 (s, 2H), 0.95 (s, 9H), 0.12 (6H).

b) [4-(tert-Butyl-dimethyl-silanyloxymethyl)-6-chloro-pyridin-2-yl]-[3-methoxy-4-(4-methyl-imidazol-1-yl)-phenyl]-amine Prepared in analogy to example 62 from 3-methoxy-4-(4-methyl-imidazol-1-yl)-phenylamine and 4-(tert-butyl-dimethyl-silanyloxymethyl)-2,6-dichloro-pyridine. The title compound was obtained as a yellowish solid (Yield=31%).
$^1$H NMR (CDCl$_3$, 300 MHz): δ (ppm)=7.64 (s, 1H), 7.36 (d, 1H), 7.17 (d, 1H), 6.95-6.85 (m, 2H), 6.75 (s, 1H), 6.73 (s, 1H), 6.68 (s broad, 1H), 4.65 (s, 2H), 3.86 (s, 3H), 2.30 (s, 3H), 0.94 (s, 9H), 0.11 (s, 6H).

c) 4-(tert-Butyl-dimethyl-silanyloxymethyl)-N-[3-methoxy-4-(4-methyl-imidazol-1-yl)-phenyl]-N'-(4-trifluoromethoxy-phenyl)-pyridine-2,6-diamine Prepared in analogy to example 62 from 4-(trifluoromethoxy)aniline and [4-(tert-butyl-dimethyl-silanyloxymethyl)-6-chloro-pyridin-2-yl]-[3-methoxy-4-(4-methyl-imidazol-1-yl)-phenyl]-amine. The title compound was obtained as a brownish gum (Yield=56%).
$^1$H NMR (CDCl$_3$, 300 MHz): δ (ppm)=7.63 (s, 1H), 7.38 (d, 2H), 7.20-7.10 (m, 4H), 6.96 (dxd, 1H), 6.87 (s, 1H), 6.42 (s, 1H), 6.35-6.25 (m, 3H), 4.62 (s, 2H), 3.74 (s, 3H), 2.30 (s, 3H), 0.93 (s, 9H), 0.10 (s, 6H).

d) [2-[3-Methoxy-4-(4-methyl-imidazol-1-yl)-phenylamino]-6-(4-trifluoromethoxy-phenylamino)-pyridin-4-yl]-methanol 4-(tert-Butyl-dimethyl-silanyloxymethyl)-N-[3-methoxy-4-(4-methyl-imidazol-1-yl)-phenyl]-N'-(4-trifluoromethoxy-phenyl)-pyridine-2,6-diamine (50 mg, 0.083 mmol) was dissolved in 1 mL of tetrahydrofurane and tetrabutyl ammonium fluoride (44 mg, 0.17 mmol) were added. The mixture was stirred at 20° C. for 2 hours, concentrated in the rotatory evaporator and diluted with water. Extraction with ethyl acetate and purification by chromatography on amino-modified silica gel (Merck HPTLC Silica Gel 60 NH2F254S) using ethyl acetate/methanol (gradient 0 to 2% methanol) gave the pure title compound as a yellowish solid (5 mg, 10%). MS ISP (m/e): 486.2 (100) [(M+H)$^+$]. $^1$H NMR (CDCl$_3$, 300 MHz): δ (ppm)=7.58 (s, 1H), 7.41 (d, 2H), 7.19 (d, 1H), 7.20-7.05 (m, 3H), 6.97 (dxd, 1H), 6.83 (s, 1H), 6.78 (s broad, 1H), 6.67 (s broad, 1H), 6.40 (s, 1H), 6.33 (s, 1H), 4.59 (s, 2H), 3.67 (s, 3H), 2.28 (s, 3H).

Example 203

{1-[4-(4-Benzyl-6-methyl-pyrimidin-2-ylamino)-phenyl]-1H-imidazol-4-yl}-methanol

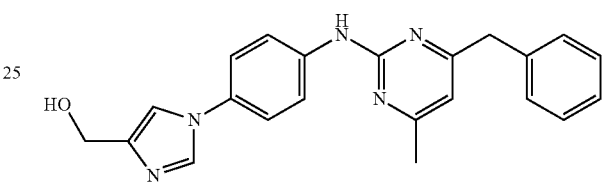

A mixture of 4-benzyl-2-chloro-6-methyl-pyrimidine (86 mg, 0.39 mmol), 1-(4-amino-phenyl)-1H-imidazol-4-yl]-methanol (75 mg, 0.39 mmol, Europ. J. Med. Chem. 19 (3), 285-7 (1984), CAS 94128-93-5) and potassium carbonate (1.10 g, 7.86 mmol) in dioxane (4 mL) and N,N-dimethylacetamide (1 mL) was degassed with nitrogen. Palladium(II) acetate (3.6 mg, 0.016 mmol) and 2-(dicyclohexylphosphino) biphenyl (12 mg, 0.031 mmol) were added and the reaction mixture was irradiated in a microwave oven at 200° C. for 25 minutes. [1-(4-Amino-phenyl)-1H-imidazol-4-yl]-methanol (43 mg, 0.19 mmol) was added and the reaction mixture was irradiated in a microwave oven at 200° C. for another 25 minutes. The reaction mixture was filtered; the filtrate was diluted with ethyl acetate, washed with water and brine, dried with magnesium sulfate and concentrated in vacuo. Purification by column chromatography on silica eluting with dichloromethane/methanol (14:1 v/v) afforded the title compound as a light yellow viscous oil (19 mg, 13%). MS ISP (m/e): 372.2 [(M+H)$^+$].

Example 204

{1-[4-(4-Benzyl-6-methyl-pyrimidin-2-ylamino)-phenyl]-1H-imidazol-2-yl}-methanol

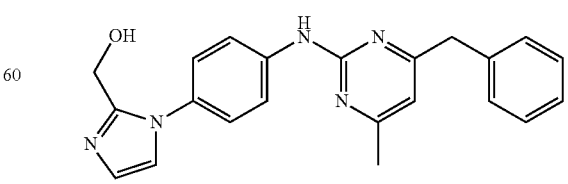

A mixture of 4-benzyl-2-chloro-6-methyl-pyrimidine (104 mg, 0.48 mmol), 1-(4-amino-phenyl)-1H-imidazol-2-yl]- methanol (90 mg, 0.48 mmol) and potassium carbonate (1.33 g, 9.5 mmol) in dioxane (4 mL) and N,N-dimethylacetamide (1 mL) was degassed with nitrogen. Palladium(II) acetate (4.3 mg, 0.019 mmol) and 2-dicyclohexylphosphino)bi-phenyl (13.6 mg, 0.038 mmol) were added and the reaction mixture was irradiated in a microwave oven at 200° C. for 30 minutes. [1-(4-Amino-phenyl)-1H-imidazol-4-yl]-methanol (43 mg, 0.19 mmol) was added and the reaction mixture was irradiated in a microwave oven at 200° C. for another 25 minutes. The reaction mixture was filtered; the filtrate was diluted with ethyl acetate, washed with water and brine, dried with magnesium sulfate and concentrated in vacuo. Purification by column chromatography on silica eluting with dichloromethane/methanol (14:1 v/v) afforded the title compound as a light yellow solid (93 mg, 52%). MS ISP (m/e): 372.2 [(M+H)⁺]. Mp 95-98° C.

Example 205

(4-Benzyl-6-methyl-pyrimidin-2-yl)-[3-methoxy-4-(3-methyl-[1,2,4]triazol-1-yl)-phenyl]-amine

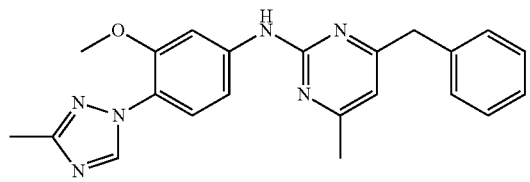 [SMILES: COc1cc(Nc2nc(C)cc(Cc3ccccc3)n2)ccc1-n1cnc(C)n1]

a) 1-(2-Methoxy-4-nitro-phenyl)-3-methyl-1H-[1,2,4]triazole

A solution of 2-chloro-5-nitroanisole (1.0 g, 5.2 mmol), 3-methyl-1H-1,2,4-triazole (1.74 g, 20.9 mmol) and potassium hydroxide (0.44 g, 7.8 mmol) in dimethyl sulfoxide (5 ML) was heated to 80° C. under an atmosphere of nitrogen for two days. Water and 1M aqueous hydrogen chloride solution was added and the reaction was stirred for 45 minutes. The precipitate was filtered off, washed with water, dissolved in dichloromethane. The aqueous layer was extracted twice with dichloromethane. The combined organic layers were washed with water, dried over sodium sulfate, filtered and the solvent was evaporated. The residue was purified by reversed preparative HPLC using acetonitril/water (0.1% formic acid) to yield the title compound as a yellow solid (77 mg, 6%). MS ISP (m/e): 235.2 (100) [(M+H)⁺]. ¹H NMR (CDCl₃, 300 MHz): δ (ppm)=8.88 (s, 1H), 8.10 (d, 1H), 7.96-8.02 (m, 2H), 4.10 (s, 3H), 2.51 (s, 3H).

b) 3-Methoxy-4-(3-methyl-[1,2,4]triazol-1-yl)-phenylamine 1-(2-Methoxy-4-nitro-phenyl)-3-methyl-1H-[1,2,4]triazole (77 mg, 0.33 mmol) was dissolved in methanol (5 mL). The flask was evacuated and flushed with nitrogen. This procedure was repeated two times. 10% Palladium on charcoal (8 mg) was added. The reaction was stirred at room temperature under an atmosphere of hydrogen over night, filtered and the filtrate was evaporated under reduced pressure to yield the title compound as a brown solid (67 mg, ca. 100%). MS ISP (m/e): 205.2 (100) [(M+H)⁺]. ¹H NMR (CDCl₃, 300 MHz): δ (ppm)=8.35 (s, 1H), 7.37 (d, 1H), 6.32-6.35 (m, 2H), 3.82 (s, 3H), 2.47 (s, 3H).

c) (4-Benzyl-6-methyl-pyrimidin-2-yl)-[3-methoxy-4-(3-methyl-[1,2,4]triazol-1-yl)-phenyl]-amine Palladium(II) acetate (5.9 mg, 0.026 mmol) and 2-(dicyclohexylphosphino)biphenyl (19 mg, 0.052 mmol) were dissolved under an atmosphere of nitrogen in dioxane (2 mL). The reaction was stirred for 25 minutes at room temperature. Sodium tert.-butylate (48 mg, 0.49 mmol), 3-methoxy-4-(3-methyl-[1,2,4]triazol-1-yl)-phenylamine (67 mg, 0.33 mmol) dissolved in dioxane (1.5 mL) and 4-benzyl-2-chloro-6-methyl-pyrimidine (79 mg, 0.36 mmol) were added. The reaction was heated three times for 30 minutes to 200° C. in a microwave oven. Water was added and the reaction was extracted twice with ethyl acetate. The combined organic layers were dried over sodium sulfate, filtered and the solvent was evaporated under reduced pressure. The residue was purified by column chromatography on silica gel using methylenechloride/methanol (19:1 v/v) as eluent to yield the title compound as a yellow gum (38 mg, 30%). MS ISP (m/e): 387.3 (100) [(M+H)⁺]. ¹H NMR (CDCl₃, 300 MHz): δ (ppm)=8.49 (s, 1H), 7.97 (s, 1H), 7.56 (d, 1H), 7.26-7.33 (m, 5H), 6.98 (d, 1H), 6.51 (s, 1H), 3.97 (s, 2H), 3.83 (s, 3H), 2.48 (s, 3H), 2.37 (s, 3H).

Example 206

(4-Benzyl-6-methyl-pyrimidin-2-yl)-[3-fluoro-4-(3-methyl-[1,2,4]triazol-1-yl)-phenyl]-amine

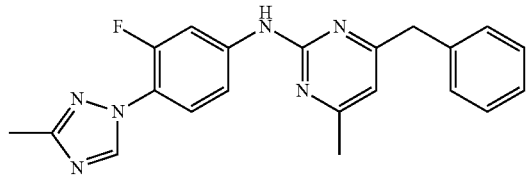 [SMILES: Cc1cc(Cc2ccccc2)nc(Nc2ccc(-n3cnc(C)n3)c(F)c2)n1]

a) 1-(2-Fluoro-4-nitro-phenyl)-3-methyl-1H-[1,2,4]triazole 3,4-Difluoronitrobenzene (514 mg, 3.23 mmol), 3-methyl-1H-1,2,4-triazole (325 mg, 3.72 mmol) and di-potassium hydrogen phosphate trihydrate (1.49 g, 6.46 mmol) in 1 dimethyl sulfoxide (5 mL) were stirred for 6 hours at 70° C. The mixture was concentrated in vacuo; the residue was diluted with water and extracted three times with ethyl acetate. The combined organic layers were washed four times with water, twice with brine, dried over magnesium sulfate and evaporated. Column chromatography (30 g silica, heptane/ethyl acetate 1:1 v/v) afforded the title compound (261 mg, 36%) as white crystals MS ISP (m/e): 223.3[(M+H)⁺]. ¹H NMR (CDCl₃, 300 MHz): δ (ppm)=8.72 (d, 1H), 8.20 (m, 3H), 2.52 (s, 3H). Mp 105-107° C.

b) 3-Fluoro-4-(3-methyl-[1,2,4]triazol-1-yl)-phenylamine 1-(2-Fluoro-4-nitro-phenyl)-3-methyl-1H-[1,2,4]triazole (250 mg, 1.13 mmol) was dissolved in tetrahydrofurane (6 mL) and triethylamine (5 mL) and stirred for 2 hours with 10% palladium on carbon (55 mg) under 1.5 bar of hydrogen. The reaction mixture was filtered and the solvent was removed under reduced pressure to yield the title compound (159 mg, 73%) as a yellow solid MS ISP (m/e): 193.3 [(M+

H)+]. 1H NMR (CDCl3, 300 MHz): δ (ppm)=8.31 (d, 1H), 7.45 (dd, 1H), 6.51 (m, 2H), 3.94 (s broad, 2H), 2.48 (s, 3H). Mp 122-125° C.

c) (4-Benzyl-6-methyl-pyrimidin-2-yl)-[3-fluoro-4-(3-methyl-[1,2,4]triazol-1-yl)-phenyl]-amine Palladium(II) acetate (5 mg, 0.022 mmol) and 2-(dicyclohexylphosphino)biphenyl (16 mg, 0.08 mmol) were stirred in dioxane (1.5 mL) while nitrogene was bubbled through the solution. A mixture of 4-benzyl-2-chloro-6-methyl-pyrimidine (120 mg, 0.55 mmol), 3-fluoro-4-(3-methyl-[1,2,4]triazol-1-O-phenylamine (105 mg, 0.55 mmol) and potassium carbonate (1.53 g, 10.9 mmol) in dioxane (5 mL) and N,N-dimethylacetamide (1.5 mL) was degassed with nitrogen, the above prepared catalyst solution was added and the reaction mixture was irradiated in a microwave oven at 200° C. for 20 minutes. The reaction mixture was partitioned between ethyl acetate and water; the water layer was extracted twice with ethyl acetate and the combined organic phases washed three times with water, once with brine, dried with magnesium sulfate and the solvent was removed in vacuo. The light brown solid was purified by trituration in heptane/ethyl acetate (9:1 v/v, 6 mL) to afford the title compound as a beige solid (140 mg, 68%). MS ISP (m/e): 375.2 [(M+H)+]. 1H NMR (CDCl3, 300 MHz): δ (ppm)=8.43 (d, 1H), 8.98 (dd, 1H), 8.66 (dd, 1H), 7.30 (m, 5H), 7.18 (m, 2H), 6.54 (s, 1H), 3.98 (s, 2H), 2.50 (s, 3H), 2.38 (s, 3H). Mp 183-185° C.

Example 207

(4-Benzyl-6-methyl-pyrimidin-2-yl)-[3-fluoro-4-(5-methyl-[1,2,4]triazol-1-yl)-phenyl]-amine

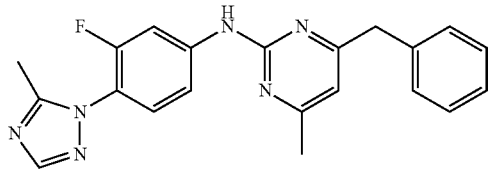 [SMILES: Cc1cc(Cc2ccccc2)nc(Nc2ccc(-n3ncnc3C)c(F)c2)n1]

a) 1-(2-Fluoro-4-nitro-phenyl)-5-methyl-1H-[1,2,4]triazole 3,4-Difluoronitrobenzene (514 mg, 3.23 mmol), 3-methyl-1H-1,2,4-triazole (325 mg, 3.72 mmol) and di-potassium hydrogen phosphate trihydrate (1.49 g, 6.46 mmol) in dimethyl sulfoxide (1.5 mL) were stirred for 6 hours at 70° C. The mixture was concentrated in vacuo; the residue was diluted in water and extracted three times with ethyl acetate. The combined organic layers were washed four times with water, twice with brine, dried with magnesium sulfate and evaporated. Column chromatography (30 g silica, heptane/ethyl acetate 1:1 v/v) afforded the title compound (160 mg, 22%) as white crystals MS ISP (m/e): 223.2[(M+H)+]. 1H NMR (CDCl3, 300 MHz): δ (ppm)=8.22 (m, 2H), 8.04 (s, 1H), 7.74 (dd, 1H), 2.48 (d, 3H). Mp 56-58° C.

b) 3-Fluoro-4-(5-methyl-[1,2,4]triazol-1-yl)-phenylamine 1-(2-Fluoro-4-nitro-phenyl)-5-methyl-1H-[1,2,4]triazole (120 mg, 0.54 mmol) was dissolved in tetrahydrofurane (6 mL) and triethylamine (10 mL) and stirred for 4 hours with 10% palladium on carbon (50 mg) under 3 bar of hydrogen. The reaction mixture was filtered and the solvent was removed in vacuo to yield the title compound (78 mg, 75%) as a yellow solid. MS ISP (m/e): 193.3 [(M+H)+]. 1H NMR (CDCl3, 300 MHz): δ (ppm)=7.93 (s, 1H), 7.16 (dd, 1H), 6.51 (m, 2H), 4.03 (s broad, 2H), 2.38 (s, 3H). Mp 106-108° C.

c) (4-Benzyl-6-methyl-pyrimidin-2-yl)-[3-fluoro-4-(5-methyl-[1,2,4]triazol-1-yl)-phenyl]-amine The title compound was prepared from 4-benzyl-2-chloro-6-methyl-pyrimidine (86 mg, 0.54 mmol) and 3-fluoro-4-(5-methyl-[1,2,4]triazol-1-yl)-phenylamine (75 mg, 0.39 mmol) using in analogous manner the procedure described in example 206c). Column chromatography (15 g silica, dichloromethane+3.5% methanol v/v) afforded the title compound as a light yellow waxy solid (100 mg, 68%). 1H NMR (CDCl3, 300 MHz): δ (ppm)=8.07 (dd, 1H), 7.97 (s, 1H), 7.27 (m, 7H), 6.56 (s, 1H), 4.00 (s, 2H), 2.42 (d, 3H), 2.39 (s, 3H). MS ISP (m/e): 375.2 [(M+H)+].

Example 208

(4-Benzyl-6-methyl-pyrimidin-2-yl)-[4-(2-methyl-oxazol-5-yl)-phenyl]-amine

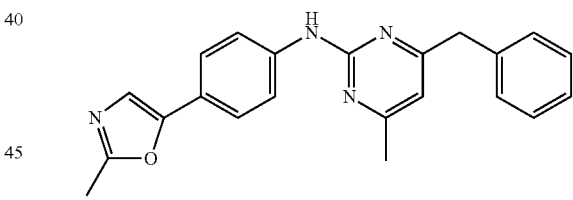

Palladium(II) acetate (9.3 mg, 0.041 mmol) and 2-(dicyclohexylphosphino)biphenyl (30 mg, 0.083 mmol) were stirred in dioxane (1.5 mL) for 15 minutes at room temperature under an atmosphere of nitrogen. Sodium tert.-butylate (76 mg, 0.78 mmol), 4-(2-methyl-oxazol-5-yl)phenylamine (90 mg, 0.52 mmol, CAS 89260-50-4) dissolved in dioxane (0.7 mL) and 4-benzyl-2-chloro-6-methyl-pyrimidine (124 mg, 0.57 mmol) were added. The reaction was heated for 30 minutes to 200° C. in a microwave oven. Water was added and the reaction was extracted twice with ethyl acetate. The combined organic layers were dried over sodium sulfate, filtered and the solvent was evaporated under reduced pressure. The residue was purified by column chromatography on silica gel using dichloromethane and then methylenechloride/methanol (19:1 v/v) as eluent to yield the title compound as a yellow solid (112 mg, 61%). MS ISP (m/e): 357.2 (100) [(M+H)+]. 1H NMR (CDCl3, 300 MHz): δ (ppm)=7.69 (d, 2H), 7.53 (d, 2H), 7.26-7.35 (m, 4H), 7.11-7.12 (m, 2H), 6.45 (s, 1H), 3.97 (s, 2H), 2.52 (s, 3H), 2.36 (s, 3H).

Example 209

(4-Benzyl-6-methyl-pyrimidin-2-yl)-[3-methoxy-4-(2-methyl-thiazol-5-yl)-phenyl]-amine

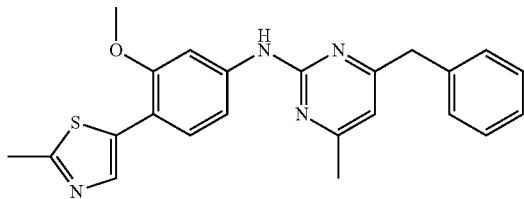 [SMILES: COc1cc(Nc2nc(C)cc(Cc3ccccc3)n2)ccc1-c1cnc(C)s1]

a) 5-(2-Methoxy-4-nitro-phenyl)-2-methyl-thiazole

In a microwave vial a mixture of 2-bromo-5-nitroanisole (800 mg, 3.38 mmol), potassium acetate (503 mg, 5.07 mmol) and tetrakis(triphenylphosphine)-palladium(0) (197 mg, 0.17 mmol) in N,N-dimethylacetamide (12 mL) were flushed with argon while 2-methylthiazole (1.71 g, 16.9 mmol) was added. The tube was sealed and the mixture irradiated two times for 30 minutes at 160° C. The red-brown mixture was partitioned between ethyl acetate and water. The water layer was re-extracted with ethyl acetate. The combined organic phases were washed three times with water, once with brine, dried with magnesium sulfate and evaporated to dryness. Column chromatography (70 g silica, heptane/ethyl acetate 7:3 v/v) afforded the title compound (360 mg, 42%) as a yellow solid. MS ISP (m/e): 251.1 [(M+H)+]. $^1$H NMR (CDCl$_3$, 300 MHz): δ (ppm)=8.15 (s, 1H), 7.90 (dd, 1H), 7.84 (s, 1H), 7.72 (d, 1H), 4.05 (s, 3H), 2.76 (s, 3H). Mp 114-117° C.

b) 3-Methoxy-4-(2-methyl-thiazol-5-yl)-phenylamine

A suspension of 5-(2-methoxy-4-nitro-phenyl)-2-methyl-thiazole (330 mg, 1.32 mmol) and anhydrous stannous chloride (1.28 g, 6.6 mmol) in ethanol (21 mL) was stirred at reflux for one hour. The yellow solution was evaporated and the residue dissolved in ethyl acetate. This solution was washed twice with 2N aqueous sodium hydroxide solution, with brine, dried with magnesium sulfate and evaporated to dryness to afford the title compound (266 mg, 91%) as an orange solid. MS ISP (m/e): 221.2 [(M+H)+]. $^1$H NMR (CDCl$_3$, 300 MHz): δ (ppm)=7.81 (s, 1H), 7.33 (d, 1H), 6.31 (m, 2H), 3.87 (s, 3H), 3.83 (m, 2H), 2.69 (s, 3H). Mp 125-129° C.

c) (4-Benzyl-6-methyl-pyrimidin-2-yl)-[3-methoxy-4-(2-methyl-thiazol-5-yl)-phenyl]-amine The title compound was prepared from 4-benzyl-2-chloro-6-methyl-pyrimidine (130 mg, 0.59 mmol) and 3-methoxy-4-(2-methyl-thiazol-5-yl)-phenylamine (131 mg, 0.59 mmol) using in analogous manner the procedure described in example 206c). Column chroma-tography (20 g silica, heptane/ethyl acetate 1:1 v/v) afforded the title compound as an off-white solid (165 mg, 69%). MS ISP (m/e): 403.2 [(M+H)+]. $^1$H NMR (CDCl$_3$, 300 MHz): δ (ppm)=7.90 (s, 1H), 7.82 (s, 1H), 7.45 (d, 1H), 7.29 (m, 5H), 7.14 (s, 1H), 6.98 (dd, 1H), 6.48 (s, 1H), 3.97 (s, 2H), 3.87 (s, 3H), 2.71 (s, 3H), 2.37 (s, 3H). Mp 138-141° C.

Example 210

(4-Benzyl-6-methyl-pyrimidin-2-yl)-[4-(2,4-dimethyl-thiazol-5-yl)-3-methoxy-phenyl]-amine

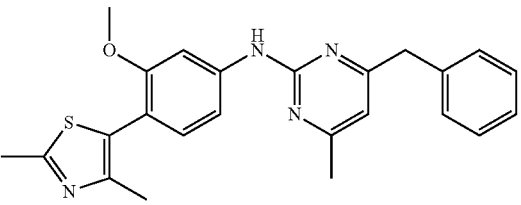 [SMILES: COc1cc(Nc2nc(C)cc(Cc3ccccc3)n2)ccc1-c1sc(C)nc1C]

5-(2-Methoxy-4-nitro-phenyl)-2,4-dimethyl-thiazole

In a microwave vial a mixture of 2-bromo-5-nitroanisole (600 mg, 2.53 mmol), potassium acetate (377 mg, 3.80 mmol) and tetrakis(triphenylphosphine)-palladium(0) (148 mg, 0.13 mmol) in N,N-dimethylacetamide (8 mL) was flushed with nitrogen while 2,4-dimethylthiazole (1.47 g, 12.6 mmol) was added. The tube was sealed and the mixture irradiated for 30 minutes at 170° C. The red-brown mixture was partitioned between ethyl acetate and water. The aqueous layer was re-extracted with ethyl acetate. The combined organic phases were washed with water, with brine, dried with magnesium sulfate and the solvent was evaporated to dryness. Column chromatography (40 g silica, heptane/ethyl acetate 7/3) afforded the title compound (415 mg, 62%) as a yellow solid. MS ISP (m/e): 265.1 [(M+H)+]. $^1$H NMR (CDCl$_3$, 300 MHz): δ (ppm)=7.90 (dd, 1H), 7.81 (d, 1H), 7.45 (d, 1H), 3.95 (s, 3H), 2.71 (s, 3H), 2.35 (s, 3H). Mp 123-125° C.

b) 4-(2,4-Dimethyl-thiazol-5-yl)-3-methoxy-phenylamine

A suspension of 5-(2-methoxy-4-nitro-phenyl)-2,4-dimethyl-thiazole (415 mg, 1.57 mmol) and anhydrous stannous chloride (1.52 g, 7.85 mmol) in ethanol (25 mL) was stirred at reflux for 3 hours. The yellow solution was evaporated and the residue dissolved in ethyl acetate. This solution was washed with 1N aqueous sodium hydroxide solution, twice with water, with brine, dried with magnesium sulfate and the solvent was evaporated to dryness. Column chromatography (50 g silica, heptane/ethyl acetate 30-60% v/v) afforded the title compound (276 mg, 75%) as a pale yellow solid. MS ISP (m/e): 235.2 [(M+H)+]. $^1$H NMR (CDCl$_3$, 300 MHz): δ (ppm)=7.04 (d, 1H), 6.31 (m, 2H), 3.80 (s broad, 2H), 3.78 (s, 3H), 2.66 (s, 3H), 2.29 (s, 3H). Mp 112-115° C.

c) (4-Benzyl-6-methyl-pyrimidin-2-yl)-[4-(2,4-dimethyl-thiazol-5-yl)-3-methoxy-phenyl]-amine The title compound was prepared from 4-benzyl-2-chloro-6-methyl-pyrimidine (130 mg, 0.59 mmol) and 4-(2,4-dimethyl-thiazol-5-yl)-3-methoxy-phenylamine (139 mg, 0.49 mmol) using in analogous manner the procedure described in example 206c). Column chromatography (20 g silica, dichloromethane/ethyl acetate 1/1 v/v) afforded the title compound (193 mg, 78%) as a light yellow waxy solid. MS ISP (m/e): 417.2 [(M+H)+]. $^1$H NMR (CDCl$_3$, 300 MHz): δ (ppm)=7.78 (d, 1H), 7.29 (m, 5H), 7.17 (d, 1H), 7.14 (s, 1H), 6.99 (dd, 1H), 6.48 (s, 1H), 3.97 (s, 2H), 3.78 (s, 3H), 2.67 (s, 3H), 2.37 (s, 3H), 2.32 (s, 3H).

Example 211

(4-Benzyl-6-methyl-pyrimidin-2-yl)-[3-methoxy-4-(1-methyl-1H-pyrazol-4-yl)-phenyl]-amine

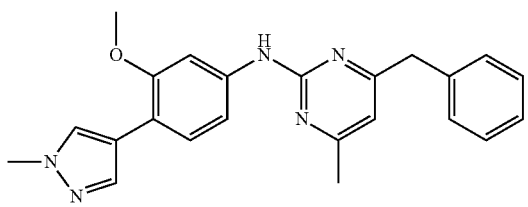 [SMILES: COc1cc(Nc2nc(C)cc(Cc3ccccc3)n2)ccc1-c1cnn(C)c1]

2-(2-Methoxy-4-nitro-phenyl)-4,4,5,5-tetramethyl-[1,3,2]dioxaborolane

A moisture of 4-bromo-5-nitroanisole (5.0 g, 21.2 mmol), bis(pinacolato)diboron (8.21 g, 31.7 mmol) and potassium acetate (6.28 g, 63.3 mmol, dried on high vacuum at 100° C.) in dioxane (75 mL) was purged for 5 minutes with nitrogen. Bis(triphenylphosphine)palladium(II)chloride (1.48 g, 2.11 mmol) was added and the mixture was heated for 18 hours to 100° C. under nitrogen atmosphere. The mixture was diluted with ethyl acetate, washed with water and brine, dried over magnesium sulfate and the solvent was evaporated. Column chromatography (330 g silica, heptane/ethyl acetate 5-60%) afforded the title compound (3.46 g, 58%) as a light brown solid. MS EI (m/e): 279 [(M+)]. $^1$H NMR (CDCl$_3$, 300 MHz): δ (ppm)=7.78 (s, 2H), 7.39 (s, 1H), 3.92 (s, 3H), 1.37 (s, 12H). Mp 75-78° C.

b) 4-(2-Methoxy-4-nitro-phenyl)-1-methyl-1H-pyrazole

A solution of 2-(2-methoxy-4-nitro-phenyl)-4,4,5,5-tetramethyl-[1,3,2]dioxaborolane (635 mg, 1.79 mmol) and 1-methyl-4-iodo-1H-pyrazole (745 mg, 3.58 mmol) in ethanol (11 mL) and toluene (26 mL) was purged with argon for 5 minutes. 1,1'-bis(diphenylphosphino)ferrocene palladium (II) chloride (73.0 mg, 0.89 mmol) was added and the mixture was heated to 80° C., then 2M aqueous sodium carbonate solution (14 mL) was added and stirring at 80° C. was continued for further 24 hours. The mixture was diluted with ethyl acetate, washed with water and brine, dried over magnesium sulfate and the solvent was evaporated. Column chromatography (20 g silica, dichloromethane) afforded the title compound (245 mg, 58%) as a yellow solid. MS ISP (m/e): 234.0 [(M+H)$^+$]. $^1$H NMR (DMSO, 300 MHz): δ (ppm)=8.35 (s, 1H), 8.08 (s, 1H), 7.85 (m, 3H), 4.03 (s, 3H), 3.90 (s, 3H). Mp 132-134° C.

c) 3-Methoxy-4-(1-methyl-1H-pyrazol-4-yl)-phenylamine

A mixture of 4-(2-methoxy-4-nitro-phenyl)-1-methyl-1H-pyrazole (240 mg, 1.03 mmol) and palladium on carbon 10% (55 mg, 0.052 mmol) in methanol (15 mL) was stirred for 2 hours at under hydrogen atmosphere. The mixture was filtrated and the solvent evaporated to afford the title compound (210 mg, 100%) as a white solid. MS ISP (m/e): 204.3.0 [(M+H)$^+$]. $^1$H NMR (CDCl$_3$, 300 MHz): δ (ppm)=7.76 (s, 1H), 7.70 (s, 1H), 7.28 (d, 1H), 6.32 (d, 2H), 3.91 (s, 3H), 3.85 (s, 3H), 3.68 (s broad, 2H). Mp 129-131° C.

d) (4-Benzyl-6-methyl-pyrimidin-2-yl)-[3-methoxy-4-(1-methyl-1H-pyrazol-4-yl)-phenyl]-amine The title compound was prepared from 4-benzyl-2-chloro-6-methyl-pyrimidine (119 mg, 0.54 mmol) and 3-methoxy-4-(1-methyl-1H-pyrazol-4-yl)-phenylamine (100 mg, 0.49 mmol) using in analogous manner the procedure described in example 206c). Column chromatography (25 g silica, dichloromethane/ethyl acetate 0-25% v/v) afforded the title compound (42 mg, 22%) as a light yellow viscous oil. MS ISP (m/e): 386.2 [(M+H)$^+$]. $^1$H NMR (CDCl$_3$, 300 MHz): δ (ppm)=7.82 (s, 1H), 7.76 (m, 2H), 7.39 (d, 1H), 7.29 (m, 5H), 7.08 (s, 1H), 6.98 (dd, 1H), 6.44 (s, 1H), 3.96 (s, 2H), 3.93 (s, 3H), 3.86 (s, 3H), 2.35 (s, 3H).

Example 212

(4-Benzyl-6-methyl-pyrimidin-2-yl)-(4-pyridin-4-yl-phenyl)-amine

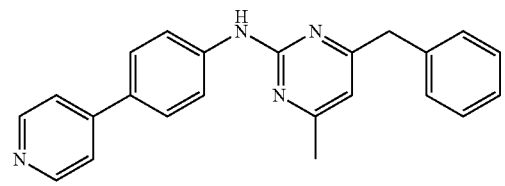 [SMILES: Cc1cc(Cc2ccccc2)nc(Nc2ccc(-c3ccncc3)cc2)n1]

Prepared in analogy to example 62 from 4-(pyridin-4-yl)aniline and 4-benzyl-2-chloro-6-methyl-pyrimidine (example 43a). The title compound was obtained as a brownish oil (Yield=31%). MS ISP (m/e): 353.1 (100) [(M+H)$^+$]. $^1$H NMR (DMSO-D$_6$, 300 MHz): δ (ppm)=9.80 (s, 1H), 8.57 (d, 2H), 7.95 (d, 2H), 7.74 (d, 2H), 7.69 (d, 2H), 7.40-7.15 (m, 5H), 6.68 (s, 1H), 3.95 (s, 2H), 2.34 (s, 3H).

Example 213

[3-Methoxy-4-(4-methyl-imidazol-1-yl)-phenyl]-(6-methyl-2-pyrrolidin-1-yl-pyrimidin-4-yl)-amine

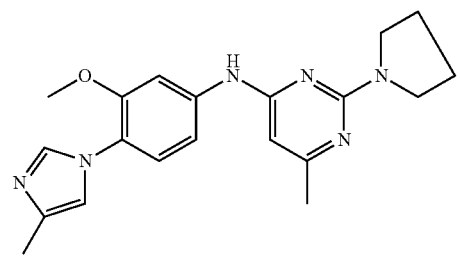 [SMILES: COc1cc(Nc2cc(C)nc(N3CCCC3)n2)ccc1-n1cnc(C)c1]

The title compound was prepared from 3-methoxy-4-(4-methyl-imidazol-1-yl)-phenylamine (61 mg, 0.30 mmol) and 4-chloro-6-methyl-2-pyrrolidin-1-yl-pyrimidine (65 mg, 0.33 mmol, example 95a) in analogous manner as described in example 90. The crude product was purified by stirring with diethyl ether. It was obtained in 58% yield as a light brown solid. MS ISP (m/e): 365.3 (100) [(M+H)$^+$]. $^1$H NMR (DMSO-D$_6$, 300 MHz): δ (ppm)=9.30 (s, 1H), 8.06 (s, 1H), 7.65 (s, 1H), 7.21 (d, 1H), 7.15 (d, 1H), 7.02 (s, 1H), 5.91 (s, 1H), 3.81 (s, 3H), 3.50 (br m, 4H), 2.15 (s, 3H), 2.14 (s, 3H), 1.90 (br m, 4H).

Example 214

[3-Methoxy-4-(4-methyl-imidazol-1-yl)-phenyl]-(6-methyl-2-piperidin-1-yl-pyrimidin-4-yl)-amine

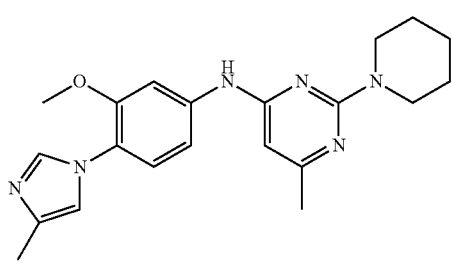 [SMILES: COc1cc(Nc2cc(C)nc(N3CCCCC3)n2)ccc1-n1cnc(C)c1]

The title compound was prepared from 3-methoxy-4-(4-methyl-imidazol-1-yl)-phenylamine (61 mg, 0.30 mmol) and 4-chloro-6-methyl-2-piperidin-1-yl-pyrimidine (70 mg, 0.33 mmol, example 97a) in analogous manner as described in example 90. The crude product was purified by stirring with diethyl ether. It was obtained in 79% yield as a grey solid. MS ISP (m/e): 379.3 (100) [(M+H)$^+$]. $^1$H NMR (DMSO-D$_6$, 300 MHz): δ (ppm)=9.29 (s, 1H), 7.88 (s, 1H), 7.65 (s, 1H), 7.22 (d, 1H), 7.04 (d, 1H), 7.03 (s, 1H), 5.89 (s, 1H), 3.80 (s, 3H), 3.74 (m, 4H), 2.15 (s, 3H), 2.14 (s, 3H), 1.60 (m, 2H), 1.50 (m, 4H).

Example 215

2-{5-Ethyl-2-[3-methoxy-4-(4-methyl-imidazol-1-yl)-phenylamino]-pyrimidin-4-yl}-propan-2-ol

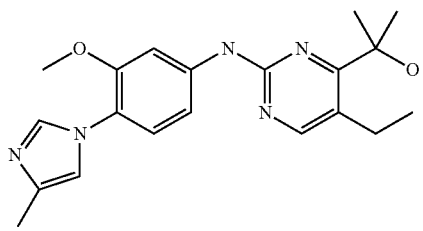 [SMILES: CCc1cnc(Nc2ccc(-n3cnc(C)c3)c(OC)c2)nc1C(C)(C)O]

A solution of ethyl 2-oxo-pentanoate (144 mg, 1.0 mmol) in N,N-dimethylformamide diethyl acetal (0.68 mL) was heated to 100° C. for 2 h. The mixture was evaporated under reduced pressure and the remaining crude ethyl 3-[1-dimethylamino-methylidene]-2-oxo-hexanoate was reacted with N-[3-methoxy-4-(4-methyl-imidazol-1-yl)-phenyl]guanidine dinitrate (298 mg, 0.80 mmol) in analogous manner as described in example 139. The resulting ethyl 5-ethyl-2-[3-methoxy-4-(4-methyl-imidazol-1-yl)-phenylamino]-pyrimidine-4-carboxylate was subjected in analogous manner to the procedure described in example 165 to give the title compound as a light yellow solid (12 mg, 3%). MS ISP (m/e): 368.2 [(M+H)$^+$]. $^1$H NMR (CDCl$_3$, 300 MHz): δ (ppm)=8.31 (s, 1H), 7.63 (s, 1H), 7.53 (d, 1H), 7.23 (s, 1H), 7.18 (d, 1H), 7.04 (dd, 1H), 6.87 (s, 1H), 5.44 (br s, 1H), 3.87 (s, 3H), 2.73 (q, 2H), 2.30 (s, 3H), 1.60 (s, 6H), 1.30 (t, 3H).

Example 216

2-{5-Isopropyl-2-[3-methoxy-4-(4-methyl-imidazol-1-yl)-phenylamino]-pyrimidin-4-yl}-propan-2-ol

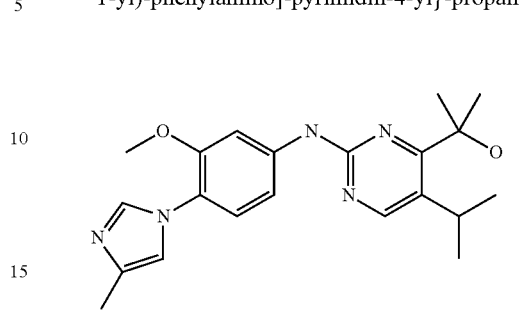

Ethyl 3-[1-dimethylamino-methylidene]-4-methyl-2-oxo-pentanoate (170 mg, 0.80 mmol) was reacted with N-[3-methoxy-4-(4-methyl-imidazol-1-yl)-phenyl]-guanidine dinitrate in analogous manner as described in example 139 and the resulting ethyl 5-isopropyl-2-[3-methoxy-4-(4-methyl-imidazol-1-yl)-phenylamino]-pyrimidine-4-carboxylate was subjected in analogous manner to the procedure described in example 165 to give the title compound as a light yellow solid (10 mg, 4%). MS ISP (m/e): 382.3 [(M+H)$^+$]. $^1$H NMR (CDCl$_3$, 300 MHz): δ (ppm)=8.45 (s, 1H), 7.64 (s, 1H), 7.53 (d, 1H), 7.25 (s, 1H), 7.18 (d, 1H), 7.04 (dd, 1H), 6.87 (s, 1H), 5.65 (br s, 1H), 3.87 (s, 3H), 3.31 (m, 1H), 2.30 (s, 3H), 1.61 (s, 6H), 1.28 (d, 6H).

Example 217

Ethyl 2-[3-fluoro-4-(4-methyl-imidazol-1-yl)-phenylamino]-6-isopropyl-pyrimidine-4-carboxylate

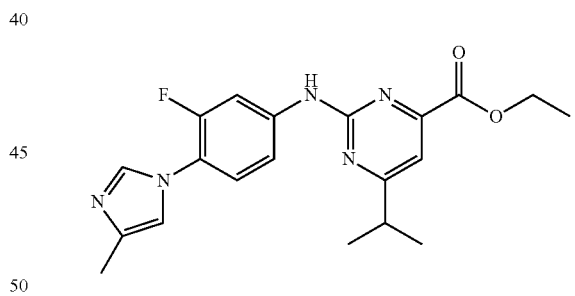

A mixture of N-[3-fluoro-4-(4-methyl-imidazol-1-yl)-phenyl]-guanidine nitrate (719 mg, 2.0 mmol), ethyl 5-methyl-2,4-dioxo-hexanoate (372 mg, 2.0 mmol) and potassium carbonate (138 mg, 1.0 mmol) in ethanol (5 mL) was heated in a sealed tube in a microwave oven to 170° C. for 0.5 h. The mixture was cooled, diluted with ethyl acetate (50 mL), and then washed with water (20 mL) and with brine (20 mL). The organic layer was dried over sodium sulfate and evaporated under reduced pressure. The residual material was purified by chromatography on silica gel using dichloromethane/0-10% methanol as eluent to give the title compound (153 mg, 20%) as a light yellow solid. MS ISP (m/e): 384.3 [(M+H)$^+$]. $^1$H NMR (CDCl$_3$, 300 MHz): δ (ppm)=8.11 (dd, 1H), 7.68 (s, 1H), 7.47 (s, 1H), 7.38 (s, 1H), 7.25-7.30 (2H), 6.94 (s, 1H), 4.48 (q, 2H), 3.05 (m, 1H), 2.31 (s, 3H), 1.46 (t, 3H), 1.36 (d, 6H).

Example 218

2-{2-[3-Fluoro-4-(4-methyl-imidazol-1-yl)-phenylamino]-6-isopropyl-pyrimidin-4-yl}-propan-2-ol

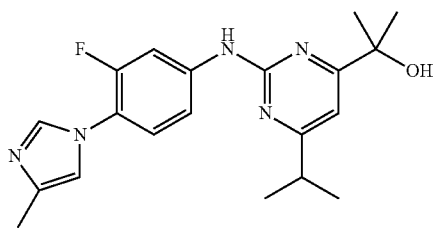 [SMILES: Cc1cn(-c2ccc(Nc3nc(C(C)C)cc(C(C)(C)O)n3)cc2F)cn1]

Using in analogous manner the procedure described in example 165, ethyl 2-[3-fluoro-4-(4-methyl-imidazol-1-yl)-phenylamino]-6-(4-trifluoromethyl-phenyl)-pyrimidine-4-carboxylate (115 mg, 0.3 mmol) was reacted with methylmagnesiumchloride to give the title compound (66 mg, 59%) as a light yellow solid. MS ISP (m/e): 370.2 [(M+H)$^+$]. $^1$H NMR (CDCl$_3$, 300 MHz): δ (ppm)=7.99 (dd, 1H), 7.64 (s, 1H), 7.25-7.35 (2H), 7.22 (s, 1H), 6.94 (s, 1H), 6.79 (s, 1H), 3.92 (br s, 1H), 2.95 (m, 1H), 2.31 (s, 3H), 1.54 (s, 6H), 1.33 (d, 6H).

Example 219

Ethyl 2-[3-fluoro-4-(4-methyl-imidazol-1-yl)-phenylamino]-6-(4-trifluoromethyl-phenyl)-pyrimidine-4-carboxylate

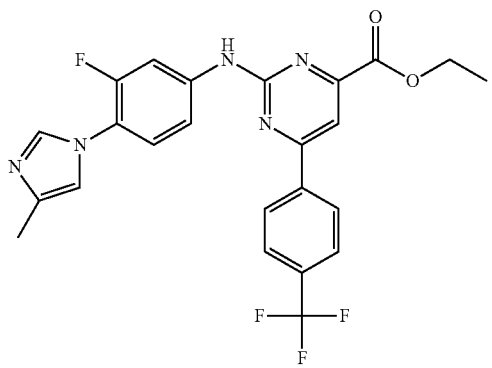 [SMILES: CCOC(=O)c1cc(-c2ccc(C(F)(F)F)cc2)nc(Nc2ccc(-n3cnc(C)c3)c(F)c2)n1]

Using in analogous manner the procedure described in example 217, but replacing ethyl 5-methyl-2,4-dioxo-hexanoate by 2,4-dioxo-4-(4-trifluoromethyl-phenyl)-butyric acid ethyl ester (576 mg, 2.0 mmol), the title compound was obtained as light yellow solid (128 mg, 13%). MS ISP (m/e): 486.2 [(M+H)$^+$]. $^1$H NMR (CDCl$_3$, 300 MHz): δ (ppm)=8.25 (d, 2H), 8.08 (dd, 1H), 7.95 (s, 1H), 7.82 (d, 2H), 7.71 (s, 1H), 7.64 (s, 1H), 7.30-7.35 (2H), 6.96 (s, 1H), 4.54 (q, 2H), 2.31 (s, 3H), 1.50 (t, 3H).

Example 220

2-[2-[3-Fluoro-4-(4-methyl-imidazol-1-yl)-phenylamino]-6-(4-trifluoromethyl-phenyl)-pyrimidin-4-yl]-propan-2-ol

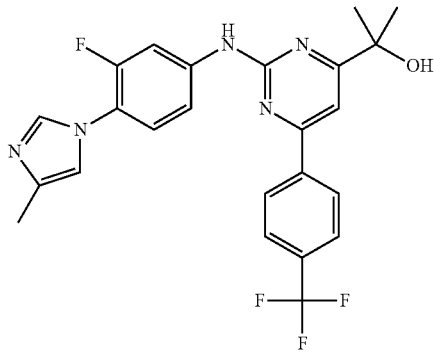 [SMILES: Cc1cn(-c2ccc(Nc3nc(-c4ccc(C(F)(F)F)cc4)cc(C(C)(C)O)n3)cc2F)cn1]

Using in analogous manner the procedure described in example 165, ethyl 2-[3-fluoro-4-(4-methyl-imidazol-1-yl)-phenylamino]-6-(4-trifluoromethyl-phenyl)-pyrimidine-4-carboxylate (87 mg, 0.18 mmol) was reacted with methylmagnesiumchloride to give the title compound (47 mg, 55%) as a light yellow solid. MS ISP (m/e): 472.2 [(M+H)$^+$]. $^1$H NMR (CDCl$_3$, 300 MHz): δ (ppm)=8.19 (d, 2H), 7.97 (dd, 1H), 7.80 (d, 2H), 7.72 (br s, 1H), 7.42 (s, 2H), 7.28-7.32 (2H), 6.98 (s, 1H), 3.68 (br s, 1H), 2.32 (s, 3H), 1.63 (s, 6H).

Example 221

2-{6-Dimethylamino-2-[3-methoxy-4-(4-methyl-imidazol-1-yl)-phenylamino]-pyrimidin-4-yl}-propan-2-ol

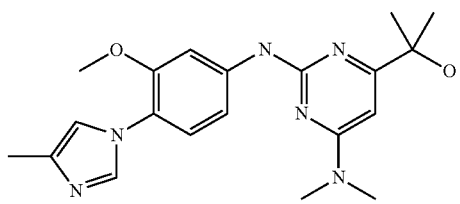 [SMILES: COc1cc(Nc2nc(N(C)C)cc(C(C)(C)O)n2)ccc1-n1cnc(C)c1]

a) 2-(2-Chloro-6-dimethylamino-pyrimidin-4-yl)-propan-2-ol

Using in analogous manner the procedure described in example 88b), but replacing ethyl 2-chloro-6-ethoxy-pyrimidine-4-carboxylate by methyl 2-chloro-6-dimethylamino-pyrimidine-4-carboxylate (645 mg, 3.0 mmol), the title compound was obtained as light yellow solid (504 mg, 78%). MS ISP (m/e): 216.2 [(M+H)$^+$].

b) 2-{6-Dimethylamino-2-[3-methoxy-4-(4-methyl-imidazol-1-yl)-phenylamino]-pyrimidin-4-yl}-propan-2-ol Using in analogous manner the procedure described in example 1e), 2-(2-chloro-6-dimethylamino-pyrimidin-4-yl)-propan-2-ol (65 mg, 0.3 mmol) was reacted with 3-methoxy-4-(4-methyl-imidazol-1-yl)-phenylamine (61 mg, 0.3 mmol) to give the title compound was obtained as light yellow foam (24 mg, 21%). MS ISP (m/e): 383.3 [(M+H)$^+$]. $^1$H NMR (CDCl$_3$, 300 MHz): δ (ppm)=7.75 (d, 1H), 7.63 (s, 1H), 7.26 (s, 1H), 7.15 (d, 1H), 6.99 (dd, 1H), 6.87 (s, 1H), 6.01 (s, 1H), 4.38 (br s, 1H), 3.86 (s, 3H), 3.16 (s, 6H), 2.30 (s, 3H), 1.51 (s, 6H).

Example 222

2-{2-[3-Methoxy-4-(4-methyl-imidazol-1-yl)-phenylamino]-6-morpholin-4-yl-pyrimidin-4-yl}-propan-2-ol

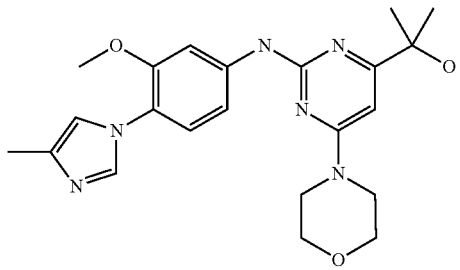 [SMILES: COc1cc(Nc2nc(N3CCOCC3)cc(C(C)(C)O)n2)ccc1-n1cnc(C)c1]

a) 2-(2-Chloro-6-morpholin-4-yl-pyrimidin-4-yl)-propan-2-ol

Using in analogous manner the procedure described in example 88b), but replacing ethyl 2-chloro-6-ethoxy-pyrimidine-4-carboxylate by methyl 2-chloro-6-morpholin-4-yl-pyrimidine-4-carboxylate (900 mg, 3.5 mmol), the title compound was obtained as light yellow solid (769 mg, 85%). MS ISP (m/e): 258.1 [(M+H)+].

b) 2-{2-[3-Methoxy-4-(4-methyl-imidazol-1-yl)-phenylamino]-6-morpholin-4-yl-pyrimidin-4-yl}-propan-2-ol Using in analogous manner the procedure described in example 1e), 2-(2-chloro-6-morpholin-4-yl-pyrimidin-4-yl)-propan-2-ol (77 mg, 0.3 mmol) was reacted with 3-methoxy-4-(4-methyl-imidazol-1-yl)-phenylamine (61 mg, 0.3 mmol) to give the title compound was obtained as light yellow foam (62 mg, 49%). MS ISP (m/e): 425.2 [(M+H)+].) 1 $^1$H NMR (CDCl$_3$, 300 MHz): (ppm)=7.82 (s, 2H), 7.16 (d, 1H), 6.98 (dd, 1H), 6.95 (s, 1H), 6.87 (s, 1H), 6.12 (s, 1H), 4.15 (br s, 1H), 3.81 (s, 3H), 3.78 and 3.65 (2 m, 2×4H), 3.16 (s, 6H), 2.30 (s, 3H), 1.51 (s, 6H).

Example 223

1-{6-(1-Hydroxy-1-methyl-ethyl)-2-[3-methoxy-4-(4-methyl-imidazol-1-yl)-phenylamino]-pyrimidin-4-yl}-4-methyl-piperidin-4-ol

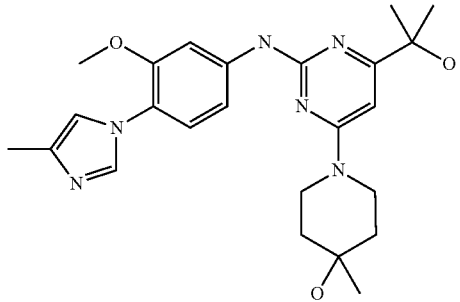 [SMILES: COc1cc(Nc2nc(N3CCC(C)(O)CC3)cc(C(C)(C)O)n2)ccc1-n1cnc(C)c1]

a) Methyl 2-chloro-6-(4-hydroxy-4-methyl-piperidin-1-yl)-pyrimidine-4-carboxylate A mixture of methyl 2,4-dichloropyrimidine-6-carboxylate (1.66 g, 8.0 mmol), 4-methyl-piperidin-4-ol (1.21 g, 8 mmol) and sodium carbonate (1.74 g, 16.0 mmol) in methanol (8 mL) was stirred for 1 h at 20° C. The mixture was partitioned between ethyl acetate and water, and the organic layer was subsequently washed with brine, dried over sodium sulfate and evaporated under reduced pressure to give crude title compound (1.70 g, 72%) as light yellow solid. MS ISP (m/e): 286.1 [(M+H)+].

b) 1-[2-Chloro-6-(1-hydroxy-1-methyl-ethyl)-pyrimidin-4-yl]-4-methyl-piperidin-4-ol Using in analogous manner the procedure described in example 88b), but replacing ethyl 2-chloro-6-ethoxy-pyrimidine-4-carboxylate by methyl 2-chloro-6-(4-hydroxy-4-methyl-piperidin-1-yl)-pyrimidine-4-carboxylate (1.71 g, 6.0 mmol), the title compound was obtained as light yellow solid (0.38 g, 22%). MS ISP (m/e): 286.1 [(M+H)+].

c) 2-{2-[3-Methoxy-4-(4-methyl-imidazol-1-yl)-phenylamino]-6-pyrrolidin-1-yl-pyrimidin-4-yl}-propan-2-ol Using in analogous manner the procedure described in example 1e), 2-(2-chloro-6-morpholin-4-yl-pyrimidin-4-yl)-propan-2-ol (77 mg, 0.3 mmol) was reacted with 3-methoxy-4-(4-methyl-imidazol-1-yl)-phenylamine (61 mg, 0.3 mmol) to give the title compound was obtained as off-white foam (70 mg, 52%). MS ISP (m/e): 453.3 [(M+H)+]. $^1$H NMR (CDCl$_3$, 300 MHz): δ (ppm)=7.73 (d, 1H), 7.62 (s, 1H), 7.14 (d, 1H), 6.97 (s, 1), 6.92 (dd, 1H), 6.87 (s, 1H), 6.14 (s, 1H), 4.28 (br s, 1H), 4.10 (m, 3H), 3.85 (s, 3H), 3.47 (m, 2H), 2.30 (s, 3H), 1.55-1.70 (m, 4H), 1.51 (s, 6H), 1.32 (s, 3H).

Example 224

2-[3-Methoxy-4-(4-methyl-imidazol-1-yl)-phenylamino]-6-(4-trifluoromethyl-phenyl)-pyrimidine-4-carboxylic acid dimethylamide

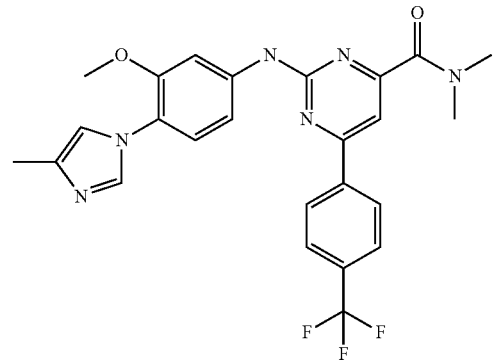

a) 2-Chloro-6-(4-trifluoromethyl-phenyl)-pyrimidine-4-carboxylic acid

Pd(dppf)Cl$_2$ (0.214 g, 0.02 mmol) was added to a mixture of methyl 2,4-dichloropyrimidine-6-carboxylate (2.07 g, 10 mmol) and 4-(trifluoromethyl)phenyl-boronic acid (1.90 g, 10 mmol) in DME (100 mL) and sat. aq. NaHCO$_3$ (20 mL), and the mixture was stirred in an atmosphere of argon at 80° C. for 3 h. The reaction mixture was cooled to 20° C. and added to ice water (100 mL). The mixture was extracted with ethyl acetate (2×100 mL) and the organic phase was extracted with saturated sodium carbonate solution (50 mL). The combined aqueous layers were acidified by the addition of 25% HCl (100 mL) and subsequently extracted with ethyl acetate (2×100 mL). The organic phase was washed with brine, dried over sodium sulfate, and the solvents were removed under reduced pressure. The residual solid was recrystallized from ethyl acetate/heptane to give the title compound (1.82 g, 60%) as light red solid. MS ISN (m/e): 301.2 [(M–H)$^-$]. $^1$H NMR (CDCl$_3$, 300 MHz): δ (ppm)=8.51 (s, 1H), 8.33 and 7.84 (2 d, 2×2H).

b) 2-Chloro-6-(4-trifluoromethyl-phenyl)-pyrimidine-4-carboxylic acid dimethylamide Oxalyl chloride (0.38 mL, 4.5 mmol) and N,N-dimethylformamide (0.03 mL) were added to a suspension of 2-chloro-6-(4-trifluoromethyl-phenyl)-pyrimidine-4-carboxylic acid (303 mg, 1.0 mmol) in dichloromethane (20 mL). The mixture was stirred at 20° C. for 3 h and then evaporated under reduced pressure. The residue was dissolved in dichloro-methane (25 mL) and the solution was stirred together with 60% aqueous dimethylamine (1.2 mL, 13.3 mmol) and saturated aqueous sodium hydrogencarbonate solution (8 mL) for 1 h at 20° C. The mixture was diluted with dichloromethane (25 mL), and the organic layer was washed with water and brine, dried over sodium sulfate, and evaporated under reduced pressure. The residual material was purified by chromatography on silica gel using heptane/0-40% ethyl acetate as eluent to give the title compound (215 mg, 65%) as a white solid. MS ISP (m/e): 330.2 [(M+H)$^+$]. $^1$H NMR (CDCl$_3$, 300 MHz): δ (ppm)=8.24 (d, 2H), 7.99 (s, 1H), 7.80 d, 2H), 3.17 (s, 6H).

c) 2-[3-Methoxy-4-(4-methyl-imidazol-1-yl)-phenylamino]-6-(4-trifluoromethylphenyl)-pyrimidine-4-carboxylic acid dimethylamide Using in analogous manner the procedure described in example 1e), 2-chloro-6-(4-trifluoromethyl-phenyl)-pyrimidine-4-carboxylic acid dimethylamide (99 mg, 0.3 mmol) was reacted with 3-methoxy-4-(4-methyl-imidazol-1-yl)-phenylamine (61 mg, 0.3 mmol) to give the title compound as yellow solid (76 mg, 51%). MS ISP (m/e): 497.4 [(M+H)$^+$]. $^1$H NMR (CDCl$_3$, 300 MHz): δ (ppm)=8.21 (d, 2H), 7.77 (d, 2H), 7.74 (d, 1H), 7.66 (s, 1H), 7.45 (s, 1H), 7.41 (s, 1H), 7.23 (d, 1H), 7.18 (dd, 1H), 6.90 (s, 1H), 3.89 (s, 3H), 3.18 and 3.15 (2 s, 2×3H), 2.31 (s, 3H).

Example 225

[2-[3-Methoxy-4-(4-methyl-imidazol-1-yl)-phenylamino]-6-(4-trifluoromethyl-phenyl)-pyrimidin-4-yl]-morpholin-4-yl-methanone

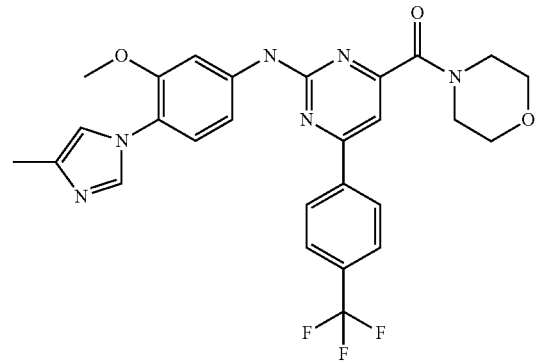 [SMILES: COc1cc(Nc2nc(C(=O)N3CCOCC3)cc(-c3ccc(C(F)(F)F)cc3)n2)ccc1-n1cnc(C)c1]

a) [2-Chloro-6-(4-trifluoromethyl-phenyl)-pyrimidin-4-yl]-morpholin-4-yl-methanone Oxalyl chloride (0.38 mL, 4.5 mmol) and N,N-dimethylformamide (0.03 mL) were added to a suspension of 2-chloro-6-(4-trifluoromethyl-phenyl)-pyrimidine-4-carboxylic acid (303 mg, 1.0 mmol) in dichloromethane (20 mL). The mixture was stirred at 20° C. for 3 h and then evaporated under reduced pressure. The residue was dissolved in dichloro-methane (25 mL) and the solution was stirred together morpholine (0.174 mL, 2.0 mmol) and saturated aqueous sodium hydrogencarbonate solution (8 mL) for 1 h at 20° C. The mixture was diluted with dichloromethane (25 mL), and the organic layer was washed with water and brine, dried over sodium sulfate, and evaporated under reduced pressure. The residual material was purified by chromatography on silica gel using heptane/0-40% ethyl acetate as eluent to give the title compound (260 mg, 66%) as a white solid. MS ISP (m/e): 372.2 [(M+H)$^+$]. $^1$H NMR (CDCl$_3$, 300 MHz): δ (ppm)=8.25 (d, 2H), 8.04 (s, 1H), 7.80 d, 2H), 3.83 (br s, 4H), 3.74 (m, 4H).

b) 2-[3-Methoxy-4-(4-methyl-imidazol-1-yl)-phenylamino]-6-(4-trifluoromethyl-phenyl)-pyrimidin-4-yl]-morpholin-4-yl-methanone Using in analogous manner the procedure described in example 1e), 2-chloro-6-(4-trifluoromethyl-phenyl)-pyrimidine-4-carboxylic acid dimethylamide (112 mg, 0.3 mmol) was reacted with 3-methoxy-4-(4-methyl-imidazol-1-yl)-phenylamine (61 mg, 0.3 mmol) to give the title compound as yellow solid (42 mg, 27%). MS ISP (m/e): 539.3 [(M+H)$^+$]. $^1$H NMR (CDCl$_3$, 300 MHz): δ (ppm)=8.21 (d, 2H), 7.77 (d, 2H), 7.69 (d, 1H), 7.67 (s, 1H), 7.57 (s, 1H), 7.48 (s, 1H), 7.2-7.3 (2H), 6.91 (s, 1H), 3.88 (s, 3H), 3.83 and 3.69 (2 m, 2×4H), 2.31 (s, 3H).

Example 226

1-[2-[3-Methoxy-4-(4-methyl-imidazol-1-yl)-phenylamino]-6-(4-trifluoromethyl-phenyl)-pyrimidin-4-yl]-cyclopentanol

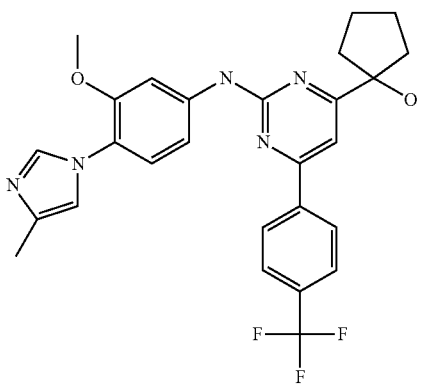 [SMILES: COc1cc(Nc2nc(-c3ccc(C(F)(F)F)cc3)cc(C3(O)CCCC3)n2)ccc1-n1cnc(C)c1]

A solution of ethyl 2-[3-methoxy-4-(4-methyl-imidazol-1-yl)-phenylamino]-pyrimidine-4-carboxylate (99 mg, 0.2 mmol) in tetrahydrofurane (2 mL) was added at 0° C. over 1 min to a 0.3 M solution of butane-1,4-bis(magnesiumbromide) in tetrahydrofurane (1.6 mL, 0.49 mmol). The reaction mixture was stirred at 0° C. for 10 min followed by 2 h at 20° C. The mixture was poured on saturated ammonium chloride solution (5 mL) and the mixture was extracted with ethyl acetate (40 mL). The organic layer was washed with brine (20 mL), dried over sodium sulfate and evaporated under reduced pressure. The residual material was purified by chromatography on silica gel using ethyl acetate as eluent to give the title compound (10 mg, 10%) as light yellow foam. MS ISP (m/e): 510.4 [(M+H)+]. $^1$H NMR (CDCl$_3$, 300 MHz): δ (ppm)=8.20 (d, 2H), 7.82 (d, 1H), 7.76 (d, 2H), 7.66 (s, 1H), 7.39 (s, 1H), 7.37 (s, 1H), 7.22 (d, 1H), 7.10 (dd, 1H), 6.90 (s, 1H), 3.89 (s, 3H), 2.31 (s, 3H), 1.85-2.25 (m, 4H).

Example 227

2-[2-[4-(3-Methyl-[1,2,4]thiadiazol-5-yl)-phenylamino]-6-(4-trifluoromethyl-phenyl)-pyrimidin-4-yl]-propan-2-ol

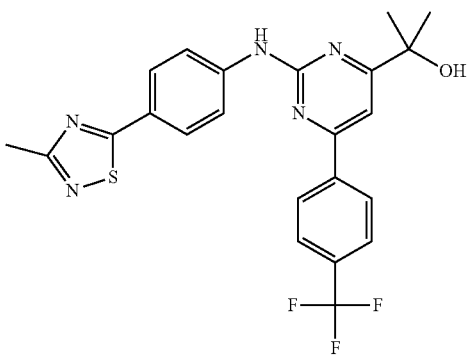 [SMILES: Cc1nsc(-c2ccc(Nc3nc(-c4ccc(C(F)(F)F)cc4)cc(C(C)(C)O)n3)cc2)n1]

a) 4-(3-Methyl-[1,2,4]thiadiazol-5-yl)-phenylamine

To a suspension of 3-methyl-5-(4-nitro-phenyl)-[1,2,4]thiadiazole (422 mg, 1.9 mmol, CAS 800408-77-9, Wilkins, D. J.; Bradley, P. A. Science of Synthesis (2004), 13, 277-295.) in ethanol (19 mL) was added under stirring tin(II) chloride (1.86 g, 9.54 mmol) and heated to 70° C. for 4 hours. The mixture was poured on cold aqueous saturated sodium hydrogen carbonate solution. The suspension was stirred for 30 minutes and the solid was filtered off, washed with water. The residue was heated two to three times with tetrahydrofurane and filtered. The aqueous layer was extracted twice with ethyl acetate. The combined organic layers were dried over sodium sulfate and the solvent was evaporated under reduced pressure. The residue was stirred with diethyl ether and the solid was filtered off and washed with diethyl ether/heptane to yield the title compound as a yellow solid (355 mg, 97%). MS ISP (m/e): 192.2 (100) [(M+H)+]. $^1$H NMR (DMSO-D$_6$, 300 MHz): δ (ppm)=7.64 (d, 2H), 6.63 (d, 3H), 6.01 (BR s, 2H, NH$_2$), 2.54 (s, 3H).

2-[2-[4-(3-Methyl-[1,2,4]thiadiazol-5-yl)-phenylamino]-6-(4-trifluoromethyl-phenyl)-pyrimidin-4-yl]-propan-2-ol Palladium(II) acetate (3.6 mg, 0.016 mmol) and 2-(dicyclohexylphosphino)biphenyl (11 mg, 0.032 mmol) were stirred in dioxane (1 mL) for 10 minutes at room temperature under an atmosphere of nitrogen. Sodium tert.-butylate (29 mg, 0.3 mmol), 4-(3-methyl-[1,2,4]-thiadiazol-5-yl)-phenylamine (38 mg, 0.20 mmol) and 2-[2-chloro-6-(4-trifluoromethyl-phenyl)pyrimidine-4-yl]-propan-2-ol (70 mg, 0.22 mmol) dissolved in dioxane (1 mL) were added. The reaction was heated for 30 minutes to 130° C. in a microwave oven. Water was added and the reaction was extracted twice with ethyl acetate. The combined organic layers were washed with brine, dried over sodium sulfate, filtered and the solvent was evaporated under reduced pressure. The residue was purified by column chromatography on silica gel using heptane/ethyl acetate (1:1 v/v) as eluent to yield the title compound as a yellow solid (26 mg, 28%). MS ISP (m/e): 472.2 (100) [(M+H)+]. $^1$H NMR (CDCl$_3$, 300 MHz): δ (ppm)=8.21 (d, 2H), 7.97 (d, 2H), 7.85 (d, 2H), 7.79 (d, 2H), 7.45 (br s, 1H, NH), 7.39 (s, 1H), 3.72 (s, 1H, OH), 2.73 (s, 3H), 1.62 (s, 6H).

Example 228

(4-Benzyl-6-methyl-pyrimidin-2-yl)-[3-methoxy-4-(2-methyl-oxazol-5-yl)-phenyl]-amine

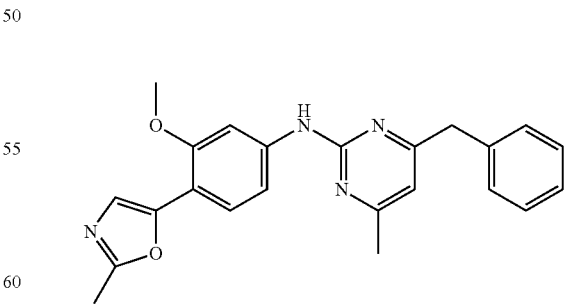

Palladium(II) acetate (5.4 mg, 0.024 mmol) and 2-(dicyclohexylphosphino)biphenyl (17 mg, 0.048 mmol) were stirred in dioxane (3 mL) for 20 minutes under an atmosphere of nitrogen. Sodium tert.-butylate (44 mg, 0.45 mmol), 3-methoxy-4-(2-methyl-oxazol-5-yl)-phenylamine (61 mg, 0.30 mmol, CAS 568556-28-5; E. J. Iwanowicz et. al. Bioorganic & Medicinal Chemistry Letters, 13(12), 2059-2063; 2003) and 4-benzyl-2-chloro-6-methyl-pyrimidine (72 mg, 0.33 mmol) were added. The reaction was heated for 30 minutes to 130° C. in a microwave oven. Water was added and the reaction was extracted three times with ethyl acetate. The combined organic layers were dried over sodium sulfate, filtered and the solvent was evaporated under reduced pressure. The residue was purified by column chromatography on silica gel using dichloromethane and then methylenechloride/methanol (19:1 v/v) as eluent to yield the title compound as a yellow solid (31 mg, 27%). MS ISP (m/e): 387.2 (100) [(M+H)$^+$]. $^1$H NMR (CDCl$_3$, 300 MHz): δ (ppm)=7.86 (s, 1H), 7.61 (d, 2H), 7.26-7.33 (m, 5H), 7.15 (br s, 1H), 6.98 (d, 1H), 6.48 (s, 1H), 3.97 (s, 2H), 3.90 (s, 3H), 2.51 (s, 3H), 2.37 (s, 3H).

Example 229

2-{6-(4-Chloro-phenyl)-2-[4-(2-methyl-oxazol-5-yl)-phenylamino]-pyrimidin-4-yl}-propan-2-ol

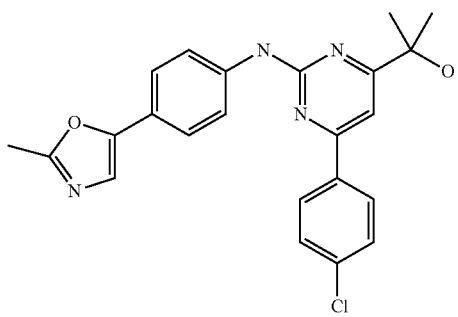 [SMILES: Cc1ncc(-c2ccc(Nc3nc(-c4ccc(Cl)cc4)cc(C(C)(C)O)n3)cc2)o1]

a) 2-Chloro-6-(4-chloro-phenyl)-pyrimidine-4-carboxylic acid

Using in analogous manner the procedure described in example 224a), but replacing 4-(trifluoromethyl)phenylboronic acid by 4-chlorophenylboronic acid (1.04 g, 5 mmol), the title compound was obtained as light yellow solid (0.78 g, 58%). MS ISN (m/e): 267.2 [(M−H)$^−$].

b) Ethyl 2-chloro-6-(4-chloro-phenyl)-pyrimidine-4-carboxylate

To a solution of 2-chloro-6-(4-chloro-phenyl)-pyrimidine-4-carboxylic acid (1.35 g, 5.0 mmol) in ethanol (50 mL) was added diethyl ether (10 mL) which had been saturated previously with hydrochloric acid gas. The reaction mixture was stirred for 24 h at 20° C. The solution was evaporated under reduced pressure and the residual oil was dissolved in ethyl acetate. The solution was washed with saturated sodium hydrogencarbonate solution and with brine, dried over sodium sulfate, and evaporated under reduced pressure. The residual material was crystallized from ethyl acetate/heptane to give the title compound (1.17 g, 78%) as light yellow solid. MS ISN (m/e): 297.1 [(M+H)$^+$]. $^1$H NMR (CDCl$_3$, 300 MHz): δ (ppm)=8.31 (s, 1H), 8.13 and 7.53 (2 d, 2×2H), 4.53 (q, 2H), 1.47 (t, 3H).

c) 2-[2-Chloro-6-(4-chloro-phenyl)-pyrimidin-4-yl]-propan-2-ol

To a solution of ethyl 2-chloro-6-(4-chloro-phenyl)-pyrimidine-4-carboxylate (297 mg, 1.0 mmol) in tetrahydrofurane (6 mL) was added at—over 2 min a 3 M solution of methylmagnesiumchloride in tetrahydrofurane (0.80 mL, 2.4 mmol). The reaction mixture was stirred at −70° C. for 30 min followed by 2 h at 0° C. The mixture was poured on saturated ammonium chloride solution (20 mL) and the product was extracted with ethyl acetate (40 mL). The organic layer was washed with brine (20 mL), dried over sodium sulfate and evaporated under reduced pressure. The residual material was purified by chromatography on silica gel using heptane/0-50% ethyl acetate as eluent to give after crystallization from ethyl acetate/heptane the title compound (185 mg, 65%) as white solid. MS ISP (m/e): 283.1 [(M+H)$^+$]. $^1$H NMR (CDCl$_3$, 300 MHz): δ (ppm)=8.07 (d, 2H), 7.80 (s, 1H), 7.49 (d, 2H), 3.16 (s, 1H), 1.62 (s, 6H).

d) 2-{6-(4-Chloro-phenyl)-2-[4-(2-methyl-oxazol-5-yl)-phenylamino]-pyrimidin-4-yl}-propan-2-ol Using in analogous manner the procedure described in example 1e), 2-[2-chloro-6-(4-chloro-phenyl)-pyrimidin-4-yl]-propan-2-ol (112 mg, 0.3 mmol) was reacted with 4-(2-methyl-oxazol-5-yl)-phenylamine (61 mg, 0.3 mmol) to give the title compound as light yellow solid (28 mg, 22%). MS ISP (m/e): 421.1 [(M+H)$^+$]. $^1$H NMR (CDCl$_3$, 300 MHz): δ (ppm)=8.04, 7.74, 7.63 and 7.50 (4 d, 4×2H), 7.20 (s, 1H), 7.23 (s, 1H), 7.15 (s, 1H), 4.01 (s, 1H), 2.53 (s, 3H), 1.61 (s, 6H).

Example 230

2-{6-(4-Chloro-phenyl)-2-[4-(2-ethyl-oxazol-5-yl)-phenylamino]-pyrimidin-4-yl}-propan-2-ol

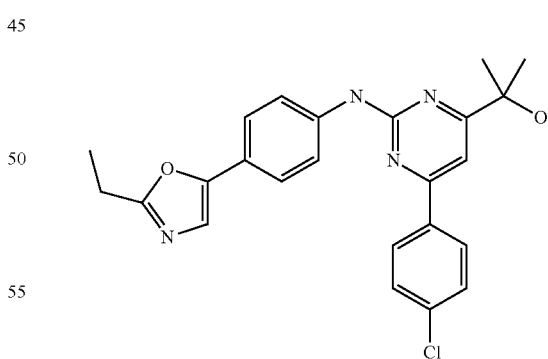

Using in analogous manner the procedure described in example 229d), but replacing 4-(2-methyl-oxazol-5-yl)-phenylamine by 4-(2-ethyl-oxazol-5-yl)-phenylamine (57 mg, 0.2 mmol), the title compound was obtained as light yellow solid (12 mg, 14%). MS ISP (m/e): 435.2 [(M+H)$^+$]. $^1$H NMR (CDCl$_3$, 300 MHz): δ (ppm)=8.04, 7.74, 7.64 and 7.50 (4 d, 4×2H), 7.17 (s, 1H), 4.01 (s, 1H), 2.86 (q, 2H), 1.60 (s, 6H), 1.40 (t, 3H).

Example 231

2-[2-[4-(2-Methyl-oxazol-5-yl)-phenylamino]-6-(4-trifluoromethyl-phenyl)-pyrimidin-4-yl]-propan-2-ol

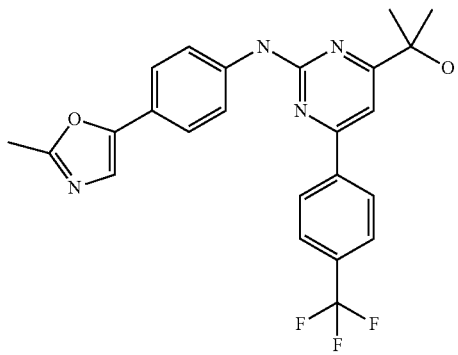 [SMILES: Cc1ncc(-c2ccc(Nc3nc(-c4ccc(C(F)(F)F)cc4)cc(C(C)(C)O)n3)cc2)o1]

a) Ethyl 2-chloro-6-(4-trifluoromethyl-phenyl)-pyrimidine-4-carboxylate

Using in analogous manner the procedure described in example 229b), but replacing 2-chloro-6-(4-chloro-phenyl)-pyrimidine-4-carboxylic acid by 2-chloro-6-(4-trifluoromethyl-phenyl)-pyrimidine-4-carboxylic acid (1.89 g, 6.0 mmol), the title compound was obtained as light yellow solid (1.83 g, 87%). MS ISP (m/e): 331.0 [(M+H)$^+$]. $^1$H NMR (CDCl$_3$, 300 MHz): δ (ppm)=8.34 (s, 1H), 8.30 and 7.82 (2 d, 2×2H), 4.55 (q, 2H), 1.48 (t, 3H).

b) 2-[2-Chloro-6-(4-trifluoromethyl-phenyl)-pyrimidin-4-yl]-propan-2-ol

Using in analogous manner the procedure described in example 229c), but replacing ethyl 2-chloro-6-(4-chloro-phenyl)-pyrimidine-4-carboxylate by ethyl 2-chloro-6-(4-trifluoromethyl-phenyl)-pyrimidine-4-carboxylate (661 mg, 2.0 mmol), the title compound was obtained as light yellow solid (486 mg, 77%). $^1$H NMR (CDCl$_3$, 300 MHz): δ (ppm)=8.23 (d, 2H), 7.89 (s, 1H), 7.78 (d, 2H), 3.12 (s, 1H), 1.64 (s, 6H).

c) 2-[2-[4-(2-Methyl-oxazol-5-yl)-phenylamino]-6-(4-trifluoromethyl-phenyl)-pyrimidin-4-yl]-propan-2-ol Using in analogous manner the procedure described in example 1e), 2-[2-chloro-6-(4-trifluoromethyl-phenyl)-pyrimidin-4-yl]-propan-2-ol (95 mg, 0.3 mmol) was reacted with 4-(2-methyl-oxazol-5-yl)-phenylamine (52 mg, 0.3 mmol) to give the title compound as light yellow solid (29 mg, 21%). MS ISP (m/e): 455.2 [(M+H)$^+$]. $^1$H NMR (CDCl$_3$, 300 MHz): δ (ppm)=8.20, 7.78, 7.75 and 7.63 (4 d, 4×2H), 7.31 (s, 2H), 7.16 (s, 1H), 3.93 (s, 1H), 2.53 (s, 3H), 1.61 (s, 6H).

Example 232

2-[2-[4-(2,4-Dimethyl-oxazol-5-yl)-phenylamino]-6-(4-trifluoromethyl-phenyl)-pyrimidin-4-yl]-propan-2-ol

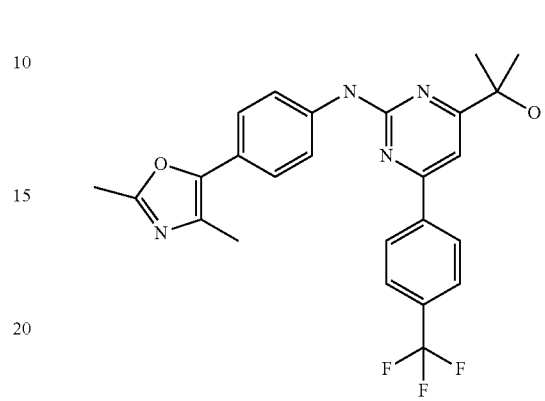

Using in analogous manner the procedure described in example 1e), 2-[2-chloro-6-(4-trifluoromethyl-phenyl)-pyrimidin-4-yl]-propan-2-ol (95 mg, 0.3 mmol) was reacted with 4-(2,4-dimethyl-oxazol-5-yl)-phenylamine (56 mg, 0.3 mmol) to give the title compound as light yellow solid (72 mg, 51%). MS ISP (m/e): 469.2 [(M+H)$^+$]. $^1$H NMR (CDCl$_3$, 300 MHz): δ (ppm)=8.20, 7.78, 7.75 and 7.63 (4 d, 4×2H), 7.31 (s, 2H), 3.93 (s, 1H), 2.53 (s, 3H), 1.61 (s, 6H).

Example 233

2-[2-[3-Methoxy-4-(2-methyl-thiazol-5-yl)-phenylamino]-6-(4-trifluoromethyl-phenyl)-pyrimidin-4-yl]-propan-2-ol

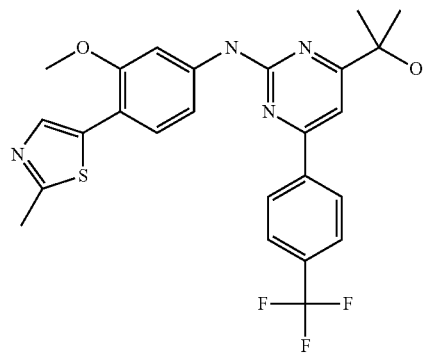 [SMILES: COc1cc(Nc2nc(-c3ccc(C(F)(F)F)cc3)cc(C(C)(C)O)n2)ccc1-c1cnc(C)s1]

Using in analogous manner the procedure described in example 1e), 2-[2-chloro-6-(4-trifluoromethyl-phenyl)-pyrimidin-4-yl]-propan-2-ol (95 mg, 0.3 mmol) was reacted with 3-methoxy-4-(2-methyl-thiazol-5-yl)-phenylamine (66 mg, 0.3 mmol) to give the title compound as light yellow solid (36 mg, 24%). MS ISP (m/e): 501.1 [(M+H)$^+$]. $^1$H NMR (CDCl$_3$, 300 MHz): δ (ppm)=8.21 (d, 2H), 7.98 (s, 1H), 7.77 (m, 3H), 7.54 (d, 1H), 7.34 (2 s, 2×1H), 7.10 (dd, 1H), 3.98 (s, 3H), 3.87 (s, 1H), 2.73 (s, 3H), 1.62 (s, 6H).

Example 234

5-[4-(1-Hydroxy-1-methyl-ethyl)-6-(4-trifluoromethyl-phenyl)-pyrimidin-2-ylamino]-2-(4-methyl-imidazol-1-yl)-benzonitrile

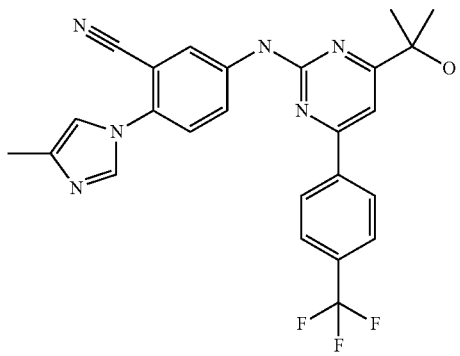 [SMILES: Cc1cn(-c2ccc(Nc3nc(-c4ccc(C(F)(F)F)cc4)cc(C(C)(C)O)n3)cc2C#N)cn1]

a) 2-(4-Methyl-imidazol-1-yl)-5-nitro-benzonitrile

A suspension of 831 mg (5 mmol) of 3-cyano-4-fluoronitrobenzene, of 0.82 g (10 mmol) 4-methylimidazol and of 1.38 g (10 mmol) potassium carbonate in acetonitrile (10 mL) was stirred for 60 h at 20° C. The solvent was evaporated and the residue was partitioned between ethyl acetate and 1N aqueous sodium hydroxide solution. The aqueous layer was extracted with ethyl acetate. The combined organic layers were washed with brine, dried over sodium sulphate, and the solvent was evaporated under reduced pressure. The crude product was crystallized from ethanol/water yielding the title compound (0.65 g, 57%) as an off-white solid. $^1$H NMR (DMSO-$D_6$, 250 MHz): δ (ppm)=8.95 (s, 1H), 8.62 (d, 1H), 8.16 (s, 1H), 7.93 (d, 1H), 7.49 (s, 1H), 2.21 (s, 3H).

b) 5-Amino-2-(4-methyl-imidazol-1-yl)-benzonitrile 0.65 g (2.84 mmol) 2-(4-methyl-imidazol-1-yl)-5-nitro-benzonitrile dissolved in ethyl acetate (10 mL) were hydrogenated under an atmosphere of hydrogen at 20° C. for 5 h in the presence of 150 mg of 10% palladium on charcoal. The catalyst was filtered off and washed with ethyl acetate. The solvent of the filtrate was evaporated under reduced pressure and dried to yield the title compound (0.45 g, 80%) as yellow solid. MS ISP (m/e): 199.1 (100) [(M+H)$^+$]. $^1$H NMR (DMSO-$D_6$, 250 MHz): δ (ppm)=7.72 (s, 1H), 7.23 (d, 1H), 7.10 (s, 1H), 6.96 (s, 1H), 6.91 (d, 1H), 2.15 (s, 3H).

c) 5-[4-(1-Hydroxy-1-methyl-ethyl)-6-(4-trifluoromethyl-phenyl)-pyrimidin-2-ylamino]-2-(4-methyl-imidazol-1-yl)-benzonitrile Using in analogous manner the procedure described in example 1e), 2-[2-chloro-6-(4-trifluoromethyl-phenyl)-pyrimidin-4-yl]-propan-2-ol (95 mg, 0.3 mmol) was reacted with 3-methoxy-4-(2-methyl-thiazol-5-yl)-phenylamine (59 mg, 0.3 mmol) to give the title compound as light yellow solid (91 mg, 63%). MS ISP (m/e): 479.1 [(M+H)$^+$]. $^1$H NMR (DMSO-$d_6$, 300 MHz): δ (ppm)=10.31 (s, 1H), 8.53 (d, 1H), 8.35 (d, 2H), 8.17 (dd, 1H), 7.94 (d, 2H), 7.92 (s, 1H), 7.78 (s, 1H), 7.61 (d, 1H), 7.28 (s, 1H), 5.52 (s, 1H), 2.19 (s, 3H), 1.54 (s, 6H).

Example 235

2-[2-[3-Methyl-4-(4-methyl-imidazol-1-yl)-phenylamino]-6-(4-trifluoromethyl-phenyl)-pyrimidin-4-yl]-propan-2-ol

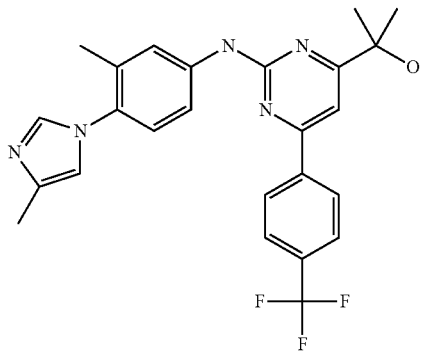 [SMILES: Cc1cn(-c2ccc(Nc3nc(-c4ccc(C(F)(F)F)cc4)cc(C(C)(C)O)n3)cc2C)cn1]

a) 4-Methyl-1-(2-methyl-4-nitro-phenyl)-1H-imidazole

A mixture of 2-chloro-5-nitro-toluene (2.0 g, 12 mmol), of 4-methylimidazole (1.0 g, 12 mmol) and of cesium carbonate (5.7 g, 17.5 mmol) in acetonitrile (20 mL) was refluxed for 15 h. The reaction mixture was cooled, quenched by addition of water and extracted with ethyl acetate. The organic layer was dried over sodium sulfate and evaporated under reduced pressure and the crude material was purified by column chromatography on silica gel using ethyl acetate as eluent to yield the title compound (1.27 g, 50%) as a slightly brownish solid. MS ISP (m/e): 218.3 (100) [(M+H)$^+$].

b) 3-Methyl-4-(4-methyl-imidazol-1-yl)-phenylamine

A mixture of 4-methyl-1-(2-methyl-4-nitro-phenyl)-1H-imidazole (1.26 g, 5.8 mmol) and of stannous chloride dihydrate (6.81 g, 30.2 mmol) in ethyl acetate (40 mL) and ethanol (20 mL) was stirred for 1 hour at 70° C. The reaction mixture was quenched by addition of water, neutralized with sodium hydrogen carbonate and extracted with ethyl acetate. The organic layer was dried over sodium sulfate and evaporated under reduced pressure to give the crude title compound (1.08 g, 99%) as a yellowish gum. MS ISP (m/e): 188.4 (100) [(M+H)$^+$].

c) 2-[2-[3-Methyl-4-(4-methyl-imidazol-1-yl)-phenylamino]-6-(4-trifluoromethyl-phenyl)-pyrimidin-4-yl]-propan-2-ol Using in analogous manner the procedure described in example 1e), 2-[2-chloro-6-(4-trifluoromethyl-phenyl)-pyrimidin-4-yl]-propan-2-ol (95 mg, 0.3 mmol) was reacted with 3-methoxy-4-(2-methyl-thiazol-5-yl)-phenylamine (56 mg, 0.3 mmol) to give the title compound as light yellow solid (38 mg, 27%). MS ISP (m/e): 468.2 [(M+H)$^+$]. $^1$H NMR (DMSO-$d_6$, 300 MHz): δ (ppm)=9.88 (s, 1H), 8.35 (d, 2H), 7.96 (s, 1H), 7.95 (d, 2H), 7.74 (dd, 1H), 7.71 (s, 1H), 7.63 (s, 1H), 7.20 (d, 1H), 7.04 (s, 1H), 5.45 (s, 1H), 2.17 (s, 3H), 2.15 (s, 3H), 1.52 (s, 6H).

Example 236

(4,6-Dimethyl-pyrimidin-2-yl)-[4-(2-methyl-pyridin-4-yl)-phenyl]-amine

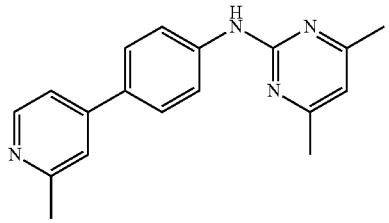 [SMILES: Cc1cc(-c2ccc(Nc3nc(C)cc(C)n3)cc2)ccn1]

a) 4-(2-Methyl-pyridin-4-yl)-phenylamine

The title compound was prepared from 4-bromo-2-methylpyridine and 4-(4,4,5,5-tetramethyl-1,2,3-dioxaborolan-2-yl)aniline by the method described in Organic Letters 8, 3421 (2006). Obtained as a brownish solid (Yield=18%). MS ISP (m/e): 185.1 (100) [(M+H)$^+$]. $^1$H NMR (DMSO-D$_6$, 300 MHz): δ (ppm)=9.80 (s, 1H), 8.57 (d, 2H), 7.95 (d, 2H), 7.74 8.34 (d, 1H), 7.51 (dxd, 2H), 7.43 (s, 1H), 7.35 (dxd, 1H), 6.65 (dxd, 2H), 5.48 (s, 2H), 2.46 (s, 3H).

b) (4,6-Dimethyl-pyrimidin-2-yl)-[4-(2-methyl-pyridin-4-yl)-phenyl]-amine

The title compound was prepared in analogy to example 62 from 4-(2-methyl-pyridin-4-yl)-phenylamine and 2-chloro-4,6-dimethylpyrimidine. Obtained as a yellowish solid (Yield=33%). MS ISP (m/e): 291.1 (100) [(M+H)$^+$]. $^1$H NMR (DMSO-D$_6$, 300 MHz): δ (ppm)=9.73 (s, 1H), 8.43 (d, 1H), 7.97 (d, 2H), 7.73 (d, 2H), 7.55 (s, 1H); 7.47 (d, 1H), 6.67 (s, 1H), 2.50 (s, 3H hidden in DMSO-peak), 2.34 (s, 6H).

Example 237

(4-Benzyl-6-methyl-pyrimidin-2-yl)-[4-(2-methyl-pyridin-4-yl)-phenyl]-amine

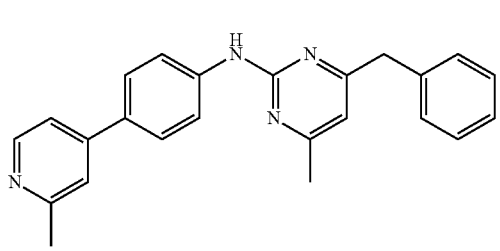 [SMILES: Cc1cc(-c2ccc(Nc3nc(C)cc(Cc4ccccc4)n3)cc2)ccn1]

The title compound was prepared in analogy to example 62 from 4-(2-methyl-pyridin-4-yl)-phenylamine and 4-benzyl-2-chloro-6-methyl-pyrimidine (example 43a). Obtained as a yellowish solid (Yield=48%). MS ISP (m/e): 367.1 (100) [(M+H)$^+$]. $^1$H NMR (DMSO-D$_6$, 300 MHz): δ (ppm)=9.77 (s, 1H), 8.45 (d, 1H), 7.93 (d, 2H), 7.71 (d, 2H), 7.55 (s, 1H), 7.47 (d, 1H), 7.35-7.20 (m, 5H), 6.67 (s, 1H), 3.95 (s, 2H), 2.51 (s, 3H), 2.33 (s, 3H).

Example 238

N4-(5-tert-Butyl-2-methyl-2H-pyrazol-3-yl)-5-fluoro-N2-[3-methoxy-4-(4-methyl-imidazol-1-yl)-phenyl]-pyrimidine-2,4-diamine

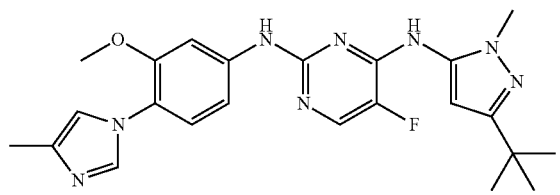 [SMILES: COc1cc(Nc2ncc(F)c(Nc3cc(C(C)(C)C)nn3C)n2)ccc1-n1cnc(C)c1]

Palladium(II) acetate (5.4 mg, 0.024 mmol) and 2-(dicyclohexylphosphino)biphenyl (17 mg, 0.048 mmol) were stirred in dioxane (2.7 mL) for 10 minutes at 20° C. under an atmosphere of nitrogen. Sodium tert.-butoxide (44 mg, 0.45 mmol), 3-methoxy-4-(4-methyl-imidazole-1-yl)-phenylamine (61 mg, 0.30 mmol) and (5-tert-butyl-2-methyl-2H-pyrazol-3-yl)-(2-chloro-5-fluoro-pyrimidin-4-yl)-amine (94 mg, 0.33 mmol, WO2008099210) were added. The reaction was heated for 30 minutes to 200° C. in a microwave oven. Palladium(II) acetate (5.4 mg, 0.024 mmol), 2-(dicyclohexylphosphino)-biphenyl (17 mg, 0.048 mmol), sodium carbonate (48 mg, 0.45 mmol), (5-tert-butyl-2-methyl-2H-pyrazol-3-yl)-(2-chloro-5-fluoro-pyrimidin-4-yl)-amine (85 mg, 0.3 mmol) and dioxane (1 mL) were added. The reaction was heated again for 30 minutes to 200° C. in a microwave oven. Water was added to the cooled reaction mixture and the mixture was extracted with ethyl acetate. The organic layer was dried over sodium sulfate and evaporated under reduced pressure. The residue was purified by column chromatography on silica gel using dichloromethane and then dichloromethane/methanol (19:1 v/v) as eluent to yield the title compound as a yellow solid (41 mg, 30%). MS ISP (m/e): 451.2 (100) [(M+H)$^+$]. $^1$H NMR (CDCl$_3$, 300 MHz): δ (ppm)=8.02 (s, 1H), 7.60 (s, 1H), 7.30 (s, 1H), 7.09 (d, 1H), 7.03 (m, 2H), 6.82 (s, 1H), 6.45 (br s, 1H, NH), 6.11 (s, 1H), 3.73 (s, 3H), 3.72 (s, 3H), 2.29 (s, 3H), 1.32 (s, 9H).

We claim:

1. A compound of formula I-A-1

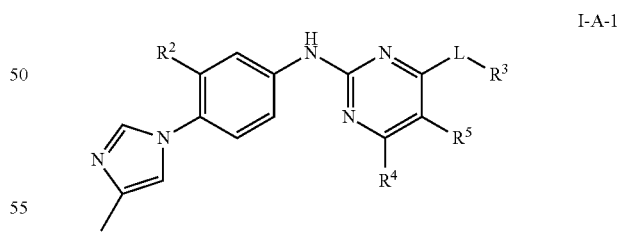

I-A-1 wherein

R$^2$ is hydrogen, lower alkoxy, lower alkyl, cyano or halogen;

R$^3$ is lower alkyl, lower alkenyl, lower alkyl substituted by fluoro, or is 4H-benzo[1,4]oxazin-3-one, cycloalkyl optionally substituted by hydroxy, or is heterocycloalkyl, which heterocycloalkyl is optionally substituted by hydroxyl, or is (CH$_2$)$_m$-aryl or is oxazol-5-yl, [1,2,4]triazol-1-yl, [1,2,4]triazol-3-yl, [1,2,3]triazol-1-yl, imidazol-1-yl, pyrazol-4-yl, pyrazol-3-yl, pyrazol-1-yl, [1,2,4]-oxadiazol-5-yl, [1,3,4]-oxadiazol-2-yl or [1,2,4]thiadiazol-5-yl which rings are optionally substituted by one or more R' for any definition of L, or is, hydroxy, for L being —CR$^6$R$^7$—, or is lower alkoxy, for L being C(O);

L is a single bond, —CR$^6$R$^7$—, —O—, or —C(O)—;

R' is halogen, lower alkyl, lower alkoxy, lower alkyl substituted by fluoro, lower alkoxy substituted by fluoro, SF$_5$, or is a five-membered heteroaryl group;

R$^4$ and R$^5$ are each independently hydrogen, halogen, lower alkyl, lower alkoxy, C(O)O-lower alkyl, lower alkyl substituted by one or more groups selected from fluoro, hydroxy, cyano and cycloalkyl, phenyl, benzyl, a five-or six-membered heteroaryl group, wherein the rings of the heteroaryl group are optionally substituted by one or more R', cycloalkyl or heterocycloalkyl, said cycloalkyl or heterocycloalkyl optionally substituted by lower alkyl and hydroxy, with the proviso that R$^4$ also optionally is NR$^8{}_2$, or wherein R$^4$ and R$^5$ together with the corresponding carbon atoms to which they are attached form an additional ring with —(CH$_2$)$_n$;

R$^6$ and R$^7$ are each independently hydrogen or lower alkyl or R$^6$ and R$^7$ together with the carbon atom to which they are attached form a C$_{3-6}$-cycloalkyl group;

R$^8$ is hydrogen or lower alkyl;

m is 0 or 1; and n is 3 or 4;

or a pharmaceutically active acid addition salt thereof.

2. The compound of claim 1, selected from the group consisting of (4-benzyl-pyrimidin-2-yl)-[3-methoxy-4-(4-methyl-imidazol-1-yl)-phenyl]-amine,

[3-methoxy-4-(4-methyl-imidazol-1-yl)-phenyl]-[4-(3,4,5-trifluoro-benzyl)-pyrimidin-2-yl]-amine,

[4-(3-chloro-benzyl)-pyrimidin-2-yl]-[3-methoxy-4-(4-methyl-imidazol-1-yl)-phenyl]-amine,

[3-methoxy-4-(4-methyl-imidazol-1-yl)-phenyl]-[5-methyl-4-(1-phenyl-ethyl)-pyrimidin-2-yl]-amine,

[3-methoxy-4-(4-methyl-imidazol-1-yl)-phenyl]-[4-methyl-6-(3,4,5-trifluoro-phenoxy)-pyrimidin-2-yl]-amine,

[4-(3,4-difluoro-phenoxy)-6-methyl-pyrimidin-2-yl]-[3-methoxy-4-(4-methyl-imidazol-1-yl)-phenyl]-amine,

[4-(4-chloro-phenoxy)-6-methyl-pyrimidin-2-yl]-[3-methoxy-4-(4-methyl-imidazol-1-yl)-phenyl]-amine,

[4-(2,6-dichloro-phenoxy)-pyrimidin-2-yl]-[3-methoxy-4-(4-methyl-imidazol-1-yl)-phenyl]-amine,

[3-methoxy-4-(4-methyl-imidazol-1-yl)-phenyl]-[4-methyl-6-(2-trifluoromethyl-phenoxy)-pyrimidin-2-yl]-amine,

[3-methoxy-4-(4-methyl-imidazol-1-yl)-phenyl]-[4-methyl-6-(3-trifluoromethoxy-phenoxy)-pyrimidin-2-yl]-amine, and

[3-methoxy-4-(4-methyl-imidazol-1-yl)-phenyl]-[4-methyl-6-(3-trifluoromethyl-phenoxy)-pyrimidin-2-yl]-amine, or a pharmaceutically active acid addition salt thereof.

3. The compound of claim 1, selected from the group consisting of [3-methoxy-4-(4-methyl-imidazol-1-yl)-phenyl]-[4-methyl-6-(3,3,4,4,4-pentafluoro-butoxy)-pyrimidin-2-yl]-amine, {4-[1-(4-chloro-phenyl)-1-methyl-ethyl]-5-methyl-pyrimidin-2-yl}-[3-methoxy-4-(4-methyl-imidazol-1-yl)-phenyl]-amine, {4-[1-(4-chloro-phenyl)-1-methyl-ethyl]-pyrimidin-2-yl}-methoxy-4-(4-methyl-imidazol-1-yl)-phenyl]-amine, {4-[1-(4-chloro-phenyl)-1-methyl-ethyl]-pyrimidin-2-yl}-fluoro-4-(4-methyl-imidazol-1-yl)-phenyl]-amine, ethyl 4-(4-chloro-phenyl)-2-[3-methoxy-4-(4-methyl-imidazol-1-yl)-phenylamino]-pyrimidine-5-carboxylate,

[3-methoxy-4-(4-methyl-imidazol-1-yl)-phenyl]-[4-(4-trifluoromethyl-phenyl)-pyrimidin-2-yl]-amine, (4-benzyl-6-methyl-pyrimidin-2-yl)-[3-methoxy-4-(4-methyl-imidazol-1-yl)-phenyl]-amine, (4-ethoxy-6-methyl-pyrimidin-2-yl)-[3-methoxy-4-(4-methyl-imidazol-1-yl)-phenyl]-amine,

[4-(4-chloro-phenyl)-5-(4-methoxy-benzyl)-pyrimidin-2-yl]-[3-methoxy-4-(4-methyl-imidazol-1-yl)-phenyl]-amine,

[3-methoxy-4-(4-methyl-imidazol-1-yl)-phenyl]-(4-methoxy-6-methyl-pyrimidin-2-yl)-amine, and (4-isopropoxy-6-methyl-pyrimidin-2-yl)-[3-methoxy-4-(4-methyl-imidazol-1-yl)-phenyl]-amine, or a pharmaceutically active acid addition salt thereof.

4. The compound of claim 1, selected from the group consisting of

[4-(4-Fluoro-phenoxy)-6-methyl-pyrimidin-2-yl]-[3-methoxy-4-(4-methyl-imidazol-1-yl)-phenyl]-amine,

[4-(4-tert-butyl-phenoxy)-6-methyl-pyrimidin-2-yl]-[3-methoxy-4-(4-methyl-imidazol-1-yl)-phenyl]-amine, 2-{6-ethoxy-2-[3-methoxy-4-(4-methyl-imidazol-1-yl)-phenylamino]-pyrimidin-4-yl}-propan-2-ol, 1-{2-[3-methoxy-4-(4-methyl-imidazol-1-yl)-phenylamino]-6-methyl-pyrimidin-4-yl}-piperidin-4-ol,

[3-methoxy-4-(4-methyl-imidazol-1-yl)-phenyl]-(4-methyl-6-pyrrolidin-1-yl-pyrimidin-2-yl)-amine,

[3-methoxy-4-(4-methyl-imidazol-1-yl)-phenyl]-(4-methyl-6-piperidin-1-yl-pyrimidin-2-yl)-amine 2-{2-[3-methoxy-4-(4-methyl-imidazol-1-yl)-phenylamino]-6-piperidin-1-yl-pyrimidin-4-yl}-propan-2-ol, 2-{2-[3-methoxy-4-(4-methyl-imidazol-1-yl)-phenylamino]-6-pyrrolidin-1-yl-pyrimidin-4-yl}-propan-2-ol,

[3-methoxy-4-(4-methyl-imidazol-1-yl)-phenyl]-(4-phenyl-pyrimidin-2-yl)-amine, 5-(4,6-dimethyl-pyrimidin-2-ylamino)-2-(4-methyl-imidazol-1-yl)-benzonitrile, and 5-[4-(4-chloro-phenyl)-pyrimidin-2-ylamino]-2-(4-methyl-imidazol-1-yl)-benzonitrile, or a pharmaceutically active acid addition salt thereof.

5. The compound of claim 1, selected from the group consisting of

[4-butyl-6-(4-chloro-phenyl)-pyrimidin-2-yl]-[3-methoxy-4-(4-methyl-imidazol-1-yl)-phenyl]-amine;

[5-ethyl-4-(4-trifluoromethyl-phenyl)-pyrimidin-2-yl]-[3-methoxy-4-(4-methyl-imidazol-1-yl)-phenyl]-amine,

[3-methoxy-4-(4-methyl-imidazol-1-yl)-phenyl]-[4-(3,4,5-trifluoro-phenyl)-pyrimidin-2-yl]-amine,

[4-(2,5-dichloro-phenyl)-pyrimidin-2-yl]-[3-methoxy-4-(4-methyl-imidazol-1-yl)-phenyl]-amine,

[4-(3,4-dichloro-phenyl)-pyrimidin-2-yl][3-methoxy-4-(4-methyl-imidazol-1-yl)-phenyl]-amine,

[4-(2,4-dichloro-phenyl)-pyrimidin-2-yl]-[3-methoxy-4-(4-methyl-imidazol-1-yl)-phenyl]-amine,

[4-(4-chloro-3-methyl-phenyl)-pyrimidin-2-yl]-[3-methoxy-4-(4-methyl-imidazol-1-yl)-phenyl]-amine,

[4-(4-chloro-phenyl)-5-propyl-pyrimidin-2-yl]-[3-methoxy-4-(4-methyl-imidazol-1-yl)-phenyl]-amine,

[3-methoxy-4-(4-methyl-imidazol-1-yl)-phenyl]-(5-methoxy-4-phenyl-pyrimidin-2-yl)-amine, and
(4-cyclopropyl-pyrimidin-2-yl)-[3-methoxy-4-(4-methyl-imidazol-1-yl)-phenyl]-amine, or a pharmaceutically active acid addition salt thereof.

6. The compound of claim 1, selected from the group consisting of ethyl 4-benzyl-2-[3-methoxy-4-(4-methyl-imidazol-1-yl)-phenylamino]-pyrimidine-5-carboxylate,
[3-methoxy-4-(4-methyl-imidazol-1-yl)-phenyl]-[4-(4-methyl-pent-3-enyl)-5-phenyl-pyrimidin-2-yl]-amine,
6-{2-[3-methoxy-4-(4-methyl-imidazol-1-yl)-phenylamino]-pyrimidin-4-yl}-4H-benzo[1,4]oxazin-3-one,
[4-(2-chloro-phenyl)-pyrimidin-2-yl]-[3-methoxy-4-(4-methyl-imidazol-1-yl)-phenyl]-amine,
(4-isobutyl-6-methyl-pyrimidin-2-yl)-[3-methoxy-4-(4-methyl-imidazol-1-yl)-phenyl]-amine,
(4,6-diethyl-pyrimidin-2-yl)-[3-methoxy-4-(4-methyl-imidazol-1-yl)-phenyl]-amine,
[3-methoxy-4-(4-methyl-imidazol-1-yl)-phenyl]-(4-methyl-6-phenyl-pyrimidin-2-yl)-amine,
(4-furan-2-yl-6-trifluoromethyl-pyrimidin-2-yl)-[3-methoxy-4-(4-methyl-imidazol-1-yl)-phenyl]-amine,
[3-methoxy-4-(4-methyl-imidazol-1-yl)-phenyl]-(4-phenyl-5,6,7,8-tetrahydro-quinazolin-2-yl)-amine,
(4,6-dimethyl-pyrimidin-2-yl)-[3-methoxy-4-(4-methyl-imidazol-1-yl)-phenyl]-amine, and
(4,6-bis-trifluoromethyl-pyrimidin-2-yl)-[3-methoxy-4-(4-methyl-imidazol-1-yl)-phenyl]-amine, or a pharmaceutically active acid addition salt thereof.

7. The compound of claim 1, selected from the group consisting of
(4-isopropyl-6-trifluoromethyl-pyrimidin-2-yl)-[3-methoxy-4-(4-methyl-imidazol-1-yl)-phenyl]-amine,
(4,6-diisopropyl-pyrimidin-2-yl)-[3-methoxy-4-(4-methyl-imidazol-1-yl)-phenyl]-amine,
[4-(2-chloro-phenyl)-6-methyl-pyrimidin-2-yl]-[3-methoxy-4-(4-methyl-imidazol-1-yl)-phenyl]-amine,
ethyl 2-[3-methoxy-4-(4-methyl-imidazol-1-yl)-phenylamino]-6-thiophen-2-yl-pyrimidine-4-carboxylate,
ethyl 6-Isopropyl-2-[3-methoxy-4-(4-methyl-imidazol-1-yl)-phenylamino]-pyrimidine-4-carboxylate,
ethyl 6-cyclopropyl-2-[3-methoxy-4-(4-methyl-imidazol-1-yl)-phenylamino]-pyrimidine-4-carboxylate,
ethyl 2-[3-methoxy-4-(4-methyl-imidazol-1-ye-phenylamino]-6-pyridin-2-yl-pyrimidine-4-carboxylate,
ethyl 2-[3-methoxy-4-(4-methyl-imidazol-1-yl)-phenylamino]-6-(4-trifluoromethyl-phenyl)-pyrimidine-4-carboxylate,
ethyl 6-(4-chloro-benzyl)-2-[3-methoxy-4-(4-methyl-imidazol-1-yl)-phenyl amino]-pyrimidine-4-carboxylate, and
2-{2-[3-methoxy-4-(4-methyl-imidazol-1-yl)-phenyl amino]-6-methyl-pyrimidin-4-yl}-propan-2-ol, or a pharmaceutically active acid addition salt thereof.

8. The compound of claim 1, selected from the group consisting of
2-{6-ethyl-2-[3-methoxy-4-(4-methyl-imidazol-1-yl)-phenylamino]-pyrimidin-4-yl}-propan-2-ol,
2-{6-isopropyl-2-[3-methoxy-4-(4-methyl-imidazol-1-yl)-phenylamino]-pyrimidin-4-yl}-propan-2-ol,
2-{6-cyclopropyl-2-[3-methoxy-4-(4-methyl-imidazol-1-yl)-phenylamino]-pyrimidin-4-yl}-propan-2-ol,
2-{6-tert-butyl-2-[3-methoxy-4-(4-methyl-imidazol-1-yl)-phenylamino]-pyrimidin-4-yl}-propan-2-ol,
2-{2-[3-methoxy-4-(4-methyl-imidazol-1-yl)-phenylamino]-6-pyridin-2-yl-pyrimidin-4-yl}-propan-2-ol,
2-{6-(4-chloro-benzyl)-2-[3-methoxy-4-(4-methyl-imidazol-1-yl)-phenylamino]-pyrimidin-4-yl}-propan-2-ol,
2-[2-[3-methoxy-4-(4-methyl-imidazol-1-yl)-phenylamino]-6-(4-trifluoromethyl-phenyl)-pyrimidin-4-yl]-propan-2-ol,
1-[2-[3-methoxy-4-(4-methyl-imidazol-1-yl)-phenylamino]-6-(4-trifluoromethyl-phenyl)-pyrimidin-4-yl]-ethanone,
3-{2-[3-methoxy-4-(4-methyl-imidazol-1-yl)-phenylamino]-pyrimidin-4-yl}-pentan-3-ol,
2-[2-[3-methoxy-4-(4-methyl-imidazol-1-yl)-phenylamino]-6-(3,4,5-trifluoro-phenyl)-pyrimidin-4-yl]-propan-2-ol, and
2-{6-(2,4-dichloro-phenyl)-2-[3-methoxy-4-(4-methyl-imidazol-1-yl)-phenylamino]-pyrimidin-4-yl}-propan-2-ol, or a pharmaceutically active acid addition salt thereof.

9. The compound of claim 1, selected from the group consisting of 2-{6-(4-chloro-phenyl)-2-[3-methoxy-4-(4-methyl-imidazol-1-yl)-phenylamino]-pyrimidin-4-yl}-propan-2-ol,
2-{6-(2-chloro-phenyl)-2-[3-methoxy-4-(4-methyl-imidazol-1-yl)-phenylamino]-pyrimidin-4-yl}-propan-2-ol,
2-{2-[3-methoxy-4-(4-methyl-imidazol-1-yl)-phenylamino]-5,6,7,8-tetrahydro-quinazolin-4-yl}propan-2-ol,
2-{2-[3-fluoro-4-(4-methyl-imidazol-1-yl)-phenylamino]-6-isopropyl-pyrimidin-4-yl}-propan-2-ol,
2-[2-[3-fluoro-4-(4-methyl-imidazol-1-yl)-phenylamino]-6-(4-trifluoromethyl-phenyl)-pyrimidin-4-yl]-propan-2-ol,
2-{6-dimethylamino-2-[3-methoxy-4-(4-methyl-imidazol-1-yl)-phenylamino]-pyrimidin-4-yl}-propan-2-ol,
1-{6-(1-hydroxy-1-methyl-ethyl)-2-[3-methoxy-4-(4-methyl-imidazol-1-yl)-phenylamino]-pyrimidin-4-yl}-4-methyl-piperidin-4-ol,
1-[2-[3-methoxy-4-(4-methyl-imidazol-1-yl)-phenylamino]-6-(4-trifluoromethyl-phenyl)-pyrimidin-4-yl]-cyclopentanol,
5-[4-(1-hydroxy-1-methyl-ethyl)-6-(4-trifluoromethyl-phenyl)-pyrimidin-2-ylamino]-2-(4-methyl-imidazol-1-yl)-benzonitrile, and
2-[2-[3-methyl-4-(4-methyl-imidazol-1-yl)-phenylamino]-6-(4-trifluoromethyl-phenyl)-pyrimidin-4-yl]-propan-2-ol, or a pharmaceutically active acid addition salt thereof.

10. A pharmaceutical composition comprising a compound of formula I-A-1

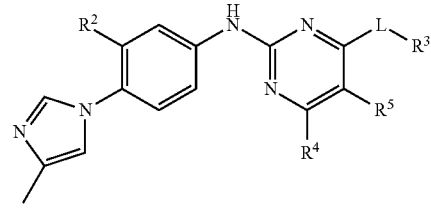

wherein
$R^2$ is hydrogen, lower alkoxy, lower alkyl, cyano or halogen;
$R^3$ is lower alkyl, lower alkenyl, lower alkyl substituted by fluoro, or is 4H-benzo[1,4]oxazin-3-one, cycloalkyl optionally substituted by hydroxy, or is heterocycloalkyl, which heterocycloalkyl is optionally substituted by hydroxyl, or is $(CH_2)_m$-aryl or is oxazol-5-yl, [1,2,4]triazol-1-yl, [1,2,4]triazol-3-yl, [1,2,3]triazol-1-yl, imidazol-1-yl, pyrazol-4-yl, pyrazol-3-yl, pyrazol-1-yl, [1,2,4]-oxadiazol-5-yl, [1,3,4]-oxadiazol-2-yl or [1,2,4]thiadiazol-5-yl which rings are optionally substituted by one or more R' for any definition of L, or is, hydroxy, for L being —$CR^6R^7$—, or is lower alkoxy, for L being C(O);

L is a single bond, —$CR^6R^7$—, —O—, or —C(O)—;

R' is halogen, lower alkyl, lower alkoxy, lower alkyl substituted by fluoro, lower alkoxy substituted by fluoro, $SF_5$, or is a five-membered heteroaryl group;

$R^4$ and $R^5$ are each independently hydrogen, halogen, lower alkyl, lower alkoxy, C(O)O-lower alkyl, lower alkyl substituted by one or more groups selected from fluoro, hydroxy, cyano and cycloalkyl, phenyl, benzyl, a five-or six-membered heteroaryl group, wherein the rings of the heteroaryl group are optionally substituted by one or more R', cycloalkyl or heterocycloalkyl, said cycloalkyl or heterocycloalkyl optionally substituted by lower alkyl and hydroxy, with the proviso that $R^4$ also optionally is $NR^8_2$, or wherein $R^4$ and $R^5$ together with the corresponding carbon atoms to which they are attached form an additional ring with —$(CH_2)_n$;

$R^6$ and $R^7$ are each independently hydrogen or lower alkyl or $R^6$ and $R^7$ together with the carbon atom to which they are attached form a $C_{3-6}$-cycloalkyl group;

$R^8$ is hydrogen or lower alkyl;

m is 0 or 1; and n is 3 or 4;

or a pharmaceutically active acid addition salt thereof and a pharmaceutically acceptable carrier.

11. The compound of claim 1 wherein said compound is [3-methoxy-4-(4-methyl-imidazol-1-yl)-phenyl]-[4-(3,4,5-trifluoro-benzyl)-pyrimidin-2-yl]-amine, or a pharmaceutically active acid addition salt thereof.

* * * * *